(12) United States Patent
Brown et al.

(10) Patent No.: US 7,195,917 B2
(45) Date of Patent: Mar. 27, 2007

(54) METHODS FOR CONTROLLING GIBBERELLIN LEVELS

(75) Inventors: Sherri M. Brown, Chesterfield, MO (US); Tedd D. Elich, Ballwin, MO (US); Gregory R. Heck, Crystal Lake Park, MO (US); Ganesh M. Kishore, St. Louis, MO (US); Eugene W. Logusch, Chesterfield, MO (US); Sherry J. Logusch, Chesterfield, MO (US); Kenneth J. Piller, St. Louis, MO (US); Sudabathula Rao, St. Louis, MO (US); Joel E. Ream, St. Louis, MO (US); Scott R. Baerson, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 538 days.

(21) Appl. No.: 10/401,321

(22) Filed: Mar. 27, 2003

(65) Prior Publication Data

US 2003/0233679 A1    Dec. 18, 2003

Related U.S. Application Data

(62) Division of application No. 09/371,307, filed on Aug. 10, 1999, now Pat. No. 6,723,897.

(60) Provisional application No. 60/137,977, filed on Jun. 7, 1999, provisional application No. 60/096,111, filed on Aug. 10, 1998.

(51) Int. Cl.
   *C12N 15/82*    (2006.01)
   *A01H 5/00*    (2006.01)
   *C12N 5/10*    (2006.01)

(52) U.S. Cl. .................. 435/468; 435/320.1; 800/290; 800/287

(58) Field of Classification Search ...................... None
   See application file for complete search history.

(56) References Cited

U.S. PATENT DOCUMENTS

| 5,107,065 | A | 4/1992 | Shewmaker et al. | 800/298 |
| 5,612,191 | A | 3/1997 | Briggs et al. | 435/69.1 |
| 5,773,288 | A | 6/1998 | Briggs et al. | 435/320.1 |
| 6,198,021 | B1 | 3/2001 | Lange | 800/278 |
| 6,670,527 | B1 * | 12/2003 | Thomas et al. | 800/290 |

FOREIGN PATENT DOCUMENTS

| EP | 0 692 537 | 1/1996 |
| WO | WO 93/16096 | 8/1993 |
| WO | WO 94/28141 | 12/1994 |
| WO | WO 95/02060 | 1/1995 |
| WO | WO 95/35383 | 12/1995 |
| WO | WO 96/05317 | 2/1996 |
| WO | WO 97/29123 | 8/1997 |
| WO | WO 97/41240 | 11/1997 |
| WO | WO 97/43419 | 11/1997 |
| WO | WO 97/46690 | 12/1997 |
| WO | WO 99/66029 | 12/1999 |
| WO | WO 9966029 A2 * | 12/1999 |

OTHER PUBLICATIONS

Falcon-Perez JM et al. 1999, J Biol Chem. 13;274(33):23584-90.*
Thomas et al. 1999, PNAS, 96:4698-4703.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Evans et al 1992, Plant Mol. Biol. 20:1019-1028.*
Aach, H., et al., ent-Kaurene synthase is located in proplastids of meristematic shoot tissues, *Planta*, 202: 211-219 (1997).
Birnberg, P.R., et al., Metabolism of Gibberellin $A_{12}$-7-Aldehyde by Soybean Cotyledons and its Use in Identifying Gibberellin $A_7$ as an Endogenous Gibberellin, *Plant Physiol.*, 82: 241-246 (1986).
Gilmore, S.J., et al., Gibberellin Metabolism in Cell-Free Extracts from Spinach Leaves in Relation to Photoperiod, *Plant Physiol.*, 82: 190-195 (1986).
Graebe, J.E., Gibberellin Biosynthesis and Control, *Ann. Rev. Plant Physiol.*, 38: 419-465 (1987).
Graebe, J.E., and Hedden, P., The Biosynthesis of a $C_{19}$-Gibberellin from Mevalonic Acid in a Cell-Free System from a Higher Plant, *Planta*, 120: 307-309 (1974).
Hedden, P. and Kamiya, Y., Gibberellin Biosynthesis: Enzymes, Genes and their Regulation, *Annu. Rev. Plant Physiol. Mol. Biol.*, 48: 431-460 (1997).
Hedden, P., et al., Modificiation of Plant Morphology by Genetic Manipulation of Gibberellin Biosynthesis, *Genetic and Environmental Manipulation of Horticultural Crops*, eds. K.E. Cockshull. D. Gray, C.B. Seymour and B. Thomas, pp. 205-217 (1998).
www.plant-hormones.bbsrc.ac.uk/gibberellin_information2.htm.
Jung, J., Plant Growth Regulation with Triazoles of the Dioxanyl Type. *Plant Growth Regul.*, 4: 181-188 (1986).

(Continued)

*Primary Examiner*—Ashwin Mehta
*Assistant Examiner*—Li Zheng
(74) *Attorney, Agent, or Firm*—M. Todd Rands; Howrey LLP

(57) ABSTRACT

Methods and materials are disclosed for the inhibition and control of gibberellic acid levels. In particular, nucleic acid sequences of copalyl diphosphate synthase. 3-β hydroxylase, and 2-oxidase and additional nucleic acid sequences are disclosed. Gibberellic acid levels may be inhibited or controlled by preparation of a chimeric expression construct capable of expressing a RNA or protein product which suppresses the gibberellin biosynthetic pathway sequence, diverts substrates from the pathway or degrades pathway substrates or products. The sequence is preferably a copalyl diphosphate synthase sequence, a 3β-hydroxylase sequence, a 2-oxidase sequence, a phytoene synthase sequence, a C20-oxidase sequence, and a 2β,3β-hydroxylase sequence. Administration of a complementing agent, preferably a gibberellin or gibberellin precursor or intermediate restores bioactivity.

10 Claims, 43 Drawing Sheets

OTHER PUBLICATIONS

Figure 1:
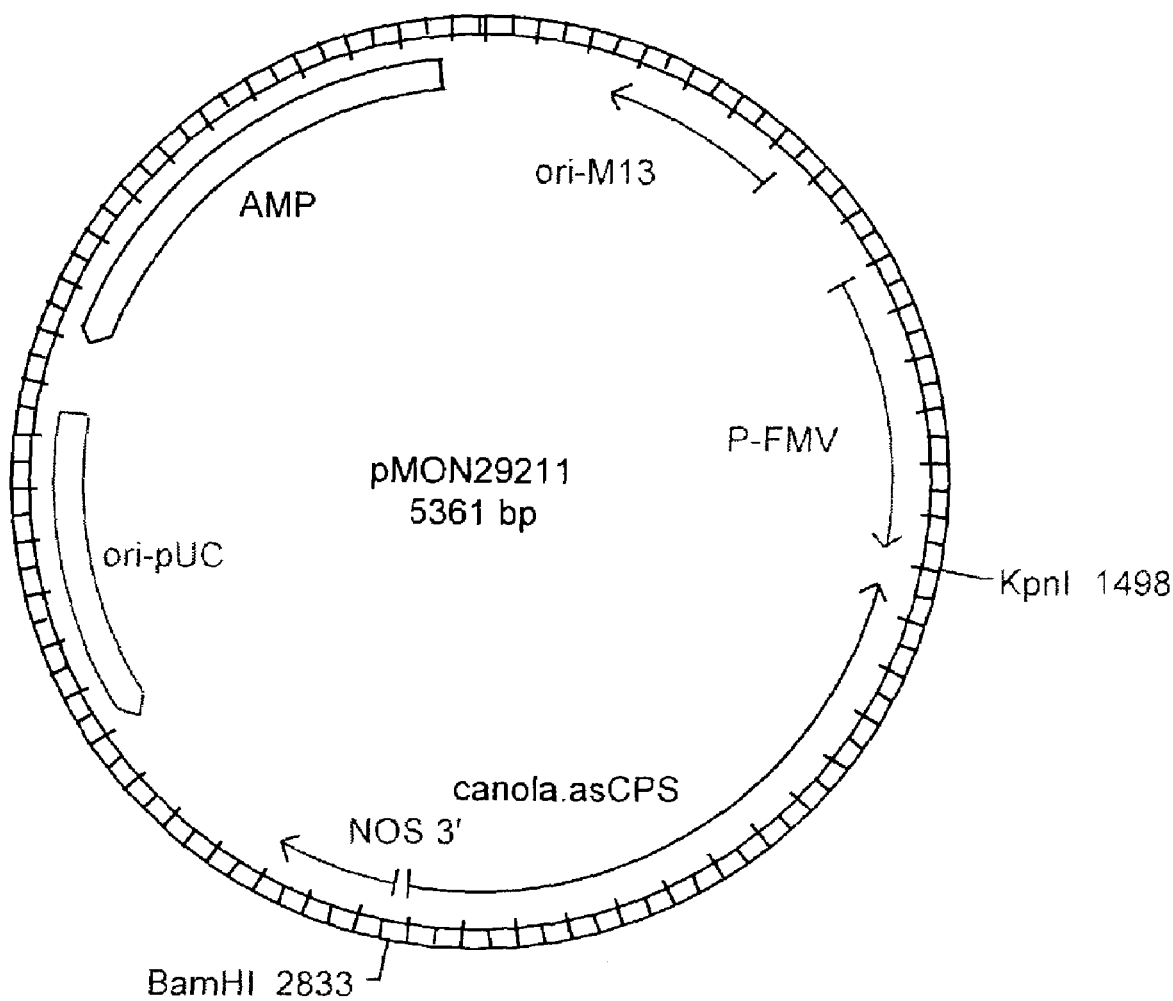

Kamiya, Y. and Graebe, J.E., The Biosynthesis of All Major Pea Gibberellins in a Cell-Free System from *Pisum Sativum*, *Phytochemistry*, 22: 681-690, (1983).

Lange, T., et al., Cloning and Expression of a Gibberellin 2β,3β-Hydroxylase cDNA from Pumpkin Endosperm, *Plant Cell*, 9: 1459-1467 (1997).

Lange, et al., Separation and charcterisation of three 2-oxoglutarate-dependent dioxygenases from *Cucurbita maxima* L. endosperm involved in gibberellin biosynthesis, *Planta*, 195: 98-107 (1994).

Owen, D.J., et al., Synthesis and Confirmation of Structure for a New Gibberellin, 2β-Hydroxy-$GA_{12}(GA_{110})$, from Spinach and Oil Palm, *Phytochemistry*, 47: 331-337 (1998).

Phillips, A.L., et al., Isolation and Expression of Three Gibberellin 20-Oxidase cDNA Clones from *Arabidopsis*, *Plant Physiol.*, 108: 1049-1059 (1995).

Rock, C.D., et al., The Role of Hormones During Seed Development, *Plant Hormones, Physiology, Biochemistry and Molecular Biology*, 2nd Edition, P.J. Davies, Ed., Kluwer Academic Publishers, Dordrecht, pp. 671-697 (1995).

Schneider, G. and Schmidt, J., Conjugation of Gibberellins in *Zea Mays*, *Plant Growth Substances*, ed. Pharis, R.P., et al., Springer-Verlag, Heidelberg, pp. 300-306 (1988).

Schwender, J., et al., Biosynthesis of isoprenoids (carotenoids, sterols, prenyl side-chains of chlorophylls and plastoquinone) via a novel pyruvate/glyceraldehyde 3-phosphate non-mevalonate pathway in the green alga *Scenedesmus obliquus*, Biochem. J., 316: 73-80 (1996).

Sheng, C., et al., Identification of Gibberellin $A_{89}$ From Bassica Campestris, *Phytochemistry*, 31: 4055-4057 (1992).

Smith and MacMillan, *Journal of Plant Growth Regulators*, 2: 251-264 (1984).

Smith, V.A., et al., Partial Purification and Characterization of the Gibberellin $A_{20}$ 3β-Hydroxylase from Seeds of *Phaseolus vulgaris*, *Plant Physiol.*, 94: 1390-1401 (1990).

Sponsel, V.M., The Biosynthesis and Metabolism of Gibberellins in Higher Plants, *Plant Hormones, Physiology, Biochemistry and Molecular Biology*, 2nd Edition, P.J. Davies, Ed., Academic Publishers, Dordrecht, pp. 66-97 (1995).

Thomas, S.G., et al., Molecular cloning and functional expression of gibberellin 2-oxidases, multifunctional enzymes involved in gibberellin deactivation, *Proc. Natl. Acad. Sci. US.A.*, 4698-4703 (1999).

Thomas, T.H., et al., Some reflections on the relationship between endogenous hormones and light-mediated seed dormancy, *Plant Growth Reg.*, 11: 239-248 (1992).

Toyomasu, T., et al., Cloning and characterization of a cDNA encoding gibberellin 20-oxidase from rice (*Oryza sativa*) seedlings, *Physiol. Plant*, 99: 111-118 (1997).

Winkler, R.G. and Helentjaris, T., The Maize Dwarf3 Gene Encodes a Cytochrome P450-Mediated Early Step in Gibberellin Biosynthesis, *Plant Cell*, 1307-1317 (1995).

Xu, Y-L., et al., Gibberellins and Stem Growth in *Arabidopsis thaliana.*, *Plant Physiol.*, 114: 1471-1476 (1997).

Zeevaart, J.A.D. and Gage, D.A., *ent*-Kaurene Biosynthesis is Enhanced by Long Photoperiods in the Long-Day Plants *Spinacia oleracea* L. and *Agrostemma githago* L., *Plant Physiol.*, 101: 25-29 (1993).

Zhang, F., et al., Application of gibberellic acid to the surface of soybean seed (*Glycine max*(L.) Merr.) and symbiotic nodulation, plant development, final grain and protein yield under short season conditions, *Plant Soil*, 188: 329-335 (1997).

Zheng, G.H., et al., Enhancement of canola seed germination and seedling emergence at low temperature by priming, *Crop Sci.*, 34: 1589-1593 (1994).

Thomas, S.G., et al., "Molecular Cloning and Functional Expression of Gibberellin 2-oxidases, multifunctional Enzymes involved in Gibberellin Deactivation", Proc. Nat. Acad. Sci. USA 96:4698-4703 (1999).

Ait-Ali, T., et al., The LS locus of pea encodes the gibberellin biosynthesis enzyme ent-kaurene synthase A, *The Plant Journal* 11(3): 443-454 (1997).

Bensen, R.J., et al., Cloning and Characterization of the Maize An1 Gene, *The Plant Cell*, 7: 75-84 (1995.

Fray, R.G., et al., Constitutive expression of a fruit phytoene synthase gene in transgenic tomatoes causes dwarfism by redirecting metabolites from the gibberellin pathway, *The Plant Journal*, 8(5): 693-701 (1995).

Hong, J.C., et al., Characterization of a Proline-rich Cell Wall Protein Gene Family or Soybean, *The Journal of Biological Chemistry*, 265(5): 2470-2475 (1990).

Kusaba, S., et al., Decreased $GA_1$ Content Caused by the Overexpression of OSH1 is Accompanied by Suppression of GA 20-Oxidase Gene Expression, *Plant Physiol.*, 117: 1179-1184 (1998).

Lester, D.R., et al., AC U85045, *EBI Database* (1997).

Lester, D.R., et al., Mendel's stem length gene (Le) encodes a gibberellin 3beta-hydroxylase, *Plant Cell*, 9: 1435-1443 (1997).

Lin, X., et al., Sequence and analysis of chromosome II of *Arabidopsis thaliana*, AC 004077, *EBI Database* (1998).

MacMillan, J., et al., Gibberellin Biosynthesis from Gibberellin $A_{12}$-Aldehyde in Endosperm and Embryos of *Marah macrocarpus*, *Plant Physiol.*, 113: 1369-1377 (1997).

Reddy, E., AC Y17556, *EBI Database* (1998).

Toyomasu, T., et al., Cloning and characterization of a cDNA encoding gibberellin 20-oxdase from rice (*Oryza sativa* L.) seedlings, AC U50333, *EBI Database* (1997).

Waycott, W. and Taiz, L., Phenotypic Characterization of Lettuce Dwarf Mutants and their Response to Applied Gibberellins, *Plant Physiol.*, 95: 1162-1168 (1991).

\* cited by examiner

*E = emergence

METHODS FOR CONTROLLING GIBBERELLIN LEVELS

CROSS REFERENCES TO RELATED APPLICATIONS

This application is a divisional of U.S. patent application Ser. No. 09/371,307, filed on Aug. 10, 1999, issued as U.S. Pat. No. 6,723.897, which claims priority from U.S. Provisional Patent Application No. 60/096,111, filed Aug. 10, 1998, and U.S. Provisional Patent Application No. 60/137,977, filed on Jun. 7, 1999. Both of these Provisional Patent priority documents are incorporated by reference in their entirety.

FIELD OF THE INVENTION

The invention relates to materials and methods for the control of seed germination and seedling growth and, more specifically, to the regulation of the gene products of the gibberellin biosynthetic pathway and restoration of normal seed germination and seedling growth by treatment with exogenously applied gibberellins or gibberellin precursors.

BACKGROUND OF THE INVENTION

Most agriculturally important crop plants are propagated by seed. The seed is planted and under favorable environmental conditions, the seed germinates and grows into crop plants. However, frequently conditions can occur in which after planting of the seed, the seed fails to germinate or germinates poorly producing a thin stand of plants with reduced yield or necessitating the replanting of the crop with new seed at considerable expense to the grower. This has been shown to occur with soybean, corn, and canola in wet and cool field conditions (Wang et al., *Enviro. Exp. Bot.* 36: 377–383, 1996; Zheng et al., *Crop Sci.* 34: 1589–1593, 1994). It is often necessary to plant more seeds than predicted to be necessary to achieve a good crop. The percent of seeds that germinate is considered good at 80%. A measurable savings in resources can be achieved if the seed germination can be controlled to achieve 90% or greater seed germination and vigorous seedling growth. Also, seeds may germinate precociously if the environmental conditions at crop maturity are such that the seed prematurely sprout. This is a problem in some wheat varieties and causes a loss of yield and quality of the harvested grain. Dormancy of seeds during storage is an important criteria for a quality product. Adequate storage and shipping characteristics of seeds is an important prerequisite for distributing food products around the world. In many developing countries storage facilities are inadequate and seed and food quality may be affected when seed dormancy is broken and the process of seed germination begins in storage. However, seeds that are chemically treated to inhibit seed germination often show characteristic traits such as reduced plant height and seedling vigor for some period of time after germination. Seed, genetically engineered for a high level of seed dormancy, can be stored more efficiently and suffer fewer side effects than chemically treated germination inhibition.

The failure of seeds to germinate uniformly and at high frequency is an important factor affecting crop yield. Soybean (*Glycine max*) is a crop species that suffers from loss of seed germination during storage and fails to germinate when soil temperatures are cool. It has been shown that the exogenous treatment of gibberellic acid will stimulate soybean seed germination under conditions that the seed will not normally germinate (Zhang et al., *Plant Soil* 188: 329–335, 1997). Sugar beet (*Beta vulgaris*) seed is often chemically treated to improve germination and plant stand which has a direct affect on the yield of the crop. Canola seed germination and seedling growth can be improved at low temperatures by treatment with gibberellic acid (Zheng et al., *Crop Sci.* 34: 1589–1593, 1994). Improved seedling vigor is observed by these treatments with the plants emerging more quickly from the soil and are more likely to establish themselves under adverse environmental conditions.

There is a need for an effective system which would couple genetically improved seed dormancy with a chemical seed treatment to induce seed germination when germination is desired. The genetic control of gibberellin activity in developing seeds, germinating seeds and during early seedling growth coupled with exogenous replacement of the activity would be an effective means to control seed germination and seedling growth.

Inhibitors of gibberellin biosynthesis suggest that de novo synthesis of GA is a prerequisite for the release from dormancy (Thomas, *Plant Growth Reg.* 11: 239–248, 1992). A key enzyme of gibberellin biosynthesis is copalyl diphosphate synthase (CPS) (formerly ent-kaurene synthetase (EKS-A)). Two enzymes, CPS and KS-B (ent-kaurene synthetase-B), catalyze the cyclization of geranylgeranyl diphosphate to ent-kaurene. CPS is the first committed step in GA biosynthesis. Plant mutants blocked at CPS show strong adverse germination/seedling vigor phenotypes that can be reversed by the application of an exogenous supply of GA. Although these mutants demonstrate the role of GA in seed germination, they do not establish the developmental timing required for expression of GA for normal seed germination and seedling growth. It has not been previously established that soybean plants require de novo biosynthesis of GA for normal seed germination and early seedling growth. It has also not been previously demonstrated that endogenous levels of GA can be affected by the expression of an antisense RNA to a gene important in the biosynthesis of GA in soybean. There are no known soybean mutants blocked in GA biosynthesis; therefore, the requirement for de novo GA biosynthesis in soybean is unknown. Inhibitors of GA biosynthesis offer a method to investigate the effect of decreased GA biosynthesis on soybean germination and seedling growth. GA biosynthesis inhibitors can block ent-kaurene biosynthesis or can block at ent-kaurene oxidation or can inhibit the late dioxygenase-catalyzed steps (Jung et al., *J. Plant Growth Regul.* 4: 181–188, 1986).

Dioxygenase enzymes modify various gibberellin substrates. The dioxygenases, 20-oxidase and 3β-hydroxylase, are involved in the biosynthesis of GA precursors and active forms. The overexpression or suppression of the GA 20-oxidase genes affect seedling growth differentially (Hedden, et al., In *Genetic and environmental manipulation of horticultural crops*. Cockshull, Gray, Seymour and Thomas eds. CAB International 1998). Degradation of bioactive GA in specific tissues of the developing seed, germinating seed and early seeding growth can also regulate GA tissue responses. Genes from *Arabidopsis* and *Phaseolus coccineus* have been identified that encode for enzymes that have gibberellin 2-oxidase activity (Thomas et al., *Proc. Natl. Acad. Sci. U.S.A.* 96: 4698–4703, 1999).

Pathways which use substrates in common with the gibberellin pathway are known. The carotenoid pathway (Encyclopedia of Plant Physiology. Secondary Plant Products Vol 8: 259, Bell and Charlwood eds.), the phytol pathway (Encyclopedia of Plant Physiology. Secondary Plant Products Vol 8: 207, Bell and Charlwood eds. ) and the gibberellin pathway each use geranylgeranyl pyrophosphate as a key precursor to the synthesis of their respective end products.

The methods of plant biotechnology provide means to express gene products in plants at particular developmental plant growth stages. Gene promoters that express during seed germination and early seedling development are a preferred embodiment of this invention. The present invention provides a method to genetically suppress seed germination and early seedling development, then by necessity restore normal germination with exogenous application of GA compounds to the seed or seedling. The present invention provides genetically-engineered gibberellin-deficient plants. In agriculture, there exists a need for improved materials and methods for the control of seed germination and seedling growth.

SUMMARY OF THE INVENTION

The present invention provides materials and methods for the control of seed germination and seedling growth through the use of plants that have altered levels of a hormone such as a gibberellin (GA) that affects seed germination and seedling growth. Such plants can be germinated and grown to maturity by treating the plants, or seeds or seedlings of such plants, a compound that restores substantially normal levels of the hormone or that has hormone activity.

According to one aspect of the invention, methods are provided for growing a transgenic plant that has a transgene that includes a promoter and, operably linked to the promoter, a sequence that, when expressed, alters the level of a hormone, for example GA. The transgene thus causes one or more abnormal phenotypes in the transgenic plant or seeds or seedlings thereof, such as a shortened hypocotyl, shortened epicotyl, or both (compared with a control, i.e., an otherwise identical except for lacking the transgene). A phenotypically normal plant can be grown from the transgenic plant after applying to the plant or to the seed or seedling thereof (for example, applying indirectly to soil or directly to the plant, seed or seedling) a composition that includes a first compound that is metabolized to produce a second compound that substantially eliminates the abnormal phenotype. In the case of GA-deficient plants, for example, use of GA precursors or biosynthetic intermediates (e.g., ent-kaurene, ent-kaurenoic acid, ent-7α-hydroxykaurenoic acid, steviol, $GA_{12}$-aldehyde, $GA_{12}$, $GA_{15}$, $GA_{24}$, $GA_9$, $GA_{53}$, $GA_{44}$, $GA_{19}$, $GA_{20}$, $GA_5$, and $GA_3$-3-acetate) helps to properly regulate the amount of bioactive GA that is available within the plants, seeds, or seedlings. Preferred compounds for administration to GA-deficient plants include $GA_9$, GA15, $GA_{19}$, $GA_{24}$, $GA_{44}$, $GA_{53}$, $GA_5$, and steviol. Several approaches are described herein for producing GA-deficient plants for which the preferred promoter is preferentially expressed in developing seeds, during seed germination, or in young seedlings.

According to one approach, such methods involve the use of transgenic plants having altered hormone levels resulting from a transgene that comprises a sequence that, when expressed, reduces expression of an enzyme in the pathway for biosynthesis of the hormone. For example, the sequence may be in an antisense orientation (i.e., an antisense construct), or suppress hormone biosynthesis as a ribozyme, triplex DNA, by cosuppression, or by any other well-known methods for reducing the expression of endogenous plant genes. For example, in order to alter GA levels, the sequence may suppress expression of an enzyme such as a copalyl diphosphate synthase, a 3β-hydroxylase, or a C-20 oxidase, such as by antisense expression of a sequence that comprises at least 12 contiguous nucleotides (and preferably at least 15, 18, 20, 24, 30, 40, or longer, up to and including the entire length of) SEQ ID NO:1, 2, 3, 4, 5, 6, or 8 or complements thereof, or, alternatively, a sequence that hybridizes under high stringency conditions to SEQ ID NO:1, 2, 3, 4, 5, 6, or 8 or complements thereof.

According to another approach, such methods involve the use of transgenic plants having altered hormone levels resulting from a transgene that comprises a sequence that inactivates the hormone. For example, plants having altered levels of a GA can be produced by expression in the plants of a sequence that encodes a GA 2-oxidase, including, but not limited to: (1) sequences having at least 85% (preferably at least 90, 95, or as much as 100%) nucleotide sequence similarity with SEQ ID NO:57, 58, 60, 62, 64, 66, 67, 68, 69, 70, or 71; (2) sequences that encode a GA 2-oxidase having at least 70% (preferably at least 75, 80, 85, 90, 95, or as much as 100%) amino acid identity with an *Arabidopsis* GA 2-oxidase 4, an *Arabidopsis* 2-oxidase 5, a soybean GA 2-oxidase 1, a soybean GA 2-oxidase 2, a cotton GA 2 oxidase-1, a cotton GA 2 oxidase-2, a cotton GA 2 oxidase-3, a maize GA 2-oxidase 1, or a maize 2-oxidase 2.

According to another approach, such methods involve the use of transgenic plants having altered hormone levels resulting from a transgene that comprises a sequence that encodes an enzyme that metabolizes a precursor of the hormone to produce a metabolite that is not a precursor of the hormone in the transgenic plant. In the case of GA, such enzymes include phytoene synthases, C-20 oxidases, and 2β,3β-hydroxylases.

According to another aspect of the invention, related methods are provided that involve the use of transgenic plants (or seeds or seedlings thereof) that have a transgene that comprises a promoter (preferably a promoter that is preferentially expressed in developing seeds, during seed germination, or in early seedlings) and, operably linked to the promoter, a sequence that, when expressed, alters the level of an enzyme in the gibberellin biosynthetic pathway and causes an abnormal phenotype in the transgenic plant or the seed or seedling thereof (compared with a control). A phenotypically normal plant can be grown after applying to the plant or to a seed or seedling thereof a composition that comprises at least one GA compound, as defined herein. For example, GA levels can be affected by altering levels of a copalyl diphosphate synthase, a 3β-hydroxylase, or a C-20 oxidase using a sequence that comprises: (1) at least 15 contiguous nucleotides of a member of the group consisting of SEQ ID NO:1, 2, 3, 4, 5, 6, 8; (2) a sequence having at least 85% (preferably at least 90, 95, or as much as 100%) nucleotide sequence identity with of a member of the group consisting of SEQ ID NO:1, 2, 3, 4, 5, 6, 8; or (3) a sequence that encodes a polypeptide having at least 70% (preferably at least 75, 80, 85, 90, 95, or as much as 100%) amino acid sequence identity with a polypeptide encoded by member of the group consisting of SEQ ID NO:1, 2, 3, 4, 5, 6, 8. Preferred GA compounds for rescuing normal plants in this case include ent-kaurene, ent-kaurenoic acid, ent-7α-hydroxykaurenoic acid, steviol, $GA_{12}$-aldehyde, $GA_{12}$, $GA_{15}$, $GA_{24}$, GA9, $GA_{53}$, $GA_{44}$, $GA_{19}$, $GA_{20}$, $GA_5$, $GA_4$, $GA_7$, $GA_3$, and $GA_3$-3-acetate, most preferably $GA_9$, $GA_{15}$, $GA_{19}$, $GA_{24}$, $GA_{44}$, $GA_{53}$, $GA_5$, and steviol.

According to another aspect of the invention, additional related methods are provided that involve the use of transgenic plants (or seeds or seedlings thereof) that have a transgene that comprises a promoter (preferably a promoter that is preferentially expressed in developing seeds, during seed germination, or in early seedlings) and, operably linked to the promoter, a sequence that encodes an enzyme such as GA 2-oxidase that inactivates an endogenous GA, that is a GA that is normally present in the plant, causing at least one abnormal phenotype in the transgenic plant or the seed or seedling thereof (compared with a control). A phenotypically normal plant can be grown after applying to the plant or to a seed or seedling thereof a composition that comprises at least one GA compound that is metabolized by the seed or seedling to produce a product having gibberellin activity that is not degraded by the enzyme. In order to produce a GA 2-oxidase, such sequences include, for example: (1) sequences having at least 85% (preferably at least 90, 95, or as much as 100%) nucleotide sequence similarity with a member of the group consisting of SEQ ID NO:57, 58, 60, 62, 64, 66, 67, 68, 69, 70, and 71; and (2) sequences that encode a GA 2-oxidase having at least 70% (preferably at least 75, 80, 85, 90, 95, or as much as 100%) amino acid identity with an *Arabidopsis* GA 2-oxidase 4, an *Arabidopsis* 2-oxidase 5, a soybean GA 2-oxidase 1, a soybean GA 2-oxidase 2, a cotton GA 2 oxidase-1, a cotton GA 2 oxidase-2, a cotton GA 2 oxidase-3, a maize GA 2-oxidase 1, and a maize 2-oxidase 2. Preferred GA compounds include $GA_4$, $GA_7$, $GA_3$, and $GA_3$-3-acetate, most preferably $GA_3$, and $GA_3$-3-acetate.

According to another aspect of the invention, additional related methods are provided that involve the use of transgenic plants (or seeds or seedlings thereof) that have a transgene that comprises a promoter (preferably a promoter that is preferentially expressed in developing seeds, during seed germination, or in early seedlings) and, operably linked to the promoter, a sequence that encodes an enzyme that metabolizes a gibberellin precursor to produce a metabolite that is not a gibberellin precursor, for example a phytoene synthase, a C-20 oxidase, or a 2β,3β-hydroxylase, thereby reducing the level of a gibberellin and causing at least one abnormal phenotype in the transgenic plant or the seed or seedling thereof (compared to a control). A phenotypically normal plant can be grown after applying to the plant or to a seed or seedling thereof a composition that comprises at least one GA compound that substantially eliminates the abnormal phenotype. In the case of phytoene synthase, the preferred GA compounds are ent-kaurene, ent-kaurenoic acid, ent-7α-hydroxykaurenoic acid, steviol, $GA_{12}$-aldehyde, $GA_{12}$, $GA_{15}$, $GA_{24}$, $GA_9$, $GA_{53}$, $GA_{44}$, $GA_{19}$, $GA_{20}$, $GA_5$, $GA_4$, $GA_7$, $GA_3$, and $GA_3$-3-acetate, most preferably $GA_9$, $GA_{15}$, $GA_{19}$, $GA_{24}$, $GA_{44}$, $GA_{53}$, $GA_5$ and steviol. In the case of C-20 oxidase, the preferred GA compounds are $GA_9$, $GA_4$, $GA_{20}$, $GA_1$, $GA_7$, $GA_3$, and $GA_3$-3-acetate, most preferably $GA_3$ and $GA_3$-3-acetate. In the case of 2β,3β-hydroxylase, the preferred GA compounds are $GA_9$, $GA_{41}$, $GA_{53}$, $GA_{44}$, $GA_{19}$, $GA_{20}$, $GA_{15}$, $GA_7$, $GA_3$, and $GA_3$-3-acetate, most preferably $GA_3$ and $GA_3$-3-acetate.

Compositions are provided that are useful in practicing the methods discussed above.

For example, nucleic acid segments are provided that comprise at least 12 contiguous nucleotides (and preferably at least 15, 18, 20, 24, 30, 40, or longer, up to and including the entire length) of a sequence selected from the group consisting of SEQ ID NO:1, 2, 3, 4, 5, 6, 8, 57, 58, 60, 62, 64, 66, 67, 68, 69, 70, 71, 75, 77, 79, and complements thereof, wherein the nucleic acid segment hybridizes specifically to the selected sequence under stringent hybridization conditions. Included are nucleic acid segments comprising sequences from SEQ ID NO:1, 2, 3, 4, 5, 6, or 8, that, when expressed in a plant cell (e.g., in an antisense orientation with respect to an operably linked promoter), reduce a level of an endogenous gibberellin compared with an otherwise identical plant cell in which the nucleic acid segment is not expressed.

In addition, nucleic acid segments are provided that comprise a sequence of at least 100 basepairs (and preferably at least 200, 300, 500, 700, 1000, or more) having at least 85% (and preferably at least 90, 95, or 100%) nucleotide sequence similarity with a member of the group consisting of SEQ ID NO:1, 2, 3, 4, 5, 6, 8, 57, 58, 60, 62, 64, 66, 67, 68, 69, 70, 71, 75, 77, 79, and complements thereof. Included among these nucleic acid segments are nucleic acid segments that encode a polypeptide with copalyl diphosphate synthase activity (SEQ ID NO:1, 2, 3, 4, and complements thereof), 3β-hydroxylase activity (SEQ ID NO:5, 6, and complements thereof), C-20 oxidase activity (SEQ ID NO:8, 77, and complements thereof), GA 2-oxidase activity ( SEQ ID NO: 57, 58, 60, 62, 64, 66, 67, 68, 69, 70, 71, and complements thereof), phytoene synthase activity (SEQ ID NO: 75 and complements thereof), and 2β,3β-hydroxylase activity (SEQ ID NO: 79 and complements thereof).

According to another aspect of the invention, nucleic acid constructs are provided that comprise a promoter that causes expression of an operably linked nucleic acid segment in a plant cell and, operably linked to the promoter, the nucleic acid segment comprising a sequence that encodes a polypeptide having a GA 2-oxidase activity. Expression of the nucleic acid segment in the plant cell results in inactivation of an endogenous gibberellin in the plant cell, thereby reducing levels of the endogenous gibberellin in the plant cell compared with an otherwise identical plant cell in which the nucleic acid segment is not expressed. For example, the sequence may encode a polypeptide having at least 70% amino acid sequence identity, preferably having only silently or conservative amino acid substitutions, and most preferably having 100% amino acid sequence identity with a polypeptide encoded by a member of the group consisting of SEQ ID NO:57, 58, 60, 62, 64, 66, 67, 68, 69, 70, 71, and complements thereof.

According to another aspect of the invention, nucleic acid constructs are provided that comprise a promoter that causes expression of an operably linked nucleic acid segment in a plant cell and, operably linked to the promoter, the nucleic acid segment comprising a sequence that encodes a polypeptide having a phytoene synthase, C-20 oxidase, or 2β,3β-hydroxylase activity. Expression of the nucleic acid segment in the plant cell results in metabolism of a gibberellin precursor in the plant cell to produce a metabolite that is not a gibberellin precursor in the plant cell, thereby reducing levels of the endogenous gibberellin in the plant cell compared with an otherwise identical plant cell in which the nucleic acid segment is not expressed. For example, the sequence may encode a polypeptide having at least 70% amino acid sequence identity, preferably having only silently or conservative amino acid substitutions, and most preferably having 100% amino acid sequence identity with a polypeptide encoded by a member of the group consisting of SEQ ID NO: 75, 77, 79, and complements thereof.

According to another aspect of the invention, a promoter that is operable in plant cells is provided that comprises at least 15, preferably 25, 50, 100, 200, 300, 500, or 1000 contiguous nucleotides or more of SEQ ID NO:7. Such a promoter is preferably preferentially expressed in seedlings.

According to another aspect of the invention, transgenic plants are provided that comprise the nucleic acid segments, constructs, and promoters mentioned above. Preferably such transgenic plants are characterized by at least one phenotype selected from the group consisting of a shortened hypocotyl, shortened epicotyl, and both a shortened hypocotyl and shortened epicotyl compared with an otherwise identical plant that lacks the nucleic acid segment.

According to another aspect of the invention, compositions are provided that comprise a seed of a plant that has a gibberellin-deficiency that results in at least one abnormal phenotype in the seed or in a seedling of the plant compared with a seed or seedling of an otherwise identical plant having wild-type levels of gibberellin; and a composition applied to a surface of the seed that comprises an amount of at least one GA compound that is effective to substantially eliminate the abnormal phenotype. The seed may be of a non-transgenic plant (e.g., a GA-deficient point or deletion mutant) or a transgenic plant comprising a transgene comprising a promoter and, operably linked to the promoter, a sequence that, when expressed, reduces gibberellin levels in the seed or seedling. The GA compound is preferably selected from the group consisting of ent-kaurene, ent-kaurenoic acid, ent-7α-hydroxykaurenoic acid, steviol, $GA_{12}$-aldehyde, $GA_{12}$, $GA_{15}$, $GA_{24}$, $GA_9$, $GA_{53}$, $GA_{44}$, $GA_{19}$, $GA_{20}$, and $GA_5$, most preferably $GA_9$, $GA_{15}$, $GA_{19}$, $GA_{24}$, $GA_{44}$, $GA_{53}$, $GA_5$ and steviol.

According to another aspect of the invention, methods are provided for reversibly controlling morphology in a seedling of a transgenic plant in which the capacity to biosynthesize at least one plant hormone that affects normal morphology in said seedling is inhibited, resulting in a deficiency in the level of said plant hormone and modification of at least one morphological trait of the seedling compared to a control seedling. A substantially normal morphology is restored by contacting seed or seedling with an amount of at least one GA compound effective to restore substantially normal morphology, permitting the plants to be grown to maturity. For example, such methods are useful for controlling elongation of a seedling tissue or tissues such as hypocotyl, epicotyl, coleoptile, and/or plumule tissue in a seedling of the transgenic plant. In GA-deficient plants, for example, normal morphology can be restored to plants that display one or more of the following morphological traits: reduced emergence, inhibited shoot growth, reduced height or stature, reduced stem growth, etc.

According to another aspect of the invention, lodging is reduced or prevented in a plant that is susceptible to lodging under conditions that are conducive to lodging by methods that employing a transgenic plant wherein the capacity to biosynthesize one or more plant hormones that affects the height of the seedling or plant is inhibited, resulting in a deficiency in the level of the hormone(s) and reduced height, compared to a control. After the conducive conditions are no longer present, the plant or a seed or seedling thereof can be grown to a normal height by contacting seed of the plant with an amount of at least one GA compound that is effective to increase the height of the seedling or plant.

DESCRIPTION OF THE FIGURES AND TABLES

The following figures and tables form part of the present specification and are included to further demonstrate certain aspects of the present invention. The invention may be better understood by reference to one or more of these drawings in combination with the detailed description of specific embodiments presented herein.

Figure 2:
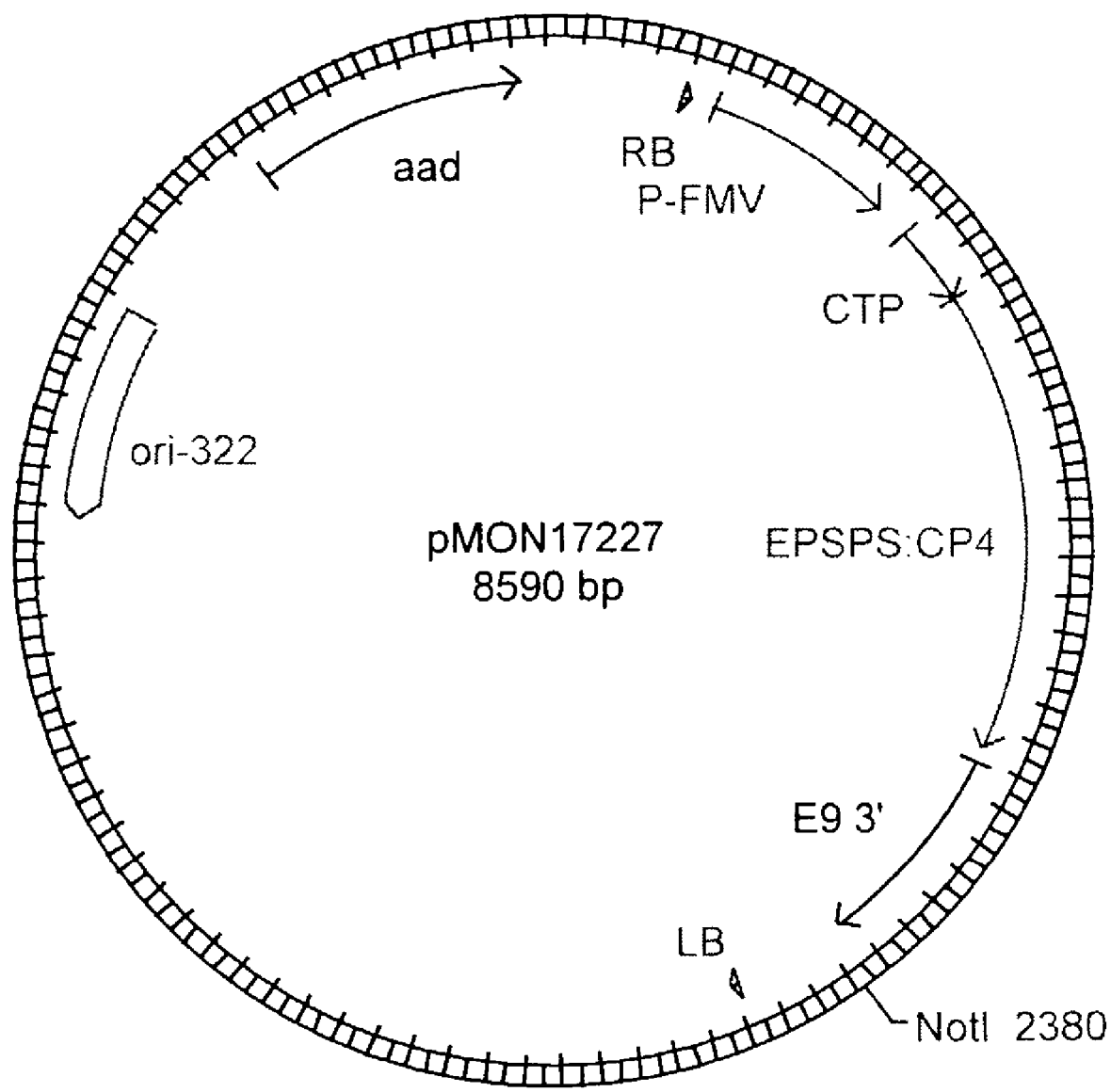
Figure 3:
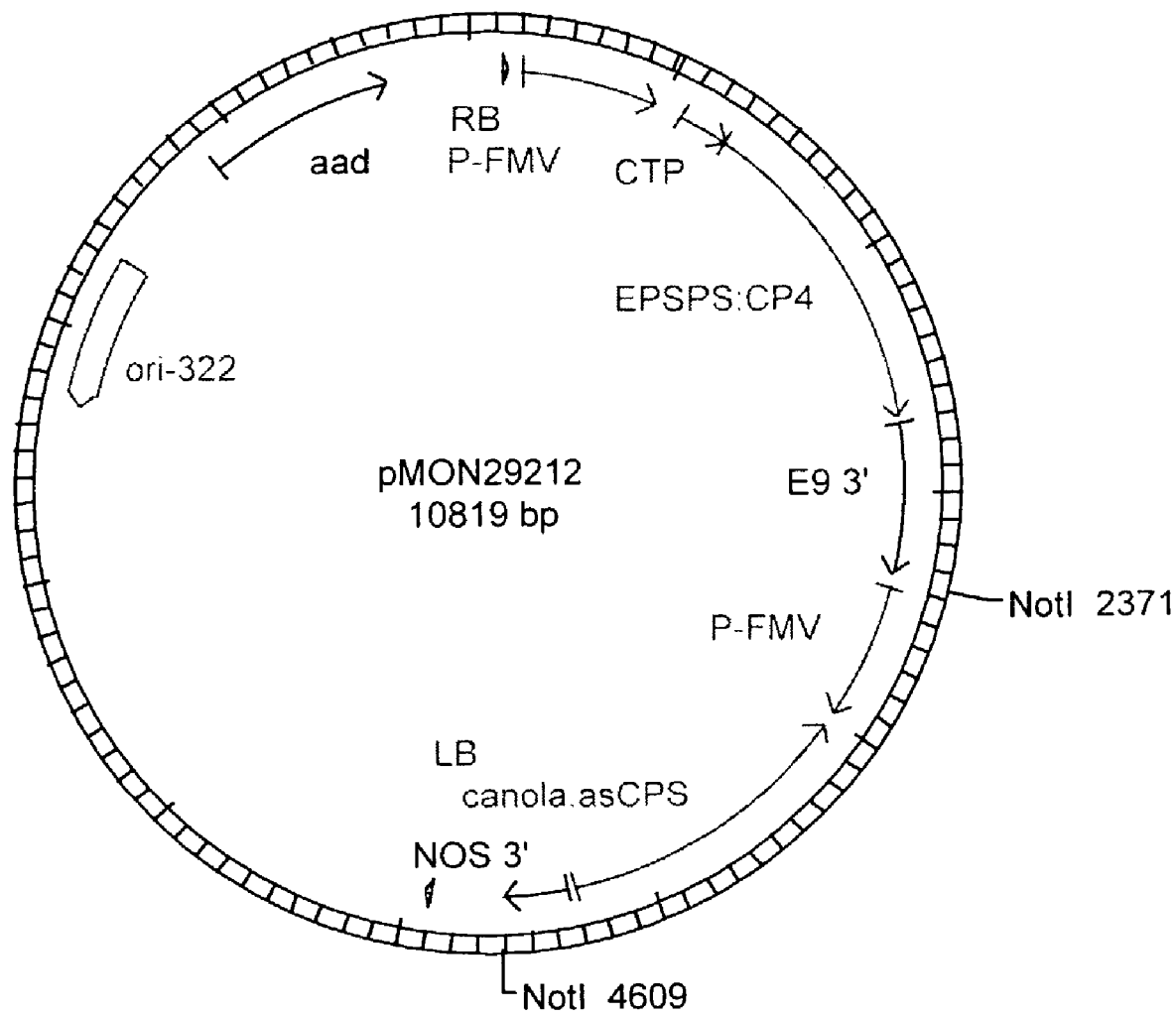
Figure 4:
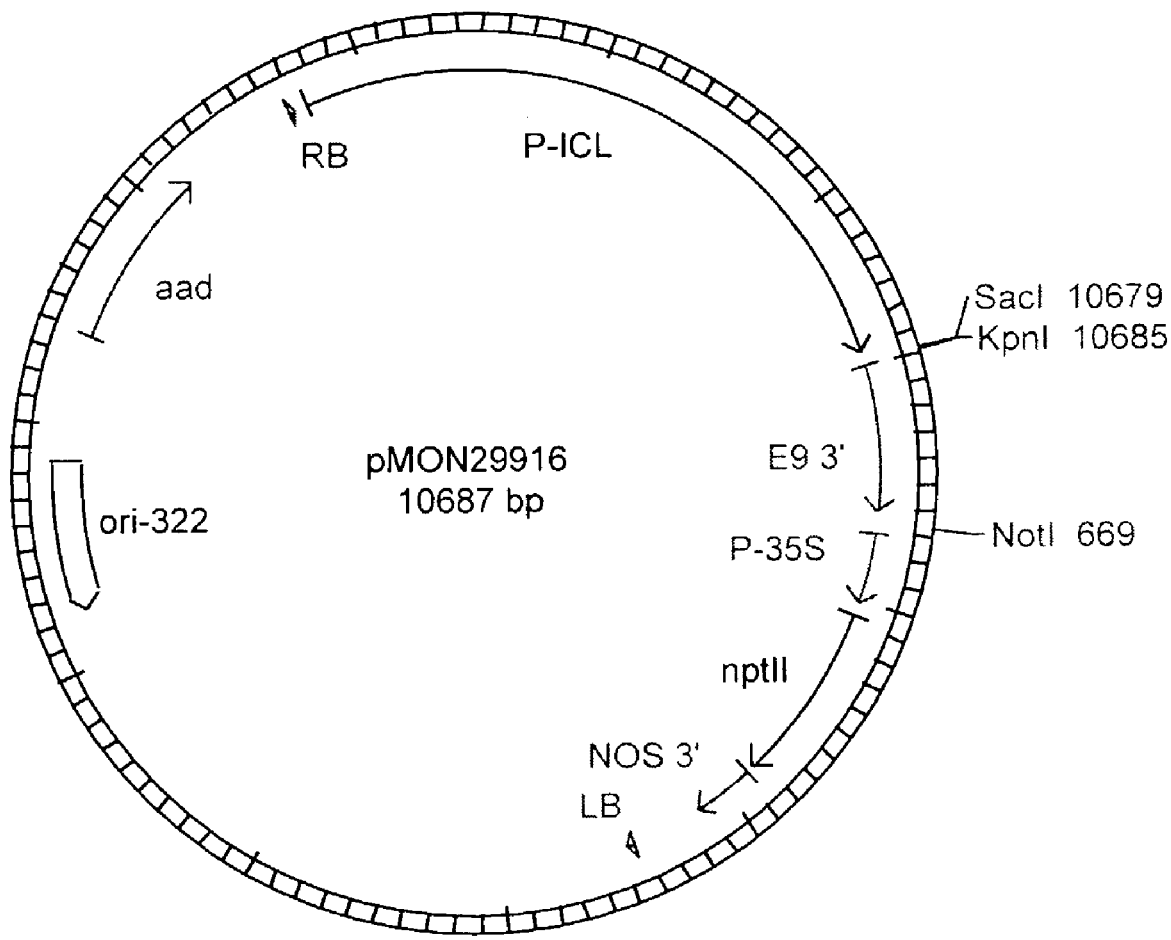
Figure 5:
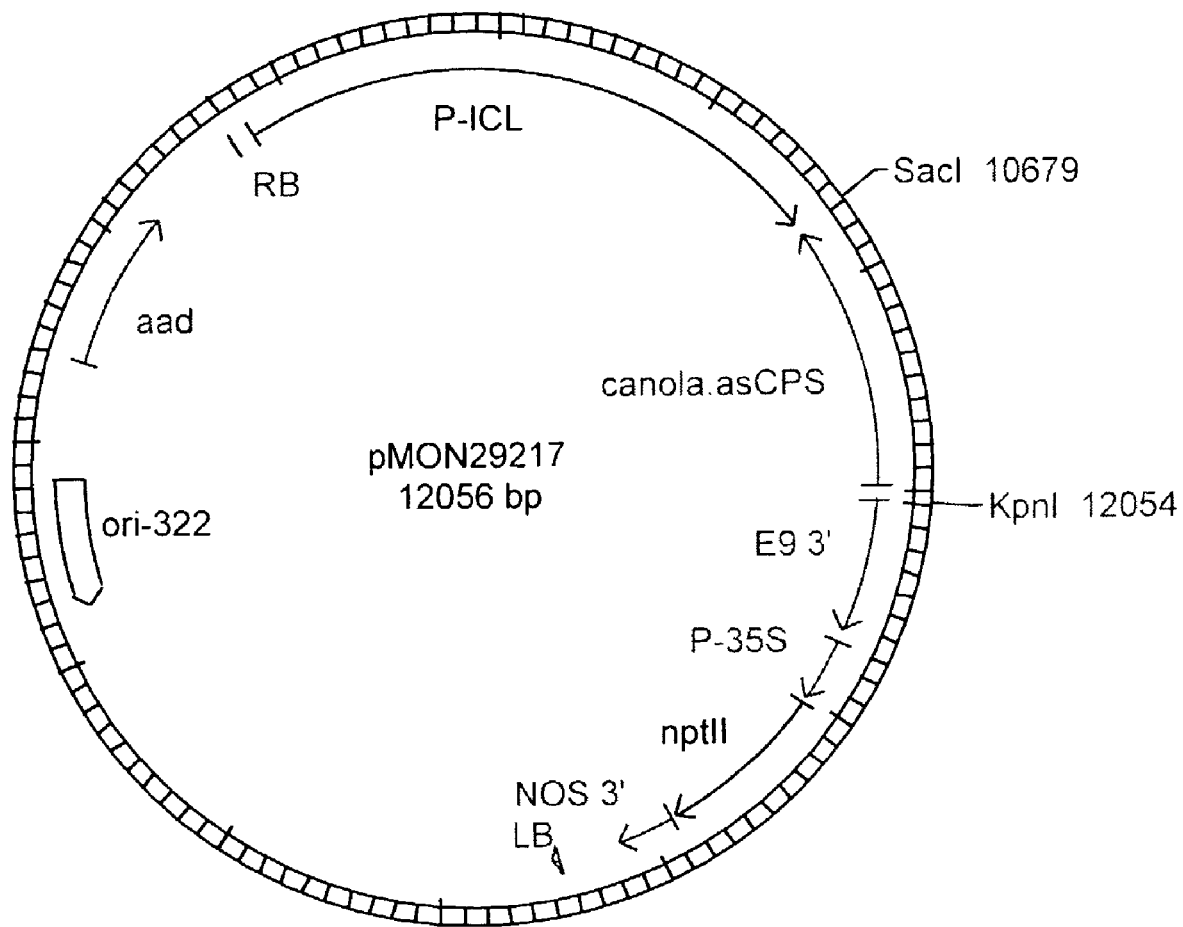
Figure 6:
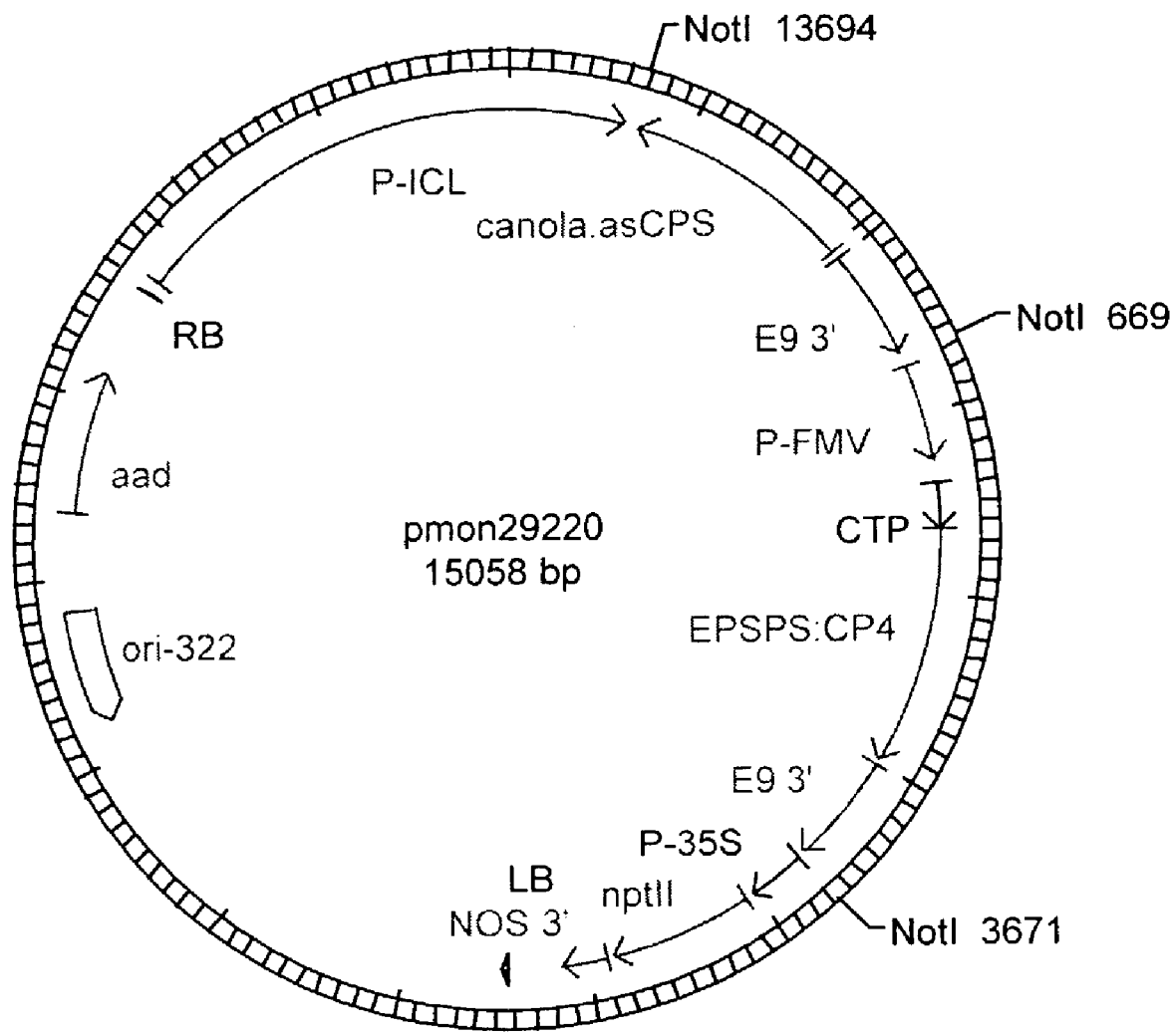
Figure 7:
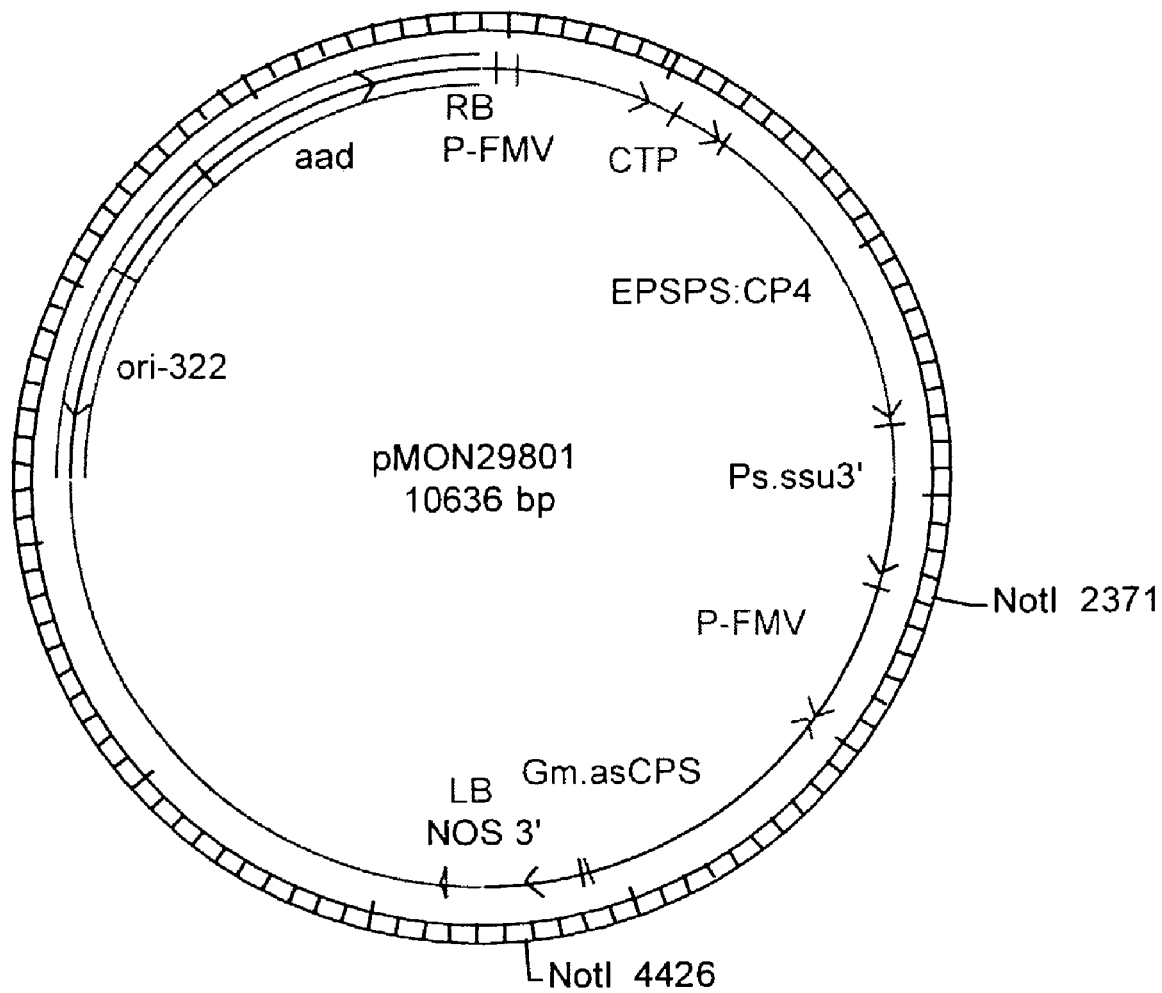
Figure 8:
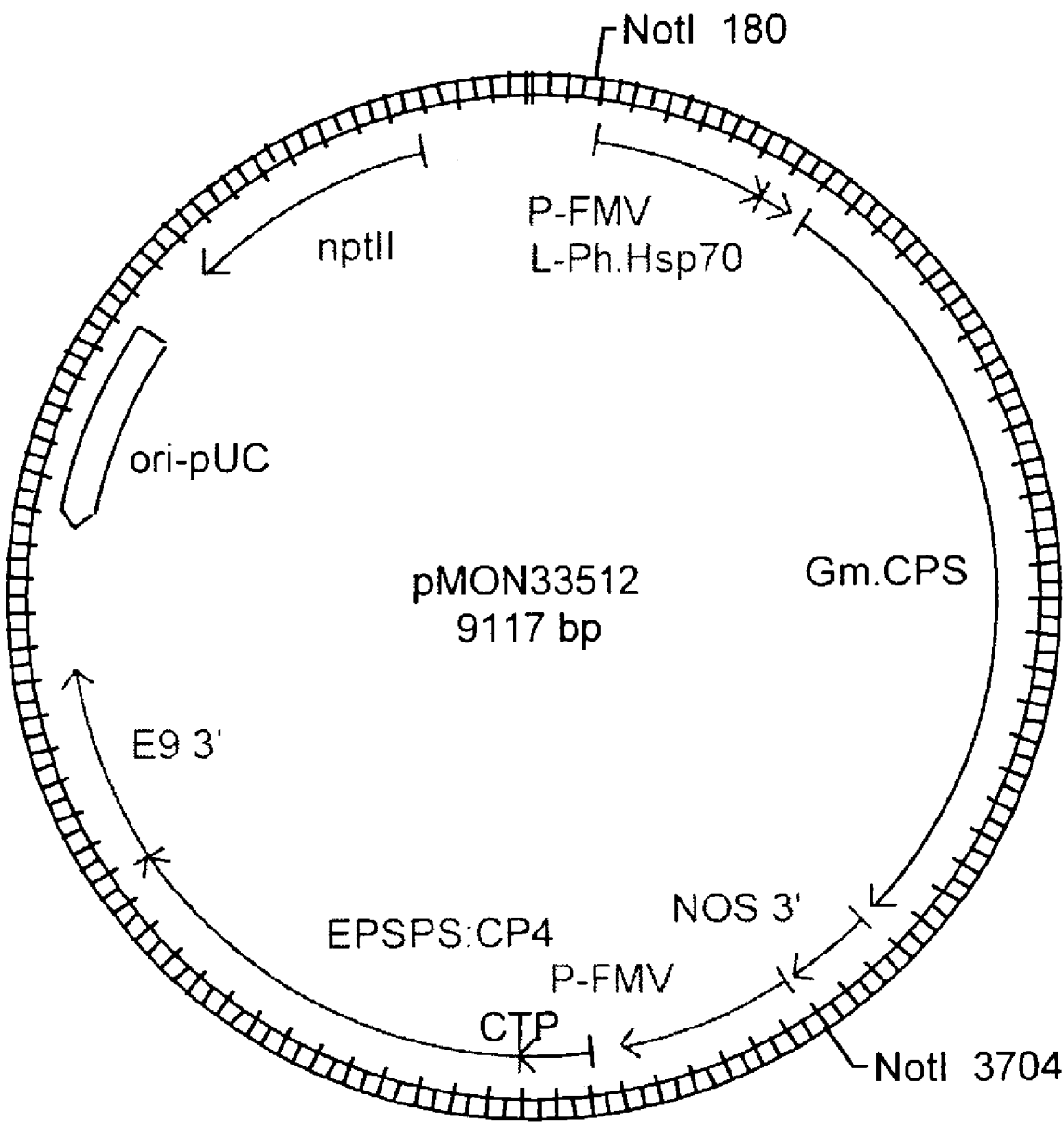
Figure 9:
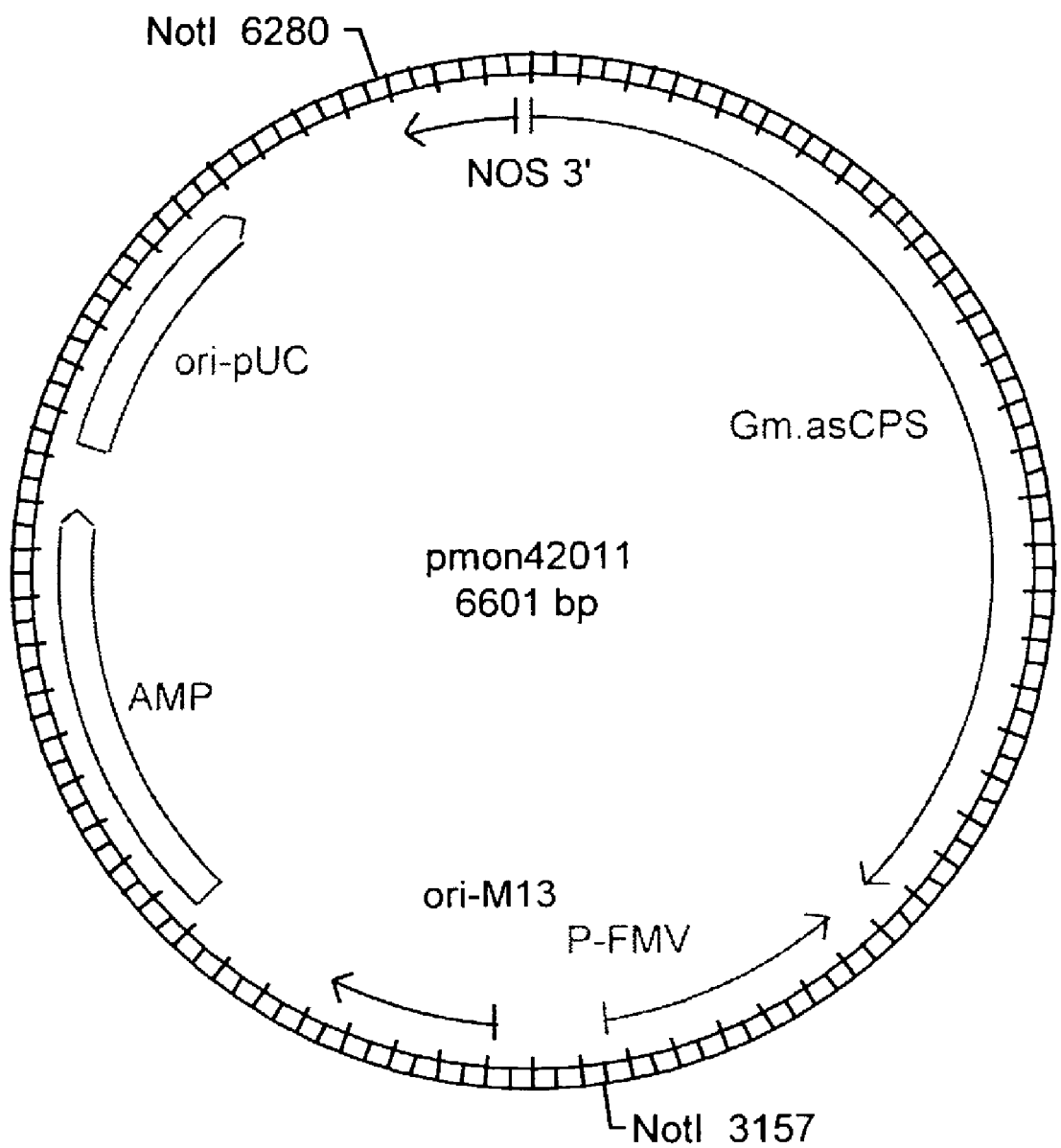
Figure 10:
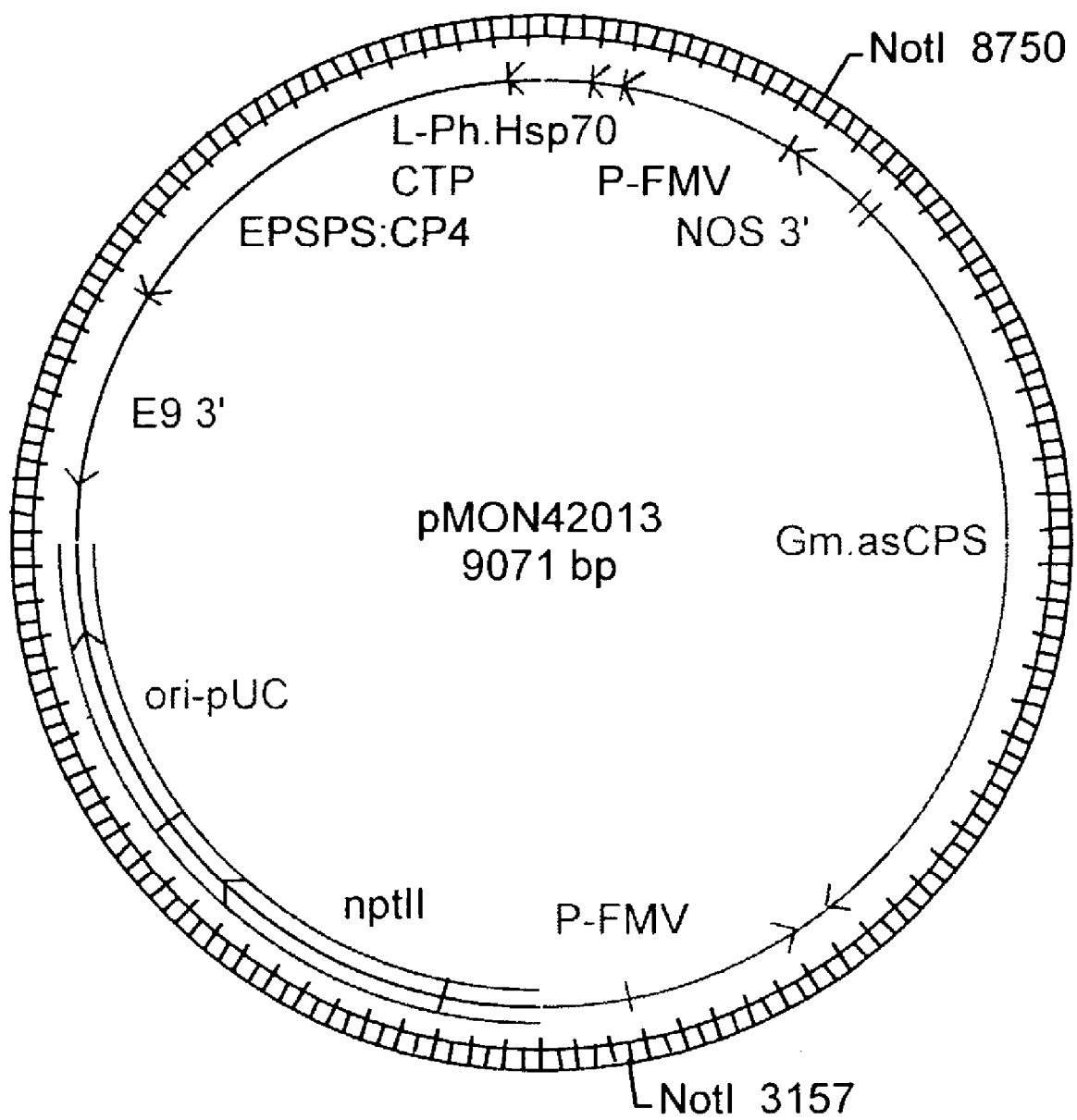
Figure 11:
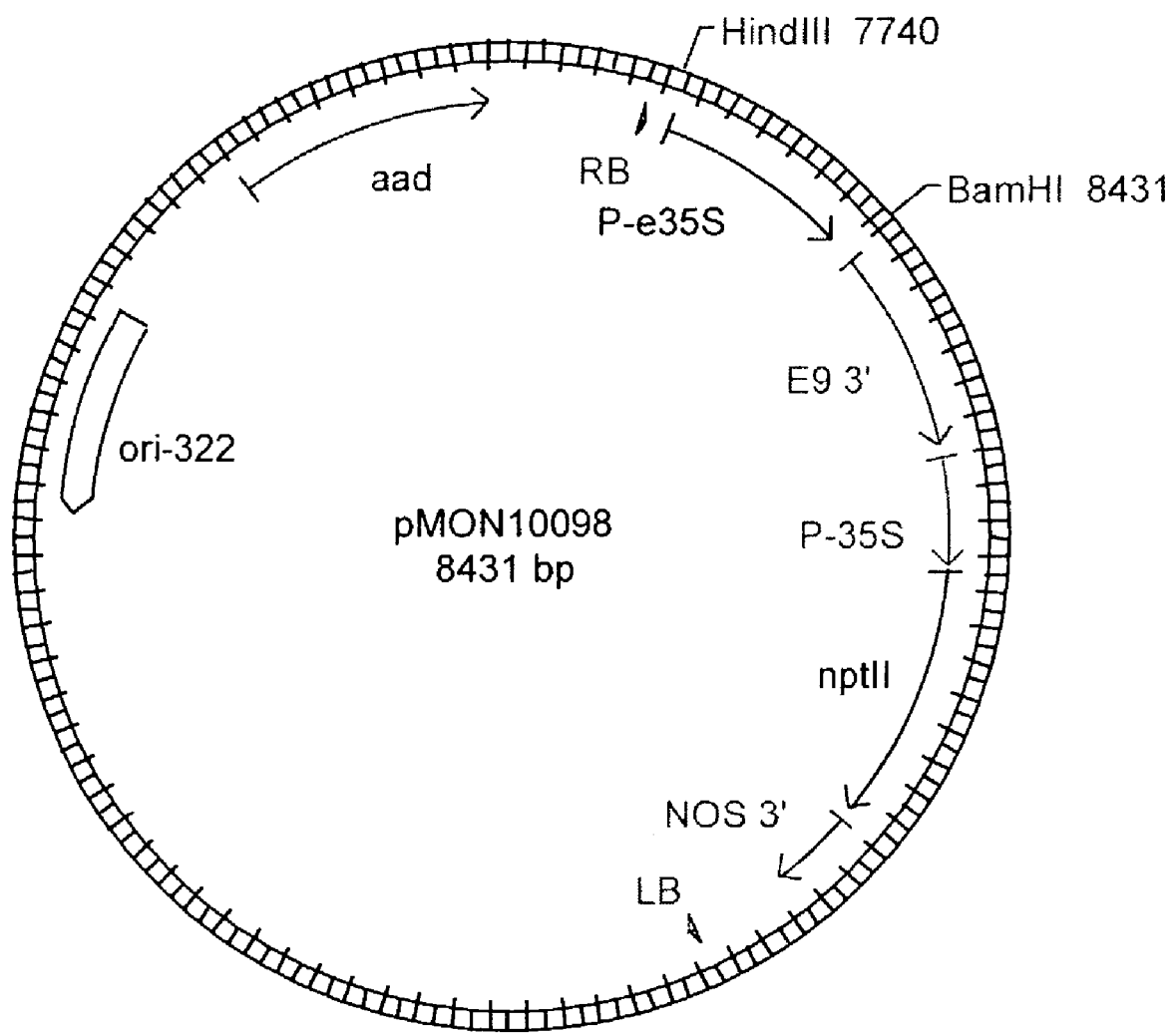
Figure 12:
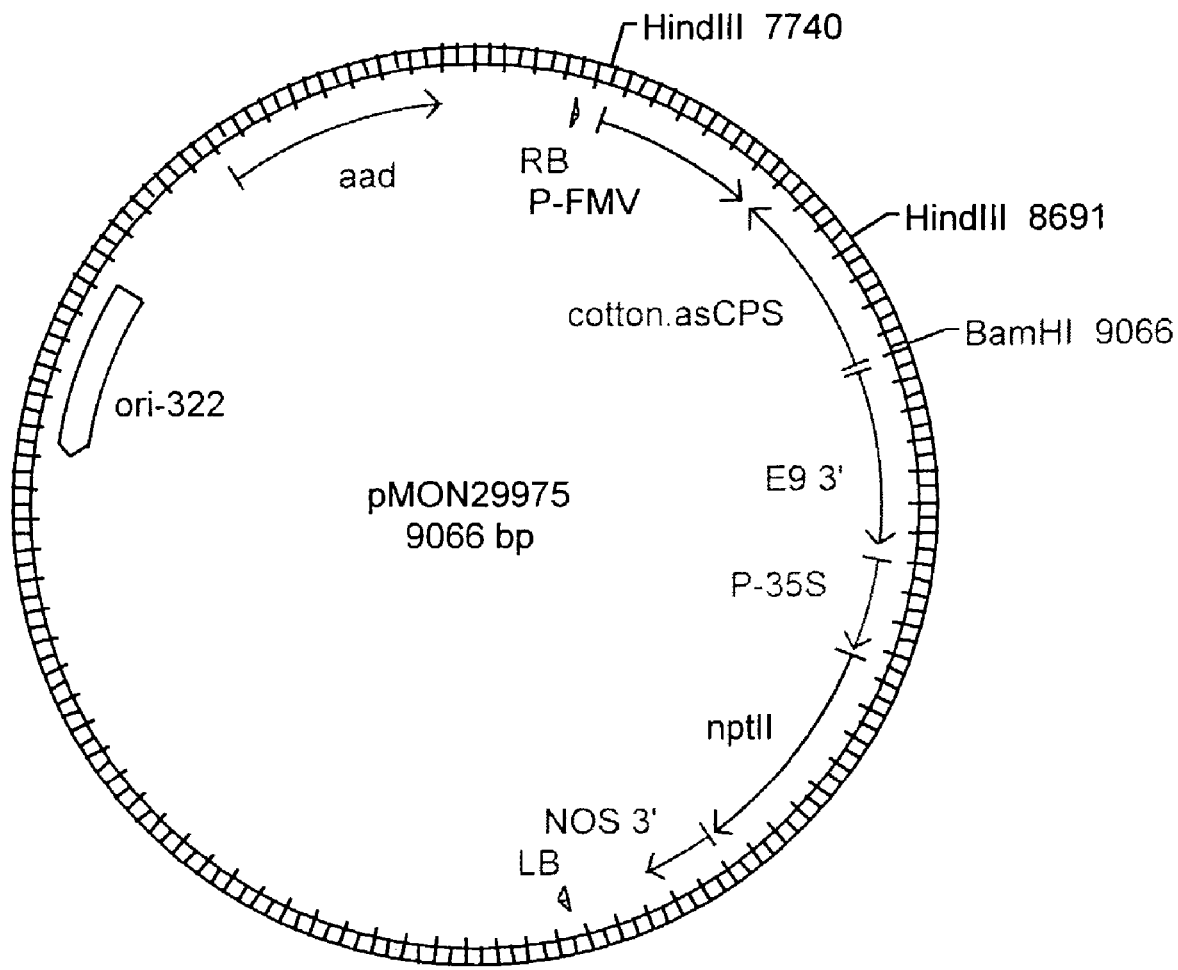
Figure 13:
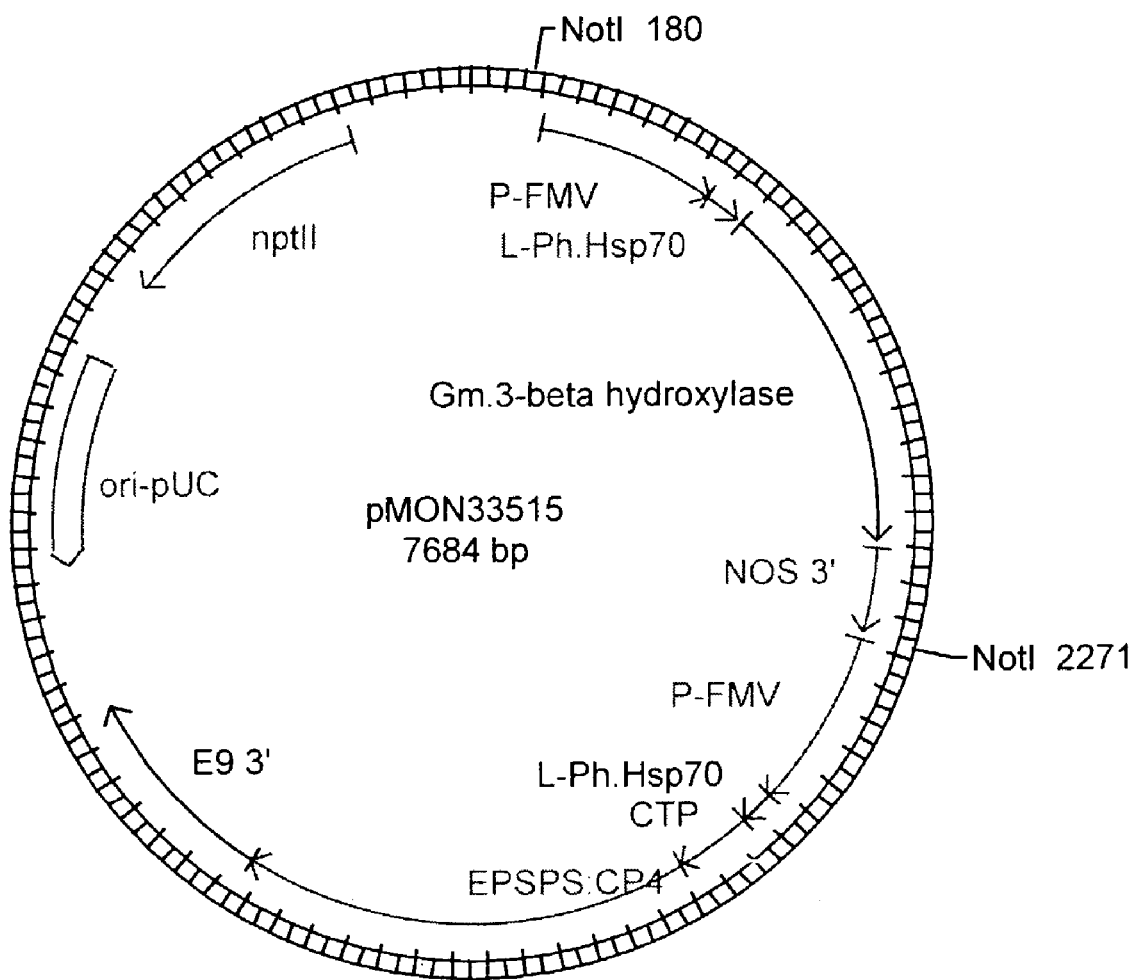
Figure 14:
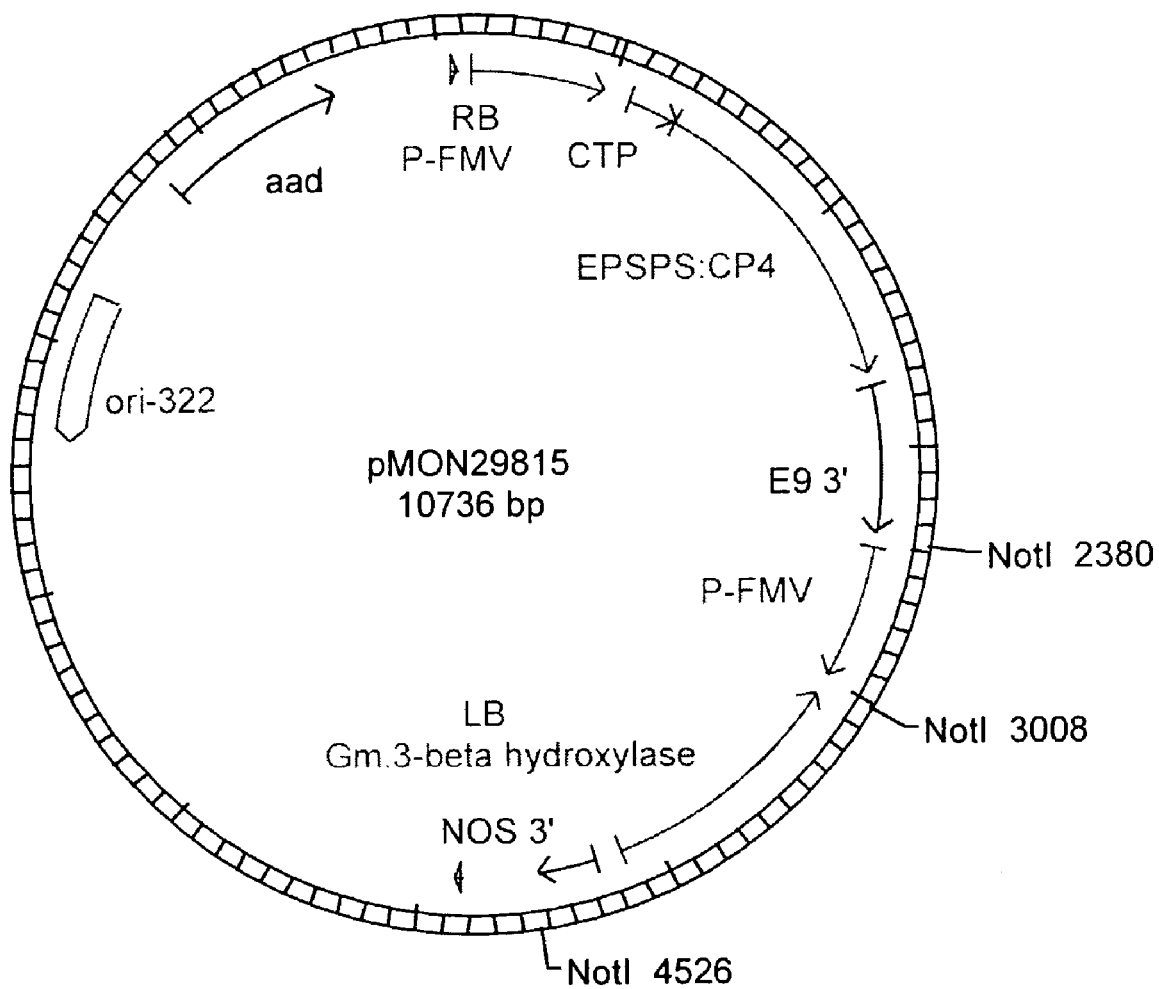
Figure 15:
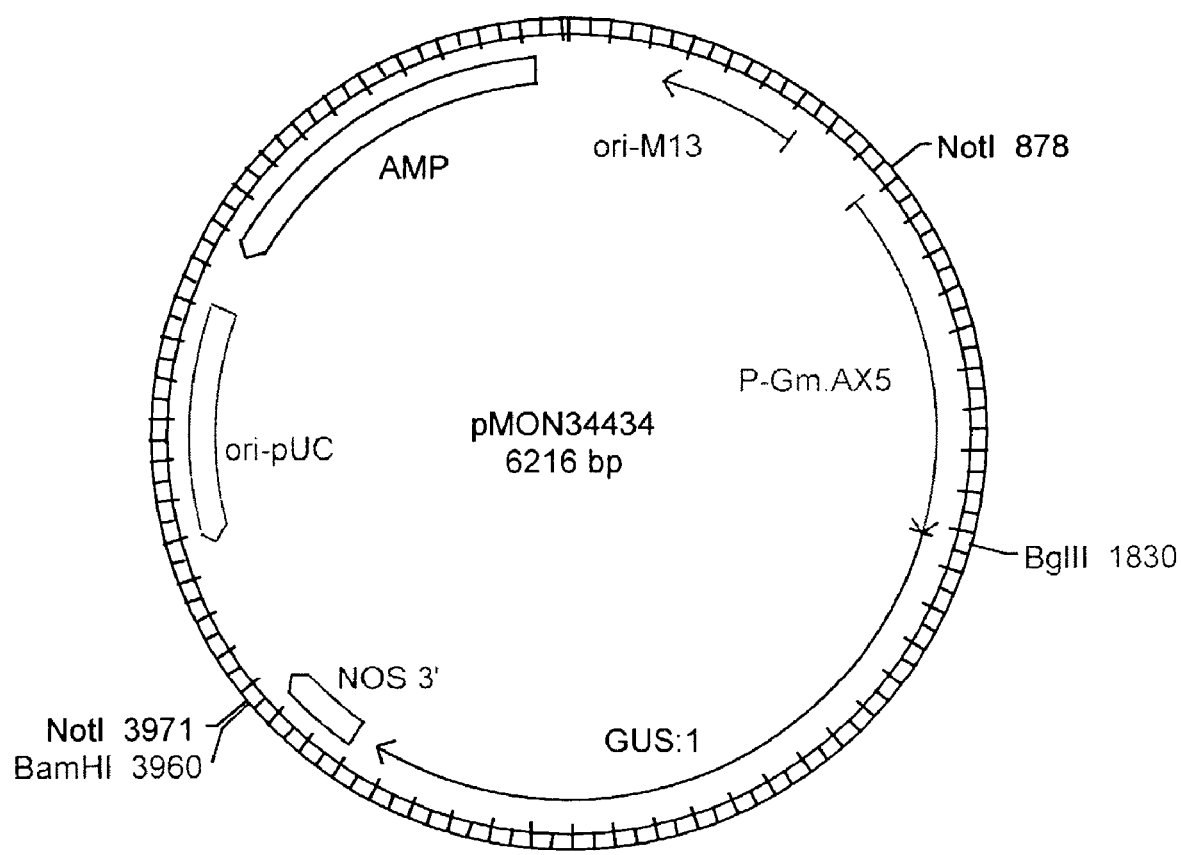
Figure 16:
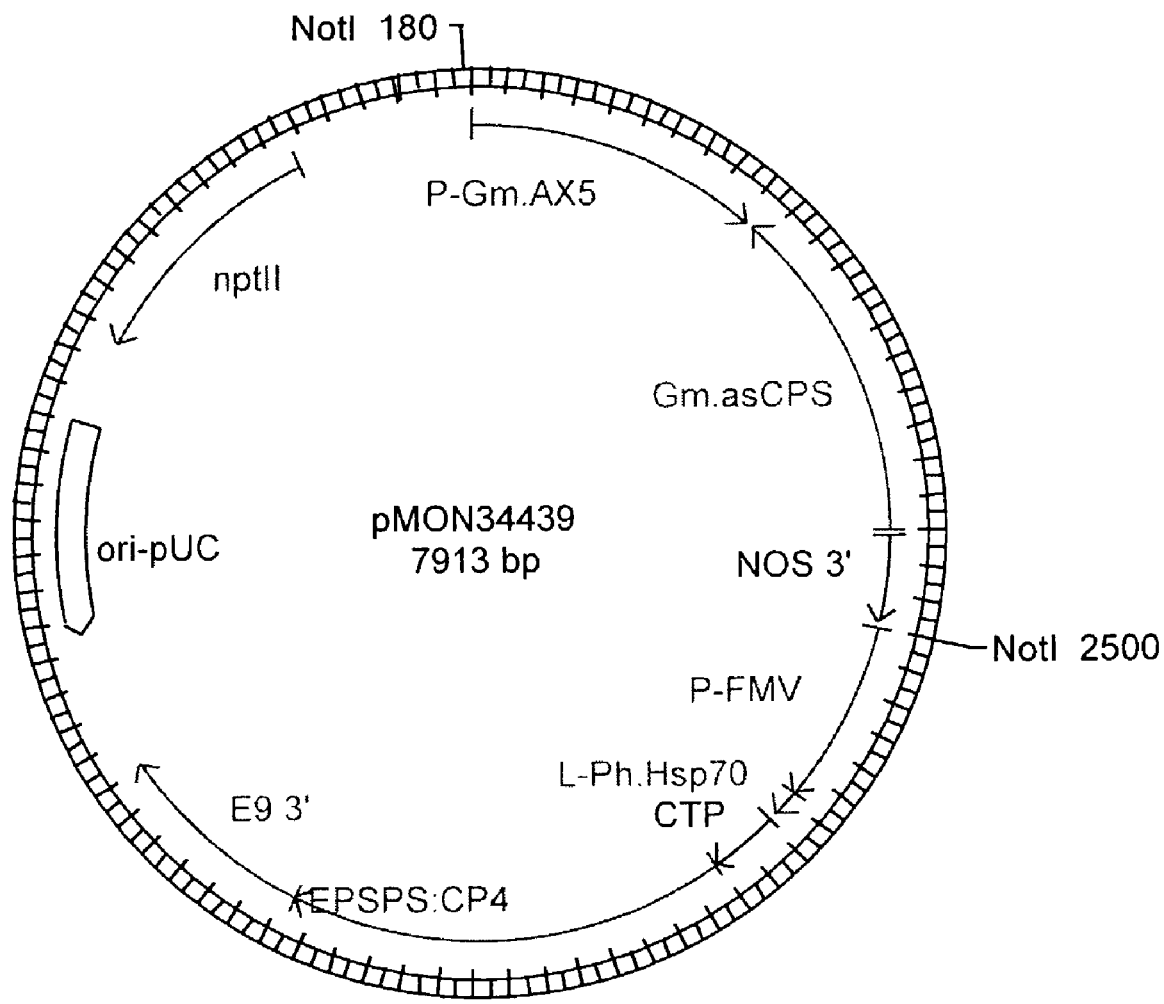
Figure 17:
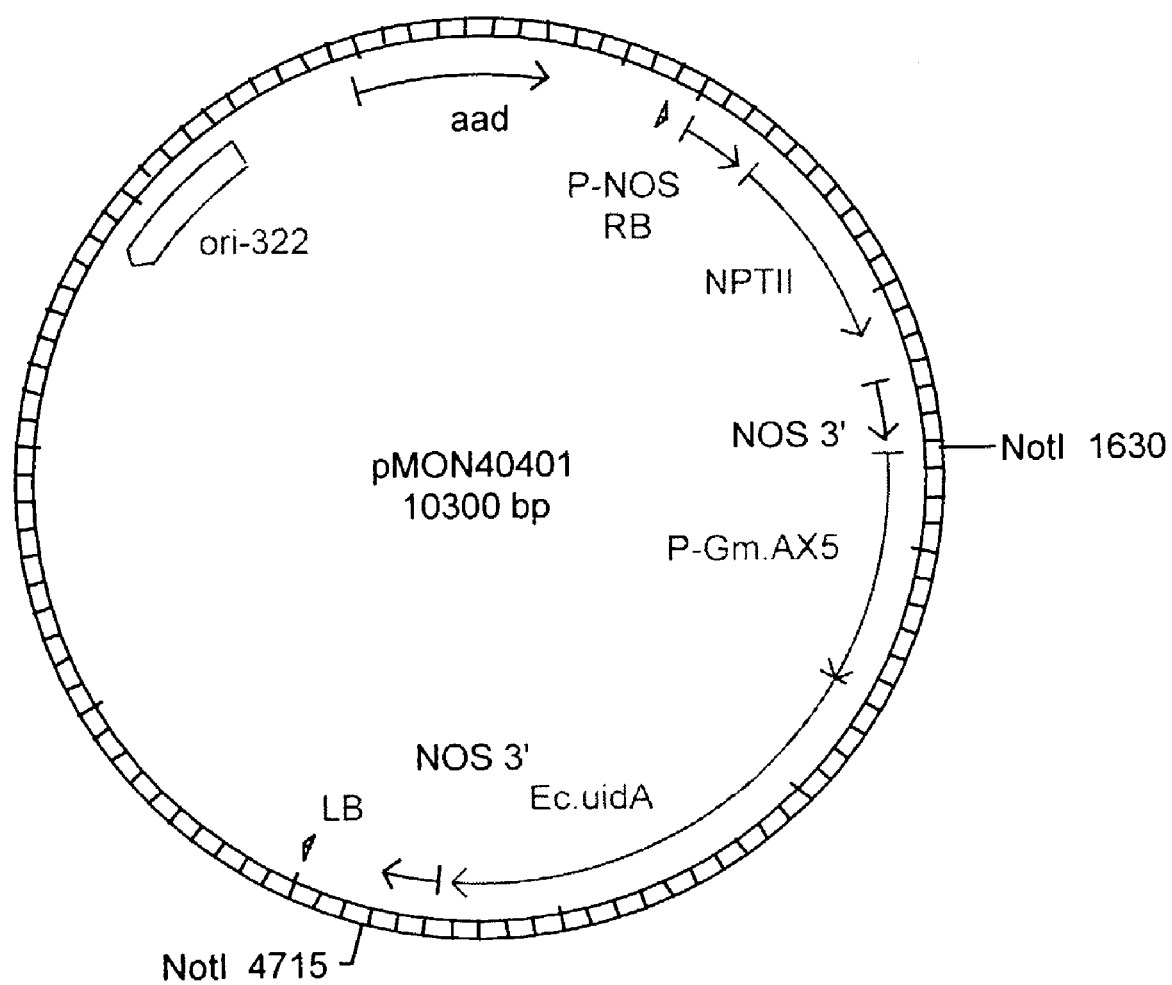
Figure 18:
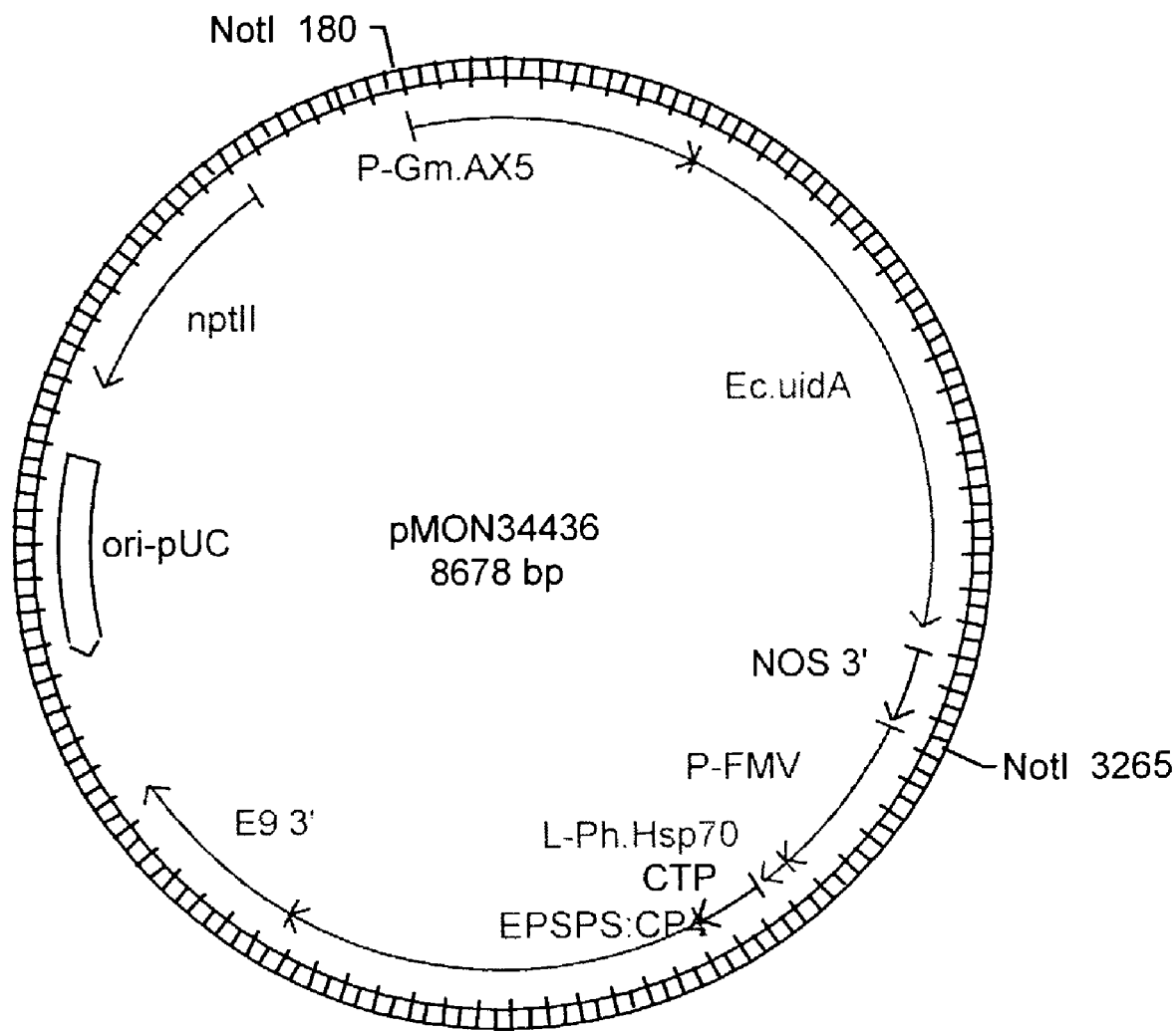
Figure 19:
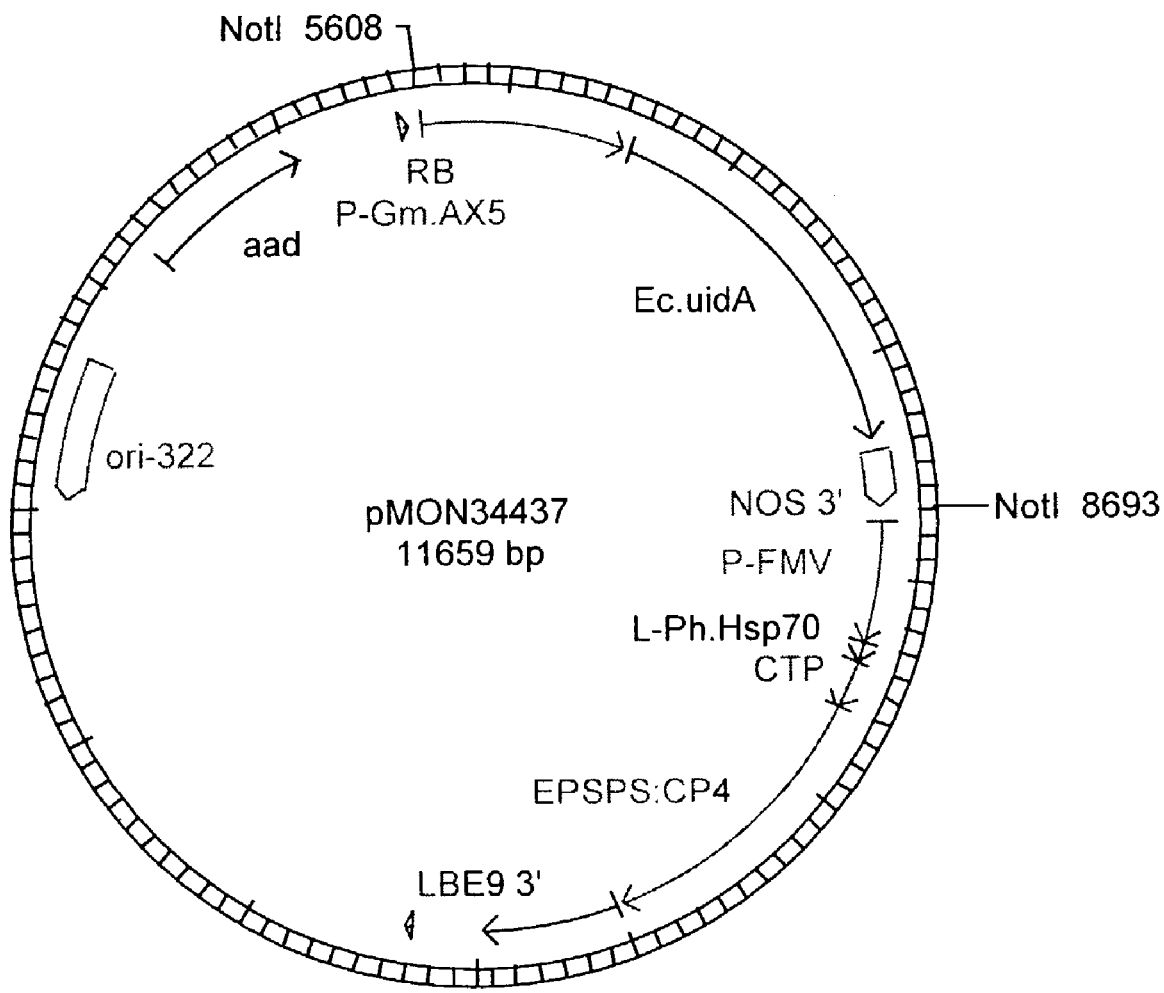
Figure 20:
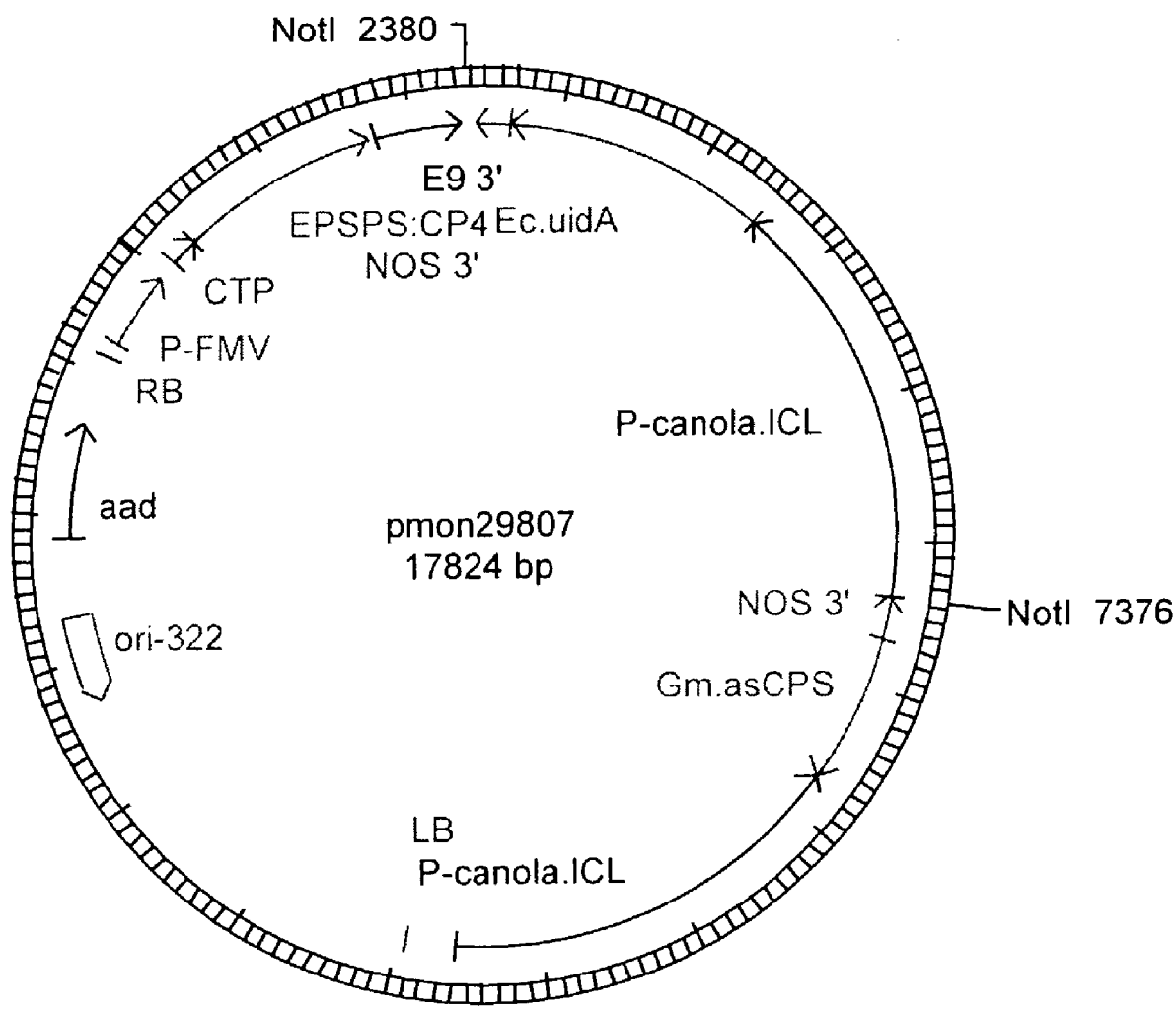
Figure 21:
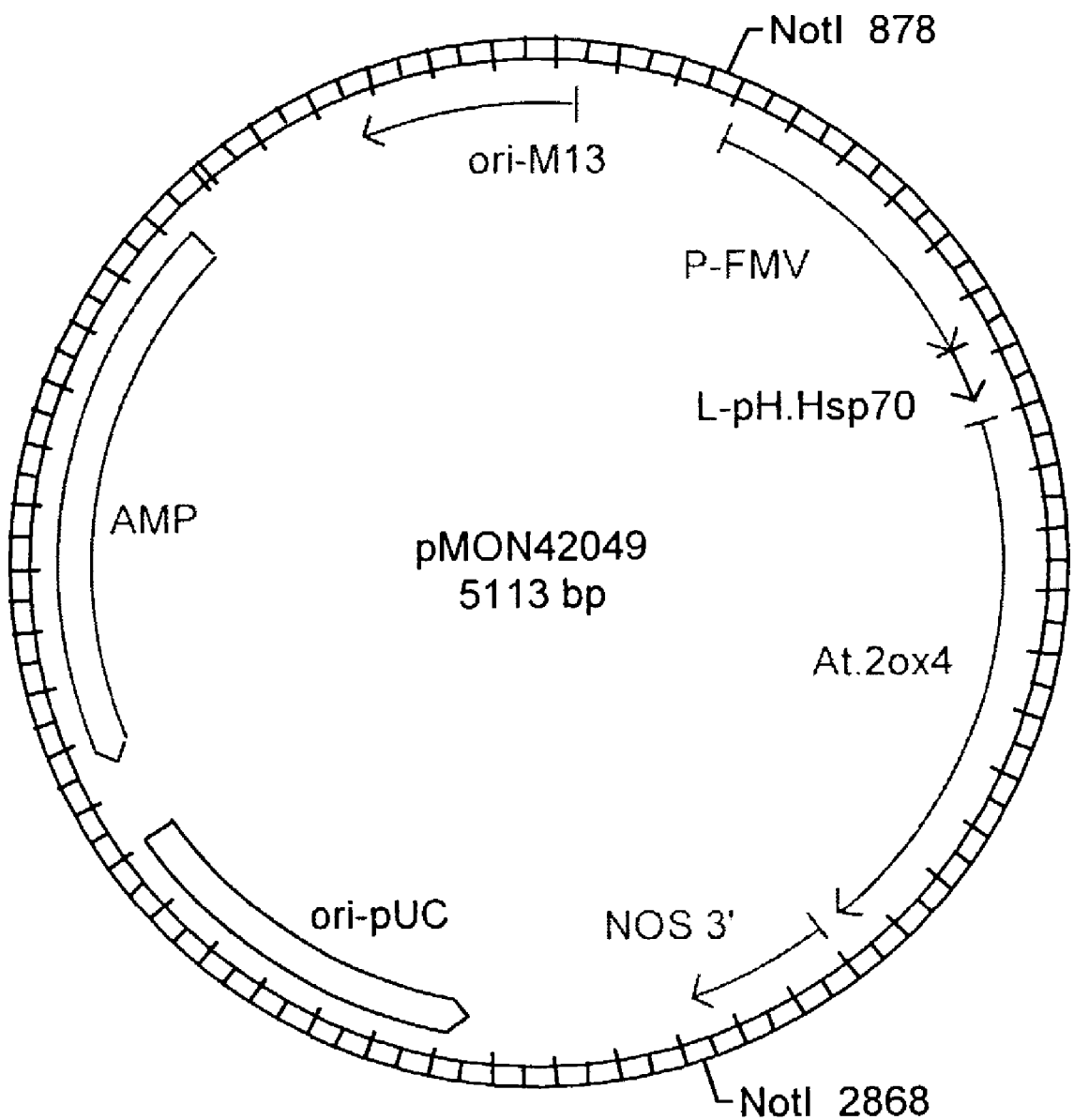
Figure 22:
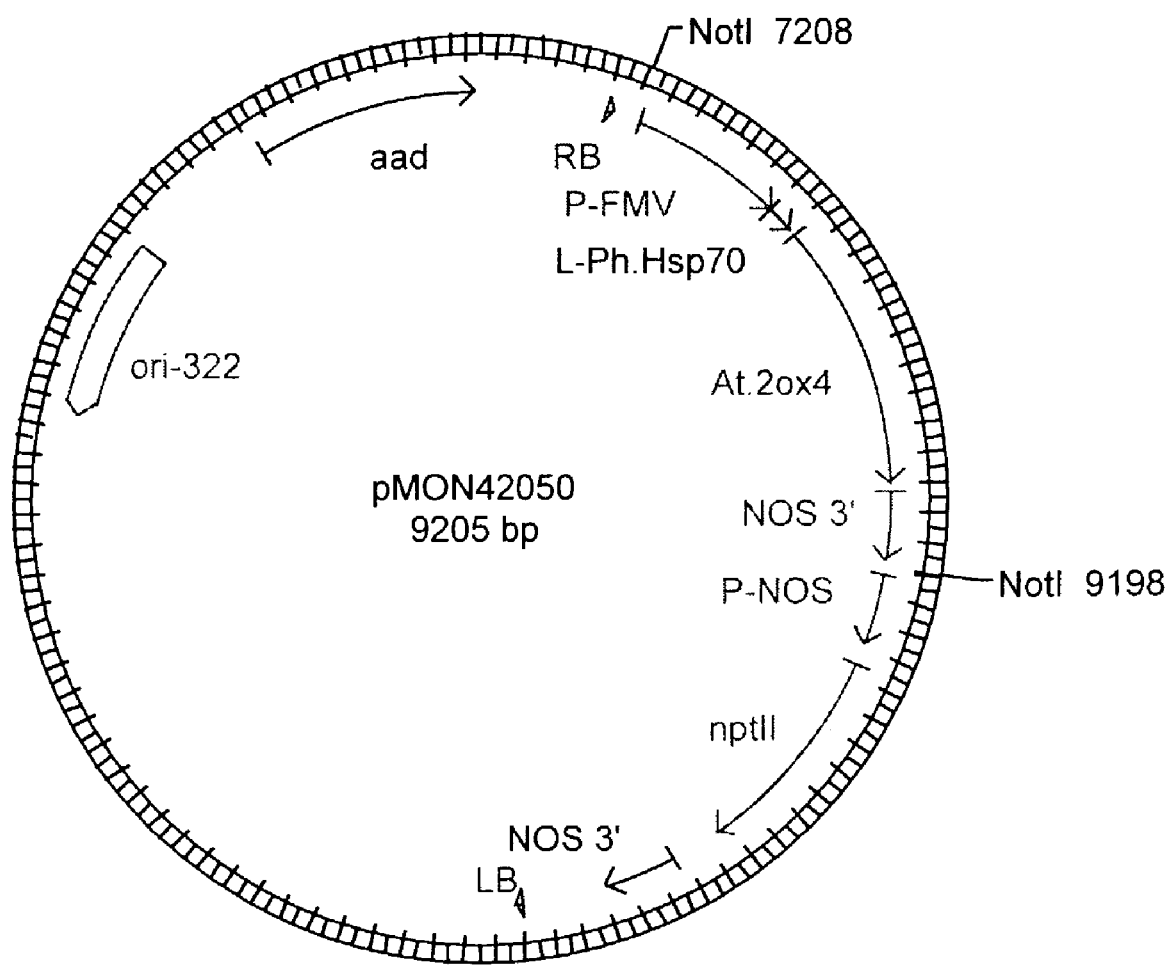
Figure 23:
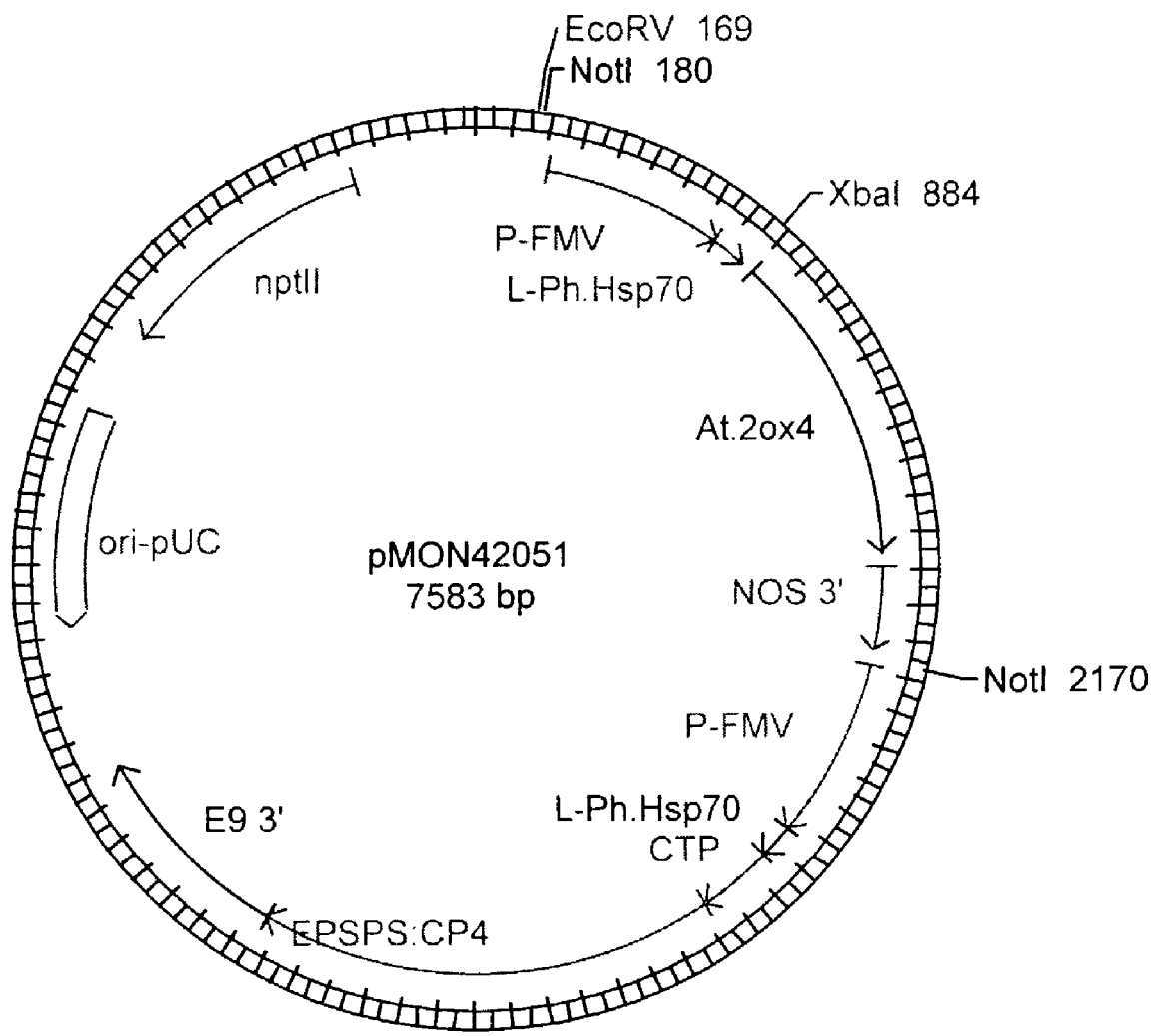
Figure 24:
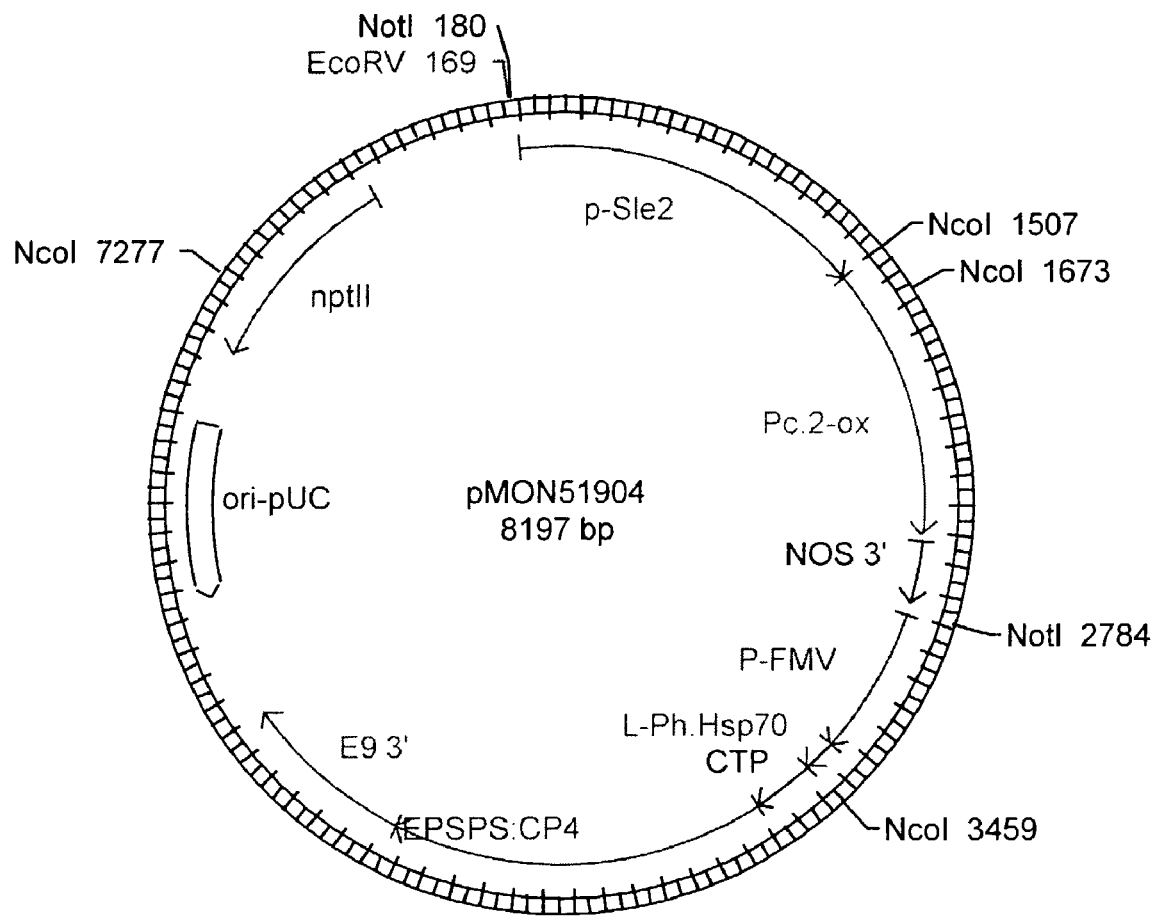
Figure 25:
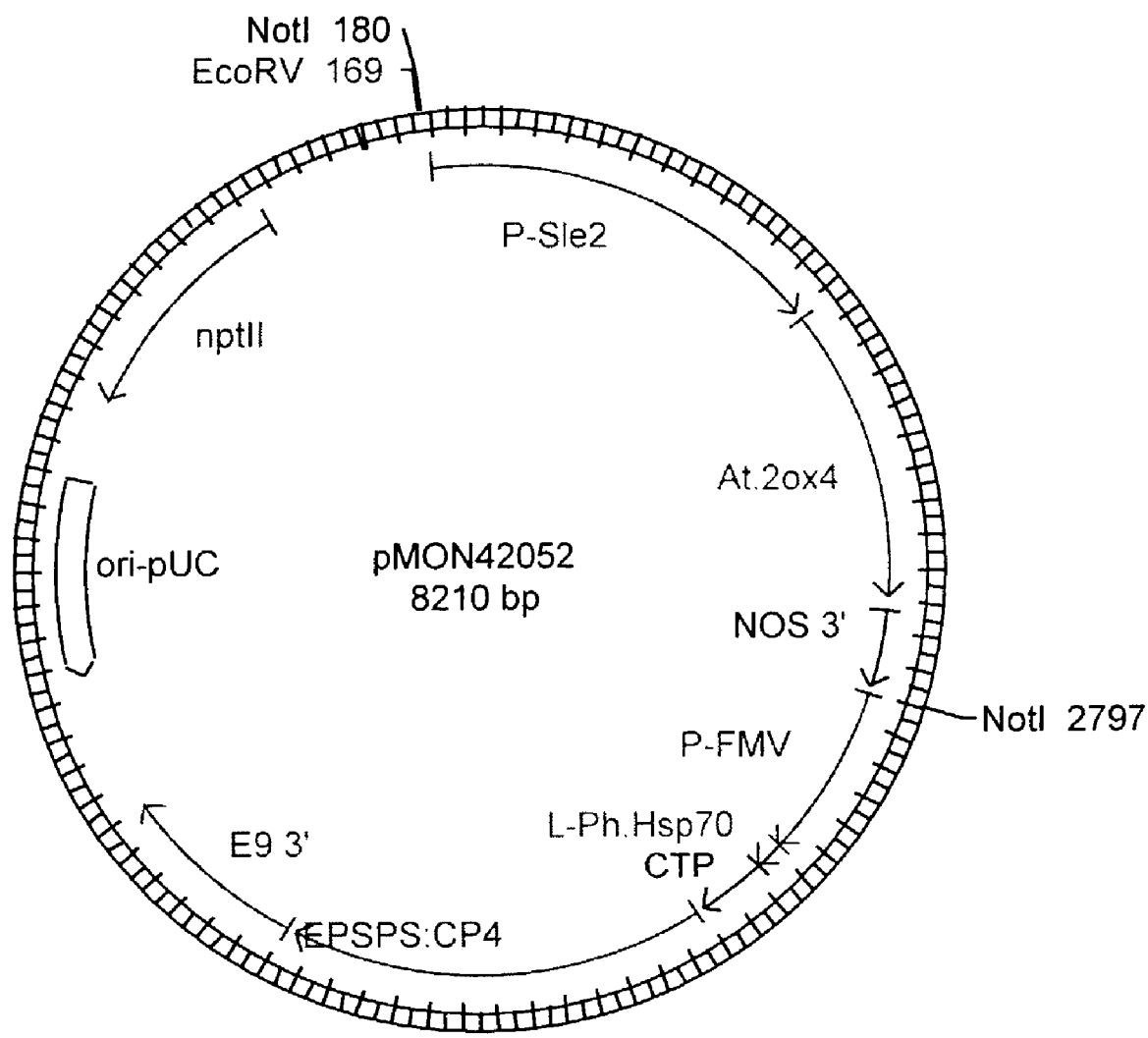
Figure 26:
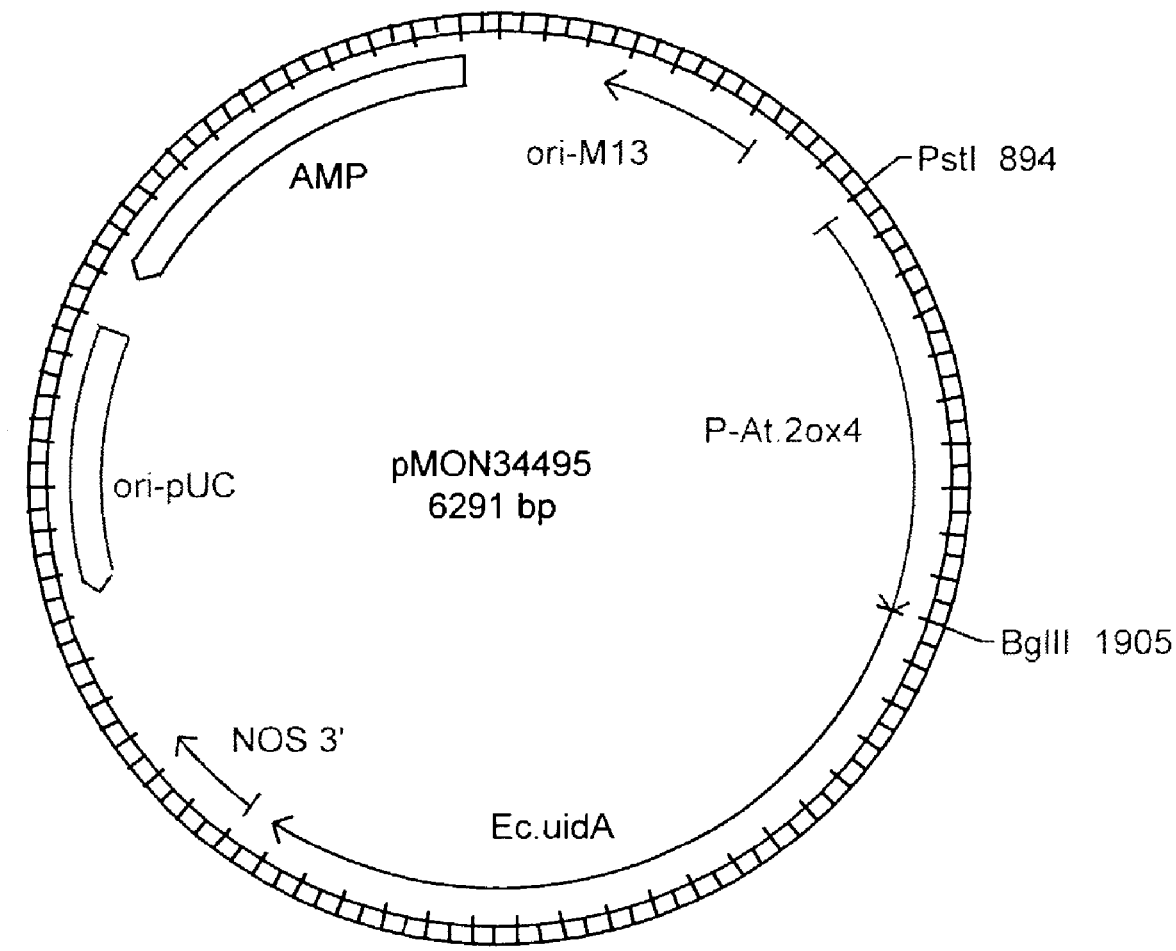
Figure 27:
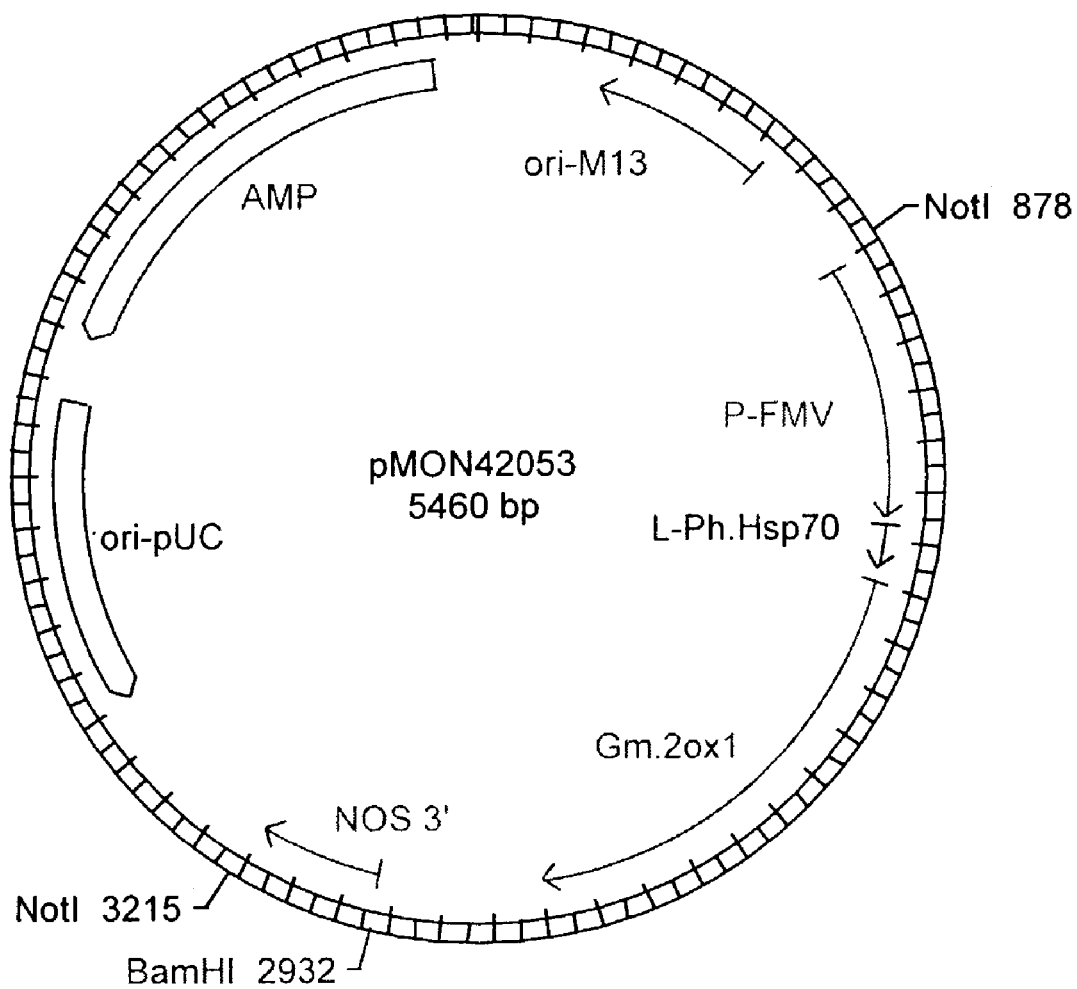
Figure 28:
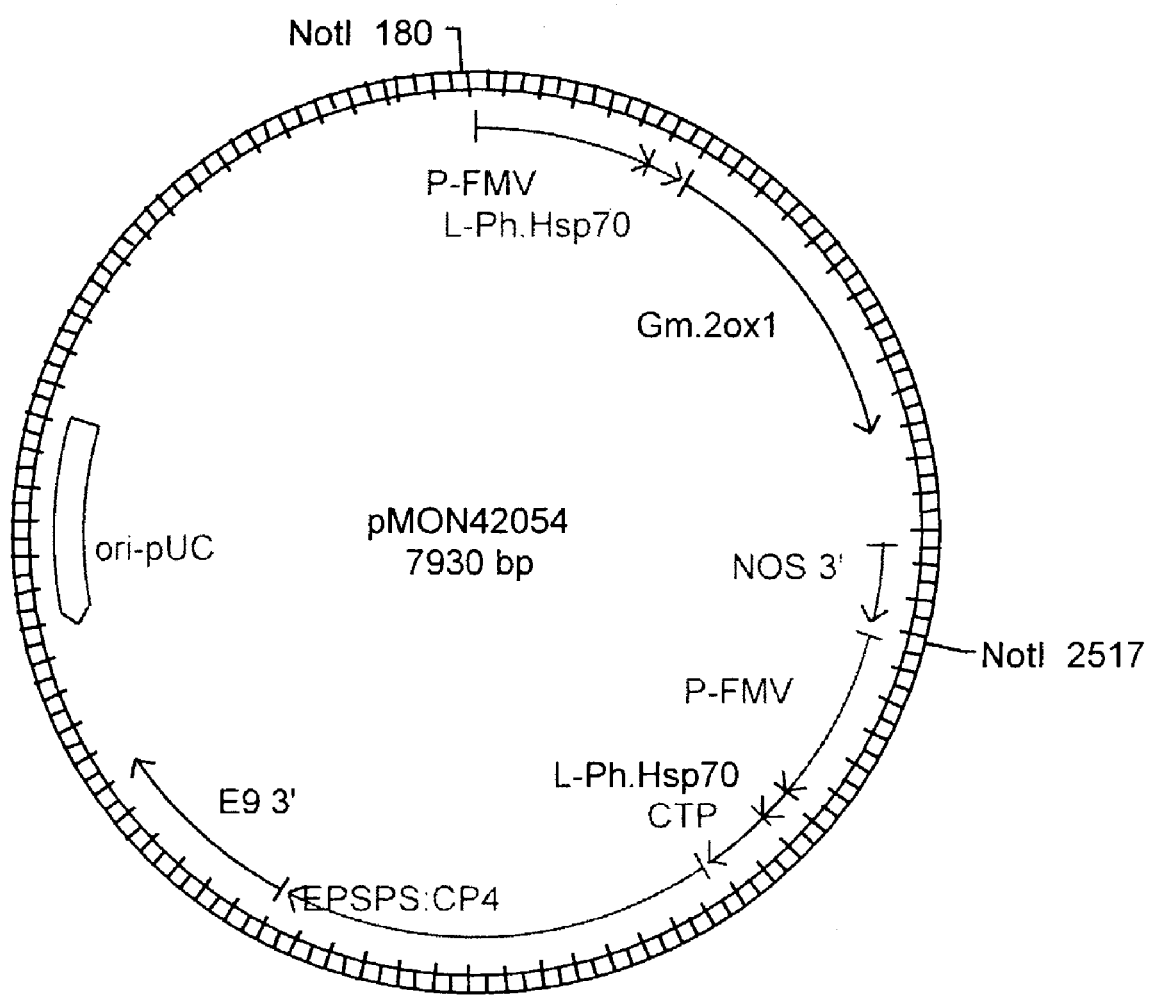
Figure 29:
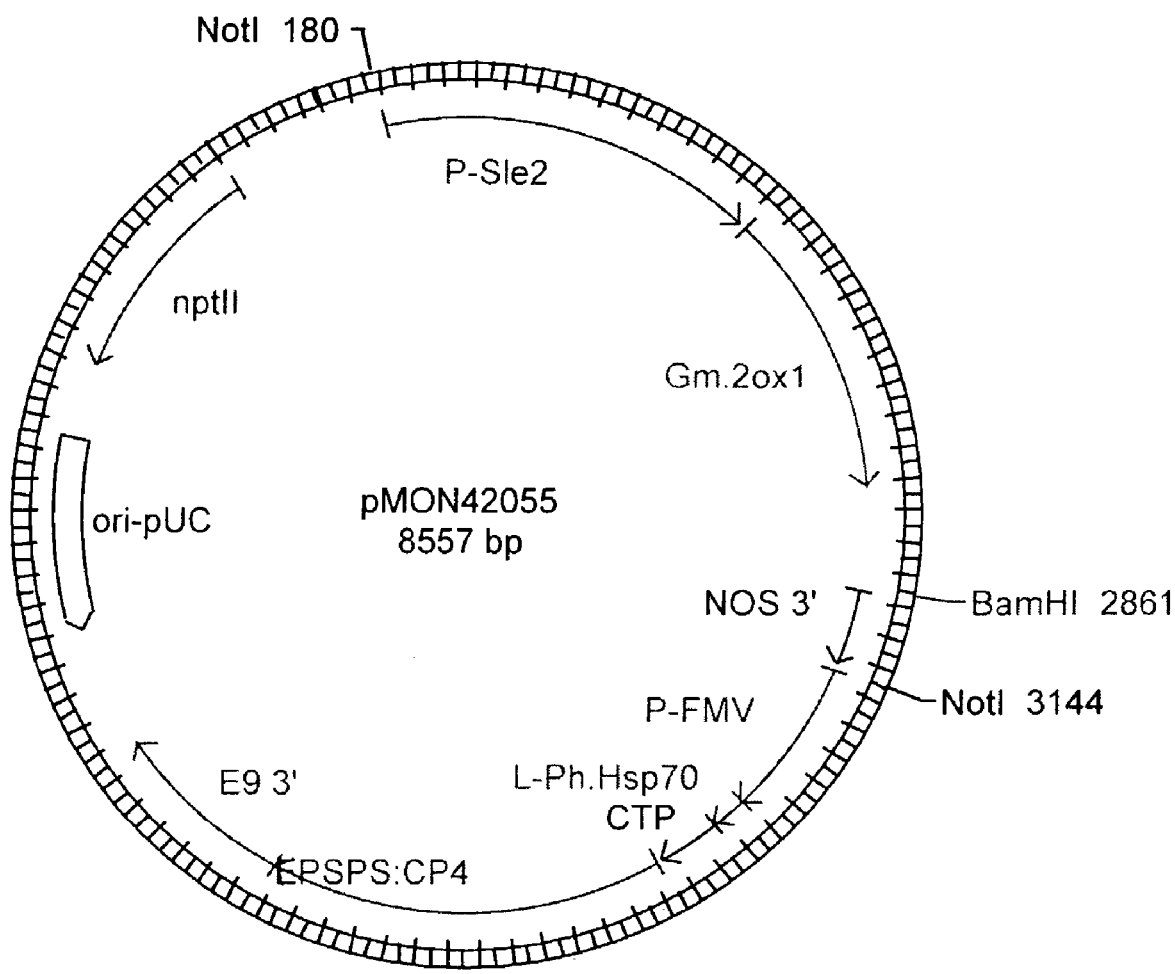
Figure 30:
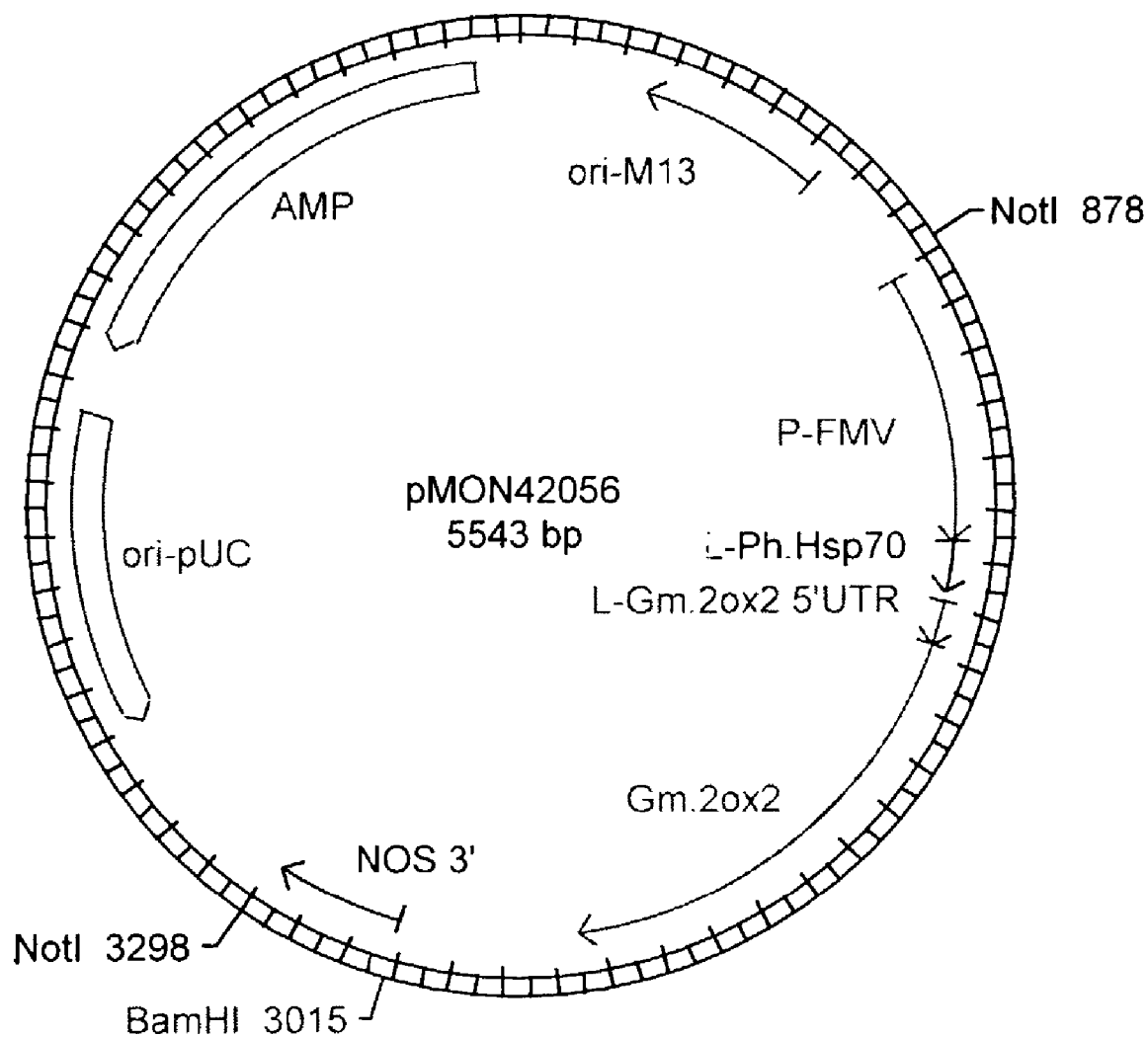
Figure 31:
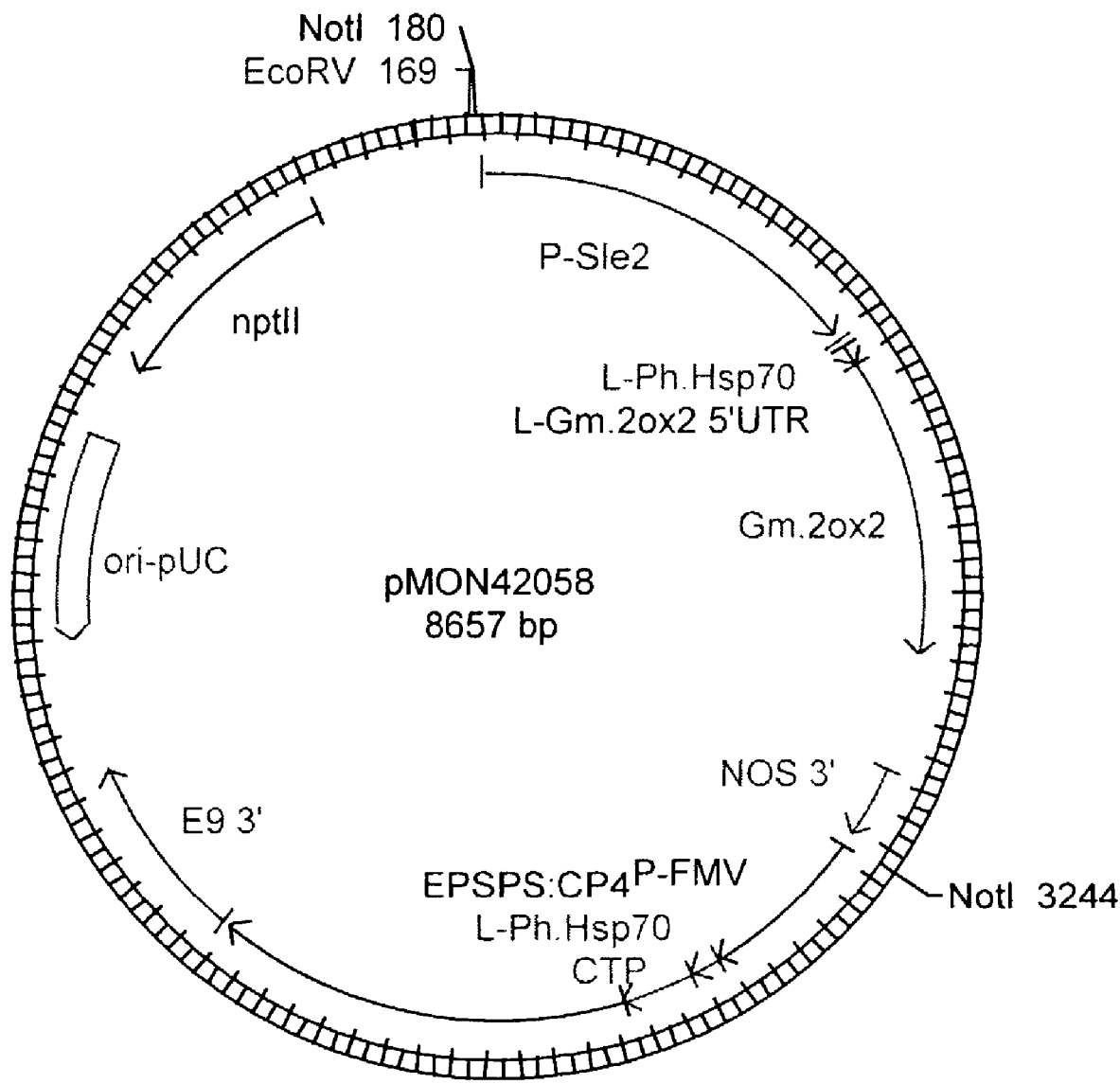
Figure 32:
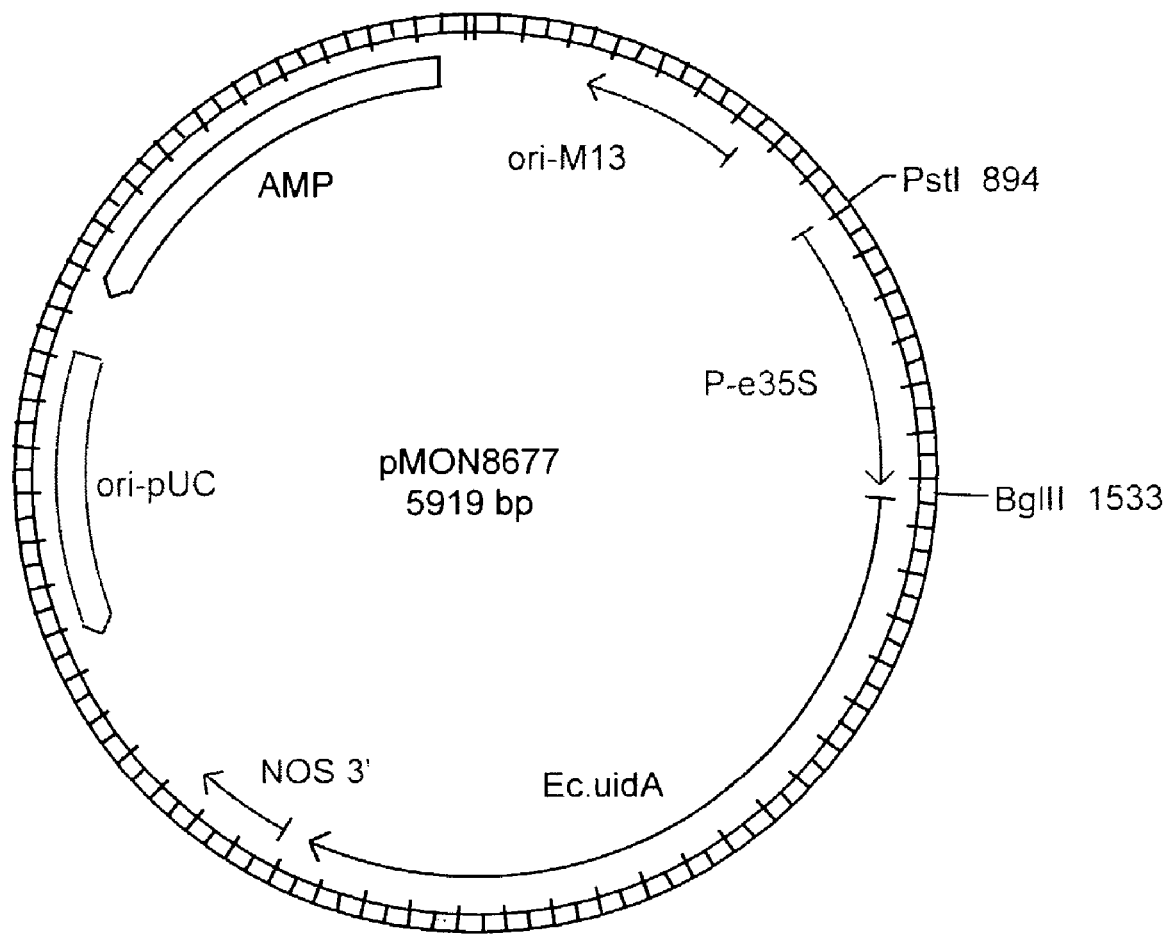
Figure 33:
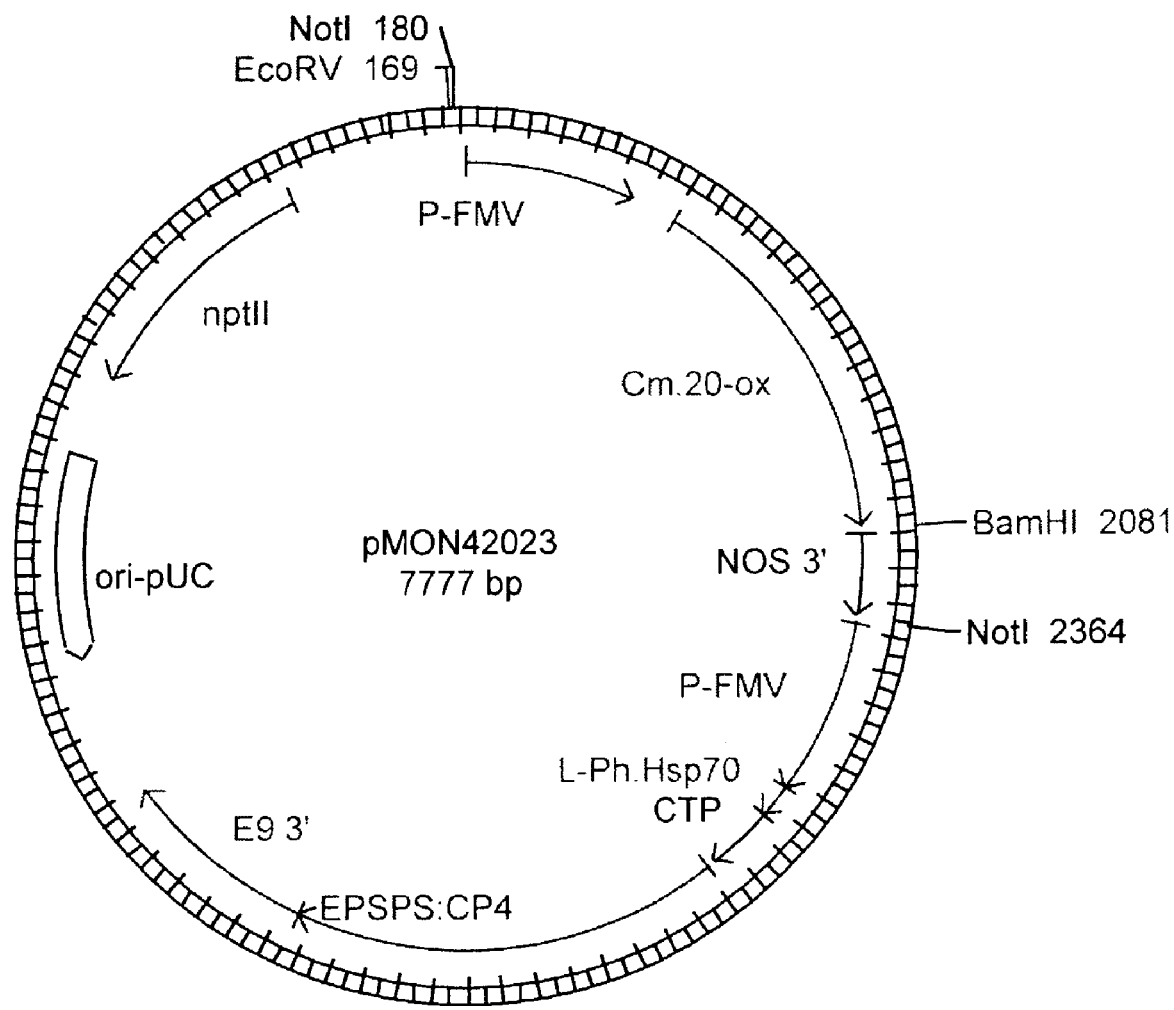
Figure 34:
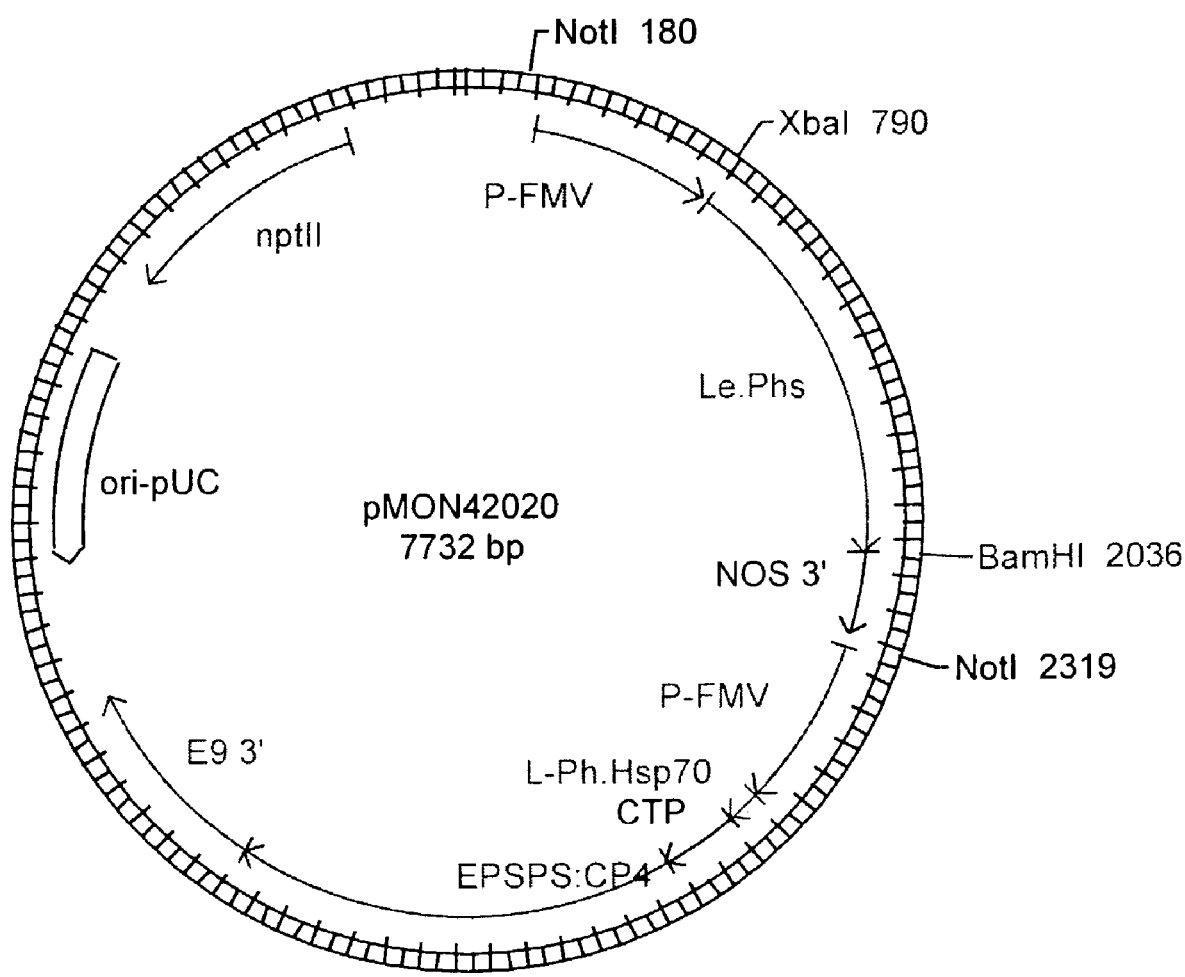
Figure 35:
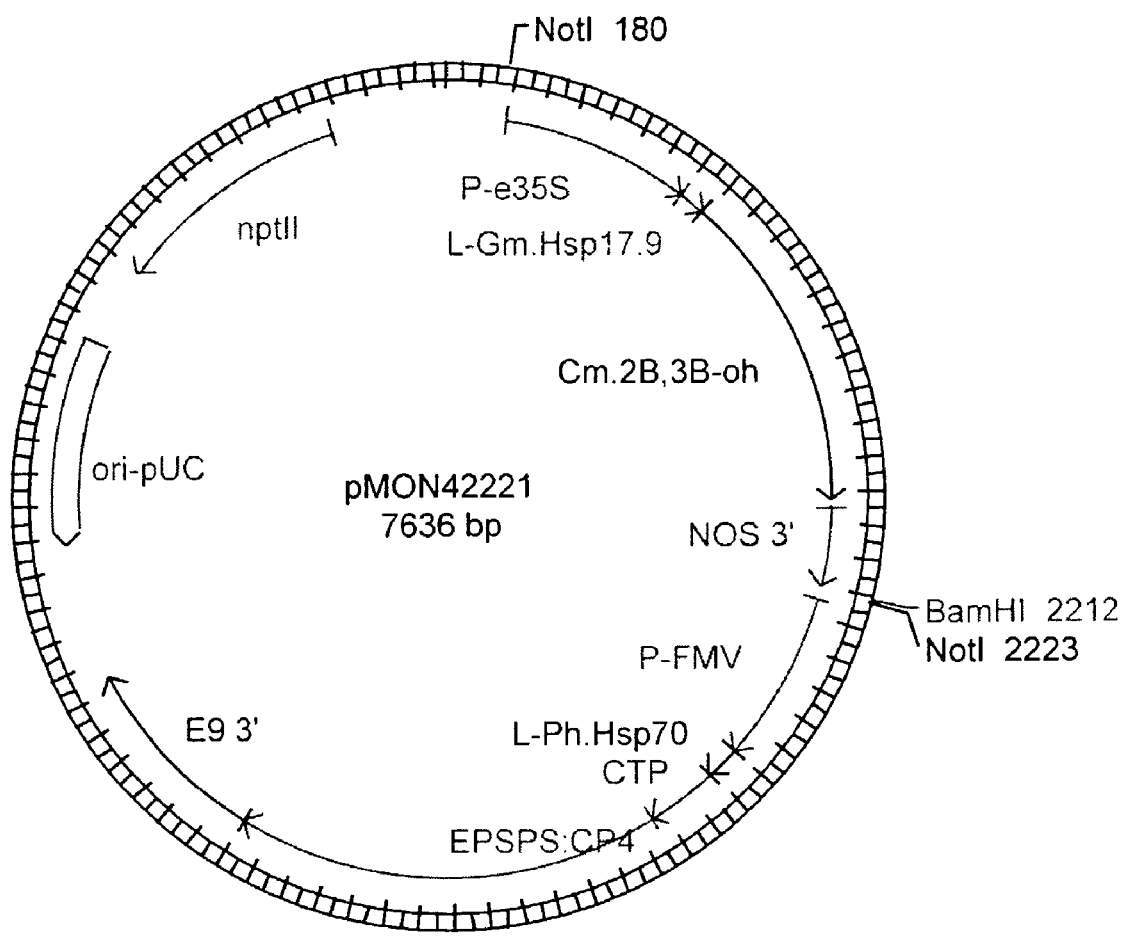
Figure 36:
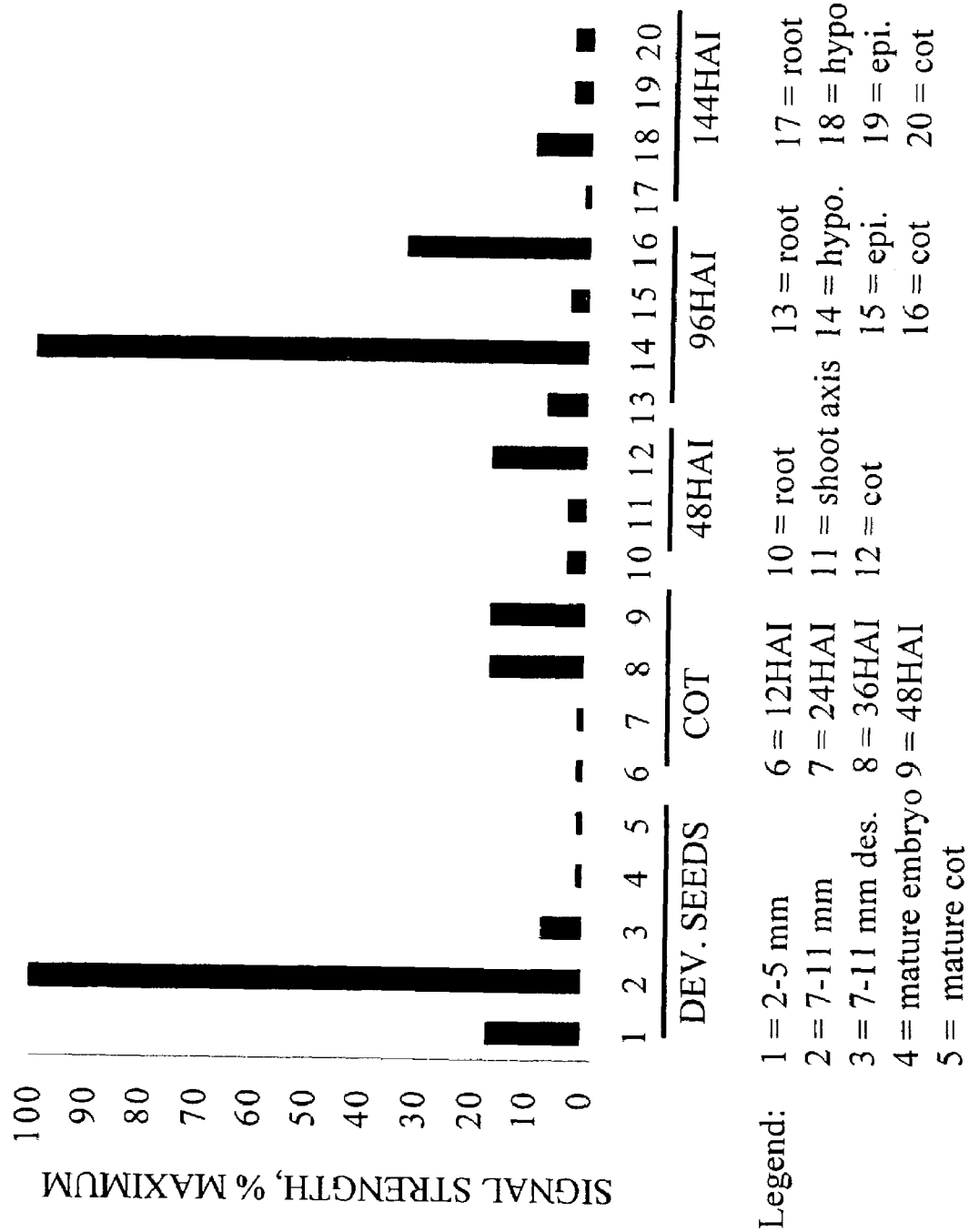
Figure 37:
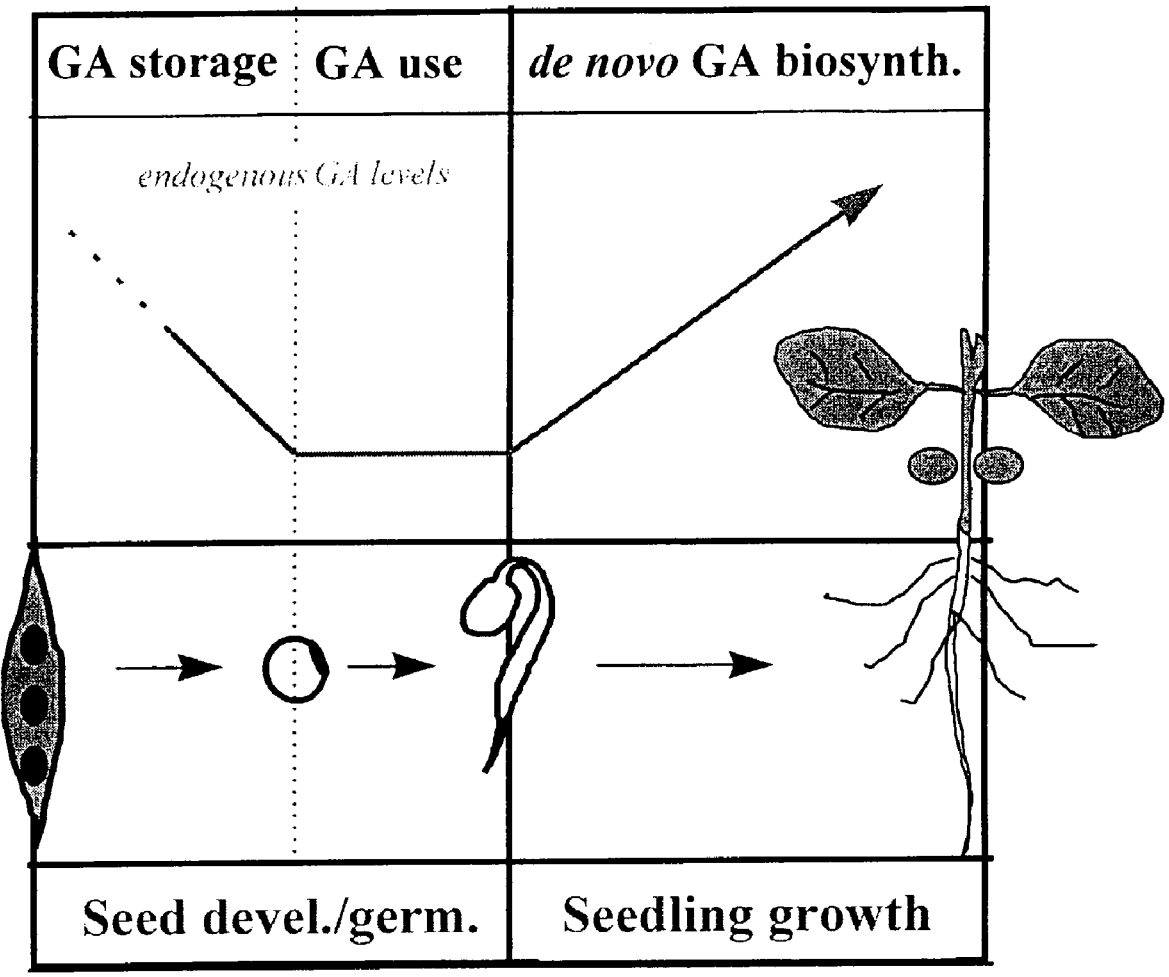
Figure 38:
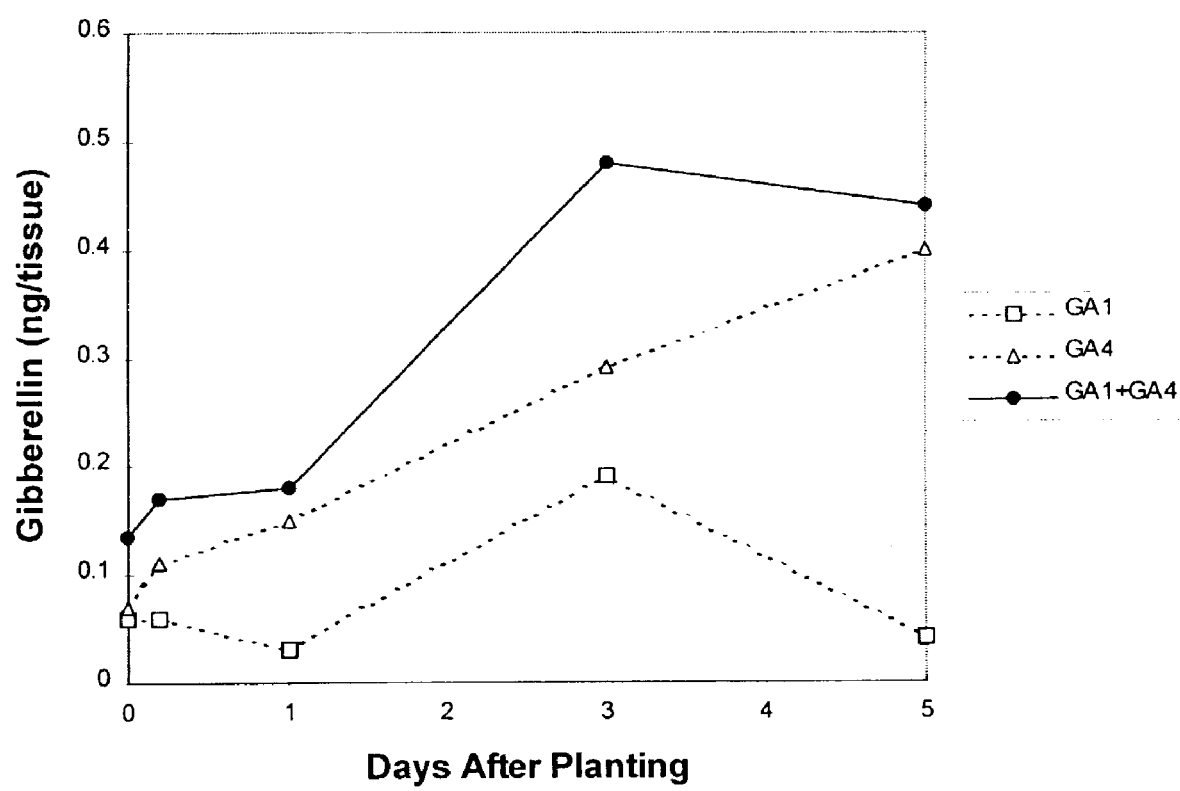
Figure 39:
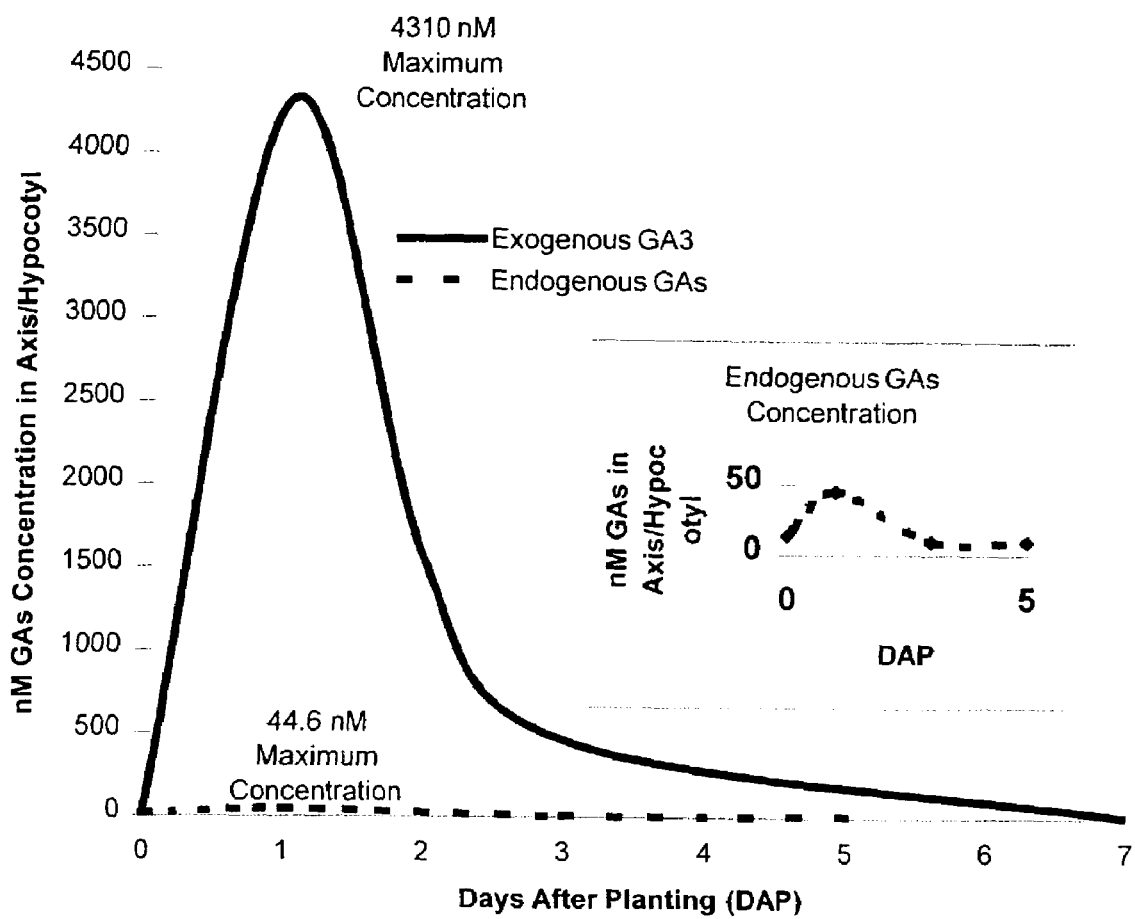
Figure 40:
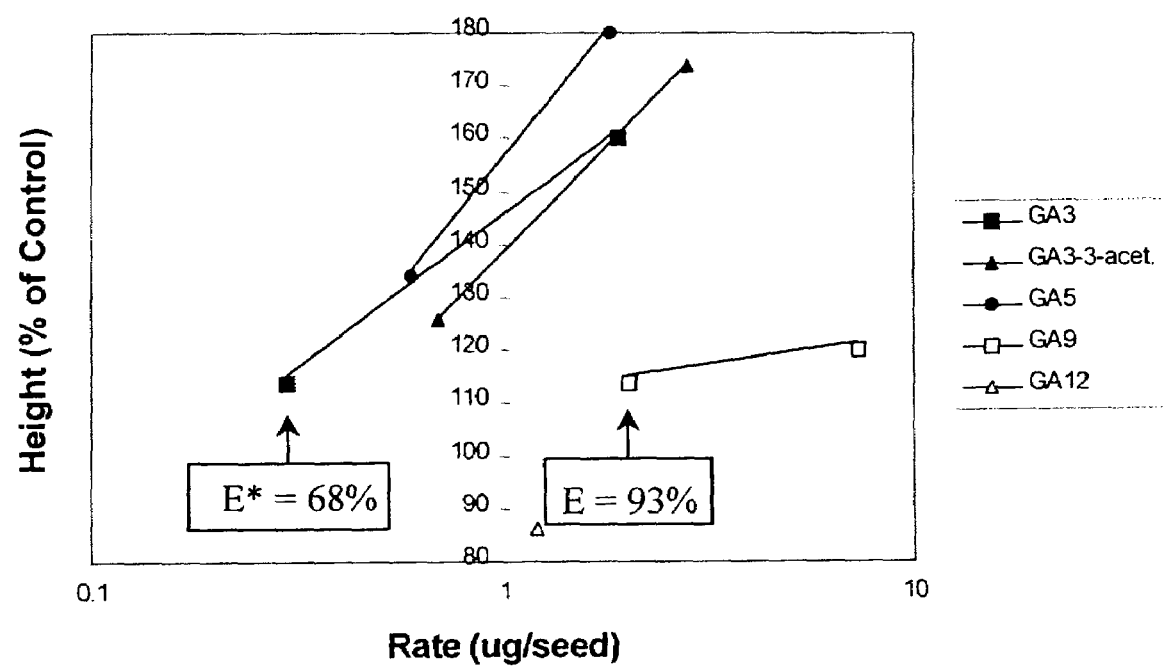
Figure 41:
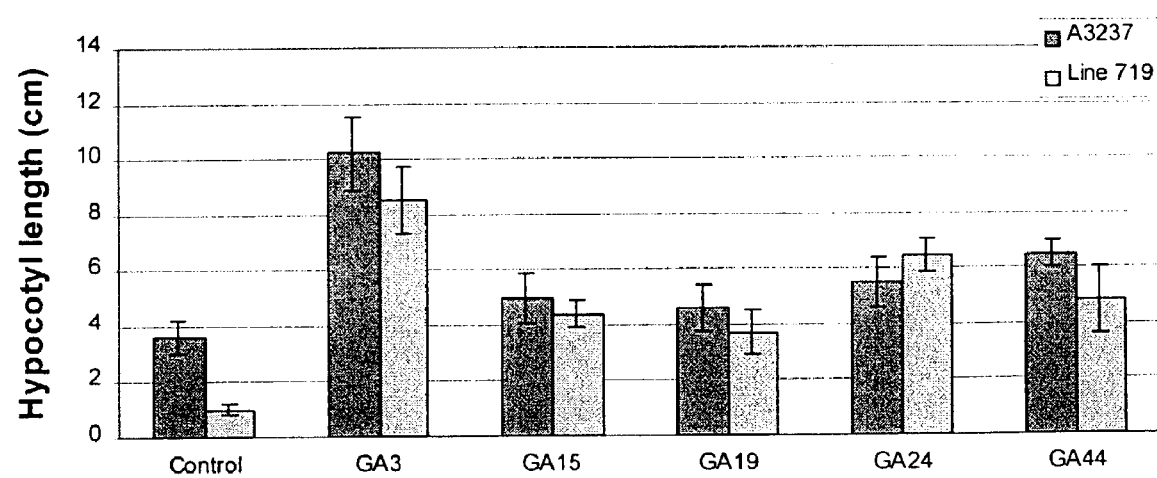
Figure 42:
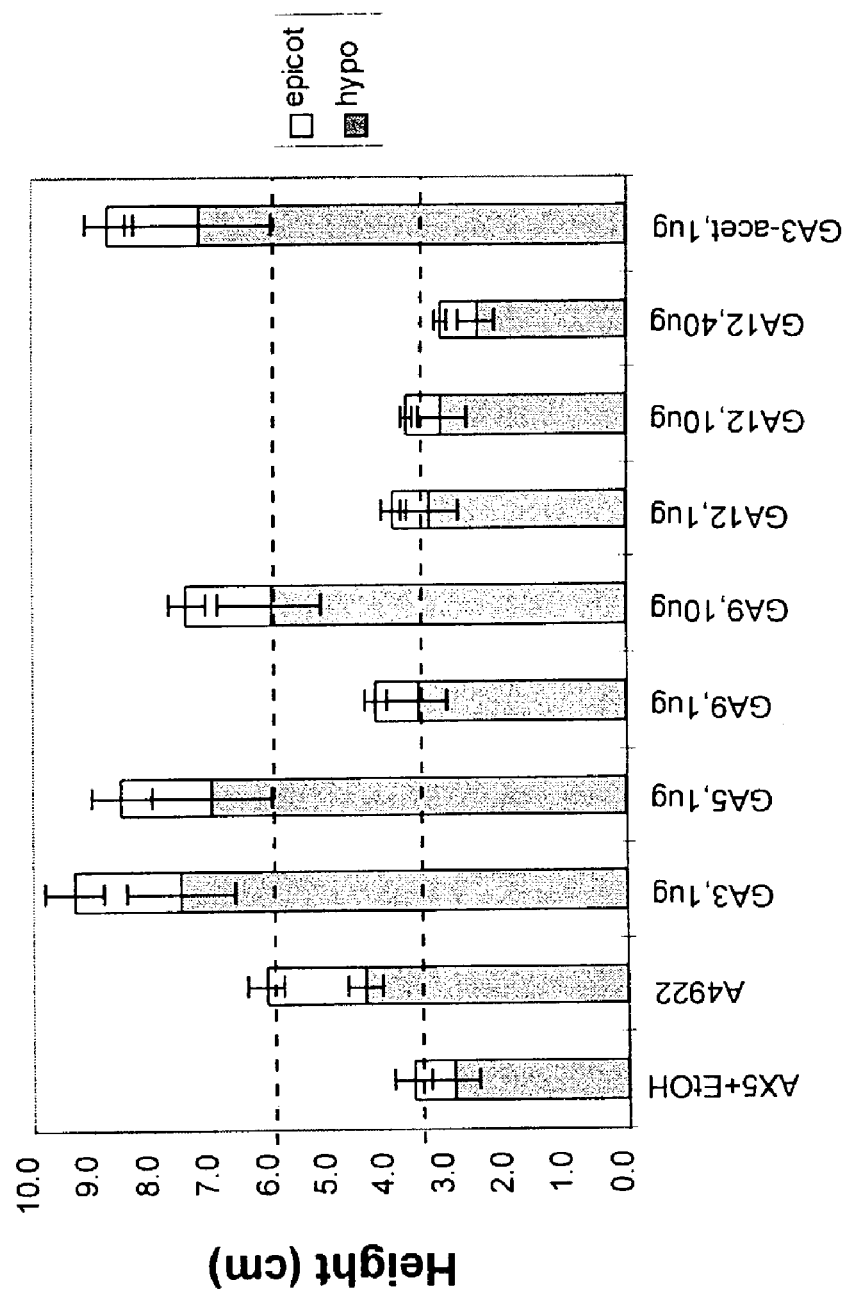
Figure 43:
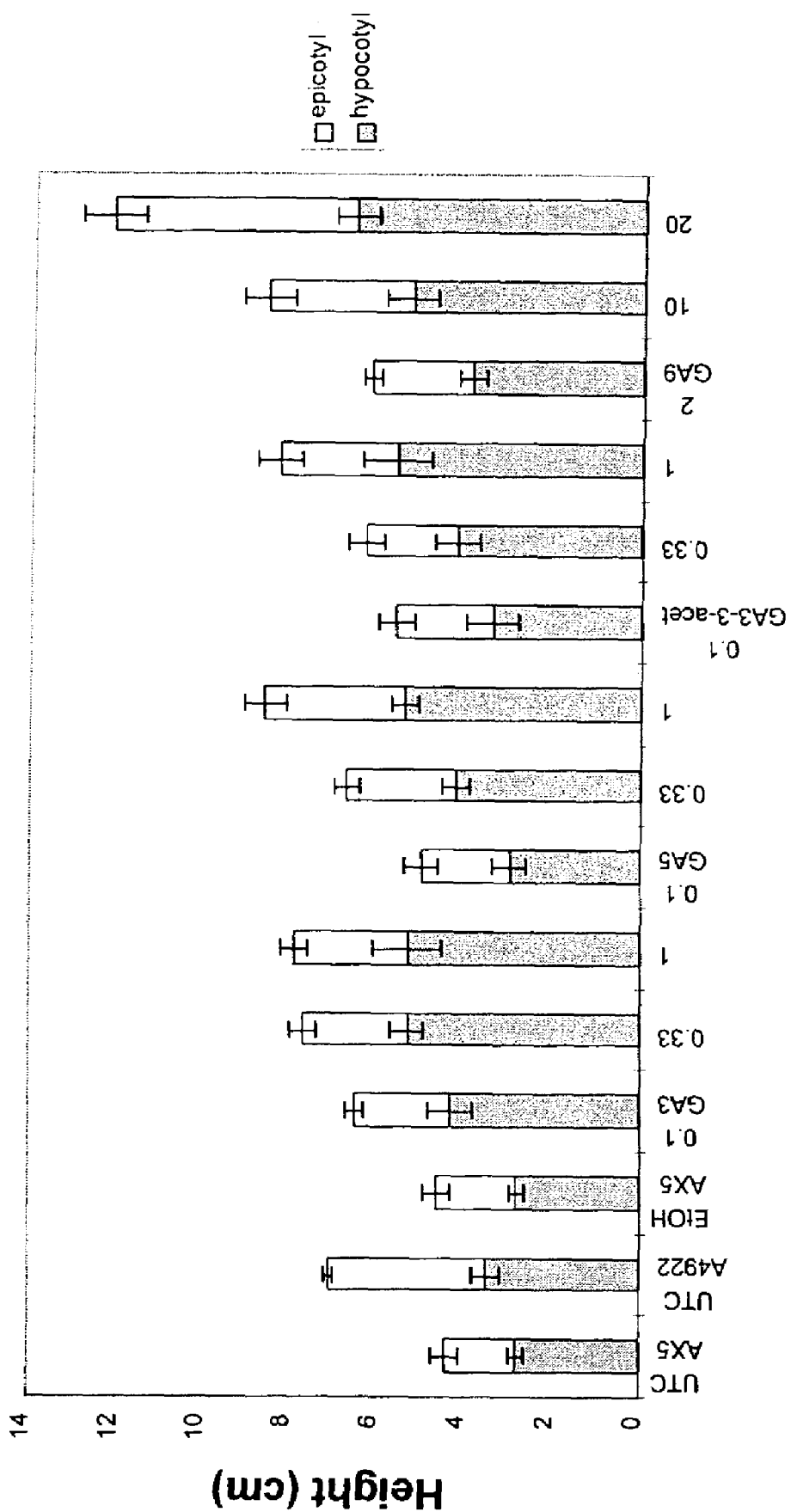

FIG. 1: A vector map of pMON29211.
FIG. 2: A vector map of pMON17227.
FIG. 3: A vector map of pMON29212.
FIG. 4: A vector map of pMON29916.
FIG. 5: A vector map of pMON29217.
FIG. 6: A vector map of pMON29220.
FIG. 7: A vector map of pMON29801.
FIG. 8: A vector map of pMON33512.
FIG. 9: A vector map of pMON42011.
FIG. 10: A vector map of pMON42013.
FIG. 11: A vector map of pMON10098.
FIG. 12: A vector map of pMON29975.
FIG. 13: A vector map of pMON33515.
FIG. 14: A vector map of pMON29815.
FIG. 15: A vector map of pMON34434.
FIG. 16: A vector map of pMON34439.
FIG. 17: A vector map of pMON40401.
FIG. 18: A vector map of pMON34436.
FIG. 19: A vector map of pMON34437.
FIG. 20: A vector map of pMON29807.
FIG. 21. A vector map of pMON42049.
FIG. 22. A vector map of pMON42050.
FIG. 23. A vector map of pMON42051.
FIG. 24. A vector map of pMON51904.
FIG. 25. A vector map of pMON42052.
FIG. 26. A vector map of pMON34495.
FIG. 27. A vector map of pMON42053.
FIG. 28. A vector map of pMON42054.
FIG. 29. A vector map of pMON42055.
FIG. 30. A vector map of pMON42056.
FIG. 31. A vector map of pMON42058.
FIG. 32: A vector map of pMON8677.
FIG. 33. A vector map of pMON42023.
FIG. 34. A vector map of pMON42020.
FIG. 35. A vector map of pMON42221.
FIG. 36: Description of relative levels of CPS mRNA in soybean developing seeds and seedling tissues.
FIG. 37. Schematic showing endogenous GA levels in wild type soybeans during seed development, germination, and seedling growth.
FIG. 38. Shows endogenous levels of $GA_1$ and $GA_4$ in developing soybean seedlings.
FIG. 39. Shows the concentration of $^{14}C$-$GA_3$ in germinating soybean seedlings when applied as a seed treatment.
FIG. 40. Summary of data from Tables 22–24.
FIG. 41. Comparison of GA compound effects on soybean hypocotyl length.
FIG. 42. Effect of GA/precursors on AX5 (Line 46, R2) soybean seedling rescue (8 DAP).
FIG. 43. Effect of GA precursors/derivatives on AX5 (line 234, R3) soybean height (10 DAP).

Table 1. Mutants and cDNA clones for GA-biosynthetic enzymes
Table 2. Nucleotide percent similarity of CPS conserved core region genes and nucleotide percent similarity of CPS full-length genes.
Table 3. Stature of FMV/asCPS soybean plants at 7 DAP.
Table 4. Distribution of plant heights in the evaluation of segregating $R_1$ FMV/asCPS soybean seeds.
Table 5. Effect of $GA_3$ soil drench on pMON29801 soybean shoot length at 7 days after planting.
Table 6. Restoration of pMON29801 soybean stature by foliar $GA_3$ treatment.
Table 7. Codon degeneracies of amino acids.
Table 8. $GA_1$ and $GA_4$ levels in soybean seeds.
Table 9. Effect of $GA_3$ seed treatment on soybean stand and yield.
Table 10. Compounds tested.
Table 11. Particulate material present in solutions after mixing Table 12. GA compound rescue of line 719

Table 13. Effect of various concentrations of selected GA compounds on constitutively GA-deficient transgenic dwarf and wild-type soybeans in the greenhouse.

Table 14. Summary of first two greenhouse experiments on the biological activity of GA compounds in constitutively GA-deficient transgenic dwarf and wild-type soybeans in constitutively GA-deficient transgenic dwarf and wild-type soybeans.

Table 15. Effect of selected GA compounds on constitutively GA-deficient transgenic dwarf soybean line 719 plants in the field.

Table 16. Effect of various GA compounds on emergence of constitutively GA-deficient transgenic dwarf soybean line 719.

Table 17. Effect of $GA_3$ on emergence, rescue and height of constitutively GA-deficient transgenic dwarf soybeans and wild-type soybeans in the field.

Table 18. Effect of $GA_3$-3-acetate on emergence, rescue, and height of constitutively GA-deficient transgenic dwarf soybeans and wild-type soybeans in the field.

Table 19. Effects of $GA_5$ on emergence, rescue and height of constitutively GA-deficient transgenic dwarf soybeans and wild-type soybeans in the field.

Table 20. Effect of GA9 on emergence, rescue, and height of constitutively GA-deficient transgenic dwarf soybeans and wild-type soybeans in the field.

Table 21. Effect of $GA_{12}$ on emergence, rescue, and height of constitutively GA-deficient transgenic dwarf soybeans and wild-type soybeans in the field.

Table 22. Effect of GA compounds on emergence, rescue, and height of soybean seedlings in different soils.

Table 23. Effect of GA compounds on emergence, rescue, and height of soybean seedlings in different soils.

Table 24. Effect of GA compounds on emergence, rescue, and height of soybean seedlings in different soils.

Table 25. Effect of soil conditions on rescue of emergence of line 719 soybeans using $GA_3$ and $GA_9$ Table 26a. $GA_3$, $GA_9$, and $GA_{12}$ half lives Table 26b. Radiolabelled $GA_3$, $GA_9$ and $GA_{12}$ in soybean tissues.

Table 27. Effect of selected GA compounds applied to the hilum of soybean seeds on seedling growth and development.

Table 28. Evaluation of the rate response of biological activity of selected GA compounds applied to the hilum of soybean seeds on seedling growth and development.

DESCRIPTION OF THE SEQUENCE LISTINGS

The following sequence listings form part of the present specification and are included to further demonstrate certain aspects of the present invention. The invention may be better understood by reference to one or more of these sequences in combination with the detailed description of specific embodiments presented herein.

SEQ ID NO:1: Canola CPS conserved core sequence.
SEQ ID NO:2: Soybean CPS full length gene nucleotide sequence.
SEQ ID NO:3: Cotton CPS core protein gene nucleotide sequence.
SEQ ID NO:4: Wheat CPS core protein gene nucleotide sequence.
SEQ ID NO:5: Soybean 3β hydroxylase.
SEQ ID NO:6: Cotton 3β hydroxylase.
SEQ ID NO:7: Soybean AX5 promoter nucleotide sequence.
SEQ ID NO:8: Soybean C20 oxidase nucleotide sequence.
SEQ ID NO:9: Primer Mot 0.
SEQ ID NO:10: Primer Mot 7.
SEQ ID NO:11: Primer soydeg1.
SEQ ID NO:12: Primer soydeg3.
SEQ ID NO:13: Primer soydeg7.
SEQ ID NO:14: Primer soydeg8.
SEQ ID NO:15: Primer soy24mer.
SEQ ID NO:16: Primer soy29mer.
SEQ ID NO:17: Primer EKS 1.
SEQ ID NO:18: Primer EKS8.
SEQ ID NO:19: Primer NN 1.3.
SEQ ID NO:20: Primer NN 7.5.
SEQ ID NO:21: Primer 3βOH1.
SEQ ID NO:22: Primer 3βOH2.
SEQ ID NO:23: Primer 3βOH3.
SEQ ID NO:24: Primer 3βOH4.
SEQ ID NO:25: Primer ARB1.
SEQ ID NO:26: Primer AX5-1.
SEQ ID NO:27: Primer AX5-5.
SEQ ID NO:28: Primer AX5-6.
SEQ ID NO:29: Primer AX5-3.
SEQ ID NO:30: Primer BOH9.
SEQ ID NO:31: Primer BOH11.
SEQ ID NO:32: Primer BOH12.
SEQ ID NO:33: Primer BOH14.
SEQ ID NO:34: Primer BOH15.
SEQ ID NO:35: Primer BOH16.
SEQ ID NO:36: Primer BOH5.
SEQ ID NO:37: Primer C20-F1.
SEQ ID NO:38: Primer C20-R1.
SEQ ID NO:39: Primer λgt10-1 ft.
SEQ ID NO:40: Primer λgt10 rt.
SEQ ID NO:41: Consensus GA 2-oxidase amino acid domain
SEQ ID NO:42: Primer 15434-2
SEQ ID NO:43: Primer 15434-3
SEQ ID NO:44: Primer 15434-7
SEQ ID NO:45: Primer 25182-1
SEQ ID NO:46: Primer 25182-2
SEQ ID NO:47: Primer 25182-5
SEQ ID NO:48: Primer 25182-6
SEQ ID NO:49: Primer 25182-7
SEQ ID NO:50: Primer 25182-8
SEQ ID NO:51: Primer 27516-2
SEQ ID NO:52: Primer 27517-3
SEQ ID NO:53: Primer AUAP
SEQ ID NO:54: Primer AP
SEQ ID NO:55: Primer T7
SEQ ID NO:56: *Arabidopsis* GA 2-oxidase 4 gene cDNA sequence
SEQ ID NO:57: *Arabidopsis* GA 2-oxidase 4 genomic clone DNA sequence
SEQ ID NO:58: *Arabidopsis* GA 2-oxidase 4 cDNA full length sequence
SEQ ID NO:59: *Arabidopsis* GA 2-oxidase 4 cDNA translation
SEQ ID NO:60: *Arabidopsis* GA 2-oxidase 5 genomic gene sequence
SEQ ID NO:61: *Arabidopsis* GA 2-oxidase 5 exon translation
SEQ ID NO:62: Soybean GA 2-oxidase 1 cDNA sequence
SEQ ID NO:63: Soybean GA 2-oxidase 1 cDNA translation
SEQ ID NO:64: Soybean GA 2-oxidase 2 cDNA sequence SEQ ID NO:65: Soybean GA 2-oxidase 2 cDNA translation
SEQ ID NO:66: Soybean GA 2-oxidase 3 cDNA sequence
SEQ ID NO:67: Cotton GA 2-oxidase 1 cDNA sequence
SEQ ID NO:68: Cotton GA 2-oxidase 2 cDNA sequence
SEQ ID NO:69: Cotton GA 2-oxidase 3 cDNA sequence
SEQ ID NO:70: Maize GA 2-oxidase 1 cDNA sequence
SEQ ID NO:71: Maize GA 2-oxidase 2 cDNA sequence
SEQ ID NO:72: Primer Gm2ox1-1
SEQ ID NO:73: Primer Gm2ox5-1
SEQ ID NO:74: Primer Gm2ox4-1
SEQ ID NO:75: Phytoene synthase cDNA sequence
SEQ ID NO:76: Phytoene synthase cDNA translation
SEQ ID NO:77: Pumpkin C20-oxidase cDNA sequence
SEQ ID NO:78: Pumpkin C20-oxidase translation
SEQ ID NO:79: Pumpkin 2beta,3beta hydroxylase cDNA
SEQ ID NO:80: Pumpkin 2beta,3beta hydroxylase translation
SEQ ID NO:81: Primer PHS1
SEQ ID NO:82: Primer PHS2
SEQ ID NO:83: Primer C20-1 oxidase
SEQ ID NO:84: Primer C20-2 oxidase
SEQ ID NO:85: Primer HOOK
SEQ ID NO:86: Primer 2β,3β-1
SEQ ID NO:87: Primer 2β,3β-2
SEQ ID NO:88: Soybean CPS full length cDNA translation
SEQ ID NO:89: Soybean 3β-hydroxylase cDNA translation Definitions The following definitions are provided in order to aid those skilled in the art in understanding the detailed description of the present invention.

"Amplification: refers to increasing the number of copies of a desired nucleic acid molecule.

"Analyte" refers to a substance or substances, either alone or in mixtures, whose presence is to be detected and, if desired, quantitated.

"3-β hydroxylase" refers to proteins which catalyze the hydroxylation of C-19 $GA_{20}$ and $GA_9$ at the 3-position.

"CPS" and "copalyl diphosphate synthase" refer to proteins which catalyze the conversion of geranylgeranyl diphosphate to copalyl diphosphate.

"2β,3β hydroxylase" refers to multifunctional proteins which hydroxylate GA intermediates at the C-2 and/or C-3 position.

"C-20 oxidase" refers to proteins which oxidize GA intermediates at the C-20 position. In the case of pumpkin 20-oxidase, the C-20 position is oxidized to a carboxylic moiety which chemically prevents GA intermediates from becoming bioactive.

"GA pathway diversion enzymes" refers to enzymes that utilize a substrate of the GA biosynthetic pathway which function when expressed in the target plant to reduce the levels of the substrate.

"Autoradiography" refers to the exposure of roentgenographic film to a blot, plate, or membrane containing a radiolabeled probe, used to locate the labeled probe on the blot.

"Bacteriophage" refers to a virus, e.g. lambda phage or M13, that infects bacteria.

"cDNA library" refers to a collection of cDNA fragments, each cloned into a separate vector molecule.

The term "chimeric" refers to a fusion nucleic acid or protein sequence. A chimeric nucleic acid sequence is comprised of two sequences joined in-frame that encode a chimeric protein. The coding regions of multiple protein subunits may be joined in-frame to form a chimeric nucleic acid sequence that encodes a chimeric protein sequence.

The phrases "coding sequence", "open reading frame", and "structural sequence" refer to the region of continuous sequential nucleic acid triplets encoding a protein, polypeptide, or peptide sequence.

"Codon" refers to a sequence of three nucleotides that specify a particular amino acid.

"Complementarity" and "complement" when referring to nucleic acid sequences, refers to the specific binding of adenine to thymine (or uracil in RNA) and cytosine to guanine on opposite strands of DNA or RNA.

"C-terminal region" refers to the region of a peptide, polypeptide, or protein chain from the middle thereof to the end that carries the amino acid having a free carboxyl group.

"Emergence" broadly refers to the event in seedling or perennial growth when a shoot becomes visible by pushing through the soil surface. As applied to seeds of plants, e.g., beans, that undergo epigeous germination wherein the cotyledons are brought aboveground, the term "emergence" refers to the presence of cotyledons raised to soil level or above. During the germination of such seeds, the hypocotyl usually first elongates, doubling up as it does so, and emerging from the seed coats as an "elbow" or hypocotyl hook. This hook elongates upward through the soil, pulling the cotyledons after it. In this case, the first structure to appear at the soil surface is the bend of the hypocotyl hook, which pulls the cotyledons aboveground soon afterwards. The hook then straightens out, and the epicotyl then grows out from between the cotyledons. As applied to seeds of monocotyledonous and dicotyledonous plants, e.g., corn and peas, respectively, that undergo hypogeous germination wherein the cotyledon(s) remain(s) underground, the term "emergence" refers, in monocots, to the presence of the coleoptile and/or first photosynthetic leaves above the soil surface; in dicots, the term "emergence" refers to the presence of the plumular hook, opening plumular hook, or plumule and young leaves above the soil surface.

The term "encoding DNA" refers to chromosomal DNA, plasmid DNA, cDNA, or synthetic DNA which encodes any of the enzymes discussed herein.

The term "endogenous" refers to materials originating from within an the organism or cell.

"Endonuclease" refers to an enzyme that hydrolyzes double stranded DNA at internal locations.

"Exogenous" refers to materials originating from outside of an organism or cell. This typically applies to nucleic acid molecules used in producing transformed or transgenic host cells and plants.

"Exon" refers to the portion of a gene that is actually translated into protein, i.e. a coding sequence.

The term "expression" refers to the transcription of a gene to produce the corresponding mRNA.

The term "translation" refers to the production the corresponding gene product, i.e., a peptide, polypeptide, or protein from a mRNA.

The term "expression of antisense RNA" refers to the transcription of a DNA to produce an first RNA molecule capable of hybridizing to a second RNA molecule encoding a gene product, e.g. a protein. Formation of the RNA-RNA hybrid inhibits translation of the second RNA molecule to produce the gene product.

The phrase "expressibly coupled" and "expressibly linked" refer to a promoter or promoter region and a coding or structural sequence in such an orientation and distance that transcription of the coding or structural sequence may be directed by the promoter or promoter region.

"GA(s)" refers to gibberellin(s).

"GA compounds" collectively refers to gibberellins, gibberellin precursors, gibberellin biosynthetic intermediates, and derivatives of any of the foregoing. Gibberellin precursors as used herein the term "precursor" refers to compounds preceding $GA_{12}$-aldehyde in the gibberellin biosynthetic pathway. "Intermediates" refers to compounds including $GA_{12}$-aldehyde and onward, toward, by not including, final bioactive gibberellins. In addition, the term "GA compounds" also includes gibberellins, gibberellin precursors, gibberellin biosynthetic intermediates, and derivatives synthetically modified to contain protecting groups on substituents attached to the gibberellane nucleus. Such protecting groups can be introduced into these compounds by methods known in the art, e.g., note Greene et al. (1991) *Protective Groups in Organic Synthesis*, Second edition, John Wiley & Sons, Inc., New York. Protected compounds can be rendered physiologically active in planta by metabolic processes, e.g., by the action of esterases, etc., depending on the nature of the protecting group.

"GA-deficient seedling or plant" refers to a monocotyledonous or dicotyledonous seedling or plant containing a reduced amount of at least one GA compound compared to the level of that compound(s) generally accepted as being normal for that seedling or plant, or usually found in a seedling or plant of that species or variety, resulting in abnormal seedling or plant morphology, e.g., dwarfism. GA-deficient seedlings or plants can be non-transgenic, wild-type plants, or transgenic seedlings or plants produced by introduction therein of anti-sense nucleic acids that interfere with the production of GA biosynthetic pathway enzymes, and therefore GA biosynthesis and/or metabolism. GA-deficient seedlings or plants can also be transgenic seedlings or plants produced by introduction therein of additional copies of nucleic acids encoding GA biosynthetic pathway enzymes, resulting in cosuppression of these enzymes, and therefore interference with GA biosynthesis and/or metabolism. GA-deficient seedlings or plants can also be transgenic seedlings or plants produced by introduction therein of nucleic acid(s) that result(s) in expression of enzymes that inactivate active GAs, GA precursors, GA biosynthetic intermediates, or derivatives thereof.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "genome" as it applies to bacteria encompasses both the chromosome and plasmids within a bacterial host cell. Encoding nucleic acids of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. Nucleic acids of the present invention introduced into plant cells can therefore be either chromosomally-integrated or organelle-localized.

"Heterologous DNA" refers to DNA from a source different than that of the recipient cell.

"Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson, et al. *Nucl. Acids Res.*, 22: 4673–4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

"Intron" refers to a portion of a gene not translated into protein, even though it is transcribed into RNA.

"N-terminal region" refers to the region of a peptide, polypeptide, or protein chain from the amino acid having a free amino group to the middle of the chain.

"Nucleic acid" refers to deoxyribonucleic acid (DNA) and ribonucleic acid (RNA).

Nucleic acid codes: A=adenosine; C=cytosine; G=guanosine; T=thymidine. Codes used for synthesis of oligonucleotides: N=equimolar A, C, G, and T; I=deoxyinosine; K=equimolar G and T; R=equimolar A and G; S=equimolar C and G; W=equimolar A and T; Y=equimolar C and T.

A "nucleic acid segment" or a "nucleic acid molecule segment" is a nucleic acid molecule that has been isolated free of total genomic DNA of a particular species, or that has been synthesized. Included with the term "nucleic acid segment" are DNA segments, recombinant vectors, plasmids, cosmids, phagemids, phage, viruses, etcetera.

"Open reading frame (ORF)" refers to a region of DNA or RNA encoding a peptide, polypeptide, or protein.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

"2-oxidase" refers to proteins which oxidize the C-2 position of bioactive and nonbioactive GAs.

"Phytoene synthase" refers to proteins which catalyze the conversion of geranylgeranyl diphosphate to phytoene.

"Plasmid" refers to a circular, extrachromosomal, self-replicating piece of DNA.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to an enzymatic technique to create multiple copies of one sequence of nucleic acid. Copies of DNA sequence are prepared by shuttling a DNA polymerase between two amplimers. The basis of this amplification method is multiple cycles of temperature changes to denature, then re-anneal amplimers, followed by extension to synthesize new DNA strands in the region located between the flanking amplimers.

The term "promoter" or "promoter region" refers to a nucleic acid sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed. Recombinant DNA constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Rescue" refers to the restoration of substantially normal growth, development, and morphology in GA-deficient seedlings and plants without causing substantial abnormal growth, development, or morphology, i.e., the phenotype of GA-deficient seedlings or plants substantially resembles that of otherwise identical, non-GA-deficient seedlings or plants. Depending upon whether their seeds undergo epigeous or hypogeous germination, GA-deficient seedlings or plants can have shortened hypocotyls or epicotyls, or both; shortened coleoptiles; or shortened plumular hooks, opening plumular hooks, or plumules. In any of these cases, rescue results in restoration of substantially normal length in these regions. Rescued GA-deficient seedlings and plants look substantially like their normal, otherwise identical non-GA deficient counterparts, and can successfully grow to maturity and bear agronomically or horticulturally valuable crop parts. "Substantially normal" refers to growth, development, and morphology, including length, that is within about ±25%, preferably about ±20%, more preferably about ±15%, more preferably about ±10%, and even more preferably about ±5% of that of otherwise identical counterpart non-GA deficient seedlings or plants. In GA-deficient dwarf seedlings in which cotyledons lie on the ground, "rescue" can refer to hypocotyl elongation such that cotyledons are raised above ground level. It should be noted that there are different degrees of "rescue."

"Restriction enzyme" refers to an enzyme that recognizes a specific palindromic sequence of nucleotides in double stranded DNA and cleaves both strands; also called a restriction endonuclease. Cleavage typically occurs within the restriction site.

"Selectable marker" refers to a nucleic acid sequence whose expression confers a phenotype facilitating identification of cells containing the nucleic acid sequence. Selectable markers include those which confer resistance to toxic chemicals (e.g. ampicillin resistance, kanamycin resistance), complement a nutritional deficiency (e.g. uracil, histidine, leucine), or impart a visually distinguishing characteristic (e.g. color changes or fluorescence).

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

"Vector" refers to a plasmid, cosmid, bacteriophage, or virus that carries foreign DNA into a host organism.

DETAILED DESCRIPTION OF THE INVENTION

A component of this invention is the specific reduction of expression of the genes responsible for normal seed germination and early seedling growth in plants. A component of this invention is that the plants have a phenotype of reduced seed germination and early seedling growth. A component of this invention is the ability to restore seed germination and early seedling growth under appropriate conditions. A seed of this invention planted by the farmer would be treated with a compound and therefore able to germinate and emerge from the soil under normal planting conditions. A plant of this invention would be treated with a compound and therefore able to develop normally under normal planting conditions. A benefit to the farmer of this technology is increased uniformity of germination, emergence, and seedling vigor provided by the treatment of the seed or the plant of the invention. A benefit to the seed producer, seed distributor or farm service agents is that normal seed germination and early seedling growth requires treatment with a compound. Untreated seed or seedlings would have reduced early seedling growth resulting in unfavorable agronomic characteristics. However, plants of reduced stature are useful in hybrid seed production as the female parent. The shortened stature of the female parent permits more efficient pollination which results in better yields of the hybrid seed. This reduces the cost of hybrid seed production.

The first component of the invention could be accomplished by inhibiting genes or functions that are essential for germination or early seedling growth and vigor. When normal germination is required, the second component in the form of a seed treatment, aerosol application, or soil incorporation would be comprised of a compound(s) capable of replacing the missing gene or its products directly or indirectly or by inducing another gene to complement the missing gene or its products. Another way to obtain germination control is to express a gene product or multiple gene products which can act alone or interact with each other or with naturally occurring plant products to affect normal germination or early seedling growth/vigor. The gene product could keep a seed in a dormant state or could influence vital processes in the germination/early seedling development phase. In this case, the seed or plant treatment would function to inhibit the expression of the inhibitor gene or its product/function or induce a secondary pathway or process that would relieve the block or bypass it.

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci. U.S.A.* 84: 5745–5749, 1987), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9: 315–324, 1987) and the CaMV 35S promoter (Odell et al., *Nature* 313: 810–812, 1985), the figwort mosaic virus 35S-promoter; the light-inducible promoter from the small subunit of ribulose-1,5-bis-phosphate carboxylase (ssRUBISCO), the Adh promoter (Walker et al., *Proc. Natl. Acad. Sci. U.S.A.* 84: 6624–6628, 1987), the sucrose synthase promoter (Yang et al., *Proc. Natl. Acad. Sci. U.S.A.* 87: 4144–4148, 1990), the R gene complex promoter (Chandler et al., *The Plant Cell* 1: 1175–1183, 1989), and the chlorophyll α/β binding protein gene promoter, et cetera These promoters have been used to create DNA constructs which have been expressed in plants; see, e.g., PCT publication WO 84/02913.

Promoters which are known or are found to cause transcription of DNA in plant cells can be used in the present invention. Such promoters may be obtained from a variety of sources such as plants and plant viruses. In addition to promoters that are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci. U.S.A.* 87: 3459–3463, 1990), the chloroplast fructose-1,6-biphosphatase (FBPase) promoter from wheat (Lloyd et al., *Mol. Gen. Genet.* 225: 209–216, 1991), the nuclear photosynthetic ST-LS1 promoter from potato (Stockhaus et al., *EMBO J.* 8: 2445–2451, 1989), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35: 773–778, 1994), the promoter for the Cab-1 gene from wheat (Fejes et al., *Plant Mol. Biol.* 15: 921–932, 1990), the promoter for the CAB-1 gene from spinach (Lubberstedt et al., *Plant Physiol.* 104: 997–1006, 1994), the promoter for the cab1R gene from rice (Luan et al., *Plant Cell.* 4: 971–981, 1992), the pyruvate, orthophosphate dikinase (PPDK) promoter from *Zea mays* (Matsuoka et al., *Proc. Natl. Acad Sci. U.S.A.* 90: 9586–9590, 1993), the promoter for the tobacco Lhcb1*2 gene (Cerdan et al., *Plant Mol. Biol.* 33: 245–255, 1997), the *Arabidopsis thaliana* SUC2 sucrose-H$^+$ symporter promoter (Truernit et al., *Planta.* 196: 564–570, 1995), and the promoter for the thylakoid membrane proteins from spinach (psaD, psaF, psaE, PC, FNR, atpC, atpD, cab, rbcS). Other promoters for the chlorophyll α/β-binding proteins may also be utilized in the present invention, such as the promoters for LhcB gene and PsbP gene from white mustard (*Sinapis alba*)(Kretsch et al., *Plant Mol. Biol.* 28: 219–229, 1995).

For the purpose of expression in sink tissues of the plant, such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter (Bevan et al., *EMBO J.* 8: 1899–1906, 1986; Jefferson et al., *Plant Mol. Biol.* 14: 995–1006, 1990), the promoter for the potato tuber ADPGPP genes, both the large and small subunits, the sucrose synthase promoter (Salanoubat and Belliard, *Gene* 60: 47–56, 1987; Salanoubat and Belliard, *Gene* 84: 181–185, 1989), the promoter for the major tuber proteins including the 22 kD protein complexes and proteinase inhibitors (Hannapel, *Plant Physiol.* 101: 703–704, 1993), the promoter for the granule bound starch synthase gene (GBSS) (Visser et al., *Plant Mol. Biol.* 17: 691–699, 1991), and other class I and II patatins promoters (Koster-Topfer et al., *Mol. Gen. Genet.* 219: 390–396, 1989; Mignery et al., *Gene* 62: 27–44, 1988).

Other promoters can also be used to express a protein in specific tissues, such as seeds or fruits. The promoter for β-conglycinin (Chen et al., *Dev. Genet.* 10: 112–122, 1989) or other seed-specific promoters such as the napin and phaseolin promoters, can be used. The zeins are a group of storage proteins found in *Zea mays* endosperm. Genomic clones for zein genes have been isolated (Pedersen et al., *Cell* 29: 1015–1026, 1982), and the promoters from these clones, including the 15 kD, 16 kD, 19 kD, 22 kD, 27 kD, and gamma genes, could also be used. Other promoters known to function, for example, in *Zea mays* include the promoters for the following genes: waxy, Brittle, Shrunken 2, Branching enzymes I and II, starch synthases, debranching enzymes, oleosins, glutelins, and sucrose synthases. A particularly preferred promoter for *Zea mays* endosperm expression is the promoter for the glutelin gene from rice, more particularly the Osgt-1 promoter (Zheng et al., *Mol. Cell Biol.* 13: 5829–5842, 1993). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins, and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

Root specific promoters may also be used. An example of such a promoter is the promoter for the acid chitinase gene (Samac et al., *Plant Mol. Biol.* 25: 587–596, 1994). Expression in root tissue could also be accomplished by utilizing the root specific subdomains of the CaMV35S promoter that have been identified (Lam et al., *Proc. Natl. Acad Sci. U.S.A.* 86: 7890–7894, 1989). Other root cell specific promoters include those reported by Conkling et al. (*Plant Physiol* 93: 1203–1211, 1990).

Germination and early seedling growth promoter specificity could be provided to drive expression of a transgene in a germination and early seedling growth specific or intensive process. Germination and early seedling growth promoters could be used specifically to affect a gene function that is essential for germination, but its gene expression is not limited to this time in the plant growth cycle. The preferred germination specific promoter would be most highly expressed in the appropriate tissues and cells at the appropriate developmental time to inhibit the germination enzyme or gene product only during germination or early seedling growth. Tissues and cells that comprise the germination and early seedling growth stages of plants may include: the radical, hypocotyl, cotyledons, epicotyl, root tip, shoot tip, meristematic cells, seed coat, endosperm, true leaves, internodal tissue, and nodal tissue. Germination-enhanced promoters have been isolated from genes encoding the glyoxysomal enzymes isocitrate lyase (ICL) and malate synthase (MS) from several plant species (Zhang et al, *Plant Physiol.* 104: 857–864, 1994; Reynolds and Smith, *Plant Mol. Biol.* 27: 487–497, 1995; Comai et al, *Plant Physiol.* 98: 53–61, 1992). Other promoters include SIP-seedling imbibition protein (Heck, G., Ph.D. Thesis, 1992, Washington University, St. Louis, Mo.) and others such as a cysteine endopeptidase promoter (Yamauchi et al, *Plant Mol. Biol.* 30: 321–329, 1996). Additionally, promoters could be isolated from other genes whose mRNAs appear to accumulate specifically during the germination process, for example class I β-1,3-glucanase B from tobacco (Vogeli-Lange et al., *Plant J.* 5: 273–278, 1994), canola cDNAs CA25, CA8, AX92 (Harada et al., *Mol. Gen. Genet.* 212: 466–473, 1988; Dietrich et al., *J. Plant Nutr.* 8: 1061–1073, 1992), lipid transfer protein (Sossountzove et al, *Plant Cell* 3: 923–933, 1991), or rice serine carboxypeptidases (Washio and Ishikawa, *Plant Phys.* 105: 1275–1280, 1994), and repetitive proline rich cell wall protein genes (Datta and Marcus, *Plant Mol. Biol.* 14: 285–286, 1990).

Seedling-enhanced promoters have utility in modifying GA biosynthesis of the present invention and accumulation of gene products and affect seed germination phase and early seedling growth and development. Seedling-enhanced promoters provide seedling enhanced transcription which provides for expression of other desirable agronomic traits. For example, the seedling portion of the plant life cycle is vulnerable to a variety plant pathogens and pests, seedling damping-off diseases caused by *Rhizoctonia* sp., *Pythium* sp., and *Sclerotium* sp. Production of antifungal proteins such as chitinase, glucanase, maganins, small basic proteins from plant seed extracts or induction of endogenous protective activities in the seedling could confer disease resistance at this sensitive stage of plant growth. Seedlings may also be subject to abiotic stresses, such as cold stress (Hake et al., *Cotton Production Manual,* Univ. of Cal. Publ. 3352, 1996); Jones, et al., *Crop Science* 16: 102–105, 1976), that negatively impact vigor, establishment in the soil, and yield. Transgenic seedlings can utilize seedling-enhanced promoters to express genes that induce cold tolerance (e.g. *Arabidopsis* CBF1, Jaglo-Ottosen et al., *Science* 280: 104–106, 1998) and restore vigor. Seedling-enhanced promoters can be used to express gene products which convert or enhance activity of agrichemicals, such as pesticides, nematocides, fungicides, chemical hybridizing agents and fertilizers, to active or more efficacious forms. These chemicals can be administered to seedlings via a seed coating, aerosol, or soil application and converted within the seedling or be secreted into the environment. Germinating seeds (sprouts) have value directly as a food source and a variety of components including phytosterols, vitamins and essential amino acids increase in abundance over the levels found in ungerminated seeds (Kurzer et al., *Ann. Rev. Nutr.* 17: 353–381, 1997; Chavan et al., *Crit. Rev. Food. Sci. Nutr.* 28: 401–437, 1989). Nutritional qualities could further be improved by using seedling-enhanced promoters to produce activities which enhance metabolic conversions or create new biosynthetic capabilities that boost the levels of the above described nutritional qualities of food during germination. A seedling promoter could also be used to provide enhanced metabolism, transport, or utilization of storage reserves. Increased lipid metabolism via seedling expression of lipase, β-oxidation, glyoxosomal, or gluconeogenesis; increased carbohydrate or nitrogen metabolism via seedling expression of glycolysis, TCA cycle, or protein metabolism such as proteases, glutamine synthase, GOGAT, glucose dehydrogenase, and asparagine synthase could provide increased growth and or vigor in the emerging seedling.

Expression of seedling specific promoters is monitored by use of a reporter gene, such as β-glucuronidase (GUS, Jefferson et al., *EMBO J.* 6: 3901–3907, 1987), luciferase (LUC, Ow et al., *Science* 234: 856–859, 1986), green fluorescent protein (GFP, Sheen et al., *Plant J.* 8: 777–784, 1995) or other suitable reporter gene cloned downstream of the promoter and transiently or stably transformed into plant cells. Detection of reporter gene activity is indicative of transcriptional activity of the promoter within the tissue.

Additional promoters that may be utilized are described, for example, in U.S. Pat. Nos. 5,378,619, 5,391,725, 5,428, 147, 5,447,858, 5,608,144, 5,608,144, 5,614,399, 5,633,441, 5,633,435, and 4,633,436. In addition, a tissue specific enhancer may be used (Fromm et al., *The Plant Cell* 1: 977–984, 1989).

Constructs or vectors may also include with the coding region of interest a nucleic acid sequence that acts, in whole or in part, to terminate transcription of that region. For example, such sequences have been isolated including the Tr7 3' sequence and the NOS3' sequence (Ingelbrecht et al., *The Plant Cell* 1: 671–680, 1989; Bevan et al., *Nucleic Acids Res.* 11: 369–385, 1983), or the like.

A vector or construct may also include regulatory elements. Examples of such include the Adh intron 1 (Callis et al., *Genes and Develop.* 1: 1183–1200, 1987), the sucrose synthase intron (Vasil et al., *Plant Physiol.* 91: 1575–1579, 1989), first intron of the maize hsp70 gene (U.S. Pat. No. 5,362,865), and the TMV omega element (Gallie et al., *The Plant Cell* 1: 301–311, 1989). These and other regulatory elements may be included when appropriate.

A vector or construct may also include a selectable marker. Selectable markers may also be used to select for plants or plant cells that contain the exogenous genetic material. Examples of such include a neo gene (Potrykus et al., *Mol. Gen. Genet.* 199: 183–188, 1985) which codes for kanamycin resistance and can be selected for using kanamycin, G418, et cetera; a bar gene which codes for bialaphos resistance; a mutant EPSP synthase gene (Hinchee et al., *Bio/Technol.* 6: 915–922, 1988) which encodes glyphosate resistance; a nitrilase gene which confers resistance to bromoxynil (Stalker et al., *J. Biol Chem.* 263: 6310–6314, 1988); a mutant acetolactate synthase gene (ALS) which confers imidazolinone or sulphonylurea resistance (European Patent Application No. 154,204, Sep. 11, 1985); and a methotrexate resistant DHFR gene (Thillet et al., *J. Biol. Chem.* 263: 12500–12508, 1988).

A vector or construct may also include a transit peptide. Incorporation of a suitable chloroplast transit peptide may also be employed (European Patent Application Publication No. 0218571). The vector may also include translational enhancers. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al. (*Plant Mol. Biol.* 32: 393–405, 1996).

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol. Rep.* 5: 387–405, 1987); an R-locus gene, which encodes a product that regulates the production of anthocyanin pigments (red color) in plant tissues (Dellaporta et al., Stadler Symposium 11: 263–282, 1988); a β-lactamase gene (Sutcliffe et al., *Proc. Natl. Acad. Sci. U.S.A.* 75: 3737–3741, 1978), a gene which encodes an enzyme for which various chromogenic substrates are known (e.g., PADAC, a chromogenic cephalosporin); a luciferase gene (Ow et al., *Science* 234: 856–859, 1986); a xylE gene (Zukowsky et al., *Proc. Natl. Acad. Sci. U.S.A.* 80: 1101–1105, 1983) which encodes a catechol dioxygenase that can convert chromogenic catechols; an α-amylase gene (Ikatu et al., *Bio/Technol.* 8: 241–242, 1990); a tyrosinase gene (Katz et al., *J. Gen. Microbiol.* 129: 2703–2714, 1983) which encodes an enzyme capable of oxidizing tyrosine to DOPA and dopaquinone which in turn condenses to melanin; and an α-galactosidase.

Included within the terms "selectable or screenable marker genes" are also genes which encode a scriptable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etcetera (Potrykus, *Ann. Rev. Plant Physiol Plant Mol. Biol.* 42: 205–225, 1991; Vasil, *Plant Mol. Biol.* 25: 925–937, 1994). For example, electroporation has been used to transform *Zea mays* protoplasts (Fromm et al., *Nature* 312: 791–793, 1986).

Other vector systems suitable for introducing transforming DNA into a host plant cell include but are not limited to binary artificial chromosome (BIBAC) vectors (Hamilton et al., *Gene* 200: 107–116, 1997), and transfection with RNA viral vectors (Della-Cioppa et al., *Ann. N.Y Acad. Sci.* 792: (Engineering Plants for Commercial Products and Applications), 57–61, 1996).

Technology for introduction of DNA into cells is well known to those of skill in the art. Four general methods for delivering a gene into cells have been described: (1) physical methods such as microinjection (Capecchi, *Cell* 22: 479–488, 1980), electroporation (Wong and Neumann, *Biochem. Biophys. Res. Commun.* 107: 584–587, 1982; Fromm et al., *Proc. Natl. Acad. Sci. U.S.A.* 82: 5824–5828, 1985; U.S. Pat. No. 5,384,253); and the gene gun (Johnston and Tang, *Methods Cell Biol.* 43: 353–365, 1994); (2) viral vectors (Clapp, *Clin. Perinatol.* 20: 155–168, 1993; Lu et al., *J. Exp. Med.* 178: 2089–2096, 1993; Eglitis and Anderson, *Biotechniques* 6: 608–614, 1988); and (3) receptor-mediated mechanisms (Curiel et al., *Hum. Gen. Ther.* 3: 147–154, 1992; Wagner et al., *Proc. Natl. Acad. Sci. U.S.A.* 89: 6099–6103, 1992).

Acceleration methods that may be used include, for example, microprojectile bombardment and the like. One example of a method for delivering transforming nucleic acid molecules to plant cells is microprojectile bombardment. This method has been reviewed by Yang and Christou, eds., *Particle Bombardment Technology for Gene Transfer*, Oxford Press, Oxford, England, 1994). Non-biological particles (microprojectiles) that may be coated with nucleic acids and delivered into cells by a propelling force. Exemplary particles include those comprised of tungsten, gold, platinum, and the like.

A particular advantage of microprojectile bombardment, in addition to it being an effective means of reproducibly transforming monocots, is that neither the isolation of protoplasts (Cristou et al., *Plant Physiol.* 87: 671–674, 1988) nor the susceptibility of *Agrobacterium* infection are required. An illustrative embodiment of a method for delivering DNA into *Zea mays* cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (*Plant Cell* 2: 603–618, 1990). The screen disperses the tungsten nucleic acid particles so that they are not delivered to the recipient cells in large aggregates. A particle delivery system suitable for use with the present invention is the helium acceleration PDS-1000/He gun is available from Bio-Rad Laboratories (Bio-Rad, Hercules, Calif.; Sanford et al., *Technique* 3: 3–16, 1991).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., (*Bio/Technol.* 3: 629–635, 1985) and Rogers et al., (*Methods Enzymol.* 153: 253–277, 1987). Further, the integration of the Ti-DNA is a relatively precise process resulting in few rearrangements. The region of DNA to be transferred is defined by the border sequences, and intervening DNA is usually inserted into the plant genome as described (Spielmann et al., *Mol. Gen. Genet.* 205: 34, 1986).

Modern *Agrobacterium* transformation vectors are capable of replication in *Escherichia coli* as well as *Agrobacterium*, allowing for convenient manipulations as described (Klee et al., In: *Plant DNA Infectious Agents*, Hohn and Schell, eds., Springer-Verlag, New York, pp. 179–203, 1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153: 253–277, 1987). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant created using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts has been reported using methods based on calcium phosphate precipitation, polyethylene glycol treatment, electroporation, and combinations of these treatments (See for example, Potrykus et al., *Mol. Gen. Genet.* 205: 193–200, 1986); Lorz et al. *Mol. Gen. Genet.* 199: 178, 1985); Fromm et al., *Nature* 319: 791, 1986); Uchimiya et al., *Mol. Gen. Genet.* 204: 204, 1986); Marcotte et al., *Nature* 335: 454–457, 1988).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnol.* 6: 397, 1988). In addition, "particle gun" or high-velocity microprojectile technology may be utilized (Vasil et al., *Bio/Technol.* 10: 667, 1992).

Using the latter technology, DNA is carried through the cell wall and into the cytoplasm on the surface of small metal particles as described (Klein et al., *Nature* 328: 70, 1987); Klein et al., *Proc. Natl. Acad. Sci. U.S.A.* 85: 8502–8505, 1988); McCabe et al., *Bio/Technol.* 6: 923, 1988). The metal particles penetrate through several layers of cells and thus allow the transformation of cells within tissue explants.

The regeneration, development, and cultivation of plants from single plant protoplast transformants or from various transformed explants is well known in the art (Weissbach and Weissbach, In: *Methods for Plant Molecular Biology*, (Eds.), Academic Press, Inc. San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863; 5,159,135; 5,518,908); soybean (U.S. Pat. Nos. 5,569,834 and 5,416,011; McCabe et. al., *Biotechnol.* 6: 923, 1988; Christou et al., *Plant Physiol.* 87: 671–674, 1988); Brassica (U.S. Pat. No. 5,463,174); peanut (Cheng et al., *Plant Cell Rep.* 15: 653–657, 1996), McKently et al., *Plant Cell Rep.* 14: 699–703, 1995); and pea (Grant et al., *Plant Cell Rep.* 15: 254–258, 1995).

Transformation of monocotyledons using electroporation, particle bombardment, and *Agrobacterium* have also been reported. Transformation and plant regeneration have been reported in asparagus (Bytebier et al., *Proc. Natl. Acad Sci. U.S.A.* 84: 5354, 1987); barley (Wan and Lemaux, *Plant Physiol* 104: 37, 1994); *Zea mays* (Rhodes et al., *Science* 240: 204, 1988; Gordon-Kamm et al., *Plant Cell* 2: 603–618, 1990; Fromm et al., *Bio/Technol.* 8: 833, 1990; Koziel et al., *Bio/Technol.* 11: 194, 1993; Armstrong et al., *Crop Science* 35: 550–557, 1995); oat (Somers et al., *Bio/Technol.* 10: 1589, 1992); orchard grass (Horn et al., *Plant Cell Rep.* 7: 469, 1988); rice (Toriyama et al., *Theor. Appl. Genet.* 205: 34, 1986; Part et al., *Plant Mol. Biol.* 32: 1135–1148, 1996; Abedinia et al., *Aust. J. Plant Physiol* 24: 133–141, 1997; Zhang and Wu, *Theor. Appl. Genet.* 76: 835, 1988; Zhang et al. *Plant Cell Rep.* 7: 379, 1988; Battraw and Hall, *Plant Sci.* 86: 191–202, 1992; Christou et al., *Bio/Technol* 9: 957, 1991); rye (De la Pena et al., *Nature* 325: 274, 1987); sugarcane (Bower and Birch, *Plant J.* 2: 409, 1992); tall fescue (Wang et al., *Bio/Technol* 10: 691, 1992), and wheat (Vasil et al., *Bio/Technol* 10: 667, 1992; U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335: 454–457, 1988; Marcotte et al., *Plant Cell* 1: 523–532, 1989; McCarty et al., *Cell* 66: 895–905, 1991; Hattori et al., *Genes Dev.* 6: 609–618, 1992; Goff et al., *EMBO J.* 9: 2517–2522, 1990). Transient expression systems may be used to functionally dissect gene constructs (see generally, Mailga et al., *Methods in Plant Molecular Biology*, Cold Spring Harbor Press, 1995). It is understood that any of the nucleic acid molecules of the present invention can be introduced into a plant cell in a permanent or transient manner in combination with other genetic elements such as vectors, promoters, enhancers, et cetera.

In addition to the above discussed procedures, practitioners are familiar with the standard resource materials which describe specific conditions and procedures for the construction, manipulation and isolation of macromolecules (e.g., DNA molecules, plasmids, et cetera), generation of recombinant organisms and the screening and isolating of clones, (see for example, Sambrook et al., *Molecular Cloning. A Laboratory Manual*, Cold Spring Harbor Press, 1989; Mailga et al., *Methods in Plant Molecular Biology*, Cold Spring Harbor Press, 1995; Birren et al., *Genome Analysis: Detecting Genes,* 1, Cold Spring Harbor, New York, 1998; Birren et al., *Genome Analysis: Analyzing DNA,* 2, Cold Spring Harbor, New York, 1998; *Plant Molecular Biology: A Laboratory Manual*, eds. Clark, Springer, New York, 1997).

Gibberellins

Gibberellins (GAs) are plant hormones that affect a wide variety of processes throughout the life cycle of plants, including seed germination, stem elongation, flower induction, anther development, and seed and pericarp growth. Plant responses to the environment can also be effected by modification of the flux through the GA biosynthetic pathway due to external stimuli. The biosynthesis and activity of GAs are therefore fundamentally important to plant development and adaptation of plants to the environment.

Gibberellins are tetracyclic diterpenoid acids found in fungi and higher plants having the ent-gibberellane ring system shown in structure (1).

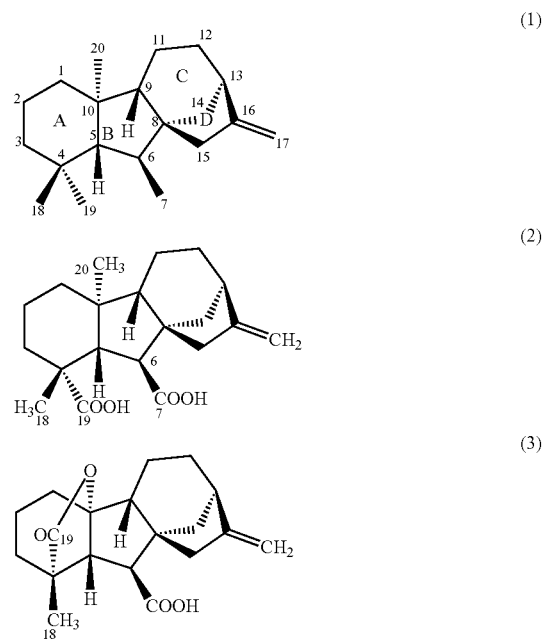

GAs were first isolated by Japanese researchers in the 1930s from cultures of the fungus *Gibberella fujikuroi* (*Fusarium moniliforme*). These secondary metabolites have been shown to be present in other fungal species, in some ferns, and in many gymnosperms and angiosperms. Of the 121 known GAs, 96 have been identified only in higher plants, 12 are present only in *Gibberella*, and 12 are present in both. As in *Gibberella*, many different GAs can be present in individual angiosperms.

Two main types of GAs exist: the $C_{20}$-GAs, which have 20 carbon atoms (structure (2), above), and the $C_{19}$-GAs, in which the twentieth carbon atom has been lost due to metabolism (structure (3)). The carboxylic acid at carbon-19 bonds to carbon-10 to produce a lactone bridge in almost all of the $C_{19}$-GAs.

The ent-gibberellane ring system can contain many structural modifications, accounting for the large number of known GAs. Naturally occurring GAs with structures that have been chemically characterized are allocated an "A number" (MacMillan et al. (1968) Nature 217:170–171). At present, 121 naturally occurring GAs of plant and fungal origin are known.

The variations in GA structure arise in several ways. Carbon-20 can exist in different oxidative states, e.g., methyl (—$CH_3$), hydroxymethyl (—$CH_2OH$), aldehyde (—CHO), or carboxylic acid (—COOH). The ent-gibberellane skeleton, especially that of $C_{19}$-GAs, can also contain additional functional groups. Hydroxyl (—OH) groups are frequently inserted into the ring system; insertion of epoxide (>O) and ketone (=O) functions also occurs, although less commonly. The position and/or stereochemistry of substituent groups affects the biochemical and physiological significance of the molecules. Substituent groups positioned above the ring plane are said to be in the β-configuration; their bonding to the ring is designated by a solid, elongated triangle. Substituent groups positioned below the ring plane are said to be in the α-configuration; their bonding to the ring is designated by a dashed, elongated triangle. The attachment of substituent groups in the plane of the ring system is indicated by a straight line.

Gibberellins can exist as conjugates, for example with a molecule of glucose, either by an ether or an ester linkage. Such conjugation may temporarily or permanently inactivate a GA.

The biological activity of different GAs varies, and various GAs within a plant can be precursors, biosynthetic intermediates, or deactivation products of active GAs. Three structural features are commonly associated with GA biological activity: a 3-hydroxyl group, a 7-carboxyl group, and a lactone ring. Broadly speaking, a compound possessing the ent-gibberellane ring system but lacking one or more of these structural features can be considered a GA precursor, intermediate, or derivative. Understanding the GA biosynthetic and metabolic pathways provides a tool for determining which GAs possess biological activity. For example, identification of GA(s) within a plant that is(are) responsible for a particular growth or developmental event is facilitated by the use of single gene dwarf mutants and chemical growth retardants that inhibit specific metabolic steps.

Sites of Gibberellin Biosynthesis in Plants

GA biosynthesis can occur in all growing, differentiated plant tissues. Developing fruits and seeds contain enzymes that can convert mevalonic acid to $C_{19}$-GAs (Graebe et al. (1974) *Planta* 120:307–309; Kamiya et al. (1983) *Phytochemistry* 22:681–690), indicating that these organs are sites of GA biosynthesis. Immature seeds exhibit two main phases of GA biosynthesis. The first phase occurs shortly after anthesis, correlates with fruit growth, and appears to involve, both qualitatively and quantitatively, GAs that are similar to those in vegetative tissues. The second phase of GA biosynthesis occurs as maturing seeds increase in size, and results in a large accumulation of GAs. In contrast to that in developing seeds, evidence for GA biosynthesis in vegetative tissues has been difficult to obtain. Based on the demonstration of several GA metabolic sequences in elongating internodes, petioles, expanding leaves, and stem apices in several plants (Gilmour et al. (1986) *Plant Physiol.* 82:190–195; Zeevaart et al. (1 993) *Plant Physiol.* 101: 25–29), it is generally accepted that these immature organs are sites of GA biosynthesis. Although GAs have been identified in root extracts, there is little evidence for GA biosynthesis in roots.

The Gibberellin Biosynthetic Pathway

The gibberellin biosynthetic pathway has been the subject of several recent reviews, to which the reader's attention is directed for additional details. Among these are the reviews by V. M. Sponsel (1995) *Plant Hormones, Physiology, Biochemistry and Molecular Biology*, $2^{nd}$ Edition, P. J. Davies, Ed., Kluwer Academic Publishers, Dordrecht, pp. 66–97, and Hedden and Kamiya (1997) *Annu. Rev. Plant Physiol. Mol. Biol.* 48:431–460.

The gibberellin biosynthetic pathway is shown in FIGS. 1 and 2 of Hedden and Kamiya (1997). *Annu. Rev. Plant Physiol. Plant Mol. Biol.* 48:431–460. Mutants and cDNA clones for GA biosynthetic enzymes are listed in Table 1.

TABLE 1

Mutants and cDNA clones for GA-biosynthetic enzymes

| Enzyme | Plant | Mutant | References | cDNA cloning | Data base |
|---|---|---|---|---|---|
| CPS | *Arabidopsis thaliana* | ga1 | 1 | 21 | U11034 |
|  | *Zea mays* | An1 | 2 | 22 | L37750 |
|  | *Pisum sativum* | ls-1 | 3 | 23 | U63652 |
|  | *Lycopersicon esculentum* | gib-1 | 4 | — | |
| KS | *Cucurbita maxima* | — | — | 24 | U43904 |
|  | *A. thaliana* | ga2 | 5 | — | |
|  | *Z. mays* | d5 | 6 | — | |
|  | *L. esculentum* | gib-3 | 7 | — | |
| ent-Kaurene oxidase | *P. sativum* | lh$^i$ | 8 | — | |
|  | *A. thaliana* | ga3 | 9 | — | |
|  | *Oryza sativa* | dx | 10 | — | |
| Monoxygenase | *Z. mays* | d3 | 11 | 25 | U32579 |
|  | *P. sativum* | na | 12 | — | |
| GA 20-oxidase | *C. maxima* | — | — | 26 | X73314 |
|  | *A. thaliana* | ga5 | 13 | 27 | U20872 |
|  |  |  |  |  | U20873 |
|  |  |  |  |  | U20901 |
|  | *A. thaliana* | — | — | 28 | X83379 |
|  |  |  |  |  | X83380 |
|  |  |  |  |  | X83381 |
|  | *P. sativum* | — | — | 29 | X91658 |
|  |  |  |  | 30 | U70471 |
|  | *P. sativum* | — | — | 31 | U58830 |
|  | *Phaseolus vulgaris* | — | — | 32 | U70530 |
|  |  |  |  |  | U70531 |
|  |  |  |  |  | U70532 |
|  | *O. sativa* | — | — | 33 | U50333 |
|  | *Spinacia oleracea* | — | — | 34 | U33330 |
| GA 3-hydroxylase | *A. thaliana* | ga4 | 14 | 35 | L37126 |
|  | *Z. mays* | dl | 15 | — | |
|  | *O. sativa* | dy | 16 | — | |

TABLE 1-continued

Mutants and cDNA clones for GA-biosynthetic enzymes

| Enzyme | Plant | Mutant | References | cDNA cloning | Data base |
|---|---|---|---|---|---|
| | P. sativum | le | 17 | — | |
| | Lathyrus odoratus | l | 18 | — | |
| GA2oxidase | P. sativum | sln | 19 | — | |
| | A. thaliana | — | 20 | — | AJ132435 |
| | | | | | AJ132436 |
| | | | | | AJ132487 |
| | | | | | AJ132438 |
| | M. macrocarpus | — | — | — | YO9113 |
| GA$_7$oxidase | — | — | — | 36 | U61386 |
| 2-β,3-β-hydroxylase | C. maxima | — | — | 37 | U63650 |

Enzyme references
1 Koornneef et al. (1983) Genet. Res. 41:57–68
2 Katsumi, M. (1964) PhD thesis, Univ. Calif., Los Angeles
3 Swain et al. (1995) Planta 195:426–33
4 Bensen et al. (1990) J. Plant Growth Regul. 9:237–42
5 Zeevaart et al. (1992) in Karssen et at., eds. Progress in Plant Growth Regulation, Dordrecht:Kluwer, pp. 34–42
6 Hedden et al.(1979) Phytochemistry 18:1475–79
7 Bensen et al. (1990) J. Plant Growth Regul. 9:237–42
8 Swain et al. (1995) Plant Cell Physiol. 36:S110
9 Zeevaart et al. (1992) in Karssen et at., eds. Progress in Plant Growth Regulation, Dordrecht:Kluwer, pp. 34–42
10 Ogawa et al. (1996) Plant Cell Physiol. 37:363–68
11 Fujioka et al. (1988) Plant Physiol. 88:1367–72
12 Ingram et al. (1987) Plant Physiol. 83:1048–53
13 Talon et al. (1990) Proc. Natl. Acad. Sci. USA 87:7983–87
14 Talon et al. (1990) Proc. Natl. Acad. Sci. USA 87:7983–87
15 Fujioka et al. (1988) Plant Physiol. 88:1367–72
16 Kobayashi et al. (1989) Plant Cell Physiol. 30:963–69
17 Ingram et al. (1984) Planta 160:455–63
18 Ross et al. (1990) Physiol. Plant. 79:453–58
19 Ross et al. (1995) Plant J. 7:513–23
20 Thomas et al (1999) Proc. Natl. Acad. Sci. USA 96:4698–4703
21 Sun et al. (1994) Plant Cell 6:1509–18
22 Bensen et al. (1995) Plant Cell 7:75–84
23 Ait-Ali et al. (1997) Plant J. 77:443–54
24 Yamaguchi et al. (1996) Plant J. 10:203–13
25 Winkler et al. (1995) Plant Cell 7:1307–17
26 Lange et al. (1994) Proc. Natl. Acad. Sci. USA 91:8522–66
27 Xu et al. (1995) Proc. Natl. Acad. Sci. USA 92:6640–44
28 Phillips et al. (1995) Plant Physiol. 108:1049–57
29 Martin et al. (1996) Planta 200:159–66
30 Garcia-Martinez et al. (1987) Plant Physiol. 85:212–16
31 Lester et al. (1996) Plant Physiol. 111:1353
32 Garcia-Martinez et al. (1987) Plant Physiol. 85:212–16
33 Toyomasu et al. (1997) Physiol. Plant. 99:111–18
34 Wu et al. (1996) Plant Physiol. 110:547–54
35 Chiang et al. (1995) Plant Cell 7:195–201
36 Lange (1997) Proc. Natl. Acad. Sci. USA 94: 6553–6558
37 Lange et al. (1997) The Plant Cell 9:1459–1467 ent-Kaurene Synthesis and the Formation of GA$_{12}$-Aldehyde

As shown in Hedden and Kamiya (1997) *Annu. Rev. Plant Physiol. Plant Mol. Biol.* 48:431–460., the fundamental ent-Kaurene nucleus is synthesized by the two-step cyclization of geranylgeranyl diphosphate (GGDP) via an ent-copalyl diphosphate (CDP) intermediate. The first reported committed step occurs when geranylgeranyl diphosphate (GGDP) is cyclized by ent-copalyl diphosphate synthase ("CPS"; also referred to as ent-kaurene synthase A) to copalyl diphosphate (CDP). GGDP is produced in plastids by the isoprenoid pathway, originating from mevalonic acid. A non-mevalonate pathway to isoprenoids involving pyruvate and glyceraldehyde-3-phosphate has been proposed in green algae (Schwender et al. (1996) *Biochem. J.* 316: 73–80), and may operate in plastids of higher plants as well in view of the difficulty in demonstrating the incorporation of mevalonate into isoprenoids in these organelles.

The second reported committed step leading to gibberellins is the cyclization of copalyl diphosphate to ent-kaurene, catalyzed by ent-kaurene synthase ("KS"; also referred to as ent-kaurene synthase B). KS exhibits amino acid homology to CPS and other terpene cyclases. Both CPS and KS are reported to be localized in developing plastids, which are generally found in vegetative tissues and seeds (Aach et al., *Planta* 197: 333–342 (1995)).

Cytochrome P-450 monooxygenases are presumed to catalyze the oxidation of ent-kaurene along the path to GA$_{12}$. The successive products of this reaction are ent-kaurenol, ent-kaurenal, and/or ent-kaurenoic acid (Hedden and Kamiya, *Ann. Rev. Plant Physiol. Plant Mol. Biol.* 48: 431–460 (1997)). An isolated *Zea mays* cytochrome P-450 monooxygenase gene has been reported (Winkler and Helentjaris, *Plant Cell* 7: 1307–1317 (1995)). Hydroxylation of ent-kaurenoic acid at position seven via a 7-hydroxylase generates ent-7-hydroxy-kaurenoic acid. A critical branchpoint in the pathway occurs at ent-7-hydroxy-kaurenoic acid. One of the subsequent products, $GA_{12}$-aldehyde, is the first-formed GA in all systems. It is formed by contraction of the B ring of ent-7-hydroxy-kaurenoic acid with extrusion of carbon-7, catalyzed by $GA_{12}$-aldehyde synthase. In contrast, the other product, i.e., ent-6,7-dihydroxykaurenoic acid, cannot be converted to GAs, and has no known function in plants. Both $GA_{12}$-aldehyde and ent-6,7-dihydroxykaurenoic acid appear to be formed from a single common intermediate (Graebe (1987) *Ann. Rev. Plant Physiol.* 38:419–465).

Biosynthetic Steps From $GA_{12}$-aldehyde

The biosynthetic pathway up to $GA_{12}$-aldehyde appears to be the same in all plants. As the conversion of $GA_{12}$-aldehyde to other GAs can vary from genus to genus, several different pathways from $GA_{12}$-aldehyde exist. However, there is a basic sequence of reactions from $GA_{12}$-aldehyde common to all pathways (Hedden and Kamiya 1997. Annu. Rev. Plant Physiol. Plant Mol. Biol. 48:431–460.).

First, carbon-7 of $GA_{12}$-aldehyde is oxidized in a reaction catalyzed by a dioxygenase or monooxygenase having GA 7-oxidase activity, producing $GA_{12}$-dicarboxylic acid ($GA_{12}$). A C-7 carboxyl group appears to be an essential feature of all biologically active GAs.

Following the formation of the C-7 carboxyl group, carbon-20 is oxidized by a GA 20-oxidase (a 2-oxoglutarate-dependent dioxygenase) through successive intermediates with the eventual loss of $CO_2$ to produce the $C_{19}$ lactone and $C_{19}$-GAs. The C-20 methyl group is first oxidized to a hydroxymethyl (—$CH_2OH$) group. Upon extraction and work-up, this hydroxymethyl group lactonises to produce $GA_{15}$; the open-lactone (—$CH_2OH$) form is probably the true intermediate. Next, the open-lactone intermediate is oxidized to the C-20 aldehyde ($GA_{24}$). The $GA_{24}$ intermediate represents another branch-point in the pathway. Carbon-20 can be oxidized to the acid, producing $GA_{25}$, or this carbon can be eliminated from the molecule as $CO_2$, producing the $C_{19}$-GA lactone, $GA_9$. This step in GA biosynthesis is a reported regulatory point that is responsive to environmental and feedback regulation (Xu et al., *Proc. Natl. Acad. Sci. U.S.A.* 92: 6640–6644 (1995)). It is the $C_{19}$-GAs that usually exhibit direct biological activity. However, $C_{20}$-GAs, for example $GA_{12}$, $GA_{53}$, and ent-kaurene, can exhibit activity, presumably due to biological conversion to more active forms of gibberellins.

Genes encoding GA 20-oxidase have been isolated from several species, including pumpkin, *Arabidopsis*, and rice. Different members of the GA 20-oxidase multigene family have been reported to be developmentally and spatially regulated (Phillips et al., *Plant Physiol.* 108: 1049–1059 (1995)). Certain GA 20-oxidases (e.g., from pumpkin, *Marah*, and *Arabidopsis*) prefer non-hydroxylated substrates to the 13-hydroxylated analogues. In contrast, a GA 20-oxidase cloned from shoots of rice oxidizes $GA_{53}$, which has a C-13 hydroxyl group, more efficiently than it does $GA_2$, which lacks the hydroxyl function at this position (Toyomasu et al. (1997) *Physiol. Plant.* 99:111–118).

Functional groups can be introduced into the GA molecule at any stage during this sequence of reactions. The position and order of insertion of these substituents differs in different plant genera. For example, early in the gibberellin biosynthetic pathway ("early 13-hydroxylation pathway"; (Hedden and Kamiya 1997. Annu. Rev. Plant Physiol. Plant Mol. Biol. 48:431–460.)), prior to the C-20 oxidation sequence described above, $GA_{12}$ can by hydroxylated at C-13 by a 2-oxoglutarate-dependent GA 13-hydroxylase. Both dioxygenase and monooxygenase forms of this enzyme have been described, and the preferred substrate for the 13-hydroxylases appears to be $GA_{12}$, although other GAs are hydroxylated to some extent. While "late" 13-hydroxylation (Hedden and Kamiya 1997. Annu. Rev. Plant Physiol. Plant Mol. Biol. 48:431–460.) has been demonstrated in the pathway during the interconversion of bioactive, non-13-hydroxylated C-19 GAs to their 13-hydroxylated derivatives (e.g., $GA_9$ $GA_{20}$ and $GA_4$ $GA_1$), this may be inefficient, and accompanied by hydroxylation at other positions on the C and D rings. Both the 13-hydroxylation and non-13-hydroxylation pathways have been demonstrated in seeds as well as in vegetative tissues. 12-hydroxylases (both monooxygenases and dioxygenases) have also been described.

3-hydroxylation results in the conversion of the $C_{19}$-GAs $GA_{20}$ and $GA_9$ to $GA_1$ and $GA_4$, respectively, in the final step in the formation of physiologically active GAs. Pumpkin GA 3-hydroxylase has properties typical of a 2-oxoglutarate-dependent dioxygenase (Lange et al. (1994) *Planta* 195:98–107). Certain 3-hydroxylases can hydroxylate more than one GA species. 3-hydroxylase enzymes can also exhibit multifunctional capabilities, catalyzing additional reactions such as 2,3-desaturation and 2-hydroxylation of GAs (Smith et al., *Plant Physiol.* 94: 1390–1401(1990); Lange et al., *Plant Cell* 9: 1459–1467 (1997)).

Gibberellins can be rendered biologically inactive by several mechanisms. 2-hydroxylation has been reported to result in the formation of inactive products. Hydroxylation of bioactive GAs by the 2-oxidase renders them inactive, while hydroxylation of biosynthetic precursors creates non-preferable substrates for GA biosynthetic enzymes. Multiple enzymes with this activity may be present in a species (Smith and MacMillan, *Journal of Plant Growth Regulators* 2: 251–264 (1984); Thomas et al., 1999. *Proc. Natl. Acad. Sci.* 96:4698–4703). A bifunctional 2,3-hydroxylase gene has been isolated from pumpkin endosperm (Lange et al., *Plant Cell* 9: 1459–1467 (1997)).

Further catabolism of 2-hydroxylated GAs to form 2-keto derivatives occurs by additional oxidation steps that can be catalyzed by 2-oxoglutarate-dependent dioxygenases. Note, for example, the conversion of $GA_{29}$ to $GA_{29}$-catabolite in Hedden and Kamiya 1997. Annu. Rev. Plant Physiol. Plant Mol. Biol. 48:431–460. GAs may also be inactivated or sequestered in planta by conjugation to sugars to form gibberellin glucosides and glucosyl ethers (Schneider and Schmidt, *Plant Growth Substances*, ed. Pharis, et al., Springer-Verlag, Heidelberg, 300 (1988)).

GA compounds, precursors, and derivatives useful in rescuing GA-deficient, transgenic dwarf plants Biological activity varies among GAs, not all GAs having high biological activity. The GAs found within a plant can include bioactive compounds, as well as precursors and deactivation products of active GAs. Understanding GA biosynthetic and metabolic pathways, and the presence and role of different GAs during seed formation and seedling growth, facilitates identification of GA compounds, precursors, and derivatives (synthetic or naturally occurring) effective in stimulating hypocotyl or epicotyl elongation in GA-deficient plants. Useful compounds can be identified by studying their effect on single gene dwarf mutants, by applying chemical growth retardants that inhibit specific steps in GA biosynthesis, and, as specifically exemplified herein, by employing transgenic plants. The genome of such plants can contain antisense nucleic acid constructs that inhibit the synthesis of particular enzymes in the GA biosynthetic pathway, or that encode GA deactivating enzymes that interfere with GA activity in planta.

Rescue compounds of the present invention, however derived, preferably possess one or more of the following properties:

(1) That are not directly or intrinsically bioactive per se;
(2) That are not immediately bioactive, or that exhibit low bioactivity compared to GA compounds naturally occurring in the species or variety of plant to which they are applied;
(3) That are available for bioconversion in the appropriate tissue, e.g., the hypocotyl and/or epicotyl, and that can be converted to bioactive gibberellins in planta in the appropriate amount as needed by the seedling at or by the appropriate developmental stage;
(4) That are sufficiently stable in planta, in soil, and on plant surfaces to exert their rescue effect;
(5) That are translocatable within the seedling or plantlet;
(6) That exhibit selective bioactivity in specific tissue(s) (tissue specificity), such as the hypocotyl and/or epicotyl. This tissue-specific bioactivity can also be developmental stage-specific or intensive (temporal specificity);
(7) That are capable of rescuing GA-deficient plants without over-supplying bioactive gibberellins during the early stages of seedling emergence;
(8) That do not cause undesirable hypocotyl or epicotyl overelongation during seedling emergence;
(9) That exhibit lower bioactivity on normal plants than on GA-deficient plants, and that therefore do not cause undesirable overelongation of normal, non-GA-deficient plants;
(10) That are capable of restoring substantially normal growth, development, and morphology in GA-deficient plants without causing substantial abnormal growth, development, and morphology due to oversupply or activity of bioactive GAs;
(11) That do not cause increased hypocotyl fragility;
(12) That do not adversely affect seedling emergence;
(13) That do not adversely affect plant stand count or yield;
(14) That do not cause stem overelongation;
(15) That do not cause thinning of stem cell walls;
(16) That do not weaken stems;
(17) That do not promote insect and disease infestation; and
(18) That are cheaply produced.

Candidate compounds for rescue of GA-deficient transgenic or non-transgenic, wild-type soybeans or other plants include $C_{19}$ and $C_{20}$ gibberellins, including the presently known 121 naturally occurring gibberellins of plant or fungal origin. The structures of GAs 1-121 naturally occurring in plant and fungi are known in the art. In addition to these compounds, the biosynthetic precursors and intermediates shown in FIGS. 1 and 2 of Hedden and Kamiya (cited above), and the metabolic intermediates leading from these biosynthetic intermediates to final gibberellin end products in plants and fungi, are also candidate rescue compounds. Chemically synthesized GA compounds, and derivatives of any of the foregoing compounds produced by biological or chemical means, are also candidates for rescue compounds useful in the present invention. Preferred esters of carboxyl groups are methyl esters; preferred derivatives of hydroxyl groups are acetate derivatives. In addition, gibberellins can exist as conjugates, for example with a molecule of glucose, either by an ether or an ester linkage. Such conjugation may temporarily or permanently inactivate a GA. Preferred conjugates are those of sugars with hydroxyl and/or carboxyl groups. GA compounds, precursors, and derivatives temporarily inactivated by conjugation are also encompassed within the scope of the present invention as such conjugation may be effective to retard conjugate activity sufficiently for the purposes disclosed herein without eliminating bioactivity entirely.

Plant growth regulators and hormones include auxins, such as indoleacetic acid and 2,4-D; gibberellins; cytokinins, such as zeatin and benzyladenine; dormins, such as abscisic acid and xanthoxin; and alkenes such as ethylene and propylene. Auxins generally promote elongation of stems and stemlike organs of higher plants. Cytokinins generally stimulate cell division. Dormins generally inhibit growth, suppress shoot elongation, induce the formation of resting buds, and promote leaf abscission. Alkenes such as ethylene generally inhibit elongation of plant tissues, promote senescence, and promote fruit ripening. Auxins include, for example, centrophenoxine, p-chlorophenoxyacetic acid, chlorogenic acid, trans-cinnamic acid, 2,4-dichlorophenoxyacetic acid, indole-3-acetic acid, indole-3-acetic acid methyl ester, indole-3-acetyl-L-alanine, indole-3-acetyl-L-aspartic acid, indole-3-acetyl-L-phenylalanine, indole-3-acetylglycine, indole-3-butyric acid, indole-3-butyryl-p-alanine, indole-3-propionic acid, α-naphthaleneacetic acid, β-naphthoxyacetic acid, phenylacetic acid, picloram, 2,4,5-tricholorophenoxyacetic acid, and 2,3,5-triiodobenzoic acid. Cytokinins include, for example, adenine, adenine hemisulfate, 6-benzylaminopurine, 6-benzylaminopurine riboside, N-benzyl-9-(2-tetrahydropyranyl)adenine, N-(2-chloro-4-pyridyl-N'-phenylurea, DL-dihydrozeatin, 6-(γ,γ-dimethylallylamino)purine, 6-(γ,γ-dimethylallylamino)purine riboside, 1,3-diphenylurea, kinetin, kinetin riboside, 1-phenyl-3-(1,2,3-thiadiazol-5-yl)urea, zeatin, trans-zeatin O-β-D-glucopyranoside, and zeatin riboside.

It should be noted that combinations of any of the foregoing GA compounds and other plant hormones and growth regulators can be used as rescue compounds in the methods of the present invention. It should be further noted that the methods of the invention can be applied to transgenic plants containing traits of agronomic importance, e.g., insect resistance, herbicide resistance, virus resistance, fungal resistance, nematode resistance, disease resistance, modified nutrient profile, yield, etc.

Terms that may be used herein to describe substituents of GA compounds useful in the present invention are defined below.

The term "hydrido" denotes a single hydrogen atom (H). This hydrido radical may be attached, for example, to an oxygen atom to form a hydroxyl radical, or two hydrido radicals may be attached to a carbon atom to form a methylene radical.

Where used, either alone or within other terms such as "haloalkyl", "alkylsulfonyl", "alkoxyalkyl" and "hydroxyalkyl", "cyanoalkyl" and "mercaptoalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, allyl, propenyl, butenyl, and 4-methylbutenyl. The terms "alkenyl" and "lower alkenyl" embrace radicals having "cis" and "trans" orientations, or alternatively, "E" and "Z" orientations. The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about six carbon atoms. Examples of alkynyl radicals include propargyl, 1-propynyl, 2-propynyl, 1-butyne, 2-butenyl, and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl, and cyclohexyl. The term "cycloalkylalkylene" embraces alkyl radicals substituted with a cycloalkyl radical. More preferred cycloalkylalkylene radicals are "lower cycloalkylalkylene" which embrace lower alkyl radicals substituted with a lower cycloalkyl radical as defined above. Examples of such radicals include cyclopropylmethyl, cyclobutylmethyl, cyclopentylmethyl and cyclohexylmethyl. The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl, and cyclohexenyl.

The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl, and polyhaloalkyl radicals. A monohaloalkyl radical, for one example, may have either an iodo, bromo, chloro, or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl, and hydroxyhexyl.

The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy, and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro, or bromo, to provide haloalkoxy radicals.

The term "aryl", alone or in combination, means a carbocyclic aromatic system containing one, two, or three rings wherein such rings may be attached together in a pendent manner, or may be fused. The term "aryl" embraces aromatic radicals such as phenyl, naphthyl, tetrahydronaphthyl, indane, and biphenyl. Aryl moieties may also be substituted at a substitutable position with one or more substituents selected independently from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, hydroxy, alkoxyalkyl, carboxyalkyl, alkoxycarbonylalkyl, aminocarbonylalkylene, acyl, carboxy, and aralkoxycarbonyl.

The term "heterocyclyl" embraces saturated, partially unsaturated, and unsaturated heteroatom-containing ring-shaped radicals, which can also be called "heterocyclyl", "heterocycloalkenyl", and "heteroaryl" correspondingly, where the heteroatoms may be selected from nitrogen, sulfur, and oxygen. Examples of saturated heterocyclyl radicals include saturated 3 to 6-membered heteromonocyclic groups containing 1 to 4 nitrogen atoms (e.g., pyrrolidinyl, imidazolidinyl, piperidino, piperazinyl, etc.); saturated 3 to 6-membered heteromonocyclic groups containing 1 to 2 oxygen atoms and 1 to 3 nitrogen atoms (e.g., morpholinyl, etc.); saturated 3 to 6-membered heteromonocyclic groups containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran, and dihydrothiazole. Heterocyclyl radicals may include a pentavalent nitrogen, such as in tetrazolium and pyridinium radicals. The term "heteroaryl" embraces unsaturated heterocyclyl radicals. Examples of heteroaryl radicals include unsaturated 3 to 6-membered heteromonocyclic groups containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; unsaturated condensed heterocyclyl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic groups containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic groups containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl groups containing 1 to 2 oxygen atoms and 1 to 3 nitrogen atoms (e.g. benzoxazolyl, benzoxadiazolyl, etc.); unsaturated 3- to 6-membered heteromonocyclic groups containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl groups containing 1 to 2 sulfur atoms and 1 to 3 nitrogen atoms (e.g., benzothiazolyl, benzothiadiazolyl, etc.), and the like. The term "heterocycle" also embraces radicals where heterocyclyl radicals are fused with aryl or cycloalkyl radicals. Examples of such fused bicyclic radicals include benzofuran, benzothiophene, and the like. Said "heterocyclyl group" may have 1 to 3 substituents such as alkyl, hydroxyl, halo, alkoxy, oxo, amino, alkylthio, and alkylamino. The term "heterocyclylalkylene" embraces heterocyclyl-substituted alkyl radicals. More preferred heterocyclylalkylene radicals are "lower heterocyclylalkylene" radicals having one to six carbon atoms and a heterocyclyl radicals. The term "alkylthio" embraces radicals containing a linear or branched alkyl radical of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio, and hexylthio.

The term "alkylthioalkylene" embraces radicals containing an alkylthio radical attached through the divalent sulfur atom to an alkyl radical of one to about ten carbon atoms. More preferred alkylthioalkylene radicals are "lower alkylthioalkylene" radicals having alkyl radicals of one to six carbon atoms. Examples of such lower alkylthioalkylene radicals include methylthiomethyl.

The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl, and hexylsulfinyl.

The term "sulfonyl", whether used alone, or linked to other terms such as "alkylsulfonyl", "halosulfonyl", etc., denotes a divalent radical, —SO2-. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl, and propylsulfonyl. The "alkylsulfonyl" radicals may be further substituted with one or more halo atoms, such as fluoro, chloro, or bromo to provide haloalkylsulfonyl radicals. The term "halosulfonyl" embraces halo radicals attached to a sulfonyl radical. Examples of such halosulfonyl radicals include chlorosulfonyl, and bromosulfonyl. The terms "sulfamyl", "aminosulfonyl" and "sulfonamidyl" denote $NH_2O_2S$—.

The term "acyl" denotes a radical provided by the residue after removal of hydroxyl from an organic acid. Examples of such acyl radicals include alkanoyl and aroyl radicals. Examples of such alkanoyl radicals include formyl, acetyl, propionyl, butyryl, isobutyryl, valeryl, isovaleryl, pivaloyl, hexanoyl, and radicals formed from succinic, glycolic, gluconic, lactic, malic, tartaric, citric, ascorbic, glucuronic, maleic, fumaric, pyruvic, mandelic, pantothenic, -hydroxybutyric, galactaric, and galacturonic acids.

The term "carbonyl", whether used alone or with other terms, such as "alkoxycarbonyl", denotes —(C=O)—. The terms "carboxy" or "carboxyl", whether used alone or with other terms, such as "carboxyalkyl", denotes —CO2H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl, and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl portions having one to six carbons. Examples of such lower alkoxycarbonyl (ester) radicals include substituted or unsubstituted methoxycarbonyl, ethoxycarbonyl, propoxycarbonyl, butoxycarbonyl, and hexyloxycarbonyl. The term "alkoxycarbonylalkyl" embraces alkyl radicals substituted with a alkoxycarbonyl radical as defined above. More preferred are "lower alkoxycarbonylalkyl" radicals with alkyl portions having one to six carbons. Examples of such lower alkoxycarbonylalkyl radicals include substituted or unsubstituted methoxycarbonylmethyl, ethoxycarbonylmethyl, methoxycarbonylethyl, and ethoxycarbonylethyl. The term "alkylcarbonyl", includes radicals having alkyl radicals, as defined herein, attached to a carbonyl radical. Examples of such radicals include substituted or unsubstituted methylcarbonyl, ethylcarbonyl, propylcarbonyl, butylcarbonyl, pentylcarbonyl, hydroxymethylcarbonyl, and hydroxyethylcarbonyl.

The term "aralkyl" embraces aryl-substituted alkyl radicals such as benzyl, diphenylmethyl, triphenylmethyl, phenylethyl, and diphenylethyl. The aryl in said aralkyl may be additionally substituted with one or more substituents selected independently from halo, alkyl, alkoxy, halkoalkyl, haloalkoxy, amino, and nitro. The terms benzyl and phenylmethyl are interchangeable.

The term "heterocyclylalkylene" embraces saturated and partially unsaturated heterocyclyl-substituted alkyl radicals (which can also be called heterocycloalkylalkylene and heterocycloalkenylalkylene, correspondingly), such as pyrrolidinylmethyl, and heteroaryl-substituted alkyl radicals (which can also be called heteroarylalkylene), such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl, and haloalkoxy.

The term "aryloxy" embraces aryl radicals attached through an oxygen atom to other radicals. The term "aralkoxy" embraces aralkyl radicals attached through an oxygen atom to other radicals.

The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which are substituted with one or two alkyl radicals. Preferred are "lower alkylamino" radicals having alkyl portions having one to six carbon atoms. Suitable lower alkylamino groups may be monosubstituted N-alkylamino or disubstituted N,N-alkylamino, such as N-methylamino, N-ethylamino, N,N-dimethylamino, N,N-diethylamino, or the like. The term "arylamino" denotes amino groups which are substituted with one or two aryl radicals, such as N-phenylamino. The "arylamino" radicals may be further substituted on the aryl ring portion of the radical. The term "aminocarbonyl" denotes an amide group of the formula —C(=O)NH2. The term "alkylaminocarbonyl" denotes an aminocarbonyl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl" and "lower N,N-dialkylaminocarbonyl" radicals with lower alkyl portions as defined above. The term "alkylcarbonylamino" embraces amino groups which are substituted with one alkylcarbonyl radicals. More preferred alkylcarbonylamino radicals are "lower alkylcarbonylamino" having lower alkylcarbonyl radicals as defined above attached to amino radicals. The term "alkylaminoalkylene" embraces radicals having one or more alkyl radicals attached to an aminoalkyl radical.

The "hydrocarbon" moieties described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl, and alkynaryl. Preferably, these moieties comprise 1 to 20 carbon atoms.

The heterosubstituted hydrocarbon moieties described herein are hydrocarbon moieties which are substituted with at least one atom other than carbon, including moieties in which a carbon chain atom is substituted with a hetero atom such as nitrogen, oxygen, sulfur, or a halogen atom. These substituents include lower alkoxy, such as methoxy, ethoxy, and butoxy; halogen, such as chloro or fluoro; ethers; acetals; ketals; esters; heterocyclyl such as furyl or thienyl; alkanoxy; hydroxy; protected hydroxy; acyl; acyloxy; nitro; cyano; amino; and amido.

The additional terms used to describe substituents of the ent-gibberellane ring system which are not specifically defined herein are defined in a manner similar to that illustrated in the foregoing definitions. As above, more preferred substituents are those containing "lower" radicals. Unless otherwise defined to contrary, the term "lower" as used herein means that each alkyl radical of an ent-gibberellane ring system substituent comprising one or more alkyl radicals has one to about six carbon atoms; each alkenyl radical of an ent-gibberellane ring system substituent comprising one or more alkenyl radicals has two to about six carbon atoms; each alkynyl radical of an ent-gibberellane ring system substituent comprising one or more alkynyl radicals has two to about six carbon atoms; each cycloalkyl or cycloalkenyl radical of an ent-gibberellane ring system substituent comprising one or more cycloalkyl and/or cycloalkenyl radicals is a 3 to 8 membered ring cycloalkyl or cycloalkenyl radical, respectively; each aryl radical of an ent-gibberellane ring system substituent comprising one or more aryl radicals is a monocyclic aryl radical; and each heterocyclyl radical of an ent-gibberellane ring system substituent comprising one or more heterocyclyl radicals is a 4–8 membered ring heterocyclyl.

The present invention also comprises compounds as disclosed herein having one or more asymmetric carbons. It is known to those skilled in the art that those GAs of the present invention having asymmetric carbon atoms may exist in diastereomeric, racemic, or optically active forms. All of these forms are contemplated within the scope of this invention. More specifically, the present invention includes all tautomers, enantiomers, diastereomers, racemic mixtures, and other mixtures thereof.

Derivatives of GA compounds useful in the present invention include structures based on various GA ring structures as follows:

Structure 1

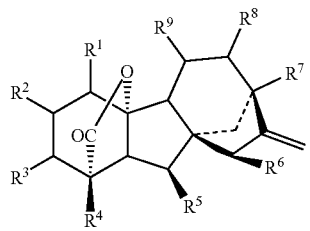

wherein $R^1$, $R^2$, $R^3$, $R^6$, $R^7$, $R^8$, and $R^9$ are each independently selected from hydrido, hydroxy, "protected" hydroxy, hydrido isotopes, alkyl, alkoxy, alkenyl, alkynyl, halo, thio, alkylthio, amino, and alkylamino;

$R^4$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^5$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

Structure 2

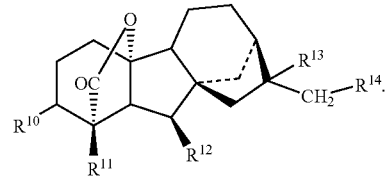

wherein $R^{10}$, $R^{13}$, and $R^{14}$ are each independently selected from hydrido, hydroxy, "protected" hydrido isotopes, alkyl, alkoxy, alkenyl, alkynyl, halo, thio, alkylthio, amino, and alkylamino;

$R^{11}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{12}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

Structure 3

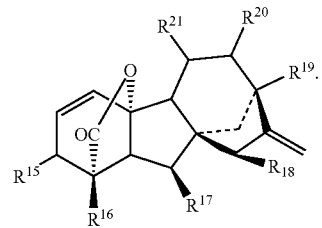

wherein $R^{15}$, $R^{18}$, $R^{19}$, $R^{20}$, and $R^{21}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{16}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{17}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

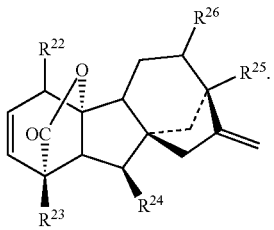

Structure 4 wherein $R^{22}$, $R^{25}$, and $R^{26}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{23}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{24}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

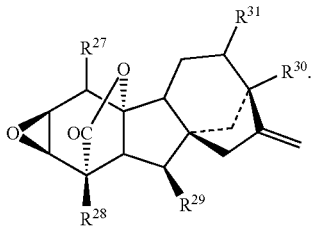

Structure 5 wherein $R^{27}$, $R^{30}$, and $R^{31}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{28}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{29}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

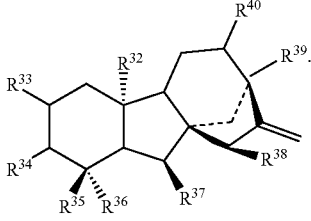

Structure 6 wherein $R^{33}$, $R^{34}$, $R^{38}$, $R^{39}$, and $R^{40}$ are each independently selected from hydrido, hydroxy, "protected" hydroxy, hydrido isotopes, alkyl, alkoxy, alkenyl, alkynyl, halo, thio, alkylthio, amino, and alkylamino;

$R_{32}$ and $R_{35}$ are each independently selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{36}$ and $R^{37}$ are each independently selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

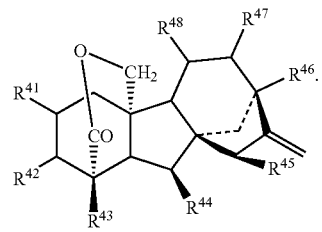

Structure 7 wherein $R^{41}$, $R^{42}$, $R^{45}$, $R^{46}$, $R^{47}$, and $R^{48}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{43}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{44}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

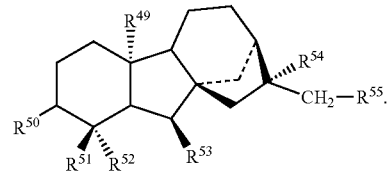

Structure 8 wherein $R^{50}$, $R^{54}$, and $R^{55}$ are each independently selected from hydrido, hydroxy, "protected" hydroxy; hydrido isotopes, alkyl, alkoxy, alkenyl, alkynyl, halo, thio, alkylthio, amino, and alkylamino;

$R^{49}$ and $R^{51}$ are each independently selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{52}$ and $R^{53}$ are each independently selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

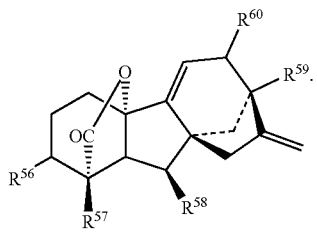

Structure 9 wherein $R^{56}$, $R^{59}$, and $R^{60}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{57}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{58}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

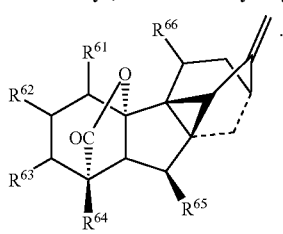

Structure 10 wherein $R^{61}$, $R^{62}$, $R^{63}$, and $R^{66}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{64}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{65}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

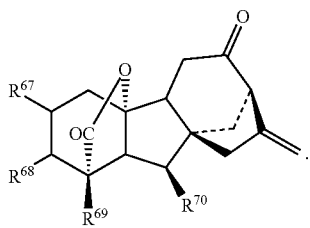

Structure 11 wherein $R^{67}$ are $R^{68}$ are each independently selected from hydrido, hydroxy, "protected" hydroxy, hydrido isotopes, alkyl, alkoxy, alkenyl, alkynyl, halo, thio, alkylthio, amino, and alkylamino;

$R^{69}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{70}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

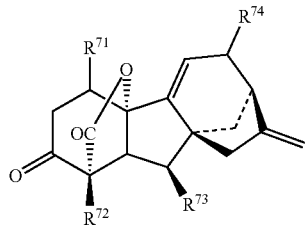

Structure 12 wherein $R^{71}$ and $R^{74}$ are each independently selected from hydrido, hydroxy, "protected" hydroxy, hydrido isotopes, alkyl, alkoxy, alkenyl, alkynyl, halo, thio, alkylthio, amino, and alkylamino; and $R^{72}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{73}$ is selected from carboxylate, "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

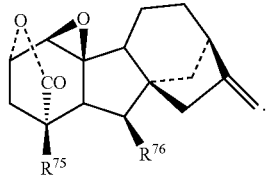

Structure 13 wherein $R^{75}$ is selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{76}$ is selected from carboxylate; "protected" carboxylate, alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

Structure 14

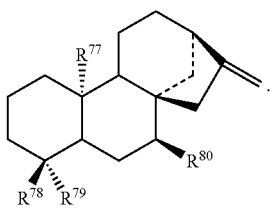

wherein $R^{80}$ is selected from hydrido, hydroxy, "protected" hydroxy, hydrido isotopes, alkyl, alkoxy, alkenyl, alkynyl, halo, thio, alkylthio, amino, and alkylamino;

$R^{77}$ and $R^{78}$ are each independently selected from alkyl, e.g., methyl, alkenyl, alkynyl, hydroxyalkyl, alkoxyalkyl, cyano, cyanoalkyl, aminoalkyl, aminocarbonyl, alkanoyl, carboxy, carboxyalkyl, and alkoxycarbonyl; and $R^{79}$ is selected from alkyl, hydroxyalkyl, alkoxyalkyl, haloalkyl, haloalkoxy, cyano, cyanoalkyl, aminoalkyl, aminocarbonyl, alkanoyl, sulfonyl, alkylsulfonyl, halosulfonyl, alkylsulfinyl, phosphonyl, phosphinyl, alkylphosphinyl, hydroxamyl, tetrazolyl, acylhydroxamino, alkylthioalkylene, arylthioalkylene, carboxy, carboxyalkyl, alkoxycarbonyl, heterocycle-substituted acyl, and aralkoxyalkyl.

Protecting Groups for Hydroxy: hydroxy groups can be protected by forming the corresponding ethers. Some examples of protecting groups include methyl, substituted methyl, substituted ethyl, substituted benzyl, and silyl groups.

Protecting Groups for Carboxylates (carboxylic acids): carboxylic acids can be protected by forming the corresponding esters. Some examples of protecting groups include methyl, phenyl, silyl, 9-fluorenylmethyl (Fm), methoxymethyl (MOM), methylthiomethyl (MTM), tetrahydrofuranyl, and methoxyethoxymethyl (MEM). Other methods to protect carboxylic acids include the formation of derivatives. Examples of derivatives include oxazoles, 2-alkyl-1, 3-oxazolines, and 4-alkyl-5-oxo-1,3-oxazolidine as well as sulfonates.

Methods for preparing gibberellin derivatives are well known in the art. Note for example: Takahashi et al. (1983) in A. Crozier, ed., Biochem. Physiol. Gibberellins, Praeger, N.Y., p. 457; Pour et al. (1998) Pure & Appl. Chem. 70:351–354; Cross et al. (1968) Tetrahedron 24:231–237; Ali et al. (1997) Z. Naturforsch., B: Chem. Sci. 52:1143–1146; Mander et al. (1997) Tetrahedron 53:2137–2162; Owen et al. (1996) Phytochemistry 42:921–925; Mander et al. (1996) Aust. J. Chem. 49:249–253; Penny et al. (1993) J. Chem. Soc., Perkin Trans. 1:541–545; Furber et al. (1992) Acta Crystallogr., Sect. C: Cryst. Struct. Commun. C48(7):1348–50; C L Willis (1990) Tetrahedron Lett. 31:6437–40.

Effective Ranges of GA Compounds for Rescuing Dwarf Plants

GA-deficient phenotypes in plants can be rescued or reversed by the exogenous application of GA compounds as described herein to seeds, seedlings, plantlets, and plants by a variety of methods, including seed coatings and other conventional seed treatments, seed imbibition, hilum treatment, soil drenches, and foliar sprays. The effective dose of the GA compound will depend on many factors, including:
the severity of the GA-deficiency;
the target tissue that is GA-deficient;
the length of time post-germination that the tissue(s) is GA-deficient;
the biotechnology method by which GA-deficiency is introduced to plants;
the environmental conditions of plant growth;
the chemical properties of the GA compound, stability and translocation;
the bioactivity of the GA compound;
the method of application of the GA compound;
the formulation of the GA compound; and
the type of plant.

For example, in side-by-side comparisons using soybean, the same dose of $GA_3$ gives substantial differences in hypocotyl elongation depending on the method of application. The relative sensitivity can be: soil drench>hilum treatment>seed imbibition). Also, the dose of $GA_3$, applied as a soil drench, that is needed to fully restore normal seedling height in ancymidol-treated soybean increases with time after planting ($10^{-7}$M at 4 DAP; greater than $10^{-5}$ M at 11 DAP).

For the application of GA compounds as a seed treatment, levels ranging between about 1 ng/seed to about 1 mg/seed would provide an effective dose to restore normal growth and development to GA-deficient plants. A more preferred effective dose is in the range between about 10 ng/seed to about 750 mg/seed. A more preferred dose is in the range between about 50 ng/seed to about 500 mg/seed. An even more preferred dose is in the range between about 75 ng/seed to about 250 mg/seed. An even more preferred dose is in the range between about 0.1 mg/seed to about 100 mg/seed. An even more preferred dose is in the range between about 0.1 mg/seed to about 50 mg/seed. An even more preferred dose is in the range between about 0.1 mg/seed to about 10 mg/seed.

For the application of GA compounds as a soil drench or foliar spray, levels ranging between about $10^{-8}$ M and $10^{-2}$ M would provide an effective dose to restore normal growth and development to GA-deficient seedlings or plants. A more preferred effective dose is in the range between about $10^{-7}$ M and about $10^{-3}$ M. An even more preferred effective dose of a GA compound in a soil drench or foliar spray is in the range between about $10^{-6}$ and about $10^{-4}$ M.

Soil drenches can be applied before planting seeds, or within 2 to 3 weeks post planting, or anytime during plant growth. Foliar applications can be made anytime after germination and during subsequent plant growth.

Formulations Comprising GA Compounds

The GA compounds of the present invention can be formulated and applied to seeds, germinating seeds, seedlings, soil, roots, stems, cotyledons, leaves, etc., by any conventional method, including but not limited to: (1) application as a seed treatment; (2) direct injection into the soil around seeds or in the root zone of developing plants, for example, at a point 2 cm deep and within a 3 cm radius of the plant crown; (3) application as a soil drench or irrigation water; and (4) application as a foliar spray, aerosol, or fumigant. In these formulations, the GA compound(s) may comprise the sole active agent, or the compound(s) can be mixed with other agrichemicals such as fungicides, insecticides, herbicides, and other plant growth regulators.

For these purposes, the GA compound formulations can be prepared in any of the relevant forms conventional in the art including, but not limited to: solid formulations, such as powders or dusts, water dispersible powders, water soluble powders, compositions for seed pelleting or seed coating, water dispersible granules (dry flowable), and impregnated granules; and liquid formulations, such as solutions, suspensions, slurries, flowable concentrates, emulsifiable concentrates, and emulsions. These liquid formulations can be prepared in an aqueous medium (e.g., water), an organic medium (e.g., ethanol or acetone), an inorganic medium, or mixtures thereof (e.g., water/ethanol or water/acetone), at a concentration of active ingredient of from about 0.5% to about 99% by weight, preferably from about 5 to about 50% by weight, based on the weight of the total liquid formulation.

Conventional biologically inactive or inert ingredients can be incorporated along with the GA compounds or in media used for producing the formulations of the present invention. Such inert ingredients include, but are not limited to: conventional sticking agents; dispersing agents, such as methylcellulose (Methocel™ A15LV or Methocel™ A15C, for example, serve as combined dispersant/sticking agents for use in seed treatments); polyvinyl alcohol (e.g., Elvanol 51-05); lecithin (e.g., Yelkinol P); polymeric dispersants (e.g., polyvinylpyrrolidone/vinyl acetate PVP/VA S-630); carriers and thickeners (e.g., clay thickeners such as Van Gel B to improve viscosity and reduce settling of particle suspensions); emulsion stabilizers; wetting agents and surfactants; antifreeze compounds (e.g., urea); dyes; colorants; and the like. Further inert ingredients useful in the formulations of the present invention can be found in McCutcheon's, Vol. 1, "Emulsifiers and Detergents," MC Publishing Company, Glen Rock, N.J., U.S.A., 1996. Additional inert ingredients useful in the formulations of the present invention can be found in McCutcheon's, Vol. 2, "Functional Materials," MC Publishing Company, Glen Rock, N.J., U.S.A., 1996.

More particularly, GA compound formulations useful in the present invention include the following:

Seed Treatments

Formulations conventionally used for seed treatment are usually either solid or liquid, and can be of the following types:

A. Solid Formulations

1. Powders for dry-seed treatment, i.e., a powder for application in the dry state directly to the seed. These are sometimes referred to as "dusts."

2. Water dispersible powders for slurry seed treatment. Such powders are usually dispersed at high concentration in water before application as a slurry to the seed. These are also called "wettable powders." While the content of water dispersible powders can vary widely due to the active ingredient, application rate, etc., they generally contain components such as wetting agents, dispersing agents, stabilizers, compatibility agents, antifoams, stickers, fillers, etc., in addition to the active ingredient.

3. Water soluble powders for seed treatment. Such powders are usually dissolved in water before application to the seed. This normally gives a clear solution of the active ingredient in water.

4. Pelleted or coated seed. In this case, the seed is embedded in a pellet, or coated in some manner to produce a treated seed.

B. Liquid Formulations

1. Flowable concentrates for seed treatment. These are stable suspensions for application to the seed either directly, or after dilution. These are also called "suspension concentrates." These types of formulations can contain high concentrations of insoluble or poorly soluble solid active ingredients dispersed in water, and usually contain wetting agents, dispersing agents, antifreezes, antifoams, thickeners, and water in addition to active ingredients. Dispersing agents permit a relatively uniform or homogeneous mixture to form. The dispersing agent preferably also provides a degree of "tackiness" or adhesion to the formulation in order for the formulation to adhere to treated seeds or other plant surfaces, such as roots, hypocotyls, epicotyls, cotyledons, leaves, etc. Suitable dispersing agents include, but are not limited to, aqueous 0.25–1.0% poly(vinyl alcohol), such as Elvanol 51-05 (DuPont) and Methocel™ A15LV.

2. Solutions for application to the seed either directly, or after dilution. Such solutions contain active ingredients in, for example, water or polar solvents miscible in water. This is the simplest and cheapest type of formulation, and can contain an active ingredient(s), a surfactant, a buffer or sequestrant, water, and a polar solvent(s). The pH can be adjusted so as to avoid solubility problems with water soluble active ingredients in the form of salts having a pH-dependent solubility. Sequestrants can be used to avoid flocculation due to salt concentration in dilution water.

3. Emulsifiable concentrates. These are liquid, homogeneous formulations applied as emulsions after dilution in water. Emulsifiable concentrates can contain active ingredients, solvents and cosolvents, emulsifiers, stabilizers, stickers, antifoams, etc.

4. Oil in water emulsions. In these emulsions, the continuous phase is water, with the oil dispersed in the water. In addition to the active ingredient, such emulsions can contain emulsifiers, antifreezes, defoamers, thickeners, biocides, and water.

In addition to the foregoing, any conventional active or inert material can be used for coating seeds with GA compounds according to the present invention, such as conventional film-coating materials including, but not limited to, water-based film coating materials such as Sepiret (Seppic, Inc., Fairfield, N.J.) and Opacoat (Berwind Pharm. Services, Westpoint, Pa.).

Examples of the preparation of these and other types of formulations are described in the literature, for example in U.S. Pat. No. 3,989,501. The GA compound formulations according to the present invention can be applied to seeds by any standard seed treatment methodology, including but not limited to, mixing in a container (e.g., a bottle or bag), mechanical application, tumbling, spraying, or immersion. Combinations of these methods can also be employed. An important consideration in the preparation of seed treatment formulations is that the ingredients be non-phytotoxic to the seed. In addition, colorants are normally added for identification purposes to protect from the direct use of treated seed in human or animal food products. Sticking agents are also commonly used to keep the formulation on the seed during handling, shipping, etc.

One embodiment of the present invention provides a GA compound composition comprising a GA compound in a polymer matrix, and an agricultural adjuvant. The composition can take a variety of forms, including a liquid suspension, a wettable powder, a granule, a water-dispersible granule, a suspension concentrate, or the like. Preferably, the GA compound composition comprises a dispersant. The composition can also comprise an adjuvant. The GA compound composition can also comprise a diluent. The diluent can be either a solid or a liquid diluent. Solid diluents can include, for example, silica, alumina, cellulose, methylcellulose, clay, or a polymer. Liquid diluents can include, for example, water, an organic solvent, or an inorganic solvent.

In addition to GA compound formulations, the present invention also encompasses processes for coating one or more GA compounds onto a seed of a plant, comprising depositing on the seed a composition comprising the GA compound(s). The GA compounds and plants useful in this embodiment are as described above. The GA compound can be used neat (that is, without adjuvants), or it can be applied in a formulated form comprising one or more adjuvants. The coating process can comprise, for example, spraying, dipping, misting, precipitation, coacervation, dusting, tumbling, granulation, or any other method which allows the GA compound to be deposited on the surface of the seed. The coating process can be used alone or in combination with other seed treating processes, such as imbibing.

Seeds can be coated using a variety of methods including imbibition, solid matrix priming, coating, spraying and dusting. Seed treatments can take a variety of forms, including suspension concentrates, solutions, emulsions, powders, granules, as well as using polymeric carriers or stickers. For example, the coating process can comprise spraying a composition comprising the GA compound(s) onto the seed while agitating the seed in an appropriate apparatus, such as a tumbler or a pan granulator.

In one embodiment, when coating seed on a large scale (for example a commercial scale), seed is typically introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the GA compound in the treatment composition, the desired concentration on the finished seed, and the like. The treatment composition can be applied to the seed by a variety of means, for example by a spray nozzle or revolving disc. The amount of liquid is typically determined by assay of the formulation and the required rate of active ingredient necessary for efficacy. As the seed falls into the treatment equipment, the seed can be treated (for example by misting or spraying with the seed treatment composition) and passed through the treater under continual movement/tumbling, where it can be coated evenly and dried before storage or use.

In another embodiment, a known weight of seed can be introduced into the treatment equipment (such as a tumbler, a mixer, or a pan granulator). A known volume of seed treatment composition can be introduced into the treatment equipment at a rate that allows the seed treatment composition to be applied evenly over the seed. During the application, the seed can be mixed, for example by spinning or tumbling. The seed can optionally be dried or partially dried during the tumbling operation. After complete coating, the treated sample can be removed to an area for further drying or additional processing, use, or storage.

In still another embodiment, seeds can be coated in laboratory size commercial treatment equipment such as a tumbler, a mixer, or a pan granulator by introducing a known weight of seeds into the treater, adding the desired amount of seed treatment composition, tumbling or spinning the seeds, and placing them on a tray to dry.

In another embodiment, seeds can also be coated by placing a known amount of seed into a narrow neck bottle or receptacle with a lid. While tumbling, the desired amount of seed treatment composition can be added to the receptacle. The seed is tumbled until it is coated with the seed treatment composition. After coating, the seed can optionally be dried, for example on a tray.

In yet another embodiment of the present invention, a GA compound can be introduced onto or into a seed by use of solid matrix priming. For example, a quantity of the GA compound can be mixed with a solid matrix material, and then the seed can be placed into contact with the solid matrix material for a period to allow the GA compound to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the GA compound for a time and releasing that compound into or onto the seed. The GA compound and the solid matrix material should be compatible with one another. For example, the solid matrix material should be chosen so that it can release the GA compound at a reasonable rate, for example over a period of minutes, hours, or days, as desired or required.

The present invention further embodies imbibition as another method of treating seed with GA compounds. For example, plant seed can be combined for a period of time with an aqueous, organic, inorganic, or mixed solvent solution comprising from about 1% by weight to about 75% by weight of the GA compound, preferably from about 5% by weight to about 50% by weight, more preferably from about 10% by weight to about 25% by weight. During the period that the seed is combined with the solution, the seed takes up (imbibes) a portion of the GA compound present in the solution. Optionally, the mixture of plant seed and solution can be agitated, for example by shaking, rolling, tumbling, or other means. After imbibition, the seed can be separated from the solution and optionally dried, for example by patting or air drying.

In yet another embodiment, a powdered GA compound can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered GA compound. The mixture can be agitated, for example by tumbling, to encourage contact of the sticking agent with the powdered GA compound, thereby causing the powdered GA compound to stick to the seed.

The present invention also encompasses a composition, comprising a seed having a surface, and a layer of one or more GA compounds deposited on the seed surface. The GA compound layer can comprise at least one GA compound and, for example, a sticking agent or coating aid. The amount or concentration of GA compound in the GA compound layer preferably comprises an amount or concentration effective to overcome any GA-deficiency in the seed or developing seedling, and/or to restore normal seedling and/or plant morphology to what would be an otherwise dwarf, GA-deficient seedling or plant. The sticking agent can be useful as an aid in sticking the GA compound to the surface of the seed. An example of a sticking agent is polyethylene glycol. The coating aid can be useful in aiding the coating ofl a layer onto the surface of the seed. An example of a useful coating agent is gelatin.

In another embodiment, the present invention provides a composition, comprising a GA compound and a sticking agent or other agent as discussed herein. Such a composition is useful for applying the GA compound to seed. Useful GA compounds in this embodiment include without limitation those disclosed herein. The amount or concentration of GA compound in the composition preferably comprises an amount or concentration effective to overcome any GA-deficiency in the seed or developing seedling, and/or to restore normal seedling and/or plant morphology to what would be an otherwise dwarf, GA-deficient seedling or plant. The sticking agent can be any material which aids in the adherence of the GA compound to the seed surface. Useful sticking agents include polyethylene glycol, gelatin, agar, polyvinyl alcohol, methyl cellulose, an alginate, a poly(vinylpyrrolidone) copolymer, a wax (such as a microcrystalline wax, beeswax, oxidized microcrystalline wax, an alkyl palmitate, carrageenan, paraffin, and the like), a lignosulfonate, a xanthan gum, mineral oil, a C9–C25 fatty acid or a salt thereof, a C9–C25 alcohol, a C9–C25 amine, lanolin, a polyglyceride, polyethylene, substituted polyethylene, ethylene bis(stearamide), a silicone oil, an ethoxylated alcohol, an ethoxylated alkylamine, an alkylpolyglucoside, and the like. A preferred sticking agent is polyethylene glycol. Polyethylene glycol useful in the present invention can have a molecular weight in the range of about 1,000 daltons to about 10,000 daltons, preferably about 2,000 daltons to about 8,000 daltons, more preferably about 2,500 daltons to about 6,000 daltons, and still more preferably about 3,000 daltons to about 4,500 daltons.

Alternatively, the composition of the present invention can comprise a GA compound and a coating agent. A useful coating agent is any material which aids in the coating of the GA compound onto the surface of the seed. Useful coating agents include gelatin, a wax, polyethylene, polyethylene glycol, polypropylene, polypropylene glycol, or the like. A preferred coating agent is gelatin.

Additional formulating aids can also be present in the seed treatment compositions of the present invention. Such formulating aids include, but are not limited to, an absorbent, an adsorbent, an anticaking agent, an antioxidant, a binder, a carrier, a chelating or sequestering agent, a colorant, a dispersant, a flocculant, a humectant, a lubricant, a plasticizer, a preservative, a release agent, a solubilizer, a solvent, a suspending agent, a thickener, a water repellent, or the like.

Foliar Sprays

The GA compounds of the present invention can also be formulated for use as foliar sprays. For this purpose, compositions containing one or more GA compounds can comprise a solvent, a carrier, and one or more surfactants, wetting agents, or emulsifiers.

The solvent can comprise water, an organic solvent, an inorganic solvent, and mixtures thereof. The organic solvent can be acetone, ethanol, or any other organic solvent in which GA compounds are known to be soluble. The organic solvent can also be an aromatic solvent. Useful aromatic solvents include benzene, toluene, o-xylene, m-xylene, p-xylene, mesitylene, naphthalene, bis(a-methylbenzyl)xylene, phenylxylylethane, and combinations thereof. Other useful solvents include substituted aromatic solvents such as chlorobenzene or ortho-dichlorobenzene. Alternatively, the solvent can comprise an aliphatic solvent such as paraffin oil. As another alternative, the solvent can comprise a phosphate solvent, preferably a triaryl phosphate or an alkyldiaryl phosphate. Particularly useful phosphate solvents include trixylenyl phosphate and 2-ethylhexyl diphenyl phosphate. Combinations of aromatic, aliphatic and phosphate solvents can also be successfully used in the present invention. Other solvents which can be used successfully in the present invention include N-methylpyrrolidone, dimethylformamide, polyvinylpyrrolidone, 4-butyrolactone, and fatty acid esters.

The carrier can be an inorganic or organic carrier. Examples of useful inorganic carriers include clay (such as bentonite, montmorillonite, or attapulgite), silica, alumina, ammonium sulfate, and diatomaceous earth. Examples of useful organic carriers include cellulose, polyethylene glycol, paraffins, and fatty acid esters such as methyl oleate or tridecyl stearate.

Surfactants, wetting agents, or emulsifiers useful in the foliar sprays of the present invention include, without limitation, an ethoxylated alkyl amine, an ethoxylated alkyl polyamine, an alkylpolyglucoside, an alkoxylated acetylenic diol, a polyoxyalkylene alkyl ether, an organosilicone, an ethoxylated alcohol, an ethoxylated Guerbet alcohol, an alkylphenol ethoxylate, a sulfated polyoxyalkylene alkylphenol, an alcohol sulfate, a polyoxyalkylene alcohol sulfate, a monoalcoholphosphate, a dialcoholphosphate, a mono(polyoxyalkylene alcohol)phosphate, a di(polyoxyalkylene alcohol)phosphate, a mono(polyoxyalkylene alkylphenol)phosphate, a di(polyoxyalkylene alkylphenol)phosphate, a polyoxyalkylene alkylphenol carboxylate, a polyoxyalkylene alcohol carboxylate, a fluorinated surfactant, an N-alkoxylated alkylpolyalkoxy amine surfactant (i.e., an etheramine surfactant), an alkylsulfonate, an alkylphenylsulfonate, an alkylsulfate, an alkylphenolsulfate, an alkyl betaine surfactant, an alkyl carboxylate (including fatty acids and fatty acid salts such as pelargonic acid), an ethoxylated alkylamide, a quaternary alkylamine, and combinations thereof. Preferred surfactants include an ethoxylated alkyl amine, an ethoxylated alkyl polyamine, an alkylpolyglucoside, a polyoxyalkylene alkyl ether an ethoxylated alcohol, an ethoxylated Guerbet alcohol, a monoalcoholphosphate, a dialcoholphosphate, a mono(polyoxyalkylene alcohol)phosphate, a di(polyoxyalkylene alcohol)phosphate, a mono(polyoxyalkylene alkylphenol)phosphate, a di(polyoxyalkylene alkylphenol)phosphate, an etheramine surfactant, an alkyl betaine surfactant, a quaternary alkylamine, and combinations thereof. Still more preferred surfactants include an ethoxylated alkyl amine surfactant, an alkylpolyglucoside surfactant, an etheramine surfactant, a quaternary alkylamine surfactant, and combinations thereof. Ethoxylated alkyl amine surfactants such as a tallowamine ethoxylate are particularly preferred. Alkoxylated acetylenic diol surfactants and polyoxyalkylene alkyl ether surfactants are also preferred in the foliar spray compositions of the present invention. Preferred alkoxylated acetylenic diols include polyethoxylated acetylenic diols, more preferably polyethoxylated tetramethyldecynediol, and still more preferably PEG-10 tetramethyldecynediol. PEG-10 tetramethyldecynediol is commercially available under the trade name Surfynol 465, available from Air Products and Chemicals, Inc. (Allentown, Pa., U.S.A.). Preferred polyoxyalkylene alkyl ethers include polyethoxyethylene-polyoxypropylene alkyl ethers, more preferably a polyethoxyethylene-polyoxypropylene-2-ethylhexyl ether such as Epan U-108 available from Dai-ichi Kogyo Seiyaku Co., Ltd. (Tokyo, Japan) or Newkalgen 4016EHB available from Takemoto Oil and Fat Co., Ltd. (Aichi, Japan). Typically the polyethoxyethylenepolyoxypropylene-2-ethylhexyl ether surfactant comprises about 5 to about 30, preferably about 10 to about 25, and more preferably about 10 to about 20 moles of ethylene oxide per mole of surfactant. Also, the polyethoxyethylenepoly-oxypropylene-2-ethylhexyl ether surfactant comprises about 5 to about 30, preferably about 10 to about 25, and more preferably about 10 to about 20 moles of propylene oxide per mole of surfactant. A particularly preferred polyethoxyethylenepolyoxypropylene-2-ethylhexyl ether surfactant comprises about 15 moles of ethylene oxide and about 15 moles of propylene oxide per mole of surfactant.

Formulations for Soil Application

Formulations for soil drenches/irrigation water can be the same as those used for foliar applications. While foliar sprays generally contain surfactants or wetting agents, drift reduction agents (if applied via airplane), and a carrier(s) in addition to active ingredients, the use of surfactants and wetting agents in soil drenches is not required. Therefore, the amount of surfactants and wetting agents can be reduced in soil drenches, or these components can be eliminated entirely. It should be noted that formulations for foliar application can be simultaneously applied to the soil.

Antisense Gene Regulation

Regulation of endogenous gene expression in plants is achievable by expression of an antisense gene (U.S. Pat. No. 5,107,065). An antisense gene is a complete (full length) coding sequence of the gene or a fragment thereof. An antisense gene may also be to a nontranslated portion of an endogenous plant gene, such as a 5' nontranslated leader region or a 3' untranslated terminator or polyadenylation region of the gene as it exists in plants. Expression of a transgenic antisense sequence allows for the regulation of the specific endogenous plant genes. This technology involves an antisense RNA introduced into the cell (via a strong promoter driving the antisense sequence or portion of a gene. The plant expression vector would contain the appropriate leader, termination, and processing signals for expression of a RNA transcript in transgenic plants. The transgene antisense RNA interacts with the endogenous sense mRNA to affect the transcription, processing, transport, turnover, and/or translation of the endogenous sense mRNA. Antisense inhibition was first reported in electroporation of carrot protoplasts with antisense and sense constructs containing the CAT reporter gene resulted in varying inhibition of CAT activity dependent on promoter strength (Ecker et al., *Proc. Natl. Acad. Sci. U.S.A.* 83: 5372–5376, 1986). A stable inheritable antisense effect is first reported in tobacco using the NOS transgene (Rothstein et al., *Proc. Natl. Acad. Sci. U.S.A.* 84: 8439–8943, 1987). Constitutive expression of antisense chalcone synthase (CHS) in transgenic tobacco and petunia plants decreased endogenous CHS RNA and protein activity demonstrating the application of this technology in regulating endogenous gene expression (van der Krol et al., *Nature* 333: 866–869, 1988; van der Krol et al., *Plant Molecular Biology* 14: 457–466, 1990). The technology is extended to show seed specific modulation of gene expression (versus leaf-specific modulation) using the B-conglycinin promoter to drive antisense expression of GUS mRNAs in transgenic tobacco (Fujiwara et al., *Plant Mol. Biol.* 20: 1059–1069, 1992). The potential commercial value of antisense technology is realized when transgenic tomato plants expressing antisense polygalacturonase (PG, an enzyme which partially solublizes cell wall pectin) showed a delay in fruit ripening (Smith et al., *Nature* 334: 724–726, 1988). Antisense technology has since been used to alter the expression of many plant genes, including ribulose bisphosphate carboxylase oxygenase in tobacco (Rodermel et al., *Cell* 55: 673–681, 1988), granule-bound starch synthase in potato (Visser et al., *Mol. Gen. Genet.* 225: 289–296, 1991), a photosystem II polypeptide in potato (Stockhaus et al., *EMBO J.* 9: 3013–3021, 1990), and TOM5 in tomato (Bird et al., *Biotechnol.* 9: 635–639, 1991).

Antisense gene expression in plants has also been useful to alter plant development via the regulation of plant hormone biosynthetic pathways and relative hormone levels. For example, expression of antisense ACC synthase and ACC oxidase RNA have been shown to inhibit fruit ripening in transgenic tomato (Oeller et al., *Science* 254: 437–439, 1991; Hamilton et al., *Nature* 346: 284–287, 1990), and cantaloupe (Ayub et al., *Nature Biotechnol.* 14: 862–866, 1996). Expression of an antisense 7 transmembrane domain (7TM) receptor homologue (GCR1) RNA reduces sensitivity to cytokinins in roots and shoots of transgenic *Arabidopsis* (Plakidou-Dymock et al., *Current Biol.* 8: 315–324, 1998). Expression of antisense prosystemin severely depressed systemic wound inducibility proteinase inhibitor synthesis in transgenic tomato and decreased resistance against insects (Schaller et al., *Bioessays* 18: 27–33, 1996). Expression of antisense catalase RNAs accumulated high levels of PR-1 proteins and showed enhanced resistance to tobacco mosaic virus (Takahashi et al., *Plant J.* 11: 993–1005, 1997) in transgenic tobacco. Thus, much success has been achieved using antisense technology to regulate biosynthetic pathways and hormone levels in plants. In this way, reduction in endogenous GA levels is induced by constitutive or by the tissue-specific antisense inhibition of expression of the endogenous GA biosynthetic enzyme mRNA molecule. Suitable and preferred features of the antisense molecule are the antisense to the nucleic acid full length or partial length of: the coding sequence, the native intron sequences, and the antisense to the intron/exon slice site region of the GA biosynthetic enzyme genes.

Another way of controlling seed germination and seedling growth involves the expression of ribozyme sequences in plants. These are small catalytic RNA molecules capable of very specific cleavage of target mRNA sequences. These RNAs are constructed to have homology with a target endogenous mRNAs such that when expressed in a transgenic plant they hybridize with the target mRNA and their specific catalytic activity inactivates the expression of this endogenous target mRNA. Ribozyme molecules targeted at mRNAs involved with GA biosynthesis and degradation are useful to affect endogenous GA levels. The first self-cleaving RNA (ribozyme) is found in *Tetrahymena* rRNA introns, however, they are now known to exist in hepatitis delta virus, plant pathogenic RNAs (such as viroids, viroid-like RNAs and satellite RNAs), and as part of the RNaseP complex. The catalytic activity is dependent upon the formation of a specific structure involving the target RNA and ribozyme sequences as well as the ribozyme catalytic center. Commonly studied self-cleaving RNAs include the hammerhead and hairpin ribozymes; both of which can form 40–50-nucleotide self-cleaving structures. In principle, a ribozyme is introduced into the cell where it hybridizes with the target sequence and cleaves the substrate. Based on natural self-cleaving RNAs, a set of rules are used to design ribozymes that specifically bind and cleave target RNA molecules in a bimolecular reaction. Hammerhead ribozymes have been shown to function transiently in tobacco protoplasts (Steinecke et al., *EMBO J.* 11: 1525–1530, 1992); Perriman et al., *Antisense Res. Dev.* 3: 253–263, 1993) to confer resistance to tobacco mosaic virus (de Feyter et al., *Mol. Gen. Genet.* 250: 329–338, 1996) in stable transgenic tobacco, and to provide resistance against the potato spindle tuber viroid in stable transgenic potatoes. Hairpin ribozymes have proven effective in delaying CaMV symptoms in transgenic Brassica (Borneman et al., *Gene* 159: 137–142, 1995). Most ribozymes are embedded within stable RNAs to increase effectiveness, and have also been effective when incorporated within tRNAs (Perriman et al., *Proc. Natl. Acad. Sci. U.S.A.* 92: 6175–6179, 1995). Thus, ribozymes could be useful to control GA hormone levels in plants by selectively binding and cleaving mRNAs which produce the enzyme involved in the biosynthetic pathway of gibberellins.

Another potential way of controlling seed germination and seedling growth is through homology-dependent gene silencing (cosuppression) of genes involved with GA biosynthesis. Specifically, overexpression of mRNAs involved with GA biosynthesis could be used to decrease GA levels. Cosuppression, also known as cosense suppression, homology-dependent gene silencing, repeat-induced gene silencing, et cetera, is the inactivation of a gene in a cell where it is normally functional (for reviews see Baulcombe et al., *Current Opinion Biotechnol.* 7: 173–180, 1996; Meyer et al., *Annu. Rev. Plant Physiol. Plant Mol. Biol.* 47: 23–48, 1996; Matzke et al., Plant Physiol. 107: 679–685, 1995). Transgene induced cosuppression in plants has been shown to have useful effects which include reduced impact of viral infection, fruit ripening, affecting flower color, inactivation of infecting transposons and retrotransposons, and editing aberrant RNA transcripts (Smyth et al., *Current Biol.* 7: 793–795, 1997; Napoli et al., *Plant Cell* 2: 279–289, 1990). Many examples of cosuppression have been reported in the literature: sense suppression of caffeic acid O-methyltransferase resulted in altered stem coloration of aspen (Tsai et al., *Plant Physiology* 117: 101–112, 1998); cosuppression of a lipoxygenase isozyme (LOX2) resulted in transgenic *Arabidopsis* plants unable to accumulate jasmonic acid following wounding (Bell et al., *Proc. Natl. Acad. Sci. U.S.A.* 92: 8675–8679, 1995); cosuppression of phytochrome-regulated chlorophyll α/β 140 RNA levels in *Arabidopsis* (Brussian et al., *Plant Cell* 5: 667–677, 1993); cosuppression of a pea cDNA encoding light-activated chloroplast NADP-malate dehydrogenase in transgenic tobacco (Faske et al., *Plant Physiol.* 115: 705–715, 1997); cosuppression of *Flaveria bidentis* NADP-MDH via heterologous sorghum NADP-MDH cDNA despite only about 71% sequence homology (Trevanion et al., *Plant Physiol.* 113: 1153–1163, 1997); cosuppression of a proline-rich glycoprotein (TTS) involved in pollen tube growth in transgenic tobacco (Cheung et al., *Cell* 82: 383–393, 1995); cosuppression of phenylalanine ammonia-lyase (PAL) in transgenic tobacco (Elkind et al., *Proc. Natl. Acad. Sci. U.S.A.* 87: 9057–9061); and cosuppression of two MADS box floral binding protein genes (FBP7 and FBP11) in petunia (Colombo et al., *Plant Cell* 9: 703–715, 1997). Cosuppression of the genes involved in GA biosynthesis will provide the same result as antisense or ribozyme inhibition of these same genes.

Many of the genes of the GA biosynthetic pathway have been cloned from various plant sources. Some of these are: ent-kaurene synthase A (CPS) from *Arabidopsis thaliana* (GenBank Accession No. U11034), *Zea mays* (GenBank Accession No. L37750), *Pisum sativum* (GenBank Accession No. U63652); ent-kaurene synthase B from *Cucurbita maxima* (GenBank Accession No. U43904); monooxygenase from *Zea mays* (GenBank Accession No. U32579); C20-oxidase from *C. maxima* (GenBank Accession No. X73314), *Arabidopsis* (GenBank Accession No. U20872, U20873, U20901, X83379, X83380, X83381), *Pisum sativum* (GenBank Accession No. X91658, U70471, U58830), *Phaseolus vulgaris* (GenBank Accession No. U70503, U70531, U70532), *Oryza sativa* (GenBank Accession No. U50333), *Spinacia oleracea* (GenBank Accession No. U33330); and 3-β-hydroxylase from *Arabidopsis* (GenBank Accession No. L37126).

The present invention is easily distinguishable from the related art (U.S. Pat. Nos. 5,773,288, 5,612,191, WO9316096, WO9605317), in that tissue and developmentally regulated promoters, not of the GA biosynthetic pathway, are directed at the seed germination and early seedling growth stages is a preferred embodiment. The present invention also provides a rescue strategy to restore normal seed germination and seedling growth.

The present invention provides an embodiment for soybean for which no previous known mutants in the GA biosynthetic pathway have been identified to suggest that down regulation of GA levels during early seedling growth would result in a dwarf plant phenotype. The present invention provides novel gene sequences of GA biosynthetic enzymes from canola (SEQ ID NO:1), soybean (SEQ ID NO:2, SEQ ID NO:5, SEQ ID NO:8), cotton (SEQ ID NO:3, SEQ ID NO:6) and wheat (SEQ ID NO:4) and methods to affect seed germination and seedling growth with these genes by genetic engineering of these crops.

The CPS gene from various plant sources contains a conserved core region. Table 2. shows a comparison of the nucleotide similarity determined for the CPS conserved core and full length coding sequences of some of the published CPS genes and the new genes (canola, soybean, cotton, wheat) isolated as part of this invention. The conserved core sequence comparisons are made for soybean, pea, *Arabidopsis*, maize, canola, cotton, and wheat and shown in the upper right half of Table 2. The full length sequence comparisons are made for soybean, pea, *Arabidopsis,* and maize and shown in the lower left portion of Table 2. Heterogeneity exists for the nucleotide sequences of all of the CPS genes compared in this table. The comparison is expressed as percent similarity using the Wilbur-Lipman algorithm (Wilbur and Lipman *Proc. Natl. Acad. Sci. U.S.A.* 80: 726–730 (1983)).

TABLE 2

Percent similarity of full length and conserved core nucleotide sequences from the CPS genes of various monocot and dicot plant species.

| | Soy | Pea | Arabidopsis | Maize | Canola | Cotton | Wheat |
|---|---|---|---|---|---|---|---|
| Soybean | 100 | 80 | 68 | 66 | 60 | 70 | 58 |
| Pea | 73 | 100 | 69 | 65 | 62 | 71 | 58 |
| Arabidopsis | 54 | 53 | 100 | 69 | 82 | 70 | 63 |
| Maize | 57 | 60 | 55 | 100 | 59 | 61 | 78 |
| Canola | | | | | 100 | 63 | 51 |
| Cotton | | | | | | 100 | 61 |
| Wheat | | | | | | | 100 |
| Full length | | | | | | | |

Conserved core (upper right); Full length (lower left)

Temporal expression of the mRNA for ent-kaurene synthase in soybean developing seeds and seedlings is determined for the purpose of identifying the target tissue and the peak times of expression. Soybean developing seeds are collected by size and maturity. Seeds in pods 2–5 mm in diameter, 7–11 mm in diameter, desiccating seeds, mature embryo and mature cotyledons. Seedling tissue is collected at various time from 12 hours to 144 hours after imbibing (HAI) mature seeds in water. The developing seed tissue and root, shoot axis, cotyledon, hypocotyl and epicotyl from the germinating seed tissue is extracted for polyA++selected mRNA and the level of CPS mRNA is determined by Northern blot analysis using standard methods (Mailga et al., *Methods in Plant Molecular Biology*, Cold Spring Harbor Press (1995)) and soybean conserved core nucleotide sequence as the radiolabeled probe (SEQ ID NO:2). The results are shown in FIG. 36 which illustrate that at the 96 hours time point, the soybean hypocotyl expressed 3–10 fold more CPS mRNA than any other tissues sampled in the developing seedling. The data indicates that the hypocotyl region should be targeted for strategies for reducing the amount of GA production in the developing seedling. The data from the developing seed also indicates that mature green seeds (7–11 mm) are producing high levels of CPS mRNA relative to the other seed development stages. Targeting this developmental stage would serve to reduce any available pool of GA in the mature desiccated seed.

The present invention also provides gene sequences from *Cucurbita maxima* (pumpkin) and tomato and methods to affect seed germination and seedling growth with these genes by genetic engineering of these and other crops. The present invention also discloses how the expression of pathway diversion enzymes that can be used to control endogenous gibberellin levels and therefore seed germination and growth in a reversible germination-control system. This invention describes the use of the pathway diversion genes to limit overexpression of the pathway diversion proteins to specific stages of seed or seedling development by using seed and/or seedling-specific promoters for the purpose of delaying and/or preventing germination in a controlled manner.

The use of the phytoene synthase enzyme in this invention functions to divert the substrate geranylgeranyl diphosphate (GGDP) from the gibberellin biosynthetic pathway to the carotenoid biosynthetic pathway. The resulting diversion results in a reduced amount of substrate available for the production of GA(s). Plants deficient in GA(s) show a reduction in seed germination and early seedling growth. Recovery of normal seed germination and seedling growth is achieved by exogenous addition of GA compounds. The present invention provides phytoene synthase sequence from tomato which when overexpressed in plants using methods of plant biotechnology reduce the availability of GGDP as a substrate for GA biosynthesis.

The present invention also provides novel GA 2-oxidase gene sequences from *Arabidopsis*, soybean, maize, and cotton and methods to affect seed germination and seedling growth with these genes by genetic engineering of these and other crops. The present invention discloses how the GA 2-oxidase gene can be used to reduce endogenous gibberellin levels and therefore seed germination and growth in a reversible germination-control system. This invention describes the use of the GA 2-oxidase gene and antisense sequence thereto to limit overexpression of the GA 2-oxidase protein to specific stages of seed or seedling development by using seed and/or seedling-specific promoters for the purpose of delaying and/or preventing germination in a controlled manner.

The GA 2-oxidase gene product functions by controlling bioactive gibberellin levels. Hydroxylation of bioactive GAs, such as $GA_1$ and $GA_4$, by 2-oxidase renders them inactive, while hydroxylation of biosynthetic precursors, such as $GA_9$ and $GA_{20}$, creates non-preferable substrates for GA biosynthetic enzymes. Overexpression of the 2-oxidase protein can therefore be used to directly inactivate GA levels or indirectly down-regulate endogenous bioactive GA levels by affecting the substrate levels, and delay or prevent seed germination. To restore germination capacity, seeds and plants can be treated exogenously with bioactive $GA_3$ or GA analogs that are not substrates for 2-oxidase. Seeds and plants can also be treated with nonpreferred substrates or by treatment with excess amounts of preferred substrates. Mature seeds contain small amounts of stored bioactive GAs. Mobilization of this stored GA is used by the seed during early seed germination. The overexpression of 2-oxidase during mid or late seed development would inactivate these GAs and reduce the pool of bioactive GA available to the seed for germination resulting in delay or inhibition of germination of these seeds. Similarly, 2-oxidase could be overexpressed during seed germination to inactivate mobilized GAs. Bioactive GAs increase during seedling growth, overexpression of GA 2-oxidase during early seedling growth could be used to inactivate bioactive GAs as they are accumulating, also delaying or preventing seedling growth after germination. Several classes of development-specific promoters could be used to drive the GA 2-oxidase gene: a) seed-intensive promoters and promoters from genes which have been shown to express during seed development such as, LEA-type promoters (Hsing et al., *Plant Physiol.* 100: 2121–2122, 1992), Per (Haslekas et al., *Plant Mol. Biol.* 36: 833–845, 1998), Sle2 (Calvo et al., *Theor. Appl. Genet.* 94:957–967, 1997) b) germination-intensive promoters such as, SIP and Acc oxidase gene, and c) seedling-specific promoters such as, AX5 from soybean axis (SEQ ID NO:7), VSPB (Mason et al., *Plant Cell* 5: 241–251, 1993), ICL, Lectin, and MS promoters It is well known in the art how to isolate the promoters and regulatory elements from genes which have been shown to express in specific plant tissue or plant cells related to seed development, seed germination and early seedling growth. The previous list is not exhaustive in describing promoters of genes which have been shown to express in the cells and tissues that are the target of this invention.

Different GA 2-oxidase genes exist whose proteins have varied substrate specificities. The known GA 2-oxidase enzymes have different substrate preferences, catalytic properties, and tissue/developmental distributions. These differences in expression and catalytic capabilities may reflect mechanisms for the fine control of specific GAs and their relative contributions to regulating plant growth and development. Additional GA 2-oxidase genes may exist in higher plants genomes as evidenced by a wide variety of GA metabolites identified (Thomas et., 1999. Proc. Natl. Acad. Sci. 96:4698–4703; Owen et al., *Phytochemistry* 97: 331–337, 1998).

The specific activities can be selected and used in combination with different developmentally regulated or tissue specific promoters to affect plant growth and development. The specific GA 2-oxidase gene chosen for overexpression should correlate with the GA being targeted and have the highest possible substrate specificity for that GA or its precursors. For example, if $GA_1$ is predominant in developing seeds, then the GA 2-oxidase protein with highest specificity for $GA_1$ and/or $GA_1$ precursors would be desired. The techniques of gene evolution (Arnold, F. H., *Acc. Chem. Res.* 31: 125–131, 1998) could be used to generate GA 2-oxidase proteins with additional specificities such as a specificity for multiple GAs, or for precursors early in the pathway. Multiple 2-oxidase sequences driven by similar or different promoters could also be expressed, such as expression of GA 2-oxidase during seed development by a LEA-type promoter and again during seedling growth with the AX5 promoter. Additionally, GA 2-oxidase could be used in conjunction with the other disclosed approaches to alter germination and seedling growth, such as, GA 2-oxidase expression during seed-development or germination in combination with antisense CPS expression, phytoene synthase expression, C20-oxidase expression or 2β,3β-hydroxylase expression during seedling growth. Restoration of seed germination and seedling growth can be controlled by balancing the specific plant expression cassette, such as a double GA 2-oxidase construct, or GA 2-oxidase plus antisense CPS cassette, or other GA biosynthetic enzyme, or pathway diversion plant expression cassette, using different tissue or developmentally regulated promoters with a specific seed treatment of GA, GA analogs or GA precursors used to restore the normal seed germination and seedling growth phenotype.

The inventive nucleic acid molecule segments, recombinant vectors, recombinant host cells, and recombinant plants may comprise structural nucleic acid sequences related to SEQ ID NOS:1, 2, 3, 4, 5, 6, 8, 56, 57, 58, 60, 62, 64, 66, 67, 68, 69, 70, 71, 75, 77, and 79. The structural nucleic acid sequences may be related to these SEQ ID NOS by percent identity. The percent identity is preferably at least about 90%, and more preferably at least about 91%, 92%, 93%, 94%, 95%, 96%, 97%, 98%, 99%, and most preferably 100%. Alternatively, the structural nucleic acid sequences may be related to these SEQ ID NOS by their hybridization properties. Preferably the structural nucleic acid sequence hybridizes under stringent hybridization conditions to the reverse complement of the SEQ ID NO.

Recombinant vectors may be plasmids, cosmids, YACs, BACs, phage, phagemids, or other forms of vectors known in the art. The vectors may be linear or circular. The vectors preferably further comprise a promoter and a 3' transcription terminator. The vectors may further comprise a selectable marker or a screenable marker. The vectors may comprise an origin of replication.

Recombinant host cells may be characterized by having a copy number of the given structural nucleic acid sequence which is higher than the copy number of the structural nucleic acid sequence in a wild type host cell of the same species. If the structural nucleic acid sequence is partially or completely exogenous to the host cell, then the copy number of the recombinant host cell is by definition higher than the copy number in the wild type host cell of the same species. If the structural nucleic acid sequence is entirely endogenous to the host cell, then successful transformation will result in a recombinant host cell with a higher copy number of the structural nucleic acid sequence than in the wild type host cell. Recombinant host cells may further comprise a selectable marker or a screenable marker to aid in the identification of recombinant host cells.

Recombinant plants may be characterized by having a copy number of the given structural nucleic acid sequence which is higher than the copy number of the structural nucleic acid sequence in a wild type plant of the same species. If the structural nucleic acid sequence is partially or completely exogenous to the plant, then the copy number of the recombinant plant is by definition higher than the copy number in the wild type plant of the same species. If the structural nucleic acid sequence is entirely endogenous to the plant, then successful transformation will result in a recombinant plant with a higher copy number of the structural nucleic acid sequence than in the wild type plant. Recombinant plants may further comprise a selectable marker or a screenable marker to aid in the identification of recombinant plants.

Methods of preparing recombinant host cells are disclosed. The methods comprise selecting a host cell, transforming the host cell with a recombinant vector, and obtaining recombinant host cells. The recombinant vector comprises a sequence related to SEQ ID NOS:1, 2, 3, 4, 5, 6, 8, 56, 57, 58, 60, 62, 64, 66, 67, 68, 69, 70, 71, 75, 77, and 79 as described above. The methods may take advantage of selectable or screenable markers to assist in the identification of recombinant host cells.

Methods of preparing recombinant plants are disclosed. The methods comprise selecting a host plant cell, transforming the host plant cell with a recombinant vector, obtaining recombinant host plant cells, and regenerating a recombinant plant from the recombinant host plant cells. The recombinant vector comprises a sequence related to SEQ ID NOS:1, 2, 3, 4, 5, 6, 8, 56, 57, 58, 60, 62, 64, 66, 67, 68, 69, 70, 71, 75, 77, and 79 as described above. The recombinant vector may further comprise a promoter, a 3' transcription terminator, and a 3' polyadenylation signal. The methods may take advantage of selectable or screenable markers to assist in the identification of recombinant host plant cells and recombinant plants.

An alternative embodiment of the invention consist of isolated proteins related to SEQ ID NOS:3, 4, 59, 61, 63, 65, 76, 78, 80, 88, or 89. The isolated proteins may be related to these SEQ ID NOS by percent identity. The percent identity is preferably at least about 90%, and more preferably at least about 91%, 92%, 93%, 94%, 95%, 96%, 97%, 98%, 99%, and most preferably 100%. Alternatively, the isolated proteins may be related to these SEQ ID NOS by their immunoreactive properties. The isolated proteins may be immunoreactive with an antibody prepared using a given SEQ ID NO as an antigen, with the antibody being immunoreactive with the given SEQ ID NO. Immunoreactivity may be determined by any method acceptable in the art, including blotting and ELISA assays.

The disclosed consensus sequence SEQ ID NO:41 may be used in methods to identify 2-oxidase amino acid sequences. The methods may comprise obtaining a library of candidate amino acid sequences; searching the library; and identifying one or more candidate amino acid sequences comprising SEQ ID NO:41. Preferably, the methods are performed by computer or any other automated method. Alternatively, SEQ ID NO:41 may be used to generate antibodies useful in ELISA, blotting, or other screening methods to identify proteins comprising SEQ ID NO:41. Candidate sequences may be screened for enzymatic activity by contacting the protein with a bioactive gibberellin or precursor that is not unsaturated at the 2- position. The isolated proteins are able to oxidize the 2-position of gibberellins that are not unsaturated at that position. For example, $GA_3$ is unsaturated at the 2-position, and thus not a substrate for 2-oxidase.

The disclosed consensus sequence SEQ ID NO:41 may further be used in methods to identify 2-oxidase nucleic acid sequences. SEQ ID NO:41 may be "back-translated" to determine possible nucleic acid sequences which may encode the amino acid sequence. The methods may comprise obtaining a library of candidate nucleic acid sequences; searching the library; and identifying one or more candidate nucleic acid sequences which encode SEQ ID NO:41. Candidate sequences may be screened for enzymatic activity by contacting the encoded protein with a bioactive gibberellin or precursor that is not unsaturated at the 2-position.

Methods for delaying seed germination in plants are disclosed. The methods comprise selecting plant cells, transforming the plant cells with a recombinant vector, selecting transformed plant cells, regenerating transformed plant cells to produce transformed plants, and selecting a transformed plant which exhibits delayed seed germination with respect to a non-transformed plant of the same species. The recombinant vector comprises a sequence related to SEQ ID NOS:1, 2, 3, 4, 5, 6, 8, 56, 57, 58, 60, 62, 64, 66, 67, 68, 69, 70, 71, 75, 77, and 79 as described above. Seed germination may be controlled by subsequently contacting the seeds with a complementing agent (rescue agent) to restore seed germination. The complementing agent may be a GA compound, tissue regulated gene expression of nucleic acid sequences which provide the necessary complementing protein product, or an antisense nucleic acid sequence to nucleic acid sequences that produce GA degrading enzymes, or any other agent effective to increase the concentration of gibberellins in the seed or during early seedling growth.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Canola (*Brassica napus*) CPS Gene

The canola (*Brassica napus*) CPS gene is isolated by identifying sequence conservation between the amino acid sequences of the maize (Bensen et al., *Plant Cell* 7: 75–84 (1995)) and *Arabidopsis* (Sun et al., *Plant Cell* 6: 1509–1518 (1994)) CPS proteins. Based on the sequence in the conserved regions, degenerate oligonucleotides are designed. These primers correspond nucleotides 439–459 and 1702–1720 in maize and nucleotides 393–413 and 1642–1660 in *Arabidopsis* in the respective referenced articles.

```
Mot 0:   TCGGCITACGAYACIGCITGG    (SEQ ID NO:9)

Mot 7:   AGCTGATGCIGAGCTTGGC      (SEQ ID NO:10)
```

Primer sequences Mot 0 and Mot 7 are used in reverse transcriptase polymerase chain reaction (RT-PCR) to isolate canola CPS sequences.

RNA is isolated from 4 day old canola seedlings and first strand cDNA is prepared using the SuperScript Preamplification System (Gibco-BRL Life Technologies) according to the manufacturer's recommendations. The cDNA synthesized is amplified by PCR using the following conditions: after an initial 3 minute denaturation at 94° C., 30 cycles are run, each with 94° C., 1 minute denaturation, followed by 1 minute annealing at 51° C., followed by 2 minute extension at 72° C. The PCR reaction resulted in a 1.2 kb fragment which is purified by agarose gel electrophoresis. The fragment is cloned into the TA vector (Invitrogen, Corp.). The insert is sequenced and the nucleotide sequence of the conserved core region is shown in SEQ ID NO:1. The canola CPS conserved core sequence has a 59% identity to the maize and an 82% identity to the *Arabidopsis* CPS conserved core sequences, respectively (Table 2).

Analysis of CPS Expression During Canola Germination

Northern analysis is performed to determine the temporal and spatial expression pattern of CPS during canola seedling growth. Total RNA is isolated from whole canola seedlings starting at 12 hours after imbibition until 6 days after imbibition. The 2 day, 4 day and 6 day samples are also divided into cotyledons, hypocotyls and roots. RNA is isolated according to the procedure of Altenbach et al, 1981. After denaturation in 50% formamide and 2.18 M formaldehyde, the RNA samples are separated on a 1% agarose gel. The gel is transferred in 10×SSC onto Hybond N nylon membrane (Amersham) which is then UV crosslinked using the UV Stratalinker (Stratagene). The Northern blot is probed with an EcoRI restriction fragment from plasmid containing the 1.2 kb canola CPS sequence. The probe is prepared by random priming using the RTS Radprime DNA labeling system from GIBCO BRL. Hybridization is performed for 35 hours at 37° C. in 50% formamide, 6×SSC, 1× Denhardts solution, 0.1% SDS and 250 µg/mL denatured salmon sperm DNA. The blot is washed by first rinsing at room temperature in 2×SSC, 0.5% SDS; followed by two 10 minute washes at room temperature in 2×SSC, 0.1% SDS; followed by two 30 minute washes at 55° C. in 0.1×SSC, 0.1% SDS. The blot is exposed with intensifying screen at −70° C. to Kodak X-OMAT film. No CPS expression is observed in dry seeds. CPS mRNA is detected as early as 1 day after imbibition. The mRNA is detected specifically in the hypocotyl tissue at 2, 4 and 6 days after imbibition. The mRNA levels increased over time with maximum levels detected at 6 days after imbibition. In all cases, the mRNA is approximately 2.6 kb in size.

Construction of Antisense Canola CPS Plant Transformation Vectors

Vectors are constructed for constitutive as well as germination enhanced expression of canola CPS in antisense orientation. For constitutive expression, the plasmid containing the CPS gene is digested using restriction enzyme EcoRI (Promega Corp.) to excise the canola CPS gene and inserted into the EcoRI restriction site of plasmid Bluescript II SK+ (Stratagene). The resulting plasmid is digested with restriction enzymes BamHI (Promega Corp.) and KpnI (Promega Corp.). This BamHI/KpnI restriction fragment is ligated into the BamHI/KpnI restriction sites of a plant expression vector to generate plasmid pMON29211 (FIG. 1). This resulted in the insertion of the canola CPS fragment in antisense orientation behind the constitutive FMV promoter (P-FMV). The plant expression cassette from plasmid pMON29211 containing P-FMV/antisense canola CPS/NOS3' end (NOS, Fraley et al., *Proc. Natl. Acad. Sci. U.S.A.* 80: 4803–4807 (1983)) is excised on a single NotI (Promega) restriction fragment and inserted into the NotI restriction site in plasmid pMON17227 (FIG. 2) to form plasmid pMON29212 (FIG. 3). In addition to the P-FMV/antisense canola CPS/NOS sequences, plasmid pMON29212 also contains a CP4-EPSPS (U.S. Pat. No. 5,633,435) expression cassette for constitutive expression in plants for use in glyphosate selection of transgenic plants and two border sequences for T-DNA transfer into the plant chromosome. Plasmid pMON29212 is introduced into *Agrobacterium tumefaciens* and utilized in canola transformations.

For germination enhanced expression, the plasmid containing the CPS gene is digested using restriction enzyme EcoRI to excise the canola CPS gene, this fragment is inserted into the EcoRI restriction site of plasmid Bluescript II SK+ (Stratagene, Corp). The orientation of the insert is opposite to that previously described. A KpnI/SacI restriction DNA fragment is inserted into the KpnI/SacI restriction sites of plasmid pMON29916 (FIG. 4) to generate plasmid pMON29217 (FIG. 5). This resulted in the insertion of the canola CPS fragment in antisense orientation behind the *Brassica napus* isocitrate lyase (ICL) promoter (Zhang et al., *Plant Physiol.* 104: 857–864 (1994)). Plasmid pMON29217 is partially digested with restriction enzyme NotI, and a NotI cassette from containing the P-FMV/ctp-CP4/E93' is inserted to form plasmid pMON29220 (FIG. 6). Plasmid pMON29220 is introduced into *Agrobacterium tumefaciens* and utilized in transformation of canola.

$R_0$ plants containing plasmid pMON29212 are examined for phenotypes. Of 63 $R_0$ plants examined, 4 plants show GA deficient phenotypes including reduced stature, delayed flowering and poor fertility. Only small amounts of $R_1$ seed or no seed is produced from these plants. The seed is analyzed for GA affected germination phenotypes by planting in soil in a greenhouse or growth chamber. The population of seeds from these plants would be segregating for the GA deficient phenotype. The seeds when planted show no delay in emergence and no reduction in hypocotyl lengths. A multigene family with sufficiently divergent gene sequence such that not all members of the family are suppressed may mask the effects of suppression of one member of that family. It may be necessary to identify and clone a representative of each member of the gene family to insure suppression of GA production. The constitutive expression of the antisense canola CPS sequence affects the fertility of the primary transformants, apparently the GA deficient phenotype does not survive well during fertilization or seed development. Tissue directed expression of the antisense CPS gene from an early seedling growth promoter in canola will reduce any effects on fertility that are observed with the constitutive expression.

Seeds are produced from plants transformed with plasmid pMON29220 (P-ICL/canola antisense CPS). These are planted and analyzed for germination phenotype. A 2 day delay in emergence is observed for 58% of the $R_1$ lines tested from pMON29220. Exogenous $GA_3$ application ($10^{-5}$ M) to the seed or soil results in rescuing the emergence delay.

Example 2

Soybean (*Glycine max*) CPS Gene

For the generation of soybean CPS gene sequences, a series of degenerate oligonucleotides are designed based on comparisons of the *Arabidopsis* and *Zea mays* sequences. Based on this information, four oligonucleotide primer pools are designed for use in PCR experiment containing mixtures potentially capable of annealing to the CPS gene coding nucleotide sequences from diverse plant species:

```
#1 soydeg1: GCITAYGAYACIGCITGGGTNGC   (SEQ ID NO:11)

#2 soydeg3: YTICAYAGYCTIGARGGIATG    (SEQ ID NO:12)

#3 soydeg7: CKRAAIGCCATIGCIGTRTCRTC  (SEQ ID NO:13)

#4 soydeg8: CATICKRTAIARIGTYTTICCIAT (SEQ ID NO:14)
```

Seeds from *Glycine max* (Asgrow, A3237) are grown in a greenhouse for 6 days. Epicotyls are collected and flash frozen with liquid nitrogen. Total cellular RNA is prepared using standard phenol-chloroform extraction procedures followed by lithium chloride precipitation to remove contaminating DNA and low molecular weight RNA species. Purified RNA precipitates are then resuspended in DEPC-treated water and stored at −80° C. until use. PolyA+ mRNA is then prepared from 1 milligram of total cellular RNA using the PolyATtract mRNA Isolation System III (Promega Corp.) according to manufacturer's instructions. First strand cDNA is then prepared by reverse transcription of 600 ng of polyA+ selected RNA using the Superscript Preamplification System (Gibco BRL) according to manufacturer's instructions.

Oligo-dT primed first-strand cDNA is prepared from 500 ng of poly(A)+ mRNA (144 hours after imbibtion) epicotyl using the SuperScript Preamplification System (Gibco-BRL Life Technologies) per the manufacturer's instructions. Polymerase chain reactions with different primer combinations are performed using the "Touchdown PCR" technique. In one set of reactions, oligonucleotide pools #1 and #3 are used in each tube and in the second set of reactions oligonucleotide pools #2 and #4 are combined. Following a 3 minutes/94° C. denaturation, annealing temperatures are decreased by 1° C. every two cycles between 60° C. and 46° C., followed by 10 cycles at 45° C., then 10 minutes/72° C. Reactions contained 2 ml first-strand cDNA, 250 picomoles of each primer, 10 mM Tris.HCl (pH 8.3), 50 mM KCl, 1.5 mM $MgCl_2$, 200 μM dNTPs, 2.5 U Taq polymerase, in a final volume of 100 μL. RT-PCR products are gel-purified, and cloned directly into the plasmid pCRII (Invitrogen). Isolation of the 5' end and 3' end of the CPS coding sequence is performed using oligonucleotides complementary to sequences obtained from the RT-PCR products (above) with the 5' RACE System for Rapid Amplification of cDNA Ends, Version 2.0, and the 3' RACE System for Rapid Amplification of cDNA Ends (GIBCO-BRL Life Technologies), respectively, per the manufacturer's instructions. For both 3' and 5' RACE reactions, 1st strand cDNAs are generated using 250 ng of poly(A)+ mRNA isolated from internode 3 of 18-day-old soybean plants (A3237).

To identify the products homologous to CPS, Southern blot analysis of the PCR reactions is performed using an *Arabidopsis* CPS cDNA as probe. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), §§ 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. PCR products which hybridized strongly with the *Arabidopsis* probe are purified by agarose gel electrophoresis and directly sequenced using the PRISM DyeDeoxy Terminator Cycle Sequencing Kit (Applied Biosystems). The sequences obtained are analyzed in all possible reading frames using the TFASTA program in the GCG sequence analysis software package.

Two oligonucleotides are designed corresponding to the 5'-most and 3'-most sequences contained within the original CPS RT-PCR products:

```
EKS1:  CCTCAATTTCCATCKAGTCTAGARTGG    (SEQ ID NO:17)

EKS8:  CCGTATTGATCAATGTAPAATCTTGTCTC  (SEQ ID NO:18)
```

Oligonucleotides EKS1 and EKS8 are used as primers in RT-PCR reactions with cDNA prepared from 6-day-old soybean epicotyl mRNA as described above. The reactions are performed using conditions: 94° C. for 1 minute, 61° C. for 1 minute, then 72° C. for two minutes, for 35 cycles. The resulting 1.1 kb PCR product is gel purified. The 1.1 kb CPS conserved core protein gene fragment (CPScc) occurs in the full length soybean CPS gene sequence (SEQ ID NO:2) between nucleotide positions 418 and 1518. The 1.1 kb gene sequence is then ligated into the pCRII T/A vector (Invitrogen). All DNA manipulations and transformations of *Escherichia coli* are performed according to standard protocols (Sambrook et al., *Molecular Cloning: A Laboratory Manual*, $2^{nd}$., Cold Spring Harbor Press (1989).

Production of Soybean Plants with Constitutive Expression of CPScc Antisense

To construct an antisense CPS transformation vector, an approximately 1.1 kb soybean CPS RT-PCR product is excised from the pCRII T/A vector by digestion with restriction enzymes BamHI and EcoRV. A plasmid which contains the *Escherichia coli* uidA gene flanked by the Figwort Mosaic Virus 35S promoter (P-FMV) (U.S. Pat. No. 5,378,619) and the nopaline synthase polyadenylation region (NOS3') is digested with restriction enzyme BamHI, then treated with mung bean nuclease, then digested with restriction enzyme BglII. The resulting vector minus the uidA coding region is then gel-purified, and ligated with the BamHI/EcoRV 1.1 kb CPS fragment, which positioned the partial CPS cDNA in antisense orientation between the P-FMV and the NOS3'. This antisense expression cassette is then excised from this plasmid by restriction enzyme NotI digestion, agarose gel-purified, then ligated into the NotI restriction site of the binary plant transformation vector pMON17227 (FIG. 2) containing a 5-enolpyruvylshikimate-3-phosphate synthase gene conferring glyphosate resistance in plants (U.S. Pat. No. 5,633,435). The resulting transformation vector pMON29801, (FIG. 7) by *Agrobacterium* mediated method is used to transform soybean (this method is described below).

Isolation of Full-length Soybean CPS Gene

Primers corresponding to sequences encompassing the predicted translation initiation and termination codons are used to RT-PCR amplify a full length CPS ORF gene using Pwo DNA polymerase (Boehringer Mannheim Biochemicals) from RNA purified from soybean seedling tissue (144 hours after imbibition). The RNA is selected for polyA+ enriched mRNA (Promega PolyATtract system). PCR primers (soy24mer and soy29mer) are then designed to amplify the full-length coding region (SEQ ID NO:2) using the Expand High Fidelity PCR System (Boehringer Mannheim Biochemicals).

```
soy24mer:
AACACTCCATGGCTTCTCACTTCC       (SEQ ID NO:15)

soy29mer:
TTAAACGACTTCATCAAACAGAACTTTGG  (SEQ ID NO:16)
```

Ten cycles are performed with 30 second denaturation at 94° C., 1 minute annealing at 60° C., and 2 minute 45 second extension at 68° C. An additional 15 cycles are performed where the extension time increased 20 seconds per cycle, followed by a final 10 minute incubation at 68° C. Multiple PCR products generated from independent amplifications are analyzed to avoid thermostable polymerase-induced sequence errors. The PCR product is subcloned into the PCR2.1 vector (Invitrogen), digested with restriction enzymes EcoRV and KpnI, and the CPS gene insert is cloned into plasmid containing P-FMV/petunia Hsp70 5' leader/NOS3' at the unique StuI and KpnI restriction sites between the leader and the NOS3' to create that contains an P-FMV/petunia HSP70 5' leader/soybean CPS/NOS3' terminator in a cassette flanked by NotI restriction sites. This plasmid is then digested with restriction enzyme NotI and cloned into the NotI digested soy linear transformation backbone to create pMON33512 (FIG. 8). Protein translation of the cDNA clone of the soybean CPS gene sequence is shown in SEQ ID NO:88.

Antisense CPS Full Length Plant Expression Vector

The vector containing the P-FMV/petunia Hsp70 5' leader/soybean CPS/NOS3' plant expression cassette is digested with restriction enzymes KpnI and BglII, and the 2547 bp insert (containing the petunia HSP leader and soybean full length CPS gene sequence) is cloned into KpnI and BamHI double digested plasmid to create plasmid pMON42011 (FIG. 9). Plasmid pMON42011 contains an FMV promoter, antisense soybean CPS, and NOS3' terminator in a cassette flanked by NotI restriction sites. Plasmid pMON42011 is then digested with restriction enzyme NotI, the expression cassette is agarose gel purified and ligated into the NotI digested, phosphatase treated plant transformation plasmid to create plasmid pMON42013 (FIG. 10). Plasmid pMON42013 is transformed into soybean to decrease the endogenous soybean CPS levels which will result in a decrease relative GA hormone levels thus altering seedling germination.

Soybean Transformation Methods

Methods for the regeneration of *Glycine max* plants from various tissue types and methods for the tissue culture of *Glycine max* are known in the art (See, for example, Widholm et al., *In vitro Selection and Culture-induced Variation in Soybean*, In Soybean: Genetics, Molecular Biology and Biotechnology, Eds. Verma and Shoemaker, CAB International, Wallingford, Oxon, England (1996)). Regeneration techniques for plants such as *Glycine max* can use as the starting material a variety of tissue or cell types. With *Glycine max* in particular, regeneration processes have been developed that begin with certain differentiated tissue types such as meristems, (Cartha et al., *Can. J. Bot.* 59: 1671–1679 (1981)), hypocotyl sections, (Cameya et al., *Plant Science Letters* 21: 289–294 (1981)), and stem node segments, (Saka et al., *Plant Science Letters*, 19: 193–201 (1980)). Cheng et al., *Plant Science Letters*, 19: 91–99 (1980) have been reported. Regeneration of whole sexually mature *Glycine max* plants from somatic embryos generated from explants of immature *Glycine max* embryos has been reported (Ranch et al., *In Vitro Cellular & Developmental Biology* 21: 11, 653–658 (1985)). Regeneration of mature *Glycine max* plants from tissue culture by organogenesis and embryogenesis has also been reported (Barwale et al., *Planta* 167: 473–481 (1986); Wright et al., *Plant Cell Reports* 5:

150–154 (1986)). *Glycine max* (A3237) transformants can be generated by *Agrobacterium tumefaciens*-mediated transformation of cotyledon explants using the method of Hinchee et al. (1988). Transformation of soybean is satisfactorily performed by the methods described in U.S. Pat. Nos. 5,120,657, 5,015,580, and 5,503,998. Enhanced shoot elongation in tissue culture may be obtained by several methods. Biological active gibberellic acid ($GA_3$, Sigma cat #G-7645) is incorporated into the media at concentrations ranging from 1–10 mM. Shoots that are elongating are removed and placed on rooting media. In addition or alternatively, shoots are removed from the media and placed in a petri dish with sterile aqueous solution of 1–1000 ppm (parts per million) of $GA_3$ in 0.05% Tween 80 or other suitable nonionic detergent or surfactant at biologically effective concentrations. They are agitated in this $GA_3$ solution for about 5–15 seconds before being placed back on the media. The shoots subjected to this dipping procedure are then assessed 1-week after treatment for shoot elongation. In addition or alternatively, shoots are sprayed with a sterile aqueous solution of 1–1000 ppm of $GA_3$ shoots are then assessed 1-week after treatment for shoot elongation. During this elongation phase of the procedure, shoots that are observed to be elongating are selected for rooting by transferring to rooting media. Rooted plants are transplanted into soil.

Analysis of Soybean with Constitutive Expression of CPS Antisense

Thirty-five soybean plants are produced by transformation with pMON29801 (FIG. 7) containing the antisense CPS conserved core (asCPScc) gene driven by constitutive FMV promoter. The seed ($R_1$) from the initial $R_0$ transgenic lines is collected. $R_1$ seeds are sown in 4-inch pots filled with commercial potting soil (Metromix 350) that is saturated with water or $GA_3$ at a rate of either $3\times10^{-6}$ or $10^{-5}$ M. Typically, 20 seeds are sown in 10 pots for each treatment, except where the seed supply is limiting. Pots are incubated in a greenhouse routinely used for soybean growth. Emergence is scored versus days after planting (DAP). Two soybean lines, 724 and 720, show a delayed emergence phenotype. Line 724 emergence is 1 to 2 days later than the control.

$R_1$ lines are also evaluated for stature reduction, a key indicator of GA-deficiency in soybean. $R_1$ seeds are grown as described above. Plant height is routinely measured at approximately one week after planting. Four lines (696, 719, 720 and 724) are identified that had overall stature reduction relative to the control (A3237) line and the control line plus ancymidol (10 mg/L), an inhibitor of GA (Table 3). As these are segregating from $R_1$ seeds, the distribution stature of the plants is evaluated. Three lines (719, 720 and 724) have a population of strong dwarf soybean plants (<25% the height of the average control plant). The segregation ratio of $R_1$ pMON29801 (FMV/asCPScc) (FIG. 7) soybean plants is checked by phenotype (stature) and for the expression of CP4 5-enolpyruvylshikimate-3-phosphate synthase by ELISA (Rogan et al., *J. Food Control*, in Press (1998)). The results for both of these analyses are fairly consistent (Table 4): Line 696 segregated at about 1:3, line 719 at about 1:2, line 720 at about 2:1 and line 724 at about 3:1. Thus, only line 724 is what could be considered normal Mendelian segregation.

TABLE 3

Stature of FMV/asCPScc soybean plants at 7 DAP

| Line | Height (% of control) | Number |
|---|---|---|
| A3237 Control | 100 | 2 |
| A3237 + ancymidol | 14 | 1 |
| 696 | 92 | 3 |
| 719 | 70 | 9 |
| 720 | 43 | 12 |
| 724 | 38 | 6 |

TABLE 4

Distribution of plant heights in the evaluation of segregating $R_1$ FMV/asCPScc (pMON29801) soybean seeds

| | Frequency of heights relative to A3237 control (%) | | | |
|---|---|---|---|---|
| Line | 0–25% | 25–50% | 50–75% | 75–100% |
| A3237 | 0 | 0 | 0 | 100 |
| A3237 + ancym. | 100 | 0 | 0 | 0 |
| 719 | 25 | 10 | 0 | 65 |
| 720 | 60 | 0 | 0 | 30 |
| 724 | 37 | 47 | 0 | 16 |

[1]Ancymidol added as a soil drench at 10 mg/L.

Levels of CPS Endogenous mRNA, Transgenic mRNA and GA in Transgenic Soybean Plants To verify the antisense effect, the CPS mRNA levels are measured by Northern blot and the endogenous GA levels analyzed by GC/MS. $R_1$ pMON29801 plants from lines 719 and 724 are grown the dark for 5 days at 30° C. These $R_1$ lines segregate into the tall and dwarf plant phenotypes. The tall plants are pooled into a single sample, the dwarf plants are pooled into a separate sample. The mRNA is purified by a method of Qiagen Corp. A Northern blot analysis is performed. The endogenous 2.9 kb mRNA is easily detected in the samples from the tall plants and from the A3237 control plant samples. The dwarf plant sample has undetectable levels of the 2.9 kb endogenous CPS mRNA, but high levels of the 1.2 kb transgenic antisense message. This results indicates that antisense expression is providing the expected effect by reducing the level of the endogenous CPS mRNA which will in turn reduce the level of GA in those plants producing the observed as a dwarf plant phenotype.

Endogenous $GA_1$ levels are measured in the upper half of hypocotyls from 5-day old etiolated soybean seedlings by a variation of the method described by Sheng, et al., (*Phytochemistry* 31: 4055–4057 (1992)). Hypocotyl lengths are measured, the upper half separated, frozen and ground into a fine powder in liquid nitrogen. For segregating transgenic lines, hypocotyl samples are separated into "tall" and "dwarf" fractions by size. Between 0.36 g and 1.30 g frozen hypocotyl powder is transferred to a glass 40-mL centrifuge tube and homogenized (Pro300D, Pro Scientific) in 80% (v/v) methanol. Deuterated $GA_1$ standard ($17,17\text{-}d_2\text{-}GA_1$, obtained from L. Mander, Australia National University) are added to levels between 0.2 and 1 ng/ml prior to homogenization. The homogenate is filtered (Whatman No. 42) and the filtrate added to a 6-mL C18 chromatography column (Bakerbond spe, J T Baker, Inc., Phillipsburg, N.J.). $GA_1$ is eluted with 2 ml 80% (v/v) methanol and the methanol is evaporated under vacuum. The remaining aqueous phase is adjusted to pH 3 with hydrochloric acid and partitioned three times against hydrated ethyl acetate. The combined ethyl acetate fractions are evaporated under vacuum, resuspended in 35% methanol containing 0.05% (v/v) acetic acid and filtered (0.25 µm, 25 mm Nylon Acrodisc, Gelman Sciences). The filtered extract is injected onto a C18 reverse-phase column (Xpertek Spherisorb ODS-2 5 µm, 4.6 mm×250 mm) and eluted at a flow rate of 1 ml/minute with a 20-minute linear gradient from 35% to 68% (v/v) acidified methanol controlled by a Waters Model 680 Gradient Controller (Waters Associates, Milford, Ma.). One-ml fractions are collected and pooled according to the expected retention of $GA_1$ as determined by previous chromatography of tritiated standard for $GA_1$ (obtained from R. Pharis, U. of Calgary). Pooled HPLC fractions are evaporated under vacuum and resuspended in 600 µl methanol. Each sample (100 µL) is methylated with diazomethane (10–20 µL) in a 1 ml reacti-vial at room temperature. Excess diazomethane and its solvent are removed with a stream of nitrogen. Each methylated sample received 1 µL of pyridine and 50 µL of BSTFA (N,O-bis(trimethylsilyl)trifluoroacetamide) and is heated at 70° C. for 45 minutes. Excess BSTFA is removed with a stream of nitrogen. An aliquot of each sample is injected into a GC for GC/SIM (selected ion monitoring)/MS. The GC is typically programmed from 100° C. to 300° C. with 10° C./min. The MS signal peak height method for endogenous $GA_1$ and the di-deuterated $GA_1$ is chosen for quantitation of $GA_1$.

Endogenous $GA_1$ levels are 62% and 88% lower in the hypocotyl segments from the dwarf transgenic lines 724 and 719, respectively relative to the A3237 control. These substantial reductions in endogenous $GA_1$ levels correlated strongly with the length of the hypocotyls from which the $GA_1$ is extracted. These results indicate the transgenic soybeans tested are shorter due to a reduction in endogenous $GA_1$ levels.

The level of $GA_1$, the gibberellin considered to be responsible for stem elongation in plants, is measured in additional two lines, 674 and 678, of transgenic antisense copalyl diphosphate synthase conserved core sequence (asCPScc) soybean and the control (A3237). The elongation region (upper half) of the hypocotyl from four-day-old etiolated soybean seedlings is lyophilized and analyzed for $GA_1$ levels in the laboratory of Dr. Richard Pharis at the University of Calgary. The control and line 674 hypocotyl tissue is extracted into 80% methanol and purified using C18 reverse phase chromatography, silica partitioning chromatography, HPLC and GC-MS. $GA_1$ recovery is calculated by the addition of deuterated $GA_1$ to the methanol extract. Gibberellin activity in the fractions collected by HPLC is detected using the microdrop dwarf rice bioassay (Nishijma et al., *Plant Cell Phys.* 30: 623–627 (1989)). For line 678, the silica partitioning step is omitted and the pooled HPLC fractions corresponding to $GA_1$, as detected using $^3H$-$GA_1$, are directly analyzed for $GA_1$ by GC-MS. The $GA_1$ levels in the two transgenic lines 674 and 678 are found to be 42% and 19%, respectively, measured in the control (A3237) hypocotyl segments.

Seed Yield from asCPScc Soybean Lines

Lines engineered for reduced GA levels produce sufficient quantities of fertile seed when treated with $GA_3$. One hundred nine soybean plants from four asCPScc lines (696, 719, 720 and 724) identified with GA-deficient phenotypes are grown to maturity and the seed harvested. Three of the lines (696, 719 and 720) required weekly spraying with $GA_3$ to restore normal vegetative growth. Line 724 showed early GA-deficiency symptoms, but then resumed normal growth and development without the need for exogenously supplied $GA_3$. Seed yield, seed weight per seed, pod number and seeds/pod data are collected for each plant. Data is collected in three groups for each line: plants that are wild-type; plants that are dwarfs and received no exogenous GA; and plants that are treated with exogenous $GA_3$. In plants that are originally dwarfs, seed yield is reduced 75% if $GA_3$ is not provided exogenously. The dwarfs treated continuously with $GA_3$ restored 70% of the yield of the wild-types for lines 696 and 719. Line 720 provides lower seed yields even with $GA_3$ treatments. Line 724 dwarf plants produces equivalent yields to the wild-type plants within this line without any external spraying. Seed weight per seed is reduced 20% to 30% in lines 696, 719 and 724 dwarf plants without GA and this reduction is nearly completely rescued by the GA treatments. Line 724 has no reduction in seed weight in dwarfs without supplying exogenous GA. These results indicate that the use of a strong constitutive promoter to constitutively reduce GA levels in soybean plants substantially reduce seed yields. Exogenous a $GA_3$ treatment strategy can restore near normal yields.

$R_2$ Plant Analysis

Sixty-six $R_2$ soybean lines selected from four gibberellin-deficient R1 lines (696, 719, 720, and 724) are evaluated for reduced emergence, reduced stature and segregation at two locations, Chesterfield, Mo. and Yauco, Puerto Rico (Table 3). The 66 lines are sent to Puerto Rico and planted in the growth chamber in Chesterfield, Mo. simultaneously to allow a detailed examination of the emergence and stature phenotypes in a controlled setting. Approximately 20 seeds per line are planted in 96-well seedling trays. Emergence timing is measured as before, and the stature data is collected on a percentage of short and tall plants to differentiate homozygous from heterozygous lines.

Thirty of the fifty dwarf lines identified at the $R_1$ generation have seedling emergence delays of one to two days in the growth chamber at Chesterfield. Fourteen of the fifty dwarf lines have a germination delay of approximately two days in Puerto Rico. A wide range of reduced stature plants are in this trial. In general, the severity of the dwarf phenotype is 719>720>696>724. Some of the progeny from line 719 are only 7% of the height of the wild-type controls in the trial in Puerto Rico.

Soybean Plants Transformed with Antisense to the Full Length Soybean CPS Sequence A linear fragment spanning the MluI restriction fragment of pMON42013 (FIG. 10) containing the P-FMV/antisense full length soybean CPS sequence/NOS3' cassette is transformed into soybean by particle gun bombardment. The shoots are subjected to the post-transformation GA treatment to induce shoot elongation. The shoots that respond to the GA treatment are rooted in rooting media then transferred to soil. A small number of $R_0$ plants show a severe GA-deficient phenotype including short stature and dark green leaves. A few more plants show a more moderate phenotype

Example 3

Cotton (*Gossypium hirsutum*) CPS

The same series of degenerate oligonucleotides that are designed based on comparisons of *Arabidopsis* and *Zea mays* CPS sequences for the cloning of the *Glycine max* CPS cDNA are used in PCR experiments to clone the CPS gene from *Gossypium hirsutum* (soydeg1 SEQ ID NO:11, soydeg7 SEQ ID NO:13).

PCR is performed on *Gossypium hirsutum*, cv. Coker-312, genomic DNA using the 'Touchdown PCR' technique (Don et al., 1991). Following a 3 minutes/94° C. denaturation, annealing temperatures are decreased by 1° C. every two cycles between 60 and 46° C., followed by 10 cycles at 45° C., then 10 minutes/72° C. Primers soydeg1 (SEQ ID NO:11) and soydeg3 (SEQ ID NO:12) generated a 1.3 kb PCR product. The PCR product is purified by agarose gel electrophoresis and subcloned into the TA cloning vector pCR$^R$2.1 (Invitrogen). The subclone is sequenced using the PRISM DyeDeoxy Terminator Cycle Sequencing Kit (Applied Biosystems). The DNA sequences obtained are analyzed using a "BLAST Search" program in the GCG sequence analysis software package. Based on the genomic sequence obtained, exact primers (NN1.3 (SEQ ID NO:19) and NN7.5 (SEQ ID NO:20)) are designed to clone the CPS cDNA by RT-PCR using the same "Touch Down PCR" technique previously described. An approximately 750 bp PCR product is produced and subcloned into the TA cloning vector pCR$^R$2.1 (Invitrogen Corp.). The cloned product is sequenced using the PRISM DyeDeoxy Terminator Cycle Sequencing Kit (Applied Biosystems). The DNA sequence from cotton (SEQ ID NO:3) is analyzed using a BLAST (GCG) and shows homology to the published *Arabidopsis thaliana* and *Zea mays* gibberellin CPS genes

Construction of Antisense CPS Construct for Expression in Cotton

Vectors are constructed for constitutive expression of the cotton CPS (SEQ ID NO:3) in antisense orientation. For constitutive expression, the plasmid containing the cloned cotton CPS cDNA is digested with restriction enzyme BamHI to excise the CPS fragment and is subcloned into the BamHI/BglII restriction site of plasmid containing a plant expression cassette. This construct resulted in the insertion of the cotton CPS fragment in the antisense orientation behind the constitutive FMV promoter. The plasmid is partially digested with restriction enzymes HindIII and BamHI, and the 1.326 kb FMV-antisense-CPS fragment subcloned into the HindIII and BamHI restriction sites of plasmid pMON10098 (FIG. 11), creating plasmid pMON29975 (FIG. 12). This plant expression cassette contains the FMV promoter driving an antisense-CPS-E9-3' construct as well as the 35s constitutive promoter driving expression of the gene for selection of transgenic plants on the antibiotic, kanamycin. Cotton transformation is conducted as described in U.S. Pat. No. 5,004,863. Enhanced shoot elongation may be obtained by several methods. Biological active gibberellic acid (GA$_3$, Sigma cat #G-7645) is incorporated into the media at concentrations ranging from 1–10 mM. Shoots that are elongating are removed and placed on rooting media. In addition or alternatively, shoots are removed from the media and placed in a petri dish with sterile aqueous solution of 1–1000 ppm (parts per million) of GA$_3$ in 0.05% Tween 80 or other suitable nonionic detergent or surfactant at biologically effective concentrations. They are agitated in this GA$_3$ solution for about 5–15 seconds before being placed back on the media. The shoots subjected to this dipping procedure are then assessed 1-week after treatment for shoot elongation. In addition or alternatively, shoots are sprayed with a sterile aqueous solution of 1–1000 ppm of GA$_3$, shoots are then assessed 1-week after treatment for shoot elongation. During this elongation phase of the procedure, shoots that are observed to be elongating are selected for rooting by transferring to rooting media. Rooted plants are transplanted into soil.

Example 4

Wheat (*Triticum aesativum*) CPS

The conserved core sequence of wheat is isolated from wheat (Ta) mRNA by using the degenerate PCR primers Mot 0 (SEQ ID NO:9) and Mot 7 (SEQ ID NO:10). The amplified fragment is purified on an agarose gel by electrophoresis. The PCR fragment is ligated into a suitable plasmid for growth in *Escherichia coli*. The fragment is subsequently purified from the plasmid, radioactively labeled and used as a probe. Alternatively, the amplified PCR fragment purified from an agarose gel is radioactively labeled and used as a probe. A lambda ZapII cDNA library (Stratagene) is made from wheat seedling leaf extracts. The radioactive probe is used to identify a 2.1 kb cDNA homologous to the PCR fragment produced using the degenerate primers Mot 0 and Mot 7. The 2.1 kb cDNA of wheat CPS DNA sequenced is determined (SEQ ID NO:4). The wheat CPS gene is excised from *E. coli* plasmid with restriction enzymes XbaI and SphI and is ligated into XbaI/SphI digested plasmid containing the plant expression cassette. The orientation of the coding sequence of the Ta CPS gene is antisense in this plant expression cassette. Transcription of the antisense Ta CPS gene in is controlled by the CaMV enhanced 35S promoter (Kay et al., *Science* 236: 1299–1302 (1987)), a *Zea mays* heat shock protein gene intron sequence, and the NOS3' terminator region in the monocot expression cassette. The P-e35S/Zmhsp70intron/antisenseTaCPS/NOS3' is transformed into wheat cells by particle bombardment (Vasil, *Plant Mol. Biol.* 25: 925–937 (1994) and transgenic plants are regenerated. Transgenic plants are selected which demonstrate the dwarf plant phenotype useful for this invention.

Example 5

Soybean (*Glycine max*) Gibberellin 3β-hydroxylase

PolyA+ selected mRNA is prepared from dry seed embryos, dry seed cotyledons; root, hypocotyl, and cotyledon from 2-day-old seedlings; root, hypocotyl, epicotyl, and cotyledon from 4-day-old seedlings; and root, hypocotyl, epicotyl, and cotyledon from 6-day-old seedlings. Approximately 5 µg of each sample is subjected to Northern analysis and probed with a 1.4 kb cDNA insert encoding a putative full-length 3-β-hydroxylase coding region. The expression pattern of this gene more closely matched that of CPS than C20-oxidase. High levels of expression are seen in cotyledons at 2 and 4 days after imbibition, which declined by day six. Roots showed strong expression at day 2, but became almost undetectable by day 4. Cotyledons had the highest 3-β-hydroxylase mRNA levels at day 6, whereas for CPS maximal expression is seen in hypocotyls at this time. These data also reveal that two distinct mRNAs of similar size are produced in soybean.

A heterologous library screening approach is used to obtain cDNA sequences from soybean homologous to gibberellin 3β-hydroxylase. A λgt10 cDNA library prepared from 10-day-old light grown soybean seedlings is obtained (Soybean 5'-STRETCH cDNA library; Clontech). Approximately 800,000 phage are plated and replicated onto nitrocellulose. Membranes are pre-hybridized and hybridized in 35% de-ionized formamide, 5× Denhardt's reagent, 5× saline citrate solution (SSC), 0.1% sodium dodecyl sulfate (SDS), and 100 µg/ml of heat-denatured, sonicated calf thymus DNA at 37° C. A PCR generated *Arabidopsis* gibberellin 3β-hydroxylase full-length cDNA (Chiang et al., *Plant Cell* 7: 195–201 (1995)) is radiolabeled with $^{32}P$ dCTP using the Redi-prime random primer labeling kit (Amersham), heat denatured, then added to heat-sealable bags containing the membranes in hybridization buffer to a concentration of 1 ng/ml. Hybridization is allowed to proceed for 24 hours at 37° C. Filters are then washed twice for 15 minutes in 2×SSC/0.2% SDS at room temperature, twice for 20 minutes in 2×SSC/0.2% SDS at 37° C., and finally once for 30 minutes in 0.2×SSC/0.2% SDS at 37° C. Washed membranes are then subjected to autoradiography overnight at −80° C. using an intensifying screen.

Twenty three recombinant phage of the 800,000 screened initially hybridized strongly with the *Arabidopsis* cDNA. From these, ten are chosen for a single round of plaque purification per manufacturer's instructions, using the above described hybridization and wash conditions for primary screening. Purified phage particles are eluted from agar plugs into SM buffer overnight at 4° C. or for one hour with shaking at 37° C.

Five microliters of each phage eluate is placed in thin-walled PCR reaction tubes and boiled for 5 minutes. PCR is then performed on the boiled eluates using oligonucleotide primers complementary to sequences flanking the λgt10 EcoRI cloning site (Clontech).

```
λgt10-lft:  AGCAAGTTCAGCCTGGTTAAGT    (SEQ ID NO:39)

λgt10 rt:   TTATGAGTATTTCTTCCAGGG     (SEQ ID NO:40)
```

PCR conditions are for 35 cycles of 94° C. for 30 seconds, then 45° C. for 1 minute, followed by 68° C. for two minutes. The PCR products obtained are then purified by agarose gel electrophoresis, then directly sequenced using the PRISM DyeDeoxy Terminator Cycle Sequencing Kit (Applied Biosystems). The sequences obtained are analyzed in all possible reading frames for homology with the *Arabidopsis* protein using the TFASTA program in the GCG sequence analysis software package. These analyses identified 5 cDNA inserts showing a high degree of homology to the *Arabidopsis* gibberellin 3β-hydroxylase (3β-OH) enzyme. The sequence of the soybean gibberellin 3β-hydroxylase is shown in SEQ ID NO:5. Phage DNA from these clones is digested with EcoRI and cloned into EcoRI digested pBluescript KS(+) (Stratagene). One clone is chosen for further characterization and digested with restriction enzymes EcoRV and KpnI and the 3β-OH insert is cloned into plasmid containing the P-FMV/petunia Hsp70 5' leader/NOS3' at the unique StuI and KpnI sites, the expression cassette is flanked by unique NOT1 sites. The plasmid is digested with restriction enzyme NotI and cloned into the NotI-digested soybean linear transformation vector to create plasmid pMON33515 (FIG. 13). The plant expression plasmid pMON33515 is transformed into soybean as previously described to affect endogenous GA levels by cosuppression. Protein translation of the soybean 3β-hydroxylase cDNA sequence is shown in SEQ ID NO:89.

The construction of plant expression vectors designed to express an antisense gene for soybean 3β-OH is performed as follows. The plasmid containing the first 3β-OH clone is digested with restriction enzymes XbaI and KpnI, and cloned into the XbaI/KpnI-sites of the plant expression cassette. This vector contains an FMV promoter, soybean antisense 3β-OH, and 3' NOS terminator in a cassette flanked by NotI restriction sites. This plasmid is then digested with restriction enzyme NotI and cloned into the NotI digested vector pMON17227 (FIG. 2) to create pMON29815 (FIG. 14). This construct contains (from 5' to 3') the right border, FMV promoter, CTP2 sequence, CP4-EPSPS gene, E9 3' terminator; FMV promoter, antisense soybean 3β-OH, NOS3' terminator, and left border. Plasmid pMON29815 is transformed into soybean by an *Agrobacterium*-mediated soybean transformation method without exogenous application of GA. Plants are regenerated, planted into soil and seeds recovered. These seeds are planted into soil and analyzed for the GA deficient phenotype. No phenotype is observed for these plants. This indicates that the exogenous application of GA during the shooting phase of plant regeneration is important for recovery of plants expression the GA deficient phenotype. An additional vector for particle gun transformation of soybean is made by cloning the KpnI/XbaI antisense 3β-OH sequence into a plant expression vector designed for linear DNA particle gun transformation. The transformation of soybean is performed with the agarose gel purified HindIII linearized vector which contains the plant expression cassettes for expression of the antisense 3β-OH sequence and the expression of the selectable marker gene (CP4, glyphosate). Transformed soybean plants are selected from those shoots that respond to exogenous GA applications at the shoot elongation stage of plant regeneration in tissue culture. These shoots are rooted, then transferred to soil.

Example 6

Cotton (*Gossypium hirsutum*) Gibberellin 3-β-hydroxylase

A series of degenerate oligonucleotides are designed based on comparisons of the *Arabidopsis* (Chiang et al., *Plant Cell* 7: 195–201 (1995)), *Glycine max* (SEQ ID NO:5), and *Pisum sativum* 3-β-hydroxylase (Martin et al., *Proc. Natl. Acad. Sci. U.S.A.* 94: 8907–8911 (1997)) sequences for the cloning of 3-β-hydroxylase from *Gossypium hirsutum*.

```
3BOH1: CTICRRGARCTICCIGAITCTTAYA    (SEQ ID NO:21)

3BOH2: GTCIGTRTGIGSKGKIAGACCCATNGC  (SEQ ID NO:22)

3BOH3: GCIATGGGTCTIRCISCICAYCANGAC  (SEQ ID NO:23)

3BOH4: GTKCSAAGRTACTCWTTCCAWGTCAC   (SEQ ID NO:24)
```

PCR is performed on *Gossypium hirsutum*, variety Coker-312, genomic DNA using the 'Touchdown PCR' technique. Following a 3 minutes/94° C. denaturation, annealing temperatures are decreased by 1° C. every cycle between 58° C. and 43° C., using a 68° C. extension at each cycle, followed by 20 cycles at 43° C., then 10 minutes/72° C.

An approximately 1.12 kb PCR product generated using oligonucleotides 3BOH1 and 3BOH4 is purified by agarose gel electrophoresis and subcloned into the TA cloning vector pCR$^R$2.1 (Invitrogen Corp.) The subclone is sequenced using the PRISM DyeDeoxy Terminator Cycle Sequencing Kit (Applied Biosystems). The partial genomic clone contains an intron of 320 base pairs (bp) and two exons of 271 bp and 530 bp. The DNA sequences obtained are analyzed using a BLAST program in the GCG sequence analysis software package. These analyses identified genomic DNA sequence (SEQ ID NO:6) showing homology to the *Arabi*- dopsis thaliana. Glycine max and Pisum sativum 3β-hydroxylase genes identifying the cotton gene as a 3β-hydroxylase cDNA Cloning of Cotton 3-β-hydroxylase Cloning of partial and full length 3β-hydroxylase cDNA clones is done using BRL Life Technologies 5' and 3' RACE Systems for Rapid Amplification of cDNA Ends, Version 2.0 as per manufacturer's instructions. Primers are designed based on the genomic clone sequences of the of the 5' exon and 3' exons for amplification.

5-RACE Primers

| BOH9: | GTGGTAGCTGAAATCTTG | (SEQ ID NO:30) |
|---|---|---|
| BOH11: | CCTGGCAAATCCATAGCC | (SEQ ID NO:31) |
| BOH12: | CCCATATCAAGGAGACTT | (SEQ ID NO:32) |
| BOH14: | CATGGTTGGTGACTTGGA | (SEQ ID NO:33) |

3'-RACE Primers

| BOH15: | AGTTAGCCGGGAGATTGATGTG | (SEQ ID NO:34) |
|---|---|---|
| BOH16: | CCTTAGGCATAATTGCCAAA | (SEQ ID NO:35) |
| BOH5: | CAGCACTAGTGGGTTGCAGGTC | (SEQ ID NO:35) |

Messenger RNA from cotton 2–4 day old seedlings is used for 5' and 3' RACE reactions as per manufacturer's instructions. For 5' RACE primer BOH9 is used for the first strand synthesis reaction followed by C-Tailing of the cDNA. A second nested primer, (BOH11, BOH12 or BOH14) that anneals to sequences located 3' (with respect to cDNA not mRNA) of BOH9 is used in conjunction with the manufacturers AUAP primer to amplify the 5' coding region of cotton 3-β-hydroxylase The 3'-RACE primer BOH15 is used on cDNA generated using the manufacturers AP primer. A second nested primer, (BOH16 or BOH5) that anneals to sequences located 3' of BOH15 (with respect to the mRNA) is used in conjunction with the manufacturer's AUAP primer to amplify the 3' coding region of cotton 3-β-hydroxylase. Both 5' and 3' PCR products are subcloned into the TA cloning vector pCR2.1 and sequenced as previously described. Following DNA sequence verification PCR primers are designed to flank the 3β-hydroxylase open reading frame which contain unique restriction sites compatible with the polylinker sites of the constitutive plant expression vector. RT-PCR using mRNA from cotton 2–4 day old seedlings is done using the high fidelity Pwo DNA polymerase (BMB) to produce a complete clone of the cotton 3β-hydroxylase open reading frame.

Vectors are constructed for constitutive expression of the cotton 3β-hydroxylase. The 3β-hydroxylase ORF PCR product previously described is digested with restriction enzymes compatible with the vector and cloned in both sense and antisense orientations. This plant expression vector contains the FMV promoter driving sense or antisense 3-β-hydroxylase with a E9 terminator.

Example 7

Soybean AX5 Promoter

A small gene family encoding repetitive proline-rich cell wall protein exists in soybean (Datta, et al., *Plant Cell* 1: 945–952 (1989); Hong, et al., *J. Biol. Chem.* 265: 2470–2475 (1990)) with individual members being expressed in distinctive patterns in different organs, stages of development, and cell types (Hong, et al., *Plant Cell* 1: 937–943 (1989); Wyatt, et al., *Plant Cell* 4: 99–11 (1992)). The AX5 cDNA is isolated from soybean (A3237) by differential screening of a 2 days after imbibition (2 DAI) axis cDNA library with first strand cDNA derived from 2 DAI axis and 9 DAI epicotyls. Several AX5 cDNAs are isolated which exhibited preferential expression in the 2 DAI axis. The AX5 cDNA is isolated based on its preferential expression within the soybean seedling axis and limited expression beyond the seedling stage of development. By Northern blot analysis, the AX5 mRNA accumulates in the axis of the soybean seedling beginning 12–24 hours after the start of imbibition at 30° C. with lower levels of AX5 mRNA accumulating in roots and cotyledons. Peak levels of AX5 accumulation in the axis are seen 3–5 days after the start of imbibition (DAI). A prolonged but decreasing level of expression occurs in the hypocotyl at least to 18 DAI with little to no detectable accumulation of AX5 in younger internodal tissue at 18 DAI. AX5 mRNA is undetectable in mature leaves. Environmental stresses (heat, drought, jasmonic acid as a surrogate for wounding, and salicylate as a surrogate for pathogenesis) does not induce AX5 mRNA in aerial portions of the plant although increased expression is observed in roots in response to heat and drought.

The AX5 promoter is PCR amplified from soybean genomic DNA (cv. A3237) by TAIL PCR (Liu and Whittier, *Genomics* 25: 674–681 (1995)) using the primers ARB1, AX5-1, and AX5-5.

| ARB1: | NTCGASTWTSGWGTT | (SEQ ID NO:25) |
|---|---|---|
| AX5-1: | TTATAAACTGGTGGTTTCTCAGTG | (SEQ ID NO:26 |
| AX5-5: | GAAGCCATGTTTCTCACGTTGTA | (SEQ ID NO:27) |

The AX5 primers for PCR are chosen to discriminate the RPRP3 gene from related cell wall protein genes in the soybean genome. The PCR conditions are set using those described by Liu et al., (*Plant J.* 8: 457–463 (1995)) in a Perkin-Elmer 9600 PCR machine. The resulting 942 bp PCR fragment (SEQ ID NO:7) is cloned into the NotI/BglII restriction sites of plasmid pMON8677 (FIG. 32) after reamplification with the primers AX5-6 (SEQ ID NO:28) and AX5-3 (SEQ ID NO:29) to introduce NotI and BglII restriction sites, respectively. The resulting construct, plasmid pMON34434 (FIG. 15), contains the AX5 promoter immediately upstream of the uidA (β-glucuronidase) reporter gene.

```
                                          (SEQ ID NO:28)
AX5-6:  AAATAGCGGCCGCGTTTCAAACAAAATGGGTGCGTGGAG (SEQ ID NO:29)
AX5-3:  GAAGATCTGGTTCTCACGTTGTAGTTG
```

The soybean AX5 promoter will express gene transcripts in a developmentally specific manner. The CPScc (conserved core) gene and CPSfl (full-length) genes are cloned in the antisense orientation into a plant expression cassette containing the soybean AX5 promoter. The XhoI restriction fragment from plasmid pMON29801 (FIG. 7) is cloned into the BglII/BamHI restriction sites of plasmid pMON34434 (FIG. 15) replacing the uidA gene with 1082 bp (base pairs +435 to +1577 of the coding sequence) of the soybean CPScc in antisense orientation. The NotI cassette of plasmid (P-AX5/asCPScc/NOS3') is then ligated into the NotI site of a plant transformation vector containing the CP4 gene for selection on glyphosate to create plasmid pMON34439 (FIG. 16). Approximately 150 transgenic soybean plants are produced, transplanted into soil and grown in a greenhouse to make seed. Sixty-four of these lines are analyzed for a GA-deficient phenotype. In this assay, 20 seeds are planted and compared to A4922 (non-transgenic control) to determine whether or not they show delayed emergence and reduced stature. From the segregating population of plants, 2 lines are identified that show severe and moderate dwarf phenotype. Line 46 has 8 severe dwarfs plants at 7 days after planting and 5 moderate dwarfs at 14 days after planting. Line 213 has 2 severe and 2 moderate dwarfs 7 days after planting and 4 severe dwarfs 14 days after planting. These 2 lines are advanced to a secondary assay. In this assay, forty seeds are planted, 20 with a soil drench of $1\times10^{-6}$ M $GA_3$ and 20 without to assess the GA-reversibility of this early seedling phenotype.

Plant expression vectors are constructed containing the NotI cassette of plasmid pMON34434 (FIG. 15) subcloned into the NotI restriction site a plant expression vector for *Arabidopsis* transformation via *Agrobacterium* to create pMON40401 (FIG. 17). For transformation via particle gun and *Agrobacterium* in soybean, plasmid pMON34436 (FIG. 18), and plasmid pMON34437 (FIG. 19), respectively. These constructs include the reporter cassette and a constitutively expressed marker for selection of transformants using kanamycin or glyphosate. Plants from the seeds of transgenic soybeans transformed with plasmid pMON34436 and plasmid pMON34437 are produced and examined for expression driven by the AX5 promoter.

The cloned AX5 promoter causes restricted expression of downstream genes in transgenic plants. *Arabidopsis* plants transformed with plasmid pMON40401 show a common histochemical pattern of expression. Expression is observed shortly after the start of germination, initially expression is present in all organs of the seedling within 1–2 days after germination (DAG). By 4 DAG, the expression becomes restricted, with the highest levels observable in cells of the cotyledon petioles, hypocotyl and the hypocotyl/root junction. Expression is also present in some epidermal cells of the mature root, often being associated with emerging lateral roots. Post-seedling organs such as rosette leaves and developing flower buds assayed at 9 DAG and in bolting plants, typically do not show the histochemical staining indicative of transcription of the reporter gene by the AX5 promoter. The AX5 promoter is responsive to mechanical wounding and drives expression immediately around the site of mechanical damage to tissues. This general pattern is consistent with the expression profile of the endogenous AX5 gene in soybean and indicates that this promoter is likely to express in a similar manner in many plant species.

Example 8

Soybean (*Glycine max*) Gibberellin 20-oxidase Gene

A gibberellin 20-oxidase is cloned from soybean by low stringency screening of a soybean library using a heterologous probe. Based on the published sequence of the 386 amino acid *C. maxima* (pumpkin) 20-oxidase cDNA sequence (Lange et al., *Proc. Natl. Acad. Sci. U.S.A.* 91: 8552–8556 (1994)), primers are designed and used to reverse transcribe and PCR-amplify the 20-oxidase cDNA from developing pumpkin seed polyA+ mRNA.

```
C20-F1:  CCATCTAGAAGATCTCATATGGCTTTGAACGGCAAGGTGGC     (SEQ ID NO:37)

C20-R1:  CCAGCATCCGGTACCTCATTAAGCAGACGGGCGCTAAT AGTGG  (SEQ ID NO:38)
```

Amplified products are radiolabeled by random priming of RT-PCR products which are gel purified for removal of vector sequences, and used as a heterologous probe to screen approximately 500,000 λGT10 phage from a commercially prepared soybean 10-day-old light-grown seedling cDNA library (Clontech Laboratories; 5'-Stretch cDNA library). Duplicate plaque lifts on 132 mm supported nitrocellulose membranes (Schleicher and Schuell) are prepared, and membranes are pre-hybridized and hybridized at 37° C. in 35% formamide, 5× Denhardt's solution (0.1% ficoll, 0.1% polyvinylpyrrolidone, 0.1% bovine serum albumin), 5×SSC, 0.1% sodium dodecyl sulfate (SDS), and 100 µg/ml sonicated herring sperm DNA. Heat denatured radiolabeled probes are added to the hybridization solution at a concentration of 1–2 ng/ml, and after hybridization for 24 hours, membranes are washed using low-stringency conditions (twice for 15 minutes at room temperature in 2×SSC, 0.2% SDS, then twice for 20 minutes in the same solution at 37° C., then finally once for 30 minutes in 0.2×SSC, 0.2% SDS at 37° C.). Positive plaques are subjected to one round of plaque purification and the inserts are PCR-amplified and directly sequenced. Five selected phage inserts are isolated and subcloned into the plasmid pBluescript KS+ (Stratagene) at the EcoRI restriction site. Of the five putative 20-oxidase cDNA sequences, one showed homology over a 1071 bp stretch to known 20-oxidase family members (Hedden and Kamiya, *Ann Rev Plant Physiol.* 48: 431–460 (1997)) and is cloned into the XbaI and KpnI restriction sites of plant expression cassette. The vector is digested with restriction enzyme NotI and the FMV promoter/petunia hsp70 leader-soybean C20 oxidase/NOS3' expression cassette is purified and ligated into NotI digested plant transformation plasmid containing the CP4 gene for transgenic plant selection on glyphosate. The sequence of the soybean gibberellin 20-oxidase is shown in SEQ ID NO:8.

Example 9

Cosuppression CPS Vector for Soybean

The soybean CPS ORF region of pMON33512 (FIG. 8) is sequenced in both directions to verify the ORF, and this vector is submitted for soybean transformation by what method. The linear DNA fragment is produced by digestion with restriction enzyme HindIII. The Hind III restriction fragment containing the plant expression cassette is agarose gel purified then transformed into soybean by the particle gun method. Developing shoots are treated with GA to promote shoot elongation as previously described. The shoots are rooted in rooting media, then transferred to soil. Plants are assayed for the GA deficient phenotype. Plants which show the GA deficient phenotype are propagated for seed and assayed in further generations for the GA deficient phenotype. Those plants that stably maintain the dwarf phenotype are introduced into a breeding program for propagation to commercial introduction.

Example 10

Cosuppression 3β-OH Soybean

The soybean 3β-OH gene sequence of plasmid pMON33515 (FIG. 13) is linearized by digestion with restriction enzyme HindIII. The Hind III restriction fragment containing the plant expression cassette is agarose gel purified then transformed into soybean by the particle gun method. Developing shoots are treated with GA to promote shoot elongation as previously described. The shoots are rooted in rooting media, then transferred to soil. Plants are assayed for the GA deficient phenotype. Plants which show the GA deficient phenotype are propagated for seed and assayed in further generations for the GA deficient phenotype. Those plants that stably maintain the dwarf phenotype are introduced into a breeding program for propagation to commercial introduction

Example 11

ICL Promoter/GUS in Soybean

A germination restricted promoter/reporter vector is constructed using the canola isocitrate lyase (ICL) promoter (from pBtIL-GUS-IL, cloned from *Brassica napus* (Zhang, et al., *Plant Physiol.* 104: 857–864 (1994)). The HindIII-PstI restriction fragment containing the 2.9 kb canola ICL promoter and the GUS gene is subcloned into the HindIII-PstI restriction sites of plant expression cassette replacing the FMV promoter and antisense CPS fragment, thereby creating the canola ICL promoter/GUS coding sequence/NOS3' terminator plant expression cassette. The plasmid is digested with Not1 and is ligated into a NotI digested and phosphatase (CIP) treated plant transformation plasmid to create plasmid pMON29807 (FIG. 20). Plasmid pMON29807 now contains the P-ICL/GUS reporter cassette plus the FMV promoter/CP4 EPSPS and the P-ICL/antisense soybean CPS/NOS3'. Soybean is transformed by an *Agrobacterium* mediated transformation method using glyphosate for transgenic plant selection and GA to promote shoot elongation as previously described.

Germinating $R_1$ seeds containing plasmid pMON29807 are examined by histochemically staining for GUS expression. GUS activity is evident in both the hypocotyl and cotyledons prior to 1 day after the start of imbibition (DAI). By 2 DAI activity is localizing in less mature portions of the hypocotyl (apical hook and elongating zone). Higher levels of expression (on an activity/mg total protein basis) are found in the cotyledons than in the axis (9 of 9 lines examined) and can be 5-fold or more greater than in the axis (4 of 9 lines examined). Lower levels of activity are also observed in root tips and associated with the vasculature of older internodes and petioles.

Example 12

Restoration of Normal Seedling Growth with GA Treatments

The timing of emergence and plant stature at for transgenic (plasmid pMON29801, FMV/asCPScc) soybean line 724 is rescued by sowing seeds in soil saturated with $3 \times 10^{-6}$ $GA_3$. At 7 days after planting (DAP), the $GA_3$ treatment to the seeds rescued plant stature to within 10% of the A3237 control. As an additional control, soybean (A3237) seeds are coated with different concentrations of a commercial formulation of $GA_3$ (Release™) blended with talc and sown in sand saturated with 3 mg/L ancymidol and grown in a greenhouse. Plant height is measured at 6 DAP. Good reversal of ancymidol inhibition of soybean stature is realized with 3 mg $GA_3$/kg seed. This rate is equivalent to approximately 62 mg $GA_3$ per acre (assuming 140,000 seeds/acre).

$GA$ treatments to the seed, soil, and foliar application restores normal growth and development of FMV/asCPScc (plasmid pMON29801) soybean plants. Three methods of addition of $GA_3$ to plasmid pMON29801 Line #719 soybean seeds restores stature to the plants when seeds are sown and plants grown in the greenhouse and field. The $GA_3$ is added to seeds as Release 10 SP (Abbott Laboratories) milled with talc powder. The $GA_3$ is also added as a one-step seed treatment with a suspension in water of Release SP, polyethylene glycol (3,000 to 20,000 MW) and talc powder. The $GA_3$ is also added as a two-step seed treatment where the soybean seed is treated first with water and polyethylene glycol (3,000 to 20,000 MW) followed by a second treatment with Release 10 SP and talc. Water/polyethylene glycol ratios from 10:1 to 1:1 are used. $GA_3$ concentrations between 5 and 20 ppm restore normal shoot height in emerged #719 soybean plants.

$GA_3$ added to plasmid pMON29801 transgenic soybean seeds as a soil drench also restores soybean emergence timing and plant height during early seedling growth. Rates of $GA_3$ between $1 \times 10^{-6}$ and $1 \times 10^{-5}$ M, when added to soil either immediately before planting or immediately after, restores normal shoot length in emerged Line #719 seedlings (Table 5).

A foliar spray of $GA_3$ restores normal stature of Line 719 plants. $GA_3$ restores normal vegetative development (Table 6) when sprayed on the foliage of GA-deficient dwarf plants during vegetative development at rates between $10^{-4}$ and $10^{-6}$ M plus a surfactant (Tween 20, 0.05% v/v).

TABLE 5

Effect of GA3 soil drench on pMON29801 soybean shoot length at 7 days after planting.

| | Plant height (cm) | |
| --- | --- | --- |
| R1 line# | −GA | $+3 \times 10^{-6}$ M GA |
| A3237 | 11.9 (0.2) | 14.9 (0.3) |
| 719 | 8.3 (1.1) | 11.3 (1.0) |
| 724 | 4.5 (0.7) | 10.9 (0.9) |

TABLE 6

Restoration of pMON29801 soybean stature by foliar GA3 treatment

| R1 plant line | Treatment | Plant height (cm) 21 DAP | 50 DAP |
|---|---|---|---|
| 719–18 | no GA[1] | 2.0 | 13 |
| 719+14 | no GA[1] | 2.5 | 13 |
| 719–10 | GA[2] | 2.5 | 61 |
| 719–15 | GA[2] | 2.5 | 56 |

[1]Plants receive a single spray treatment at 21 DAP with GA and then are not further sprayed.
[2]Plants are sprayed approximately every week starting at 21 DAP.

Two out of 59 transgenic soybean lines transformed with construct pMON34439 (AX5 promoter/antisense CPScc, FIG. 26), lines 46 and 202, show a reduced stature during early seedling growth and then resume normal vegetative growth. Twenty seeds of each line are sown in Metromix 350 soil in 3" plastic pots in the greenhouse, approximately 40% of the seedlings are reduced in stature for line 46 and 25, 35% for line 202. Normal growth rate of seedlings in these two lines is at least partially restored by the addition of $1 \times 10^{-6}$ M $GA_3$ as a soil drench treatment immediately before planting in addition to a foliar $1 \times 10^{-5}$ M $GA_3$ spray.

Example 13

Identification of GA 2-oxidase Consensus Sequence and Cloning of Two Novel *Arabidopsis* GA 2-oxidases Known dioxygenases which are involved in GA biosynthesis or catabolism are aligned using the PileUp program in the GCG software package (Wisconsin Package Version 10.0-UNIX, Genetics Computer Group, Madison, Wis.). Sequences included gibberellin 7-oxidases, C20 oxidases, 3β-hydroxylases, 2,3β-hydroxylases, and GA 2-oxidases identified in a variety of dicot and monocot species (Genbank accession numbers: X73314, U61385, y09112, Y14007, Y14008, Y14009, U70532, U58830, U70471, X91658, U70530, U70531, X83380, X83379, X83381, Y09113, At132435, At132436, At132437, At132438, Af010167, L37126, U85045, U63650, U61386). The results of this alignment indicated general conservation at the amino acid level among these dioxygenases with particular regions in the GA 2-oxidases being diagnostic of this subfamily. The consensus amino acid sequence is shown in SEQ ID NO:41.

GFGEHTDPQ(I/L)IS(L/V)LRSNXTXGLQI(C/N)(L/V)
XDG(S/T)W(I/V)XV(P/T)PD(H/Q)(S/T)SFFXNVGDX-
LQVMTNGRFKSV(K/R)

This is an example of a region which has higher amino acid identity and overall similarity between GA 2-oxidase members (>60% identity) than amongst other dioxygenases which utilize GAs or their biosynthetic intermediates as substrates. The conserved regions in GA 2-oxidase sequences are used to screen the sequence databases for new family members. All 3 *Arabidopsis* GA 2-oxidase sequences (EMBL database Nos: AJ132435, AJ132436, AJ132437) are used to search an *Arabidopsis* genomic sequence database using the TBLASTN and TBLASTX search algorithms (Altschul, et. al., *J. Mol. Biol.* 215:403–410, 1990). Two novel *Arabidopsis* GA 2-oxidases (At2ox4 and At2ox5) are identified which have amino acid identity of greater than 50% to the consensus sequence constructed from all GA oxidases (SEQ ID NO:41). *Arabidopsis* GA 2-oxidase 4 (At2ox4) nucleotide sequence is shown in SEQ ID NO:58, its amino acid translation shown in SEQ ID NO:59. *Arabidopsis* GA 2-oxidase 5 (At2ox5) gene nucleotide sequence is shown in SEQ ID NO:60, its exon amino acid translation shown in SEQ ID NO:61. These genes are overall distinct from the previously described *Arabidopsis* sequences (Thomas, et al., *Proc. Natl. Acad. Sci. U.S.A.* 96: 4698–4703, 1999) and from each other at the nucleotide and amino acid level when compared in their entirety.

Isolation of genomic clones containing the new sequences is performed to allow complete determination of the coding region, exon/intron structure, and regulatory regions such as 5' promoter sequence. An *Arabidopsis* genomic library is constructed in the λFIX II vector (Stratagene, La Jolla, Calif.,) following the manufacturer's protocol. *Arabidopsis* genomic DNA from the *Landsberg erecta* ecotype is partially digested with restriction enzyme Sau3A and then partially filled-in with dGTP and dATP using *E. coli* polymerase I (Klenow) fragment. Fragments in the 9–23 kbp size range are gel purified and ligated into the arms of the λFIX II vector according to manufacturer's instruction. The resulting library is amplified in the *E. coli* strain XL1-Blue MRA P2 (Stratagene, LaJolla, Calif.) for amplification prior to screening. For screening, phage are plated at approximately 133–200 pfu/cm². One hundred square segments (10×10) of agar (1.5 cm²) are isolated from the plates and phage are eluted in 1.5 ml of SM buffer [100 mM NaCl, 8 mM $MgCl_2$, 50 mM Tris-HCl pH7.5, 0.01% (w/v) gelatin. Superpools (pooled rows and columns of eluted phage) are then screened by PCR using primers sets, 15434-2 (SEQ ID NO:42) and 15434-3 (SEQ ID NO:43); 25182-1 (SEQ ID NO:45) and 25182-2 (SEQ ID NO:46); 27516-2 (SEQ ID NO:51) and 27516-3 (SEQ ID NO:52), which specifically amplify each of the new GA 2-oxidase sequences. One μL of each superpool is amplified in a 25 μL reaction using the following conditions: 1×PCR buffer (Sigma RedTaq), 200 mM dNTPs, 0.5 mM each primer, 1.25 units Taq polymerase; amplification parameters: one cycle of 94° C. for 2 min; 32 cycles of 94° C.—15 s, 60° C.—15s, 68° C.—30 s, one cycle of 68° C.—5 min. At least one positive superpool and corresponding individual pool are found for each of the amplifications attempted. Expected fragments for the 15434-2 and -3 and 25182-1 and -2 primer sets are amplified from the same individual pools. Digoxigenin-labeled probe (Boehringer Mannheim Biochemicals Corp.) made for SEQ ID NO:56 (PCR amplified with primers 15434-2 and 15434-3), is used to screen low density platings of positive pools according to stringent hybridization conditions (Boehringer Mannheim EasyHyb hybridization solution, 42° C.—overnight, final wash: 0.2×SSC, 0.1% SDS, 68° C.—15 minutes). Individual positive plaques are isolated and grown in liquid culture to isolate the corresponding DNA (Lech, K. *Current Protocols in Molecular Biology*, 1.12.2, 1990).

Mapping of the positive phage DNA with XbaI digests, indicated an approximately 1.4 kbp XbaI fragment and an approximately 2.8 kbp XbaI fragment. DNA sequencing of these fragments revealed them to be contained within a genomic clone for *Arabidopsis* GA 2-oxidase 4 (SEQ ID NO:57). Sequencing primer 25182-6 (SEQ ID NO:48) is be used to sequence a portion of the genomic DNA of the At2ox4 gene. The putative start of translation of the GA 2-oxidase open reading frame is located at position 1002 in SEQ ID NO:57 estimated by homology with known GA 2-oxidases. However, in the genomic clone an in-frame upstream translation initiation codon also occurs at position 852. Two introns are present, positions 1348–2247 and 2613–2931. The open reading frame terminates at position 3179.

A cDNA for *Arabidopsis* GA 2-oxidase 4 (At2ox4) (SEQ ID NO:58) is isolated to confirm exon/intron structure of the gene. *Arabidopsis* ecotype Columbia bolting rosette first-strand cDNA is prepared according to manufacturer's instructions for first-strand cDNA synthesis using the AP primer (SEQ ID NO:54) (3' RACE Kit, GIBCO/BRL, Gaithersburg, Md.). The AUAP (SEQ ID NO:53) and 25182-8 (SEQ ID NO:50) primers are used to perform a first round of PCR, 1×PCR buffer (Boehringer High Fidelity), 200 mM dNTPs, 0.5 mM each primer, 2.5 units Boehringer High Fidelity Taq polymerase (Boehringer Mannheim, Indianapolis, Ind.); cycle parameters: one cycle of 94° C. for 2 min; 9 cycles of 94° C.—15 s, 72° C.—30s, 68° C.—1 min 15 s, decreasing annealing temperature every cycle by 2° C.; 27 cycles of one cycle of 94° C. for 2 min; 27 cycles of 94° C.—15 s, 60° C.—15 s, 68° C.—1 min 15 s; one cycle of 68° C.—5 min. Two microliters of a 1:1000 dilution of the first round PCR reaction is used with a nested primer set, 25182-7 (SEQ ID NO:49) and 15434-7 (SEQ ID NO:44) and same amplification parameters are used to amplify the cDNA of *Arabidopsis* GA 2-oxidase 4 (using same cycle parameters as described in the first strand reaction).

The cDNA is cloned into plasmid pCR2.1 (Invitrogen, Carlsbad, Calif.) by the TA cloning procedure of the manufacturer. The vector is digested with restriction enzymes EcoRI and EcoRV, followed by agarose purification of the DNA fragment containing the GA 2-oxidase. Vector pET-30A(+) (Invitrogen, Carlsbad, Calif.) is digested with restriction enzymes EcoRI and EcoRV, and ligated using T4 DNA ligase. The clone is fully sequenced and the cDNA protein translation produced (SEQ ID NO:59). A plant expression vector, pMON42049 (FIG. 21), is constructed to express the At 2-oxidase 4 cDNA in transgenic plants. The At2ox4 is excised from pET-30A(+) as an EcoRI/EcoRV endonuclease digested fragment, blunted and ligated using T4 DNA ligase into a plasmid which is previously digested with restriction endonucleases StuI and treated with alkaline phosphatase (Promega Corp, Madison, Wis.). An aliquot of the ligation reaction is transformed into *E. coli* XL-1 blue competent cells (Stratagene, LaJolla Calif.), transformed cells are selected on 50 μg/ml ampicillin, and screened for the DNA insert by mini-DNA plasmid preparation (Wizard®, Promega Corp, Madison, Wis.) and restriction endonuclease digestion. Plasmid pMON42049 contains the FMV promoter linked to the At2ox4 gene linked to the nos 3' terminator region. An *Agrobacterium* binary transformation vector is constructed by digestion of pMON42049 with restriction enzyme NotI, followed by agarose gel purification of the DNA fragment (Wizard® PCR Preps, Promega Corp., Madison, Wis.), digestion of a plant expression vector with restriction enzyme NotI followed by alkaline phosphatase treatment, then ligation of the agarose gel purified fragment with the plant expression plasmid to make plasmid pMON42050 (FIG. 22). The transformation vector useful for particle bombardment transformation is constructed by digesting plasmid pMON42049 with restriction enzyme NotI and agarose gel purification of the plant expression cassette DNA fragment. The plasmid is linearized with restriction enzyme NotI, treated with phosphatase, and ligated with the pMON42049 gel purified fragment. An aliquot of the ligation reaction is transformed into *E. coli* competent cells and selected on kanamycin, and screened for the DNA insert by miniprep DNA plasmid preparation and restriction endonuclease digestion. The resulting vector is pMON42051 (FIG. 23) which contains the FMV promoter linked to At2ox4 gene and the nos 3' terminator and the plant expression cassette for conferring resistance to glyphosate.

Tissue specific expression of the At2ox4 gene is achieved by digestion of pMON42051 with restriction enzymes EcoRV and XbaI, followed by filling the 5' overhang with DNA polymerase I (Klenow enzyme) and dNTPs, isolating the large vector DNA fragment by agarose gel electrophoresis. Plasmid pMON51904 (FIG. 24) is digested with restriction enzymes EcoRV and NcoI, fill in the overhang using DNA polymerase I and dNTPs, and isolate the Sle2 promoter DNA fragment by agarose gel purification. The vector fragment is ligated to the Sle2 promoter DNA fragment with T4 DNA ligase. An aliquot of the ligation reaction is transformed into competent *E. coli* cells, selected on 50 μg/ml kanamycin, and the vector which contains the Sle2 promoter/At2ox4/nos3' and the plant expression cassette is selected for glyphosate resistance. This vector is pMON42052 (FIG. 25). The plant expression vector is mated into *Agrobacterium* ABI by the triparental mating procedure (Ditta et al., *Proc. Natl. Acad. Sci. USA.* 77: 7347–7351, 1980) and confirmed by recovery of the vector and endonuclease restriction mapping. The transgene plant expression cassette is transferred into plants by an *Agrobacterium* mediated transformation method. Transformation methods for soybean, cotton, canola, sugarbeets, rice, wheat, maize using *Agrobacterium* are well know in the art. Methods using particle gun bombardment of regenerable plant tissue using circular or linear DNA containing the plant expression cassette is also well known in the art. Addition of GA3 or GA analog which is not a substrate of GA 2-oxidase, or addition of excess bioactive GA to the shooting media may be necessary to promote shoot elongation during the regeneration phase of plant tissue culture. Alternatively, GA3 or suitable analog, or excess bioactive GA may be applied as a soil drench or foliar spray to promote shoot elongation during the plant growth phase of propagation after transfer of rooted shoots to soil or artificial potting media.

Expression of these genes in the tissues of developing seeds, germinating seeds and during early seedling growth will result in a delay or inhibition of seed germination or reduced seedling stature. To recover seed germination and seedling height it is necessary to add exogenous bioactive gibberellic acid which is not a substrate for inactivation by GA 2-oxidases. Exogenous bioactive GA is preferably added as a seed treatment, alternatively, bioactive GA is applied as a foliar spray or soil drench to promote shoot elongation.

A promoter/reporter construct is prepared to analyze expression of the *Arabidopsis* GA 2-oxidase 4 gene upon reintroduction into *Arabidopsis* via stable transformation. Histochemical staining of such transgenic plant material for β-glucuronidase activity revealed developmental, spatial and temporal patterns of expression driven by the transcriptional activity of the GA 2-oxidase 4 promoter. A 991 bp (position 1–991 of SEQ ID NO:57) genomic sequence containing 5' untranslated sequences and transcriptional regulatory elements is used as template and the primers, 25182-5 (SEQ ID NO:47) and T7-promoter (SEQ ID NO:55) (other reaction components same as for cDNA for amplification, but template concentration is approximately 1 ng of plasmid; cycle parameters: one cycle of 94° C. for 2 min; 22 cycles of 94° C.—15 s, 60° C.—15 s, 68° C.—1 min; one cycle 72° C.—5 min). The resulting amplification product is digested with restriction enzymes PstI and BglII and ligated into PstI/BglII digested pMON8677 (FIG. 32) to generate pMON34495 (FIG. 26), containing the promoter and 5' untranslated region of the *Arabidopsis* GA 2-oxidase 4 gene immediately upstream of the β-glucuronidase open reading frame. The pMON34495, P-At2ox4:GUS:NOS-terminator construct may be removed as a NotI cassette for insertion into appropriate *Agrobacterium* mediated plant transformation vectors. The temporal expression of transgenes using the At2ox4 promoter is useful for modification of GA substrates, modification of GA 2-oxidase activity, and expression of other genes useful for affecting plant development.

A genomic clone for *Arabidopsis* GA 2-oxidase 5 (At2ox5) corresponding to SEQ ID NO:20 is identified in the *Arabidopsis* genomic library and a corresponding individual phage isolate is obtained. Phage DNA is isolated and primers complementary to the DNA sequence are used to obtain additional sequence of the DNA. The amino acid translation of the exon sequence from the At2ox5 genomic gene sequence is shown in SEQ ID NO:61.

Example 14

Isolation of Soybean GA 2-oxidase Sequences

Soybean (*Glycine max*) cDNA libraries are searched for GA 2-oxidase consensus sequence and several candidate sequences are found in seed, root, flower and leaf libraries. Based on these cDNA sequences, nucleotide primers for PCR are designed to amplify the full reading frames plus 5' untranslated regions (AUAP; SEQ ID NO:53) and the respective primers: Gm2ox1-2 (SEQ ID NO:72) for soybean GA 2-oxidase 1; Gm2ox5-1 (SEQ ID NO:73) for soybean GA 2-oxidase 2; Gm2ox4-1 (SEQ ID NO:74) for soybean GA 2-oxidase 3). First-strand cDNA is made from soybean seedling axes from seeds imbibed for 2 days in 100 mM abscisic acid in water using the same method which generated rosette cDNA for cloning *Arabidopsis* GA 2-oxidase 4. Amplifications are performed as for the amplification of the *Arabidopsis* GA 2-oxidase 4 cDNA, but with altered amplification parameters (one cycle of 94° C. for 2 min; 9 cycles of 94° C.—15 s, 72° C.—30 s, 68° C.—1 min 30 s, decreasing annealing temperature every cycle by 2° C.; denature 94° C.—2 min for one cycle; "touchdown"conditions—94° C. (15 sec)—72° C. (30 sec)—68° C. (90 sec) for 9 cycles with 2° C. reduction per cycle; amplification at 94° C. (15 sec), 60° C. (30 sec)—68° C. (90 sec) for 27 cycles, then 72° C.—5 min. Two cDNAs which represent distinct GA 2-oxidase genes, soybean GA 2-oxidase 1 (SEQ ID NO:62 and SEQ ID NO:63) and soybean GA 2-oxidase 2 (SEQ ID NO:64 and SEQ ID NO:65), are amplified and inserted into the pCR2.1 vector by the TA cloning method (Invitrogen, Carlsbad, Calif.). The soybean GA 2-oxidase 3 gene (SEQ ID NO:66), a contig of cDNA sequences GM2417 and 700556244H1 contained in a soybean cDNA library database, is identified by homology to the GA 2-oxidase consensus sequence (SEQ ID NO:41). Plant expression vectors are constructed by digestion of a plasmid with restriction enzymes BamHI and StuI followed by isolation of the large vector fragment by agarose gel electrophoresis. The plasmid is digested with restriction enzyme NcoI, filled with Klenow and dNTPs, and digested with restriction enzyme BamHI. The Gm2ox1 sequence is isolated by agarose gel purification. The vector fragment and the Gm2ox1 gene are ligated and transformed into competent *E. coli*, and selected on 50 μg/ml ampicillin. Isolated DNA is screened with endonucleases to verify insertion. The resulting vector is pMON42053 (FIG. 27). Plasmid pMON42053 is digested with restriction enzyme NotI, followed by isolation of the plant expression cassette containing the Gm2ox-1 gene by agarose gel purification. The cassette is ligated into NotI digested, alkaline phosphatase treated vector, creating pMON42054 (FIG. 28). This vector provides for glyphosate selection of transformed plants. Tissue specific expression of Gm2ox1 can be achieved by digesting pMON42054 with restriction enzymes EcoRV and XbaI, filling in with DNA polymerase I and dNTPs and isolating the large vector fragment by agarose gel purification. Plasmid pMON51904 is digested with restriction enzymes EcoRV and NcoI, filled with Klenow and dNTPs, and the Sle2 promoter DNA fragment is isolated by agarose gel purification. The vector backbone from pMON42054 is ligated to the Sle2 promoter DNA fragment using T4 DNA ligase. The mixture is transformed into competent *E. coli*, and selected on 50 μg/ml kanamycin. DNA preparation from isolated colonies is screened with restriction endonucleases for the Sle2 promoter insertion. The resulting vector is pMON42055 (FIG. 29). The Gm2ox2 gene is inserted into a plant expression cassette by digestion of with restriction enzymes StuI and BamHI and isolation of the large vector DNA fragment by agarose gel electrophoresis. The plasmid is digested with restriction enzymes BamHI and DraI and the Gm2ox2 gene is isolated by agarose gel purification. The two DNA fragments are ligated together with T4 DNA ligase. An aliquot of the ligation mix is transformed into competent *E. coli*, selected on 50 μg/ml ampicillin, and screened by endonuclease restriction analysis of mini preparation plasmid DNA. The resulting plant expression cassette is pMON42056 (FIG. 30). A plant expression vector containing the Gm2ox2 gene and a plant expression cassette for selection of plants resistant to glyphosate is constructed by digestion of pMON42056 with restriction enzyme NotI and isolating the plant expression cassette containing the Gm2ox2 gene. The plasmid is digested with restriction enzyme NotI, treated with alkaline phosphatase, and an aliquot is ligated to the NotI fragment isolated from pMON42056 using T4 DNA ligase. An aliquot of the ligation reaction is transformed into competent *E. coli*, selected on 50 μg/ml ampicillin, screened for the insert by endonuclease restriction digestion. The resulting vector which contains the Gm2ox2 gene in a plant expression cassette and a plant expression cassette which confers glyphosate resistance to plants. Tissue specific expression of Gm2ox2 gene is achieved by digestion of the vector with restriction enzyme EcoRV, then partially digestion with restriction enzyme DraI and isolation of the approximate 7315 bp vector DNA fragment by agarose gel purification. Plasmid pMON51904 is digested with restriction enzymes EcoRV and NcoI, filled with DNA polymerase I (Klenow) and dNTPs, and the Sle2 promoter DNA fragment isolated by agarose gel purification. Ligation of the vector DNA fragment and the Sle2 promoter DNA fragment creates pMON42058 (FIG. 31). Plasmid pMON42058 contains the tissue specific expression promoter Sle2 driving the Gm2ox2 gene and the plant expression cassette conferring glyphosate resistance to plants. Expression of these genes in the tissues of developing seeds, germinating seeds and during early seedling growth result in a delay or inhibition of seed germination or reduced seedling stature. To recover seed germination and seedling height it is necessary to add exogenous bioactive gibberellic acid which is not a substrate for inactivation by GA 2-oxidases.

Example 15

Isolation of Cotton GA 2-oxidases Sequences

A cotton (*Gossypium hirsutum*) cDNA database is searched for GA 2-oxidase sequences using the *Arabidopsis* GA 2-oxidase 4 amino acid sequence (At2ox4) and the TBLASTN algorithm. Several candidates are found with at least 50% identify over 85 amino acids or which had sequence homologous to the conserved GA 2-oxidase domain. Two distinct genes are represented by cDNA sequences LIB3166-002-Q1-n 1 -B5 (SEQ ID NO:67), and LIB3147-022-Q1-K1-H9 (SEQ ID NO:68). A third cDNA, LIB3048-028-Q1-L1-G9 (SEQ ID NO:69), representing an N-terminal portion of a GA 2-oxidase is identified and could not be linked to the other cotton GA 2-oxidase genes based on available sequence. These sequences are found in seedling axis (SEQ ID NO:67 and SEQ ID NO:68) and abscission zone libraries (SEQ ID NO:67 and SEQ ID NO:69). The methods used for cloning genomic DNA and full length cDNA clones of the *Arabidopsis* and soybean GA 2-oxidases as well as the methods for making plant expression vectors can be applied to clone the cotton GA 2-oxidase full length genes contained in a cDNA database of sequences contained in seedling axis and abscission zone cDNA libraries of cotton plants. Expression of these genes in the tissues of developing seeds, germinating seeds and during early seedling growth will result in a delay or inhibition of seed germination or reduced seedling stature. To recover seed germination and seedling height it is necessary to add exogenous bioactive gibberellic acid which is not a substrate for inactivation by GA 2-oxidases.

Example 16

Isolation of Corn GA 2-oxidase Sequences

A corn (*Zea mays*) cDNA database is searched for the GA 2-oxidase consensus sequence. Two cDNA sequences, L1892837 (SEQ ID NO:70) and L30695722 (SEQ ID NO:71), are found in leaf and 18 hour post-pollination libraries, respectively. L1892837 and L30695722 both exhibit 53% identity over 117 amino acids of At2ox1 which contains the consensus sequence found among GA 2-oxidases (SEQ ID NO:41). The methods used for cloning genomic DNA and full length cDNA clones of the *Arabidopsis* and soybean GA 2-oxidases as well as the methods for making plant expression vectors can be applied to clone the corn genes contained in a cDNA database of sequences contained in leaf and post-pollination cDNA libraries of corn plants. Those skilled in the art would know how to optimize expression of transgenes in monocots, such as use of introns, codon preference, monocot tissue and developmentally regulated promoters. Expression of these genes in the tissues of developing seeds, germinating seeds and during early seedling growth will result in a delay or inhibition of seed germination or reduced seedling stature. To recover seed germination and seedling height it is necessary to add exogenous bioactive gibberellic acid which is not a substrate for inactivation by GA 2-oxidases.

Example 17

Isolation of *Cucurbita maxima* C20-oxidase Gene

Young developing seeds of *Cucurbita maxima* (pumpkin) are extracted for total RNA (Triazol Reagent, BRL) and polyA mRNA isolation (Qiagen polyA kit). The HOOK primer (SEQ ID NO:85) is incubated with approximately 1 µg of polyA selected mRNA first strand synthesis reaction (Superscript Kit, Bethesda Research Labs) according to manufacturer's instructions. The primers C20-1 (SEQ ID NO:83) and C20-2 (SEQ ID NO:84) are used in a high fidelity PCR reaction in the following conditions to yield a cDNA product suitable for cloning. The reaction mix is the same as previously described containing dNTPs, and reaction buffer, and polymerase. The PCR reaction product (Stratagene Robocycler) is 1 cycle at 94° C. for 3 minutes, then 25 cycles of: 94° C., 1 minute; 56° C.—66° C. (gradient block), 1 minute; 72° C., 1 minute. The DNA product from the 60° C. annealing step is incubated at 70° C. for 10 minutes with approximately 5U Taq polymerase to add A nucleotides to the ends of the DNA The DNA product is cloned into the TOPO TA cloning vector. The DNA product is sequenced (SEQ ID NO:77) and amino acid deduced (SEQ ID NO:78). This plasmid contains the C.m. C20-oxidase gene which is further inserted into a plant expression vector with T4 DNA ligase as a BamHI/EcoRV DNA fragment into a BamHI/StuI digested vector plasmid. This expression cassette is combined with the expression cassette for glyphosate resistance to create pMON42023 (FIG. 34).

Example 18

Isolation of *Lycopersicum esculentum* Phytoene Synthase Gene

Total RNA is isolated from developing tomato fruit using Triazol reagent and following the manufacturer's methods (BRL). The RNA is selected for polyA RNA using the Qiagen polyA kit (Qiagen Corp). The first strand cDNA reaction is conducted using the Superscript kit (BRL), followed by high fidelity PCR with the PHS1 (SEQ ID NO:81) and PHS2 (SEQ ID NO:82) primers. The conditions are as described in Example 17 for the production of the PCR DNA product and cloning into the TA vector. The DNA product is sequenced (SEQ ID NO:75) and identified as phytoene synthase gene of tomato (GenBank #M84744). This sequence (SEQ ID NO:75) is modified by site directed mutagenesis to change -nucleotide 1029 from T to A and nucleotide 1058 from T to G. The deduced amino acid sequence is shown in SEQ ID NO:76. The phytoene synthase gene DNA is digested with XbaI/BamHI and ligated into XbaI/BamHI digested plant expression cassette to make P-FMV/Le.Phs/NOS3'. This expression cassette is combined with the expression cassette for glyphosate resistance to create pMON42020 (FIG. 34).

Example 19

Isolation of *Cucurbita maxima* 2β,3β-hydroxylase

PolyA selected RNA is made by the method described in Example 17 from young tissue of *Cucurbita maxima* (pumpkin). First strand cDNA synthesis is conducted using the HOOK primer (SEQ ID NO:85), as previously described, followed by high fidelity PCR using Cm 2β,3β-1 (SEQ ID NO:86) and Cm 2β,3β-2 (SEQ ID NO:87). The DNA fragment is sequenced (SEQ ID NO:79) and amino acid sequence deduced (SEQ ID NO:80). The TA vector containing DNA product is digested with XbaI/BamHI, blunted using Klenow fragment and ligated into BglII/blunted plant expression vector to make p35S/C.m.2b,3b-oh/NOS3'. This expression cassette is combined with the expression cassette for glyphosate resistance to create pMON42221 (FIG. 35)

Example 20

Alternative Nucleic Acid and Protein Sequences

Sources other than those disclosed may be used to obtain the sequences used to generate a 2-oxidase nucleic acid sequence, and the encoded 2-oxidase protein. Furthermore, sequences from different organisms may be combined to create a novel 2-oxidase sequence incorporating structural, regulatory, and enzymatic properties from different sources.

Example 21

Nucleic Acid Mutation and Hybridization

Variations in the nucleic acid sequence encoding a 2-oxidase protein may lead to mutant 2-oxidase protein sequences that display equivalent or superior enzymatic characteristics when compared to the sequences disclosed herein. This invention accordingly encompasses nucleic acid sequences which are similar to the sequences disclosed herein, protein sequences which are similar to the sequences disclosed herein, and the nucleic acid sequences that encode them. Mutations may include deletions, insertions, truncations, substitutions, fusions, shuffling of subunit sequences, and the like.

Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, T. *Proc. Natl. Acad. Sci. U.S.A.*, 82: 488–492, 1985), unique site elimination (Deng and Nickloff, *Anal. Biochem.* 200: 81, 1992), nick protection (Vandeyar, et al. *Gene* 65: 129–133, 1988), and PCR (Costa, et al. *Methods Mol. Biol.* 57: 31–44, 1996). Random or non-specific mutations may be generated by chemical agents (for a general review, see Singer and Kusmierek, *Ann. Rev. Biochem.* 52: 655–693, 1982) such as nitrosoguanidine (Cerda-Olmedo et al., *J. Mol. Biol.* 33: 705–719, 1968; Guerola, et al. *Nature New Biol.* 230: 122–125, 1971) and 2-aminopurine (Rogan and Bessman, *J. Bacteriol.* 103: 622–633, 1970), or by biological methods such as passage through mutator strains (Greener et al. *Mol. Biotechnol.* 7: 189–195, 1997).

Nucleic acid hybridization is a technique well known to those of skill in the art of DNA manipulation. The hybridization properties of a given pair of nucleic acids is an indication of their similarity or identity. Mutated nucleic acid sequences may be selected for their similarity to the disclosed nucleic acid sequences on the basis of their hybridization to the disclosed sequences. Low stringency conditions may be used to select sequences with multiple mutations. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed sequences. Conditions employed may include about 0.02 M to about 0.15 M sodium chloride, about 0.5% to about 5% casein, about 0.02% SDS and/or about 0.1% N-laurylsarcosine, about 0.001 M to about 0.03 M sodium citrate, at temperatures between about 50° C. and about 70° C. More preferably, high stringency conditions are 0.02 M sodium chloride, 0.5% casein, 0.02% SDS, 0.001 M sodium citrate, at a temperature of 50° C.

Example 22

Determination of Homologous and Degenerate Nucleic Acid Sequences

Modification and changes may be made in the sequence of the proteins of the present invention and the nucleic acid segments which encode them and still obtain a functional molecule that encodes a protein with desirable 2-oxidase properties. The following is a discussion based upon changing the amino acid sequence of a protein to create an equivalent, or possibly an improved, second-generation molecule. The amino acid changes may be achieved by changing the codons of the nucleic acid sequence, according to the codons given in Table 7.

TABLE 7

| Codon degeneracies of amino acids | | | |
|---|---|---|---|
| Amino acid | One letter | Three letter | Codons |
| Alanine | A | Ala | GCA GCC GCG GCT |
| Cysteine | C | Cys | TGC TGT |
| Aspartic acid | D | Asp | GAC GAT |
| Glutamic acid | B | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of enzymatic activity. It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, *J. Mol. Biol.*, 157: 105–132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0 ±1); serine (+0.3); asparagine/glutamine (+0.2); glycine (0); threonine (−0.4); proline (−0.5 ±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted in functional fusion proteins.

Example 23

GA Compounds as "Rescue Agents" for Transgenic, GA-deficient Dwarf Soybeans and Other Self-fertile Plants GA Synthesis and Accumulation During Seed Formation and Seedling Growth Conceptually, the development of seeds and seedlings in soybeans and other plants can be divided into three phases: seed development, seed germination, and seedling growth. The endogenous GA levels in wild-type soybeans during seed development, germination, and seedling growth are shown schematically in FIG. 37.

In soybean, GAs increase through mid-seed development, and then decline as the seed matures (Birnberg et al. (1986) *Plant Physiol.* 82:241–246). This trend is similar to that observed in other legumes. There does not appear to be any net increase in gibberellins in the seed during germination. This is supported by the following observations (data not shown). First, ancymidol, an inhibitor of gibberellin biosynthesis at ent-kaurene oxidase, does not reduce soybean axis elongation during the first one to two days of growth; afterwards, the hypocotyl becomes substantially shorter than that of controls (data not shown). This observation suggests that de novo gibberellin biosynthesis is not required for early axis elongation. Secondly, as detected by Northern blotting, expression of mRNA for copalyl diphosphate synthase, the early GA pathway enzyme that catalyzes the conversion of geranylgeranyl diphosphate to copalyl diphosphate (FIG. 1. of Hedden and Kamiya 1997. *Annu. Rev. Plant Physiol. Plant Mol. Biol.* 48:431–460.), begins about 1.5 days after planting (data not shown). This is well after germination and axis elongation have begun. Both of these observations support the hypothesis that soybean seed germination and early axis elongation are not dependent on de novo gibberellin biosynthesis.

In fact, as shown in the following experiment, mature soybean seeds contain quantities of bioactive gibberellins that may be sufficient to fuel seed germination and seedling axis elongation. The experimental procedures are as follows.

Plant Material

A3237 soybean seeds (Asgrow Seed Company, Des Moines, Iowa), are sown in vermiculite, and plants are grown in a growth chamber under a 12-hour light cycle. Seedlings are harvested at specific time points, and rinsed under cool tap water. Seedlings are cut into tissue fractions with a scalpel, and the tissue fractions kept on ice during the fractionation process. After tissue fractionation, samples are frozen in liquid nitrogen or placed at −80° C. overnight and lyophilized to dryness. Dry seeds are lyophilized directly. Imbibed seeds are placed on moist absorbent paper in trays, covered and placed in the growth chamber for five hours. For 0 DAP and imbibed seed (0.2 DAP), whole seed is extracted. For 1 DAP time point, data for the axis only is shown on this FIG. 38. For 3 and 5 DAP, data presented is for the hypocotyl. Data for the whole seedling is not presented because the one sample set, the cotyledon fraction of the 3 DAP seedlings, did not provide usable endogenous gibberellin data.

Extraction and Purification

Method A. Frozen tissue is ground to a fine powder in a mortar and pestle in liquid nitrogen. Cold 80% methanol is added to the frozen powder. Two nanograms of deuterated standards of $GA_1$ and $GA_4$ (17,17-$d_2$-$GA_1$ and 17,17-$d_2$-$GA_4$, provided by Lew Mander, Australian National University) are added to the methanol plus tissue powder prior to grinding. The homogenate is filtered (Whatman No. 42), the retentate is re-ground in fresh 80% cold methanol and filtered, and the filtrates are combined. The 80% methanol extract is added to a $C_{18}$ chromatography column (Baker-bond spe, J T Baker, Inc., Phillipsburg, N.J.). Gibberellins are eluted with 80% methanol, and the methanol is evaporated under vacuum. The aqueous portion of the extract is adjusted to approximately pH 3 with HCl and partitioned three times against hydrated ethyl acetate. The combined ethyl acetate fractions are evaporated under vacuum, resuspended in 35% acidified (0.05% v/v glacial acetic acid) methanol, filtered (0.25 mm, 25 mm Nylon Acrodisc, Gelman Sciences), and injected onto a C18 reverse-phase HPLC column (Xpertek Spherisorb ODS 4.6 mm×250 mm). $GA_1$ and $GA_4$ are eluted a flow rate of 1 ml/min using a 40-min linear gradient from 35% (v/v) acidified (0.05% v/v acetic acid) methanol; 65% acidified (0.05% v/v acetic acid) water to 100% acidified methanol into 1-ml fractions. Fractions containing $GA_1$ and $GA_4$ are pooled based on the elution of tritiated standards ($^3H$-$GA_1$, $^3H$-$GA_4$ and $^3H$-$GA_9$ (provided by R. Pharis, University of Calgary) injected previously. Pooled HPLC fractions are evaporated under vacuum and resuspended in methanol.

Method B. Tissue is frozen with dry ice and ground with a Waring blender to a fine meal. After sublimation of the carbon dioxide and weighing, the frozen powder is ground with a blender in 80% methanol/water after addition of deuterated $GA_1$ and $GA_4$ standards. The homogenate is filtered using a prewashed glass fiber filter pad and 2 ml of 0.1 N $NH_4OH$ is added. The extract is added to an equilibrated anion exchange chromatography column (AG-1-X8, 200–400 mesh, chloride form, Bio-Rad Laboratories, Richmond, Calif.). The column (1.7 cm OD×22 cm, topped with a 3 cm OD×8 cm reservoir) plus extract is washed with 100 ml deionized water and 100 ml methanol at high flow rates. These eluates are discarded. $GA_1$ and $GA_4$ are eluted with 100 ml 2% (v/v) HOAC/MeOH. The first 15 ml of the eluate is discarded. The anion exchange column eluate is evaporated under vacuum to dryness, dissolved in 5 ml deionized water, and added to a 20 cc Alltech Hi-Load $C_{18}$ column. The column plus sample is rinsed with water and hexane. The water and hexane washes are discarded. $GA_1$ and $GA_4$ are eluted with 10 ml of 25% and 50 ml of 50% ETOC/hexane with slow vacuum. The eluate is evaporated to dryness and resuspended in methanol.

GC/MS. GA samples in methanol are methylated with diazomethane and excess diazomethane and its solvent are removed with a stream of nitrogen. Each methylated sample is heated at 70° C. for approximately 45 minutes in BSTFA (N,O-bis(Trimethylsily)trifluroracetamide) and pyridine. Excess BSTFA is removed with a stream of nitrogen. An aliquot is injected into a gas chromatograph from GC/SIM (selected ion monitoring). The GC is typically programmed from 100° C. to 300° C. at 10° C./min. $GA_1$ and $GA_4$ levels are quantified by comparison of peaks for deuterated standards and endogenous $GA_1$ and $GA_4$ peaks.

Both $GA_1$ and $GA_4$ are detected in mature soybean seeds in the first experiment; the presence of $GA_1$ is confirmed in two subsequent experiments using two different GA purification methods (Table 8). $GA_4$ is not detected in the second two experiments. Based on three experiments, $GA_1$ levels in mature A3237 soybean seeds are between 0.14 and 0.85 ng/g fwt. $GA_4$, detected in one experiment only, is present at 0.33 ng/g fwt.

TABLE 8

Measurement of $GA_1$ and $GA_4$ in mature A3237 soybean seeds

| Experiment | Method | $GA_1$ (ng/gfwt) | $GA_4$ |
|---|---|---|---|
| 1 | A | 0.29 | 0.33 |
| 2 | A | 0.85 | n.d. |
| 3 | B | 0.14 | n.d. |

Gibberellin levels are calculated on a "ng/g fresh tissue weight" basis to provide information on the total increase/decrease in specific gibberellins during the course of development of a single soybean plant. $GA_1$ and $GA_4$ levels are also calculated on fresh weight, dry weight, and estimated in vivo concentration bases. $GA_1$ levels, measured on a ng/tissue basis, increased to a maximum at 3 days after planting (DAP) and then declined by 5 DAP (FIG. 38). In contrast, $GA_4$ levels increased to similar levels by 3 DAP and continued to increase by 5 DAP. Since both $GA_1$ and $GA_4$ are bioactive, a summary profile of bioactive gibberellin levels versus plant development is shown in FIG. 38. The combined levels of $GA_1$ and $GA_4$ stays approximately the same through 1 DAP, rises to a maximum at 3 DAP, and then stays approximately the same through 5 DAP.

The presence of significant amounts of bioactive gibberellins in mature soybean seeds is surprising. This result suggests that soybeans may store residual bioactive gibberellins from seed development in the mature seed. The levels detected are very low, but $GA_1$ has been detected three times using two different GA purification protocols. This level of gibberellins may be sufficient to increase axis elongation during germination/early seedling growth. Measurement of the levels of both $GA_1$ and $GA_4$ in seeds and seedlings demonstrates an increase after imbibition, and that the level $GA_1$ in hypocotyls correlates with hypocotyl elongation, which occurs between approximately 1–3 days after planting (FIG. 38). Measured gibberellin levels are initially low, and increase in the axis/hypocotyl about one to two days after imbibition. Presumably, the stored gibberellins promote very early seedling growth prior to de novo GA biosynthesis. FIG. 3 suggests that there is a lag of approximately 1 day in de novo gibberellin biosynthesis. This lag period is consistent with other data suggesting that soybean seedlings with impaired de novo GA biosynthesis, either through treatment with inhibitors or expression of an antisense construct of a key biosynthetic gene (CPS), do germinate and begin early seedling growth before substantial growth inhibition is observed. The results shown in FIG. 38 suggest that $GA_1$ levels correlate well with hypocotyl elongation; hypocotyl elongation is essentially complete by 5 DAP.

These results support the hypothesis that soybean seeds utilize gibberellins present in the mature seed for germination and/or early seedling growth until de novo gibberellin biosynthesis is sufficient to drive stem elongation after 1.5 days after planting. These results also provide insight into the endogenous levels in soybean that an optimal seed treatment, developed to restore normal growth and development to GA-deficient soybeans without oversupplying bioactive gibberellins during seedling emergence, would provide.

Control of Seedling Growth by Modification of GA Biosynthesis and Accumulation in planta The presence of bioactive gibberellins in mature seeds (e.g., Birnberg et al. (1986) *Plant Physiol.* 82:241–246; Rock et al. (1995) *Plant Hormones, Physiology, Biochemistry and Molecular Biology*, $2^{nd}$ Edition, P. J. Davies, Ed., Kluwer Academic Publishers, Dordrecht, pp. 671–697) and their presumed role in driving germination and seedling emergence, present a novel opportunity to create GA-deficient phenotypes of soybean and other self-fertile, non-hybrid plants, e.g., peas, beans, peppers, cucumbers, cotton, wheat, canola, rice, and tomato, of varying severity and developmental stage specificity in which endogenous GA levels can be manipulated so as to produce plants in which seed germination and early seedling growth can be reversibly inhibited. Understanding the identity, presence, and distribution over time of GAs in plant seeds, seedlings, and plants permits the selection of appropriate genes and promoters that can be used to produce transgenic seedlings and plants containing selectively modified GA levels, and therefore modifications in seed germination and early seedling growth phenotypes. Transgenic techniques can be used to produce plants in which inhibited seed germination/early seedling growth can be rescued (reversed) by the use of a GA "rescue agent." If, in fact, gibberellins stored in the seed are necessary to support very early seedling emergence growth, then transgenic approaches that interfere with this process may well provide desirable phenotypes. Conceivably, severe interference with these processes could produce plants that do not emerge at all.

Targeting of seed-stored and early seedling gibberellins in soybeans and other self-fertile, non-hybrid plants to produce phenotypes that are unable to emerge, or that emerge poorly, provides a number of different opportunities to develop seed rescue treatments. Restricting the requirement for exogenously-applied GA compounds to seed germination/seedling emergence/early seedling growth by transgenic techniques makes these developmental time frames attractive for a seed rescue treatment by GA compounds. The gibberellins studied to date are rapidly taken up by germinating seeds, and have a very short half-life in planta, i.e., about one day. This imposes a particular set of technical requirements in epicotyl-intensive GA-deficient soybeans, such as those containing the AX5/asCPScc cassette, which require more exogenous GA at about five to eight days after planting. In contrast, targeting the GA-deficient phenotype to the period from zero to about three days after planting facilitates the use of GA compounds on seeds/germinating seedlings at a time when these compounds can be conveniently made available to the germinating seed, and after which they dissipate rapidly in the seedling. This permits the use of $GA_3$ and/or other GA compounds in low amounts as a seed treatment system, soil drench, or foliar spray to rescue transgenic GA-deficient dwarf soybeans and other self-fertile, non-hybrid plants.

Transgenic plant technology permits the targeting, among others, of three stages of plant/seedling development: seed development, seed germination, and seedling growth, as well as throughout the plant life cycle when using a constitutive promoter. These stages can be targeted alone, or in various combinations. Such targeting can be achieved, for example, by employing promoters that drive gene expression during specific growth stages. For example, the Lea9 promoter is active during seed development (Galau et al. (1987) *Dev. Biol.* 123:213–221), the SIP promoter is active during seed imbibition (Heck et al. (1996) *Plant Mol. Biol.* 30:611–622), and the AX5 promoter is active during seedling growth (described above).

Growth stage-specific promoters can be used in combination with nucleic acid sequences encoding GA biosynthesis enzymes for cosuppression of endogenous GA biosynthetic pathway genes, and antisense DNAs to GA biosynthesis genes, such as the CPS gene, to produce transgenic plant lines with controllable seedling morphology. In addition, other GA pathway genes can be employed to effect control over GA levels, and therefore control over seedling growth and development. For example, the enzyme GA 2-oxidase inactivates endogenous gibberellins by catalyzing the addition of a hydroxyl group at carbon-2 of the A ring. Coding sequences for GA inactivating enzymes can be used alone or in combination with one another, or in various combinations with CPS gene antisense DNA and other GA biosynthetic enzyme antisense DNAs, and GA biosynthetic enzyme-encoding DNAs to achieve cosuppression, to control seedling growth and development. GA levels in transgenic plants produced by these methods can be reduced anywhere from about 90%, about 80%, about 70%, about 60%, about 50%, about 40%, about 30%, about 20%, or about 10% of normal, to levels below the limits of detection by current methods. This can be achieved by affecting GA biosynthesis, accumulation, or both.

The use of different developmental stage-specific promoters in combination with CPS antisense DNA, the GA 2-oxidase gene, and other GA-related DNAs permits the production of transgenic plants in which seedling growth and development can be selectively modified in multiple, different ways to affect the biosynthesis and accumulation of storage gibberellins during seed formation, as well as de novo biosynthesis during seed germination and seedling growth. This can be achieved by transforming plants with single promoter/gene constructs, or combinations of promoter/gene constructs to achieve the desired effect on morphology. Various of the above combination strategies can be employed to introduce these DNAs into transgenic plants. Cross pollination to produce a hybrid plant containing a mixture of the DNA constructs resulting in the desired phenotype. Sequentially transforming plants with plasmids containing each of the encoding DNAs of interest. Simultaneously cotransforming plants with plasmids containing each of the encoding DNAs. Transforming plants with a single plasmid containing two or more DNAs of interest. Transforming plants by a combination of any of the foregoing techniques in order to obtain a plant that expresses a desired combination of DNAs of interest.

Endogenous GA Levels in Germinating Soybean Seeds, and the Effect of Exogenously-applied $GA_3$ Application of $^{14}C$-$GA_3$ to Asgrow 3237 soybeans as a seed treatment via the hilum at a rate (5–20 ppm) within the range effective in rescuing the hypocotyl of dwarf, GA-deficient plants causes a substantial oversupply in the level of $GA_3$ compared to the levels of endogenous bioactive gibberellins $GA_1$ and $GA_4$ in germinating soybean seeds (FIG. 39). The data upon which FIG. 39 is based are taken from the experiment described below in the section entitled "Determination of half-lives and distribution of $^{14}C$-labeled GA compounds in planta". More particularly, the data in FIG. 39 are taken from the experiment in which $^{14}C$-$GA_3$ is applied to the hilum at 20 ppm.

As can be seen from the results presented in FIG. 39, at an application rate of 20 ppm, the calculated concentration of $GA_3$ delivered to the seedling axis at one day after planting (DAP) is approximately 100 times higher than the combined levels of endogenous bioactive GAs present in similar untreated tissue (4310 nM vs. 44.6 nm, respectively). The concentration of $GA_3$ in the seedling axis appeared to be directly proportional to the amount of $GA_3$ applied to the seed.

Effect of $GA_3$ on Stand Count and Yield in Soybeans $GA_3$ is highly active when applied to germinating soybean seeds, and can cause stand count and yield reduction under conditions of compacted soil and soil crusting prior to emergence. Note the data presented in Table 9. This may be due to over dosing of $GA_3$ at the wrong stage during germination and emergence, and/or the fact that $GA_3$ is not a natural growth regulator in soybeans.

TABLE 9

Effect of $GA_3$ seed treatment on soybean stand count and yield

| Seed Treatment | Plants per Acre | Yield (bushels/acre) |
|---|---|---|
| Untreated Control | 44,971 | 49.7 |
| 5 ppm $GA_3$ | 41,458 | 41.6 |
| 10 ppm $GA_3$ | 35,133 | 31.9 |
| 15 ppm $GA_3$ | 30,566 | 31.4 |

In this experiment seed of wild-type soybean variety A4922 (Asgrow) is treated with an aqueous solution of $GA_3$ using a Hege 11 seed treater (Hans-Ulrich Hege GmbH & Co., Waldenburg, Germany). Treated seed is planted about 1 inch deep in previously disced soil using a cone planter. The rows are about 30 inches (76.2 cm) apart, and 15 feet (457.2 cm) long. Seeds are spaced about 3 inches (7.62 cm) apart within the rows. The emerged plants are counted periodically, and seed yields are obtained at harvest. The plant counts and yields are converted to a per acre basis. As can be seen from the data in Table 9, plants per acre and yield both decreased as $GA_3$ dose in the seed treatment increased. The decrease in plant population per acre is due to lack of emergence, in part due to broken and unhooked hypocotyls. In addition, some of the emerged plants are abnormal, e.g., with small, broken cotyledons, etc. Other seeds germinated, but seedlings did not emerge out of the ground.

Desirable Properties of GA "Rescue" Compounds $GA_3$ may not be a preferred GA for rescuing GA-deficient dwarf soybeans.

Preferred compounds for rescuing transgenic soybeans and other plants exhibiting symptoms of GA deficiency are GAs or other GA compounds having one or more of the following properties:

(1) That are not directly or intrinsically bioactive per se;

(2) That are not immediately bioactive, or that exhibit low bioactivity compared to GA compounds naturally occurring in the species or variety of plant to which they are applied;

(3) That are available for bioconversion in the appropriate tissue, e.g., the hypocotyl and/or epicotyl, and that can be converted to bioactive gibberellins in planta in the appropriate amount as needed by the seedling at or by the appropriate developmental stage;

(4) That are sufficiently stable in planta, in soil, and on plant surfaces to exert their rescue effect;

(5) That are translocatable within the seedling or plantlet;

(6) That exhibit selective bioactivity in specific tissue(s) (tissue specificity), such as the hypocotyl and/or epicotyl. This tissue-specific bioactivity can also be developmental stage-specific or intensive (temporal specificity);

(7) That are capable of rescuing GA-deficient plants without over-supplying bioactive gibberellins during the early stages of seedling emergence;

(8) That do not cause undesirable hypocotyl or epicotyl overelongation during seedling emergence;

(9) That exhibit lower bioactivity on normal plants than on GA-deficient plants, and that therefore do not cause undesirable overelongation of normal, non-GA-deficient plants;

(10) That are capable of restoring substantially normal growth, development, and morphology in GA-deficient plants without causing substantial abnormal growth, development, and morphology due to oversupply or activity of bioactive GAs;

(11) That do not cause increased hypocotyl fragility;

(12) That do not adversely affect seedling emergence;

(13) That do not adversely affect plant stand count or yield;

(14) That do not cause stem overelongation;

(15) That do not cause thinning of stem cell walls;

(16) That do not weaken stems;

(17) That do not promote insect and disease infestation; and

(18) That are cheaply produced.

Such compounds will "rescue" transgenic or non-transgenic GA-deficient plant lines, but will not cause overelongation in GA-deficient and non-GA-deficient lines. In essence, these GA compounds will permit seedlings and plants to self-regulate the biosynthesis of GA compounds, such as physiologically active GAs, therefrom to overcome any GA deficit where, when, and to the extent, necessary to substantially restore normal seedling and plant morphology. In some cases, it is desirable that the GA compound only partially restores a morphological trait such as height. Such "partial rescue" is defined as restoration of a morphological trait, such as height, in an amount in the range of from about 5% to about 70%, or from about 10% to about 60%, or from about 20% to about 50%, or from about 30% to about 40%, compared to that in an otherwise identical seedling or plant in which the capacity to biosynthesize a GA is not inhibited. As shown below, such a GA compound is $GA_{12}$. In the case of soybeans, the appropriate time frame for activity is in the range of from about one day after planting to about three days after planting, preferably at about two days after planting. Such compounds can be applied to transgenic seeds, seedlings, or plants designed to contain a lesion or other modification in GA biosynthesis resulting in a GA deficiency. If a GA compound is used for rescue of GA-deficient soybeans or other plants, then the seedlings or plants may convert the inactive or poorly active GA compound to a physiologically bioactive GA compound such as a GA as needed, thus eliminating the possibility of detrimental overexposure at an inappropriate time during growth and development. It is also possible, of course, that the GA compound itself exhibits the desired activity profile, and therefore requires no further modification in planta.

As shown in FIGS. 38 and Table 8, $GA_1$ and $GA_4$ are major GAs present in mature soybean seeds and germinating seedlings. The level of $GA_1$ correlates with hypocotyl elongation. As shown in FIG. 38, treatment of soybean seeds with $GA_3$ at 20 ppm greatly oversupplies this gibberellin compared to the levels of endogenous $GA_1$ and $GA_4$, and results in reduced stand count (number of fully emerged, healthy seedlings with fully expanded cotyledons) and yield reduction under conditions of compacted soil and soil crusting prior to emergence. One can therefore hypothesize that while $GA_3$ may not be an appropriate rescue agent for all GA-deficient dwarf soybeans under these conditions, it may be useful on some transgenic GA-deficient lines or plants. On the other hand, $GA_1$ and $GA_4$, or precursors or biosynthetic intermediates thereof, or derivatives of any of these compounds, may be appropriate rescue agents. In the case of $GA_1$ deficiency, review of the gibberellin biosynthetic pathway suggests that $GA_{12}$, $GA_{53}$, $GA_{44}$, $GA_{19}$, and/or $GA_{20}$, may be appropriate rescue agents for GA-deficient soybeans exhibiting retarded hypocotyl elongation. In the case of $GA_4$ deficiency, $GA_{12}$, $GA_{15}$, $GA_{24}$, and/or $GA_9$ may be appropriate rescue agents.

In order to evaluate the ability of a variety of different GA compounds to rescue constitutively GA-deficient transgenic dwarf soybeans transformed with the FMV/asCPScc cassette, several greenhouse and field tests are conducted. The first two tests are conducted in the greenhouse, and are aimed at determining the biological activity of the compounds and their ability to rescue constitutively GA-deficient transgenic dwarf soybean without elongating wild-type soybeans. Three later tests are conducted in the field to confirm the greenhouse results, and to determine the ability of selected GA compound leads to provide rescue of constitutively GA-deficient transgenic dwarfs without loss of stand and/or without elongation of wild-type soybeans in compacted soil.

The initial compounds tested are $GA_3$, $GA_1$, $GA_{20}$, $GA_9$, $GA_3$-3-acetate, kaurenoic acid, $GA_{12}$, $GA_5$, kaurene, $GA_7$-methyl ester, $GA_4$-methyl ester, ent-7,13-dihydroxy-kaurenoic acid (steviol), $GA_{12}$-aldehyde, and $GA_4$. These compounds are selected to represent a wide spectrum of locations within the gibberellin biosynthetic pathway (Hedden and Kamiya (1997) *Annu. Rev. Plant. Physiol Plant Mol. Biol.* 48:431–460) after the step catalyzed by copalyl diphosphate synthase (CPS), which is targeted for inhibition by antisense constructs. These compounds are evaluated by three criteria: 1) Their effectiveness in rescuing hypocotyls of GA-deficient soybean plants; 2) Their ability to avoid causing overelongation of hypocotyls of wild-type soybeans at a concentration that rescues hypocotyls of GA-deficient soybean plants. This is important because overelongation can lead to hypocotyl breakage, lodging of plants, disease susceptibility, and poor stature (abnormal phenotype); and 3) Whether they produce less emergence drag (reduced emergence of seedlings above ground level due, for example, to weak or broken hypocotyls, etc.) than $GA_3$. Based on the greenhouse and field results, four compounds, i.e., $GA_3$-3-acetate, $GA_5$, $GA_9$, and $GA_{12}$, are shown to provide acceptable to good rescue of constitutively GA-deficient transgenic dwarf soybeans (an equal mixture of transgenic lines 719–2 and 719+17) with acceptable stand count, without causing excessive elongation of wild-type soybeans (varieties A3237 and A4922). In these experiments, the other compounds either did not exhibit substantial biological activity, or provided rescue of constitutive transgenic dwarfs while causing some or excessive elongation of wild-type soybeans. Some difficulty is encountered in solubilizing several of the test compounds in the treatment solutions, which might have led to the conclusion that they are not biologically active. Subsequent experiments are carried out to solubilize those compounds prior to testing them again as seed treatments. Parameters that can be varied to improve solubility include the nature of the carrier solvent and pH. In any event, appropriate carrier solvents are those that are non-phytotoxic.

Four additional field tests are conducted with $GA_3$, $GA_3$-3-acetate, $GA_5$, $GA_9$, and $GA_{12}$. Two tests are performed in a light textured soil, while two other tests are conducted in a heavy textured soil. In each soil type, two tests are conducted, one each with constitutively GA-deficient transgenic dwarf soybean line 719 and with wild-type line A4922. The objectives of these studies are to determine: a) if the selected precursors/derivatives provide rescue of constitutively GA-deficient transgenic dwarf soybeans when applied as seed coat treatments; b) the rate ranges that can provide rescue of constitutively GA-deficient transgenic dwarfs; and c) the rate ranges that cause reduced stand and/or overelongation of wild-type plants. $GA_3$, $GA_3$-3-acetate, $GA_5$, and $GA_9$ each provided rescue of constitutively GA-deficient transgenic dwarfs with crop safety. Although $GA_{12}$ is effective in rescuing constitutive transgenic dwarfs, plants are short in stature.

Preparation of Stock Solutions for Biological Testing

Stock solutions of selected GA compounds are prepared for use in evaluating their potential to restore normal hypocotyl elongation in constitutively GA-deficient transgenic dwarf soybean seedlings without over-elongating wild-type soybeans. Selected compounds are initially dissolved in ethanol for testing on soybean. Three separate stock solutions are prepared for three separate experiments (Experiments I-III).

TABLE 10

GA Compounds Tested
Selected GA compounds are obtained from Sigma Chemical Company, St. Louis, MO, or from Lew Mander, Australian National University, Canberra, Australia, as indicated below.

| Compound | Source | Product Number | Lot Number |
|---|---|---|---|
| $GA_3$ | Sigma | G-7645 | 46H0994 |
| $GA_1$ | Mander | | |
| $GA_{20}$ | Mander | | |
| $GA_9$ | Mander | | |
| kaurene | Mander | | |
| $GA_7$ methyl ester | Sigma | G-0143 | 72H3805 |
| $GA_4$ methyl ester | Sigma | G-9892 | 82H3838 |
| $GA_3$-3-acetate | Sigma | G-3268 | 115H37931 |
| kaurenoic acid | Mander | | |
| steviol | Mander | | |
| $GA_{12}$-aldehyde | Mander | | |
| $GA_{12}$ | Mander | | |
| $GA_5$ | Mander | | |
| $GA_4$ | Mander | | |

Solutions for Experiment I

Each of the compounds noted above is weighed to the nearest 0.1 mg in a pre-tarred 1.5-ml polypropylene vial with a screw-top lid. Absolute ethanol is added to the weighed powder to prepare a 25 mg/ml solution. Solutions are thoroughly mixed using a vortex mixer. A stainless steel spatula is used to crush any particulate material remaining after extensive mixing. Vials are left overnight at room temperature, and then remixed to form the concentrated ethanol stock solutions. The presence of undissolved material is noted throughout this procedure. In addition, the solubility of 0.25 mg/ml compound in water is tested. The results are shown in Table 11.

TABLE 11

Particulate material present in solutions after mixing

| Compound | Initial Mixing | O/N Incubation | 100× Diln w/water |
|---|---|---|---|
| $GA_3$ | NO | NO | NO |
| $GA_1$ | NO | NO | NO |
| $GA_{20}$ | NO | NO | NO |
| $GA_9$ | NO | NO | YES |
| kaurene | YES | YES | YES |
| $GA_7$, methyl ester | NO | NO | YES |
| $GA_4$, methyl ester | NO | NO | NO |
| $GA_3$-3-acetate | NO | NO | NO |
| kaurenoic acid | NO | NO | YES |
| steviol | YES | NO | YES |
| $GA_{12}$-aldehyde | NO | NO | YES |

TABLE 11-continued

Particulate material present in solutions after mixing

| Compound | Initial Mixing | O/N Incubation | 100× Diln w/water |
|---|---|---|---|
| $GA_{12}$ | YES | YES | NO |
| $GA_5$ | NO | NO | NO |
| $GA_4$ | NO | NO | NO |

Solutions for Experiment II

A subset of the compounds tested in Experiment I is selected for further evaluation in Experiment II: kaurenoic acid, $GA_1$, $GA_3$, $GA_3$-3-acetate, $GA_5$, $GA_9$, $GA_{12}$, and $GA_{20}$. Stock solutions (25 mg/ml) in ethanol are prepared as described for Experiment I. For GA9 only, a 12.5 mg/ml stock solution is prepared instead of a 25 mg/ml solution due to limited compound availability. The $GA_{12}$ stock solution contained particulate matter after the overnight incubation, as noted in Experiment I. The 25 mg/ml stock solutions are further diluted to 2.5 and 0.25 mg/ml with ethanol. 0.3 ml of each concentration of each gibberellin/precursor is supplied for biological testing.

Solutions for Experiment III

A subset of the compounds tested in Experiment II is selected for further evaluation in Experiment III: kaurenoic acid, $GA_3$, $GA_3$-3-acetate, $GA_5$, $GA_9$, and $GA_{12}$. 25 mg/ml stock solutions in ethanol are prepared as in Experiments I and II. Due to limited compound availability, a 14 mg/ml stock of $GA_9$ is prepared instead of a 25 mg/ml solution. Freshly prepared stock solutions are mixed with previously prepared solutions (Experiments I and II, stored at −20° C. in ethanol) to obtain a sufficient supply for biological testing. Stock solutions (25 mg/ml) are supplied for biological testing.

Experiment I: Greenhouse Test

The objective of this experiment is to determine if any of the selected GA compounds exhibit biological activity on constitutively GA-deficient transgenic dwarf soybeans (line 719) or wild-type (line A3237) soybeans at a concentration of 0.25 mg/ml.

Compounds are first prepared as 25 mg/ml solutions in ethanol as described above, and then diluted into 40 ml of water to prepare the final 0.25 mg/ml treatment solutions. Visual observations on solubilities (milky, clear, etc.) of the treatment solutions are noted. The treatment solutions are divided into two 20 ml portions, each in 50 ml plastic centrifuge tubes. In addition to treating seeds with solutions containing the test compounds, untreated seeds and seeds imbibed in ethanol-water solution (300 μl ethanol in 30 mls of water) are also included in this experiment as controls. In the latter case, 20 seeds are imbibed in 30 mls of solution for six hours.

Two soybean varieties are selected for testing: constitutively GA-deficient transgenic dwarf soybean line 719 (plasmid pMON29801, constitutive FMV promoter/asCPScc; which is a mixture of 719-2 and 719+17), and A3237, the wild-type parent material. The line 719 seed used in these early experiments consisted of a segregating population of three different phenotypes: seed producing seedlings with normal-looking morphology, including hypocotyls of normal length as in wild-type plants; seed producing seedlings having hypocotyls shorter than those in wild-type plants, but in which cotyledons do not rest on the soil, i.e., "intermediate dwarfs"; and seed producing seedlings having little or no hypocotyls, wherein the cotyledons touch the ground, i.e., "extreme dwarfs." Twenty seeds of each variety are imbibed in 30 mls of the test solutions for 5 hours. After imbibition, seeds are removed from the test tubes, placed on wax paper to dry, and planted in bread pans containing farm soil amended with fertilizer at 20 seeds/pan. Seeds are covered with 0.5" of vermiculite. Pans are transferred to the greenhouse, which had day/night temperatures of 86/68° F. (30/20° C.), and subirrigated. Illumination is at a light intensity of 300–400 $\mu molm^{-2}s^{-1}$ photosynthetic photon flux; 16 hours light/8 hours dark. Subsequent waterings are also through sub-irrigation until the test is terminated three weeks later. Observations included the number of dwarf, intermediate, and tall plants; plant height; uniformity of rescue; and any visual effects. The results are shown in Table 12.

TABLE 12

Effect of Various GA Compounds at 0.25 mg/ml on Constitutively GA-Deficient Transgenic Dwarf Soybeans and Wild-Type Soybeans in the Greenhouse

| GA Compound | Trt # | *Observation on Transgenic Line 719 | Trt # | *Observation on Wild-Type Line A3237 |
|---|---|---|---|---|
| $GA_3$ | 1 | 3 | 17 | 3 |
| $GA_1$ | 2 | 4 | 18 | 4 |
| $GA_{20}$ | 3 | 4 | 19 | 4 |
| $GA_9$ | 4 | 3 | 20 | 3 |
| Kaurene | 5 | 0 | 21 | 0 |
| $GA_7$-methyl ester | 6 | 2 | 22 | 1 |
| $GA_4$-methyl ester | 7 | 1 | 23 | 1 |
| $GA_3$-3-acetate | 8 | 3 | 24 | 3 |
| Kaurenoic acid | 9 | 1, some rescue | 25 | 0 |
| Steviol | 10 | 0 | 26 | 0 |
| $GA_{12}$-aldehyde | 11 | 0 | 27 | 0 |
| $GA_{12}$ | 12 | 1, Rescued, shorter plants; no over-elongation | 28 | −1 |
| $GA_5$ | 13 | 4 | 29 | 4 |
| $GA_4$ | 14 | 2 | 30 | 2 |
| Untreated Control | 15 | 0 | 31 | 0 |
| Ethanol | 16 | 0 | 32 | 0 |

*−1 = treated plants are shorter as compared to untreated plants; 0 = treated plants had the same stature as untreated plants; 1 = treated plants are slightly elongated as compared to untreated plants; 2 = treated plants are moderately elongated as compared to untreated plants; 3 = treated plants are highly elongated as compared to untreated plants; 4 = treated plants are extremely elongated as compared to untreated plants.

The data in Table 12 demonstrate that at 0.25 mg/ml, $GA_3$, $GA^1$, $GA_{20}$, $GA_9$, $GA_3$-3-acetate, and $GA_5$ caused excessive elongation in both the constitutive transgenic dwarf and wild-type soybean lines. $GA_7$-methyl ester, $GA_4$-methyl ester, and $GA_4$ at this concentration caused slight to medium elongation in both lines. Kaurene, steviol, and $GA_{12}$ aldehyde exhibited no substantial activity in either line when applied via imbibition. $GA_{12}$ and kaurenoic acid resulted in rescue (elongated hypocotyls) with very little elongation. It should be noted that several of the compounds, i.e., $GA_9$, kaurene, kaurenoic acid, steviol, $GA_4$-methyl ester, $GA_{12}$, and $GA_{12}$-aldehyde, are less soluble in water during imbibition, perhaps contributing to some lower activity and differential activity among the various compounds in this experiment.

Experiment II: Second Greenhouse Test

The objective of this test is to evaluate further the results of the initial greenhouse test with respect to a subset of the compounds tested in Experiment I, i.e., kaurenoic acid, $GA_1$, $GA_3$, $GA_3$-3-acetate, $GA^5$, GA9, $GA_{12}$, and $GA_{20}$, at concentrations equal to or below those used in Experiment I.

Company, Marysville, Ohio ), and covered with 0.5" Metromix. Covered pans are transferred to the greenhouse and subirrigated. Illumination is at a light intensity of 300–400 $\mu molm^{-2}s^{-1}$ photosynthetic photon flux; 16 hours light/8 hours dark. Subsequent waterings are also through subirrigation until the test is terminated three weeks later. Observations included the number of dwarf, intermediate, and tall plants; plant height; uniformity of rescue; and any visual effects. Digital photographs are also taken. The results are shown in Table 13.

TABLE 13

Effect of Various Concentrations of Selected GA Compounds on Constitutively GA-Deficient Transgenic Dwarf and Wild-Type Soybeans in the Greenhouse

| GA Compound, mg/ml Concentration | Trt # | Significant Visual Observations on Line A3237 | Trt # | Significant Visual Observations on Line 719 |
|---|---|---|---|---|
| $GA_3$ 0.25 | 1 | Poor emergence | 28 | Excessive elongation |
| $GA_3$ 0.025 | 2 | | 29 | Excessive elongation |
| $GA_3$ 0.0025 | 3 | | 30 | Excessive elongation |
| $GA_1$ 0.25 | 4 | Excessive elongation | 31 | |
| $GA_1$ 0.025 | 5 | | 32 | Good rescue of dwarfs |
| $GA_1$ 0.0025 | 6 | | 33 | Good rescue of dwarfs |
| $GA_{20}$ 0.25 | 7 | Excessive elongation | 4 | Excessive elongation |
| $GA_{20}$ 0.025 | 8 | | 35 | Good rescue of dwarfs |
| $GA_{20}$ 0.0025 | 9 | | 36 | Good rescue of dwarfs |
| $GA_9$ 0.125 | 10 | Normal height | 37 | Good rescue, no elongation |
| $GA_9$ 0.0125 | 11 | | 38 | Good rescue of dwarfs |
| $GA_9$ 0.00125 | 12 | | 39 | Poor rescue |
| $GA_3$-3-Actetate 0.25 | 13 | | 40 | Excessive elongation |
| $GA_3$-3-Acetate 0.025 | 14 | | 41 | Poor rescue |
| $GA_3$-3-Acetate 0.0025 | 15 | Normal height | 42 | Good rescue, no elongation |
| Kaurenoic Acid 0.25 | 16 | | 43 | Poor rescue |
| Kaurenoic Acid 0.025 | 17 | | 44 | Poor rescue |
| Kaurenoic Acid 0.0025 | 18 | | 45 | Poor rescue |
| $GA_{12}$ 0.25 | 19 | Short plants | 6 | Good rescue, no elongation, short plants |
| $GA_{12}$ 0.025 | 20 | | 47 | Incomplete rescue |
| $GA_{12}$ 0.0025 | 21 | | 48 | Poor rescue |
| $GA_5$ 0.25 | 22 | Excessive elongation | 49 | Excessive elongation |
| $GA_5$ 0.025 | 23 | Normal height | 50 | Good rescue, no elongation |
| $GA_5$ 0.0025 | 24 | | 51 | Good rescue of dwarfs |
| Water | 25 | | 52 | |
| Ethanol | 26 | | 53 | |
| Dry seed | 27 | | 54 | |

All compounds are tested at final concentrations of 0.25, 0.025, and 0.0025 mg/ml except for $GA_9$, which is tested at 0.125, 0.0125, and 0.00125 mg/ml. (The compounds are tested in Experiment I at only one concentration, i.e., 0.25 mg/ml). Test tubes contained 300, 30, or 3 ml of ethanol solution per tube. Final volumes are made up to 30 ml with deionized water. After shaking, the treatment solutions (15 ml each) are transferred to each of two 50 ml test tubes. Treatments 1 to 27 are performed on wild-type line A3237; treatments 28 to 54 are performed on constitutively GA-deficient transgenic dwarf soybean line 719 (a mixture of 719-2 and 719+17). Twenty seeds are used in each treatment. Dry seed, ethanol/water-imbibed seed (1% ethanol in water, v/v), and water-imbibed seeds are included as controls. Seeds are imbibed for 6 hours in the test solutions, then planted in bread pans containing Metromix 350 (The Scotts The results presented in Table 13 demonstrate that in this experiment, $GA_9$ at 0.125 mg/ml, $GA_3$-3-acetate at 0.0025 mg/ml, $GA_{12}$ at 0.25 mg/ml, and $GA_5$ at 0.025 mg/ml resulted in good rescue, with no overelongation, in constitutive dwarf transgenic line 719. The improved results with $GA_9$ in this experiment compared with that obtained in the first experiment may have been due to the lower concentrations used. Similarly, in this experiment, $GA_3$-3-acetate at 0.0025 mg/ml and $GA_5$ at 0.025 mg/ml yielded improved results compared to the same compounds used at 0.25 mg/ml in experiment I, i.e., concentrations 1/100 and 1/10, respectively, of those used in experiment I. This suggests that concentration may be a result-affective variable. Finally, the results with $GA_{12}$ are roughly comparable between this and the preceding experiment.

The results of the first two greenhouse experiments are summarized in Table 14.

TABLE 14

Summary of First Two Greenhouse Experiments on the Biological Activity of GA Compounds in Constitutively GA-Deficient Transgenic Dwarf and Wild-Type Soybeans

| GA Compound | Concentration, mg/ml solution (ethanol-water) | *Rescue of GA-deficient soybeans | **Elongation of wild-type soybeans |
|---|---|---|---|
| $GA_3$ | 0.25 | + | + |
|  | 0.025 | + | + |
|  | 0.0025 | + | + |
| $GA_1$ | 0.25 | + | + |
|  | 0.025 | + | + |
|  | 0.0025 | + | − |
| $GA_{20}$ | 0.25 | + | + |
|  | 0.025 | + | + |
|  | 0.0025 | + | + |
| $GA_9$ | 0.25 | + | + |
|  | 0.125 | + | 0 |
|  | 0.0125 | + | 0 |
|  | 0.00125 | 0 | − |
| $GA_3$-3-acetate | 0.25 | + | + |
|  | 0.025 | + | + |
|  | 0.0025 | + | 0 |
| Kaurenoic Acid | 0.25 | ? | − |
|  | 0.025 | 0 | 0 |
|  | 0.0025 | 0 | 0 |
| $GA_{12}$ | 0.25 | + | − |
|  | 0.025 | + | − |
|  | 0.0025 | 0 | 0 |
| $GA_5$ | 0.25 | + | + |
|  | 0.025 | + | 0 |
|  | 0.0025 | + | 0 |
| Kaurene | 0.25 | 0 | 0 |
| $GA_7$-methyl ester | 0.25 | 0 | + |
| $GA_4$-methyl ester | 0.25 | 0 | + |
| Steviol | 0.25 | 0 | 0 |
| $GA_{12}$-aldehyde | 0.25 | 0 | 0 |
| $GA_4$ | 0.25 | + | + |

*+ = transgenic soybeans are rescued; 0 = transgenic soybeans are not rescued
**+ = wild type soybeans are elongated; 0 = wild type soybeans are not affected;
− = wild type soybeans are shorter than untreated plants

Experiments III and IV: Field Tests

The objective of these experiments is to determine if there is a greenhouse to field translation of results with selected GA compounds with respect to rescue of constitutively GA-deficient transgenic dwarf soybeans and elongation of wild-type plants. Experiment III is carried out on wild-type line A3237; experiment IV is carried out on constitutively GA-deficient transgenic dwarf soybean line 719 (719−2 and 719+17). For the first field trial, the solutions previously used for the second greenhouse test, and stored in the freezer, are employed. The solutions used for imbibing line A3237 and constitutively GA-deficient transgenic dwarf soybean line 719 in greenhouse test 2 are pooled to produce approximately 30 ml of solution. For comparison, freshly prepared solutions of $GA_3$ are also employed. The compounds tested included kaurenoic acid, fresh $GA_3$, stored $GA_3$, $GA_3$-3-acetate, $GA_5$, $GA_9$, and $GA_{12}$. The concentrations tested are 0.25, 0.025, and 0.0025 mg/ml. Seeds of line A3237 are imbibed for 8 hours. Untreated dry seeds served as controls. After imbibition, the remaining solutions are returned to the freezer. Seeds are kept on the benchtop at room temperature overnight. At 7 PM the next day, they are planted. Fifty seeds are planted 1 inch (2.54 cm) deep in two five foot (152.4 cm) rows, and the soil is compacted following planting. Seeds of constitutive transgenic dwarf line 719 are imbibed for 8 hours using the same solutions as used for line A3237, and 25 seeds are planted 1 inch (2.54 cm) deep in 5 foot (152.4 cm) rows behind the A3237 study. Untreated dry seeds served as controls. Following planting line 719, all plots (both A3237 and line 719) are compacted by driving an all-terrain vehicle over the planted rows twice, and watered. All GA solutions are discarded. The results are shown in Table 15 for constitutively GA-deficient transgenic dwarf line 719 only as insufficient A3237 germinated to make any useful observations. Observations included number of plants that germinated, number rescued, and visual observations.

Two points should be noted concerning the data in Table 15. First, there are no entries in the "% of dwarfs rescued" column for treatments 1 and 2, i.e., the untreated controls. As explained previously, the line 719 seed used in these early experiments consisted of a segregating population of three phenotypes, i.e., seed producing seedlings with essentially normal morphology; seed producing "intermediate dwarfs"; and seed producing "extreme dwarfs." The number of dwarfs not "rescued" among untreated controls 1 and 2 represent extreme dwarfs; no dwarfs are actually rescued since no GA compound is applied to these seeds. Secondly, "% of dwarfs rescued" for treatments 3–23 is calculated as follows: The number of true dwarfs per plot is calculated as the average of the number of dwarfs not rescued in treatments 1 and 2, i.e., as 8+9/2=8.5. Next, the number of dwarfs not rescued in any treatment is subtracted from 8.5. Thus, for example, in treatment 4, one dwarf is not rescued; 8.5−1=7.5. Finally, the percentage of dwarfs rescued is calculated as 7.5/8.5×100=88.2%.

TABLE 15

Effect of Selected GA Compounds on Constitutively GA-Deficient Transgenic Dwarf Soybean Line 719 Plants in the Field

| Trt No. | GA Compound, mg/ml | Total Plants | No. of Dwarfs Not Rescued | % of Dwarfs Rescued | Visual Observations on Transgenic Line 719 |
|---|---|---|---|---|---|
| 1 | Untreated control | 22 | 8 | — |  |
| 2 | Untreated control | 21 | 9 | — |  |
| 3 | $GA_3$ fresh 0.0025 | 13 | 0 | 100 |  |
| 4 | $GA_3$ fresh 0.025 | 13 | 1 | 88.2 |  |
| 5 | $GA_3$ fresh 0.25 | 1 | 0 | 100 |  |
| 6 | $GA_3$ stored 0.25 | 7 | 0 | 100 | Extremely elongated plants |
| 7 | $GA_3$ stored 0.025 | 9 | 0 | 100 | Extremely elongated plants |

TABLE 15-continued

Effect of Selected GA Compounds on Constitutively GA-Deficient Transgenic Dwarf Soybean Line 719 Plants in the Field

| Trt No. | GA Compound, mg/ml | Total Plants | No. of Dwarfs Not Rescued | % of Dwarfs Rescued | Visual Observations on Transgenic Line 719 |
|---|---|---|---|---|---|
| 8  | $GA_3$ stored 0.0025 | 14 | 0 | 100 | |
| 9  | $GA_9$ stored 0.25 | 17 | 0 | 100 | Slightly elongated plants |
| 10 | $GA_9$ stored 0.025 | 22 | 0 | 100 | Not uniform in height, 1 broken plant |
| 11 | $GA_9$ stored 0.0025 | 20 | 7 | 17.6 | |
| 12 | $GA_3$-3-Ac stored 0.25 | 3 | 0 | 100 | Extremely elongated plants |
| 13 | $GA_3$-3-Ac stored 0.025 | 1 | 0 | 100 | |
| 14 | $GA_3$-3-Ac stored 0.0025 | 21 | 0 | 100 | Not uniform in height, 2 broken plants |
| 15 | Kaurenoic acid stored 0.25 | 22 | 6 | 29.4 | |
| 16 | Kaurenoic acid stored 0.025 | 17 | 4 | 52.9 | |
| 17 | Kaurenoic acid stored 0.0025 | 23 | 5 | 41.2 | |
| 18 | $GA_{12}$ stored 0.25 | 20 | 0 | 100 | Uniform in height, 3 broken plants, Short rescued plants |
| 19 | $GA_{12}$ stored 0.025 | 22 | 4 | 52.9 | |
| 20 | $GA_{12}$ stored 0.0025 | 20 | 5 | 41.2 | |
| 21 | $GA_5$ stored 0.25 | 7 | 0 | 100 | Extremely elongated plants |
| 22 | $GA_5$ stored 0.025 | 20 | 0 | 100 | Not uniform in height, 1 broken plant, slightly elongated |
| 23 | $GA_5$ stored 0.0025 | 25 | 8 | 5.9 | |

The rate response (dose response) data for $GA_3$, $GA_3$-3-acetate, and $GA_5$ in Table 14 indicate that low rates result in less stand reduction than high rates (note the "Total plants" column). There is a good rate response with $GA_5$ with respect to plant count and rescue. Rescue is observed with the high rate (0.25 mg/ml) of $GA_{12}$. Treatment with $GA_{12}$ resulted in good emergence. All $GA_{12}$-treated plants are rescued with no excessive elongation and excellent plant height uniformity at 0.25 mg/ml. $GA_{12}$-treated plants appeared shorter than untreated ones. There is no rate response to $GA_{12}$ with respect to stand, and there is no overelongation of plants. Treatment with $GA_3$ resulted in poor emergence at all rates. While all emerged plants are rescued, there is excessive elongation at all rates. Treatment with $GA_9$ resulted in slight elongation, and no uniformity in height. Treatment with $GA_3$-3-acetate resulted in excessive elongation, and no uniformity in plant height. $GA_5$ treatment resulted in slight to excessive elongation, and no uniformity in plant height. Finally, kaurenoic acid treatment resulted in poor uniformity in plant height.

Fifth and Sixth Field Tests

The objective of these tests is to determine the highest concentrations of the available GA compounds that do not adversely affect emergence of constitutive transgenic dwarf soybean seedlings (line 719).

Fresh stock solutions of compounds are prepared for this test. Kaurenoic acid is tested at 0.025 and 0.25 mg/ml; $GA_3$ is tested at 0.025, 0.25, and 0.5 mg/ml; $GA_3$-3-acetate at 0.025 and 0.25 mg/ml; $GA_5$ at 0.025 and 0.25 mg/ml; $GA_9$ at 0.025 and 0.04 mg/ml; and $GA_{12}$ at 0.025 and 0.25 mg/ml. Stock solutions are prepared in ethanol in 50 ml plastic centrifuge tubes; deionized water is then added to make up the volumes to 30 ml. The final solutions contained 300 µl ethanol in 30 mls. 50 seeds of constitutively GA-deficient transgenic dwarf soybean line 719 are placed in each vial. Seeds are imbibed for 6 hours, and planted 1" deep in a single row in moist to wet soil. They are then covered with dry soil, and the row is compacted twice with an all-terrain vehicle. Untreated dry seeds served as controls. The GA solutions are placed on dry ice until reuse the next day.

The next day, additional seeds of constitutive transgenic dwarf line 719 (50 seeds/treatment) are imbibed in the remaining treatment solutions for 5 hours, and planted in moist soil. The rows are compacted twice. The results are shown in Table 16.

TABLE 16

Effect of Various GA compounds on emergence of constitutively GA-deficient transgenic dwarf soybean line 719

| Trt. No. | GA Compound, g/ml | Total Emerged | Visual Observations on Transgenic Line 719 |
|---|---|---|---|
| 1  | Untreated control | 21 | Poor and erratic emergence |
| 2  | $GA_3$ 0.025 | 15 | Hypocotyl hooks and broken plants; over elongation |
| 3  | $GA_3$ 0.25 | 9 | Hypocotyl hooks and broken plants; over elongation |
| 4  | $GA_3$ 0.5 | 1 | Hypocotyl hooks only; rate response |
| 5  | $GA_9$ 0.025 | 24 | No dwarfs in plots |
| 6  | $GA_9$ 0.04 | 11 | |
| 7  | $GA_3$-3-Ac 0.025 | 2 | |
| 8  | $GA_3$-3-Ac 0.25 | 1 | Overelongation |
| 9  | Kaurenoic acid 0.025 | 20 | Poor rescue |
| 10 | Kaurenoic acid 0.25 | 10 | Poor stand |
| 11 | $GA_5$ 0.025 | 21 | Good emergence; no dwarfs in plot; good |

TABLE 16-continued

Effect of Various GA compounds on emergence of constitutively GA-deficient transgenic dwarf soybean line 719

| Trt. No. | GA Compound, g/ml | Total Emerged | Visual Observations on Transgenic Line 719 |
|---|---|---|---|
| 12 | $GA_5$ 0.25 | 3 | uniformity; good rescue; good stand Poor emergence; frozen and broken hypocotyl hooks; overelongation |
| 13 | $GA_{12}$ 0.025 | 28 | Good emergence; good stand; poor rescue |
| 14 | $GA_{12}$ 0.25 | 9 | Poor emergence; frozen and broken hypocotyl hooks; no overelongation; good uniformity; good rescue; poor stand |
| 15 | Untreated control | 16 | Poor and erratic emergence; only 1 dwarf |

The first set of seeds did not emerge due to frost, and this study is terminated. In the second planting of 50 seeds, a few untreated plants emerged, but emergence is erratic. This is attributed to cold weather soon after planting. Better emergence is observed at lower concentrations of GA compounds than at higher concentrations. Frozen hypocotyl hooks and broken plants occurred frequently with $GA_3$. There are only hooks (no broken or normal plants) with the highest $GA_3$ concentration. $GA_{12}$ at low rate (0.025 mg/ml) resulted in good emergence but poor rescue; at high rate (0.25 mg/ml), there is poor emergence, good rescue, good plant height uniformity, and a few broken plants. $GA_9$ at 0.025 mg/ml and GA5 at 0.025 mg/ml provided good emergence with good rescue.

Seventh Through Eleventh Field Tests $GA_3$, $GA_3$-3-acetate, $GA_5$, $GA_9$, and $GA_{12}$ are evaluated in further field trials. The first trial (data reported in Tables 16–20) provided information on appropriate application rates. The objectives of these tests are: 1) to determine if seed coatings, as compared to imbibition, of GA compounds facilitate rescue of constitutively GA-deficient transgenic dwarf soybeans (transgenic lines 719–2 plus 719+17) without causing elongation of wild-type soybeans (line A4922), and 2) to determine the seed treatment rate ranges for each of the selected GA compounds that would provide rescue of constitutively GA-deficient transgenic dwarf soybeans (transgenic lines 719–2 plus 719+17) without causing elongation of wild-type soybeans (line A4922).

The second trial (data reported in Tables 22–24) tested the precursors under conditions of soil compaction.

Determination of Appropriate Application Rates for $GA_3$, $GA_3$-3-acetate, $GA_5$ $GA_9$, and $GA_{12}$ Seeds are treated with $GA_3$, GA5, $GA_9$, $GA_{12}$, and $GA_3$-3-acetate at rates of 0, 0.1, 1, 10, and 100 µg/seed. These GA compounds are applied to the seeds using a Hege 11 seed treater (Hans-Ulrich Hege GmbH & Co., Waldenburg, Germany); 100% acetone is used as the carrier solvent. The amount of liquid introduced into the seed treater is six fluid ounces/100 lbs seed rate. In addition, $GA_{12}$ is tested at 50 µg/seed. The untreated control (UTC) consisted of dry, untreated seeds. Seeds of constitutively GA-deficient transgenic dwarf soybean line 719 and wild-type A4922 are sown in both light and heavy soil. The planting depth is 0.5 to 1 inch (1.27 to 2.54 cm); watering is via drip irrigation. The experiment is carried out in three repetitions, using 25 seeds/plot (one five foot (152.4 cm) long row) for line 719, and 75 seeds/plot (two eight foot (243.8 cm) rows) for line A4922. Observations included total emergence, number of dwarfs not rescued, uniformity in plant height, average plant height, visual notes, and digital photos. The results are shown in Tables 16 through 20. In these tables, treatment means within a given column followed by the same letter are not significantly different from each other at the 0.05 level of probability.

In all the experiments reported in Tables 17–24, treatments are replicated three times in a randomized block design. Data are analyzed using LSD (least significant difference) 0.05 probability using the PRM 5.0 Statistical Analysis Program (SAS Institute, North Carolina).

TABLE 17

Effect of $GA_3$ on Emergence, Rescue, and Height of Constitutively GA-Deficient Transgenic Dwarf Soybeans and Wild-Type Soybeans in the Field

| Treatment # | µg Compound per seed | No. 719 Emerged Light soil | No. 719 Heavy soil | No. 719 Not Rescued Light soil | No. 719 Not Rescued Heavy soil | 719 Height, cm Light soil | 719 Height, cm Heavy soil | No. A4922 Emerged Light soil | No. A4922 Emerged Heavy soil | A4922 Height, cm Light soil | A4922 Height, cm Heavy soil |
|---|---|---|---|---|---|---|---|---|---|---|---|
| 1 | UTC | 23.0a | 21.3abc | 9.7a | 7.0a | 4.3fg | 4.3d–h | 63.3a | 59.3a | 5.3g–j | 5.0fgh |
| 23 | Acetone | 21.7abc | 19.7a–d | 0g | 0.3ef | 5.0efg | 4.7d–g | 43.7d–i | 49.0ab | 6.3fgh | 6.3efg |
| 2 | $GA_3$ 0.1 | 21.3abc | 19.7a–d | 1.0fg | 0f | 5.7ef | 5.7cd | 42.7e–i | 28.0c–g | 6.7fg | 5.7efg |
| 3 | $GA_3$ 1 | 20.7abc | 17.3b–e | 0g | 0.3ef | 5.7ef | 5.3cde | 36.3i | 16.7g | 8.3ef | 6.0efg |
| 4 | $GA_3$ 10 | 21.0abc | 18.3a–e | 0g | 0f | 11.7bc | 10.3a | 39.7f–j | 28.7c–g | 12.7d | 10.3d |
| 5 | $GA_3$ 100 | 16.7cd | 8.0f | 0g | 0f | 13.7a | 9.3ab | 38.0hi | 19.7efg | 27.0ab | 21.0a |
| *** | LSD 0.05 | 4.27 | 7.06 | 1.77 | 2 | 1.46 | 2.26 | 8.21 | 18.8 | 2.79 | 2.37 |

The results shown in Table 17 demonstrate that the acetone blank did not reduce the emergence of transgenic line 719. Rescue (hypocotyl elongation) is observed in line 719 seeds treated with the acetone blank; it is subsequently discovered that the acetone blank is contaminated with a GA compound. There is no other sample contamination. All GA$_3$ rates rescued line 719 seedlings. Only the 100 μg rate reduced line 719 emergence. Only the 10 and 100 μg rates caused overelongation in line 719. The acetone blank reduced emergence of line A4922 seedlings at one site (light soil). All GA$_3$ rates reduced A4922 seedling emergence. The treatments that gave the best results in line 719 are numbers 2 and 3; the treatment that gave the best results in line A4922 is number 2. In this experiment, preferred rates for GA$_3$ appeared to be in the range of from about 0.1 to about 1 μg per seed.

TABLE 18

Effect of GA$_3$-3-Acetate on Emergence, Rescue, and Height of Constitutively GA-Deficient Transgenic Dwarf Soybeans and Wild-Type Soybeans in the Field

| Treatment # | μg Compound per seed | No. 719 Emerged Light soil | No. 719 Emerged Heavy soil | No. 719 Not Rescued Light soil | No. 719 Not Rescued Heavy soil | 719 Height, cm Light soil | 719 Height, cm Heavy soil | No. A4922 Emerged Light soil | No. A4922 Emerged Heavy soil | A4922 Height, cm Light soil | A4922 Height, cm Heavy soil |
|---|---|---|---|---|---|---|---|---|---|---|---|
| 1 | UTC | 23.0a | 21.3abc | 9.7a | 7.0a | 4.3fg | 4.3d–h | 63.3a | 59.3a | 5.3g–j | 5.0fgh |
| 23 | Acetone | 21.7abc | 19.7a–d | 0g | 0.3ef | 5.0efg | 4.7d–g | 43.7d–i | 49.0ab | 6.3fgh | 6.3efg |
| 19 | GA$_3$-3 Acetate 0.1 | 21.0ab | 18.7a–d | 0.7fg | 0.3ef | 5.3efg | 3.3e–i | 40.0f–i | 46.0abc | 7.7fg | 6.7efg |
| 20 | GA$_3$-3 Acetate 1 | 21.7ab | 21.3abc | 0.3fg | 0f | 6.3e | 6.0cd | 47.7b–f | 38.3b–e | 8.3ef | 8.0de |
| 21 | GA$_3$-3 Acetate 10 | 20.3a–d | 17.7a–e | 0g | 0f | 9.3d | 9.0ab | 40.0f–i | 29.0c–g | 13.0d | 13.0c |
| 22 | GA$_3$-3 Acetate 100 | 17.7b–f | 16.7b–e | 0g | 0f | 12.0b | 8.7ab | 39.3ghi | 36.3b–f | 25.7b | 21.7a |
| *** | LSD 0.05 | 4.27 | 7.06 | 1.77 | 2 | 1.46 | 2.26 | 8.21 | 18.8 | 2.79 | 2.37 |

The results shown in Table 18 demonstrate that the acetone blank did not reduce the emergence of transgenic line 719. Rescue (hypocotyl elongation) is observed in line 719 seeds treated with the acetone blank; it is subsequently discovered that the acetone blank is contaminated with a GA compound. There is no other sample contamination. All GA$_3$-3-acetate rates rescued line 719 seedlings. GA$_3$-3-acetate at 1 μg and above caused elongation in line 719 seedlings. The 100 μg rate reduced emergence of line 719. The acetone blank reduced the emergence of line A4922 at one site (light soil). All rates reduced line A4922 emergence. GA$_3$-3-acetate at 1 μg and above elongated line A4922 seedlings. The treatment that gave the best results in lines 719 and A4922 is treatment 20. In this experiment, the preferred rate for GA$_3$-3-acetate appeared to be about 1 μg per seed.

TABLE 19

Effect of GA$_5$ on Emergence, Rescue, and Height of Constitutively GA-Deficient Transgenic Dwarf Soybeans and Wild-Type Soybeans in the Field

| Treatment # | μg Compound per seed | No. 719 Emerged Light soil | No. 719 Emerged Heavy soil | No. 719 Not Rescued Light soil | No. 719 Not Rescued Heavy soil | 719 Height, cm Light soil | 719 Height, cm Heavy soil | No. A4922 Emerged Light soil | No. A4922 Emerged Heavy soil | A4922 Height, cm Light soil | A4922 Height, cm Heavy soil |
|---|---|---|---|---|---|---|---|---|---|---|---|
| 1 | UTC | 23.0a | 21.3abc | 9.7a | 7.0a | 4.3fg | 4.3d–h | 63.3a | 59.3a | 5.3g–j | 5.0fgh |
| 23 | Acetone | 21.7abc | 19.7a–d | 0g | 0.3ef | 5.0efg | 4.7d–g | 43.7d–i | 49.0ab | 6.3fgh | 6.3etg |
| 6 | GA$_5$ 0.1 | 21.7ab | 22.0ab | 4.3c | 1.7def | 4.3fg | 5.0def | 51.7bcd | 32.3b–g | 6.0fgh | 4.3ghi |
| 7 | GA$_5$ 1 | 22.7a | 21.0abc | 0g | 0.7ef | 6.3e | 4.7d–g | 47.3c–g | 37.3b–f | 7.3fg | 7.0ef |
| 8 | GA$_5$ 10 | 20.0a–d | 20.0a–d | 0.7fg | 0.3ef | 11.3bc | 7.3be | 45.7c–h | 32.7b–g | 16.3c | 17.3b |
| 9 | GA$_5$ 100 | 14.3f | 12.3ef | 0g | 0f | 12.0b | 9.0ab | 46.7c–g | 38.3b–e | 29.7a | 22.3a |
| *** | LSD 0.05 | 4.27 | 7.06 | 1.77 | 2 | 1.46 | 2.26 | 8.21 | 18.8 | 2.79 | 2.37 |

The results shown in Table 19 demonstrate that the acetone blank did not reduce the emergence of transgenic line 719. Rescue (hypocotyl elongation) is observed in line 719 seeds treated with the acetone blank; it is subsequently discovered that the acetone blank is contaminated with a GA compound. There is no other sample contamination. $GA_5$ at the rate of 1 pg and above resulted in good rescue in line 719 seedlings. Only the 100 µg rate reduced line 719 seedling emergence. The 10 and 100 µg rates caused excessive elongation of line 719 seedlings. The acetone blank reduced the emergence of line A4922 at one site (light soil). All $GA_5$ rates reduced line A4922 emergence. $GA_5$ at the rates of 10 and 100 µg/seed resulted in overelongation of line A4922. The treatment that gave the best results in line 719 is treatment 7; treatments 6 and 7 gave the best results in line A4922. In this experiment, preferred rates for $GA_5$ appeared to be in the range of from about 0.1 to about 1 µg per seed

TABLE 20

Effect of $GA_9$ on Emergence, Rescue, and Height of Constitutively GA-Deficient Transgenic Dwarf Soybeans and Wild-Type Soybeans in the Field

| # | Treatment | | No. 719 Emerged | | No. 719 Not Rescued | | 719 Height, cm | | No. A4922 Emerged | | A4922 Height, cm | |
|---|---|---|---|---|---|---|---|---|---|---|---|---|
| | | µg Compound per seed | Light soil | Heavy soil | Light soil | Heavy soil | Light soil | Heavy soil | Light soil | Heavy soil | Light soil | Heavy soil |
| 1 | UTC | | 23.0a | 21.3abc | 9.7a | 7.0a | 4.3fg | 4.3d–h | 63.3a | 59.3a | 5.3g–j | 5.0fgh |
| 23 | Acetone | | 21.7abc | 19.7a–d | 0g | 0.3ef | 5.0efg | 4.7d–g | 43.7d–i | 49.0ab | 6.3fgh | 6.3efg |
| 10 | $GA_9$ | 0.1 | — | — | — | — | — | — | 48.3b–e | 41.0a–d | 5.7f–i | 5.7efg |
| 11 | $GA_9$ | 1 | — | — | — | — | — | — | 46.7c–g | 43.0a–d | 6.3fgh | 6.3efg |
| 12 | $GA_9$ | 10 | 21.7ab | 16.3b–e | 0.3fg | 0.7ef | 5.0efg | 4.0d–i | 46.0c–h | 26.3d–g | 7.3fg | 6.7efg |
| 13 | $GA_9$ | 100 | 19.0a–e | 20.3a–d | 0g | 0f | 10.3cd | 8.3ab | 40.0f–i | 28.3c–g | 11.0de | 10.3d |
| *** | LSD 0.05 | | 4.27 | 7.06 | 1.77 | 2 | 1.46 | 2.26 | 8.21 | 18.8 | 2.79 | 2.37 |

The results shown in Table 20 demonstrate that the acetone blank did not reduce the emergence of line 719. Rescue (hypocotyl elongation) is observed in line 719 seeds treated with the acetone blank; it is subsequently discovered that the acetone blank is contaminated with a GA compound. There is no other sample contamination. Seedlings of seeds treated with 0.1 and 1 µg per seed $GA_9$ appeared unusually abnormal. These seedlings are slow in developing, and remained short, as if they had been treated with paclobutrazol, high rates of $GA_{12}$, or had prolonged exposure to solvents. Both the 10 and 100 µg rates produced no stand reduction in line 719; both rates rescued line 719 seedlings. The acetone blank reduced the emergence of line A4922 seedlings at one site (light soil). $GA_9$ at 0.1 and 1 µg/seed caused stand reduction in line A4922 seedlings at only one site. $GA_9$ at 10 and 100 µg/seed caused stand reduction at both sites. The treatment that gave the best results in line 719 is number 12; treatments 10, 11, and 12 gave the best results in line A4922. Because of the lack of reliable data on line 719 at the 0.1 and 1 µg/seed rates in this experiment, no preferred rate for $GA_9$ could be determined.

TABLE 21

Effect of $GA_{12}$ on Emergence, Rescue, and Height of Constitutively GA-Deficient Transgenic Dwarf Soybeans and Wild-Type Soybeans in the Field

| # | Treatment μg Compound per seed | No. 719 Emerged Light soil | No. 719 Emerged Heavy soil | No. 719 Not Rescued Light soil | No. 719 Not Rescued Heavy soil | 719 Height, cm Light soil | 719 Height, cm Heavy soil | No. A4922 Emerged Light soil | No. A4922 Emerged Heavy soil | A4922 Height, cm Light soil | A4922 Height, cm Heavy soil |
|---|---|---|---|---|---|---|---|---|---|---|---|
| 1 | UTC | 23.0a | 21.3abc | 9.7a | 7.0a | 4.3fg | 4.3d–h | 63.3a | 59.3a | 5.3g–j | 5.0fgh |
| 23 | Acetone | 21.7abc | 19.7a–d | 0g | 0.3ef | 5.0efg | 4.7d–g | 43.7d–i | 49.0ab | 6.3fgh | 6.3efg |
| 14 | $GA_{12}$ 0.1 | 22.3a | 20.7a–d | 6.3b | 4.3bc | 4.0g | 4.0d–i | 45.7c–h | 24.3d–g | 5.7f–i | 5.3fg |
| 15 | $GA_{12}$ 1 | 22.0a | 21.0abc | 3.7cd | 5.3ab | 4.0g | 3.3e–i | 55.7ab | 48.0ab | 5.0g–i | 5.7efg |
| 16 | $GA_{12}$ 10 | 21.0ab | 22.3ab | 1.7efg | 1.7def | 2.3h | 3.0f–i | 46.3c–g | 19.0fg | 3.7hij | 5.0fgh |
| 17 | $GA_{12}$ 50 | 22.3a | 23.7a | 3.0cde | 5.0bc | 2.3h | 3.3e–i | 51.3bcd | 40.0bcd | 3.0ij | 2.7hi |
| 18 | $GA_{12}$ 100 | 21.3ab | 20.7a–d | 1.0fg | 2.0de | 2.0h | 2.7ghi | 53.0bc | 38.7bcd | 2.7j | 2.3i |
| *** | LSD 0.05 | 4.27 | 7.06 | 1.77 | 2 | 1.46 | 2.26 | 8.21 | 18.8 | 2.79 | 2.37 |

The results shown in Table 21 demonstrate that the acetone blank did not reduce the emergence of transgenic line 719 seedlings. Rescue (hypocotyl elongation) is observed in line 719 seeds treated with the acetone blank; it is subsequently discovered that the acetone blank is contaminated with a GA compound. There is no other sample contamination. There is no reduction in line 719 seedling emergence due to $GA_{12}$ at any rate, although emergence is delayed. Due to the short stature of seedlings, it is difficult to determine the rescue count. It appeared that $GA_{12}$ at 10 μg and above resulted in rescue of line 719 seedlings. $GA_{12}$ at 10 μg and above reduced the height of line 719 seedlings. The acetone blank reduced the emergence of line A4922 seedlings at one site (light soil). All $GA_{12}$ rates reduced line A4922 seedling emergence. $GA_{12}$ at 10 μg and above reduced the height of A4922 seedlings. In general, as the rate of $GA_{12}$ application increased, seedling height decreased.

Effect of GA3, GA3-3-acetate, GA5, GA9, and GA12 on Seedling Emergence and Rescue in Compacted Soil As noted above, the second trial tested the noted precursors under conditions of soil compaction. These experiments are performed in the same manner as in the first trial, except that the soil is compacted with an all-terrain vehicle. The GA compounds are tested on both transgenic line 719 and non-transgenic line A4922.

The results are shown in Tables 22–24. In these tables, treatment means within a given column followed by the same letter are not significantly different from each other. "Height" equals total plant height in cm. Selected data from Tables 22–24 are summarized in FIG. 40 and Table 25.

TABLE 22

Effect of GA Compounds on Emergence, Rescue, and Height of Soybean Seedlings in Different Soils

| No. | Treatment, μg/seed Target rate | Actual rate A4922 | Actual rate 719 | Light-soil - Compacted A4922 Count | Light-soil - Compacted A4922 Height | Light-soil - Compacted Line 719 Count | Light-soil - Compacted Line 719 Dwarfs | Heavy soil - loose A4922 Count | Heavy soil - loose A4922 Height | Heavy soil - loose Line 719 Count | Heavy soil - loose Line 719 Dwarfs |
|---|---|---|---|---|---|---|---|---|---|---|---|
| 1 | Untreated | | | 41a | 5.0efg | 37a–d | 8.0a | 32abc | 4.0g | 35abc | 10.0a |
| 3 | $GA_5$ 0.5 | 0.26 | 0.13 | 28bcd | 5.7def | 22efg | 0d | 25cde | 5.0efg | 27cd | 2.0cde |
| 4 | $GA_3$ 2.0 | 1.91 | 2.01 | 13ef | 8.0a | 19fg | 0d | 21ef | 6.7bcd | 25de | 0.7cde |
| 6 | $GA_5$ 0.5 | 0.57 | 0.58 | 37abc | 6.7d | 39abc | 0d | 32abc | 5.3d–g | 32bcd | 2.0cde |
| 7 | $GA_5$ 2.0 | 1.75 | 1.66 | 22de | 9.0c | 30a–f | 0d | 25cde | 6.7bcd | 32bcd | 0.7ede |
| 9 | $GA_9$ 2.0 | 2.02 | 3.11 | 38abc | 5.7def | 38abc | 0.7cd | 33ab | 5.3d–g | 42a | 2.0cde |
| 10 | $GA_9$ 8.0 | 7.38 | 4.89 | 22de | 6.0de | 27b–f | 0d | 29a–d | 6.3cde | 35abc | 0.7cde |
| 14 | $GA_{12}$ 40.0 | 16 | 21.5 | 41a | 4.3g | 42a | 3.7bc | 33ab | 4.3g | 35abc | 3.3c |
| 15 | $GA_3$-3-Ac 0.5 | 0.68 | 0.45 | 28bcd | 6.3d | 25def | 0d | 29a–d | 5.3d–g | 31bcd | 3.3c |
| 16 | $GA_3$-3-Ac 2.0 | 2.77 | 2.11 | 18def | 8.7c | 22efg | 0d | 15f | 6.0c–f | 27cd | 0.3de |

Based on the data presented in Table 22 with respect to seedling emergence under conditions of soil compaction, wide margin of selectivity, ability to rescue seedlings without causing overelongation, and consistency across tests, the tested GA compounds showed the best to least selectivity in the order $GA_9 > GA_5 > GA_3$-3-acetate $> GA_3$.

TABLE 23

Effect of GA Compounds on Emergence, Rescue, and Height of Soybean Seedlings in Different Soils

| | Treatment, μg/seed | | | Heavy soil - Loose | | | | Heavy soil-compacted | | | |
|---|---|---|---|---|---|---|---|---|---|---|---|
| | | Actual rate | | A4922 | | Line 719 | | A4922 | | Line 719 | |
| No. | Target rate | A4922 | 719 | Count | Height | Count | Dwarfs | Count | Height | Count | Dwarfs |
| 1 | Untreated | | | 31.7a–d | 4.0g | 34.7abc | 10.0a | 16.7ab | 4.0de | 11.7b–e | 4.0a |
| 2 | Ethanol-water | | | 27.7b–e | 4.0g | 33.7bc | 8.3ab | 12.7abc | 4.0de | 16.0a–d | 4.3a |
| 3 | $GA_3$ 0.5 | 0.26 | 0.13 | 25.0cde | 5.0efg | 27.3cd | 2.0cdc | 8.3cd | 4.3b-e | 7.7efg | 0.3cd |
| 4 | $GA_3$ 2.0 | 1.91 | 2.01 | 21.3ef | 6.7bcd | 24.7de | 0.7cde | 2.0de | 6.0bc | 7.3efg | 0d |
| 5 | $GA_3$ 4.0 | 3.60 | 3.28 | 24.7de | 8.7a | 14.3f | 0e | 4.0de | 8.0a | 3.3fg | 0d |
| 6 | $GA_5$ 0.5 | 0.57 | 0.58 | 32.0abc | 5.3d–g | 31.7bcd | 2.0ede | 13.7abc | 4.7cde | 18.3ab | 0d |
| 7 | $GA_5$ 2.0 | 1.75 | 1.66 | 24.7de | 6.7bcd | 32.3bcd | 0.7cde | 9.0bcd | 6.7ab | 9.0d–g | 0d |
| 8 | $GA_5$ 4.0 | 4.00 | 5.61 | 26.7b–c | 9.0a | 30.3bcd | 0c | 6.7cdc | 6.7ab | 7.0cfg | 0d |
| 9 | $GA_9$ 2.0 | 2.02 | 3.11 | 32.7ab | 5.3d–g | 42.0a | 2.0cde | 13.3abc | 5.3b–c | 17.3abc | 0d |
| 10 | $GA_9$ 8.0 | 7.38 | 4.89 | 29.3a–d | 6.3cde | 35.3abc | 0.7cde | 9.7a–d | 6.0bc | 8.7d–g | 0d |
| 11 | $GA_9$ 16.0 | 15.90 | 11.50 | 24.7de | 7.0bc | 30.7bcd | 0e | 6.3cde | 6.7ab | 12.0b–c | 0d |
| 12 | $GA_{12}$ 1.0 | 0.94 | 1.03 | 36.0a | 4.7fg | 36.0ab | 10.0a | 17.0a | 4.3cde | 18.7ab | 4.0a |
| 13 | $GA_{12}$ 10.0 | 6.82 | 12.10 | 26.7b–c | 4.0g | 35.3abc | 7.0b | 12.3abc | 3.7e | 13.0b–c | 2.0b |
| 14 | $GA_{12}$ 40.0 | 16.00 | 21.50 | 33.0ab | 4.3g | 35.3abc | 3.3c | 13.7abc | 4.0de | 22.7a | 1.3bc |
| 15 | $GA_3$-3-Ac 0.5 | 0.68 | 0.45 | 29.0a–d | 5.3d–g | 31.3bcd | 0.3de | 4.0de | 5.3b–c | 10.3c–f | 0.3cd |
| 16 | $GA_3$-3-Ac 2.0 | 2.77 | 2.11 | 15.3f | 6.0c–f | 27.3cd | 0e | 6.0cde | 5.7bcd | 7.3cfg | 0d |
| 17 | $GA_3$-3-Ac 4.0 | 3.38 | 4.96 | 7.0g | 8.0ab | 18.3ef | 0e | 0e | *** | 2.0g | 0d |

Treatment means, within a given column, followed by the same letter are not significantly different from each other.
Height = total plant height in cm. Dwarfs = number of dwarfs/number of dwarfs not rescued.

The results shown in Table 23 are consistent with those in Table 22. Based on the data presented in Table 23 with respect to seedling emergence under conditions of soil compaction, wide margin of selectivity, ability to rescue seedlings without causing overelongation, and consistency across tests, the tested GA compounds again showed the best to least selectivity in the order $GA_9 > GA_5 > GA_3$-3-acetate $> GA_3$.

TABLE 24

Effect of GA Compounds on Emergence, Rescue, and Height of Soybean Seedlings in Different Soils

| | Treatment, μg/seed | | | Light soil - Loose | | | | Light soil - compacted | | | |
|---|---|---|---|---|---|---|---|---|---|---|---|
| | | Actual rate | | A4922 | | Line 719 | | A4922 | | Line 719 | |
| No. | Target rate | A4922 | 719 | Count | Height | Count | Dwarfs | Count | Height | Count | Dwarfs |
| 1 | Untreated | | | 46.3a | 4.7hi | 47.0a | 20.a | 40.7a | 5.0efg | 37.3a–d | 8.0a |
| 2 | Ethanol-water | | | 43.7abc | 4.0hi | 47.0a | 19.0ab | 35.7abc | 4.7fg | 29.7a–f | 5.3ab |
| 3 | $GA_3$ 0.5 | 0.26 | 0.13 | 43.0abc | 7.0ef | 45.0ab | 0e | 28.3bcd | 5.7def | 12.0g | 0 d |
| 4 | $GA_3$ 2.0 | 1.91 | 2.01 | 38.3bc | 9.0cd | 43.7ab | 0e | 12.7ef | 8.0c | 19.3fg | 0d |
| 5 | $GA_3$ 4.0 | 3.60 | 3.28 | 37.7c | 10.3b | 39.3b | 0e | 7.7 f | 10.3b | 26.3c–f | 0d |
| 6 | $GA_3$ 0.5 | 0.57 | 0.58 | 44.7ab | 6.0fg | 46.3a | 1.0e | 36.7abc | 6.7d | 39.0abc | 0d |
| 7 | $GA_3$ 2.0 | 1.75 | 1.66 | 41.0abc | 10.0bc | 43.3ab | 0e | 21.7de | 9.0c | 30.3a–f | 0d |
| 8 | $GA_5$ 4.0 | 4.00 | 5.61 | 43.3abc | 12.7a | 45.0ab | 0e | 18.7def | 11.7a | 32.7a–e | 0d |
| 9 | $GA_9$ 2.0 | 2.02 | 3.11 | 41.3abc | 5.0gh | 48.0a | 2.3e | 38.0abc | 5.7def | 38.3abc | 0.7cd |
| 10 | $GA_9$ 8.0 | 7.38 | 4.89 | 39.3bc | 7.0ef | 49.0a | 0e | 21.7de | 6.0de | 27.3b–f | 0d |
| 11 | $GA_9$ 16.0 | 15.90 | 11.50 | 39.0bc | 8.0de | 45.0ab | 0e | 20.0de | 8.3c | 29.7a–f | 0d |
| 12 | $GA_{12}$ 1.0 | 0.94 | 1.03 | 43.7abc | 4.0hi | 46.3a | 17.3b | 39.3ab | 4.3g | 40.3a | 8.3a |
| 13 | $GA_{12}$ 10.0 | 6.82 | 12.10 | 47.7a | 3.7i | 48.3a | 11.3c | 41.7ab | 4.0g | 40.0ab | 4.3b |
| 14 | $GA_2$ 40.0 | 16.00 | 21.50 | 44.0abc | 4.0hi | 46.0a | 7.7d | 41.0a | 4.3g | 42.0a | 3.7bc |
| 15 | $GA_3$-3-Ac 0.5 | 0.68 | 0.45 | 44.3abc | 6.3f | 45.3ab | 0.3e | 27.7cd | 6.3d | 25.3def | 0d |
| 16 | $GA_3$-3-Ac 2.0 | 2.77 | 2.11 | 42.0abc | 9.7bc | 43.3ab | 0c | 18.0def | 8.7c | 22.0efg | 0d |
| 17 | $GA_3$-3-Ac 4.0 | 3.38 | 4.96 | 42.3abc | 10.3b | 42.7ab | 0c | 22.7dc | 11.0ab | 33.7a–e | 0d |

Treatment means, within a given column, followed by the same letter are not significantly different from each other.
Height = total plant height in cm. Dwarfs = number of dwarfs/number not rescued.

The results shown in Table 24 are consistent with those in Tables 22 and 23. Based on the data presented in Table 24 with respect to seedling emergence under conditions of soil compaction, wide margin of selectivity, ability to rescue seedlings without causing overelongation, and consistency across tests, the tested GA compounds again showed the best to least selectivity in the order $GA_9 > GA_5 > GA_3$-3-acetate $> GA_3$.

TABLE 25

Effect of soil conditions on rescue and emergence
of line 719 soybeans using $GA_3$ and $GA_9$

| Compound | Rate (μg/seed) | Light Soil-Compact | | Heavy Soil-Loose | |
|---|---|---|---|---|---|
| | | % Rescue | % Emergence | % Rescue | % Emergence |
| $GA_3$ | 0.1 | 100 | 59 | 80 | 78 |
| | 2.0 | 100 | 51 | 93 | 66 |
| $GA_9$ | 3.1 | 91 | 103 | 80 | 103 |
| | 4.9 | 100 | 73 | 93 | 91 |

The results shown in FIG. 40 and Table 25 are based on selected data in Tables 22–24. As shown in FIG. 40, $GA_5$ and $GA_3$-3-acetate yielded dose/response curves similar to that of $GA_3$ with respect to plant height in wild-type soybean line A4922. $GA_{12}$ inhibited plant height at ten days after planting. $GA_9$ is less active than $GA_3$, $GA_3$-3-acetate, and $GA_5$, and produced a dose/response curve having a lower slope in compacted soil. In addition, at approximately equivalent biological response (height), $GA_9$ resulted in higher emergence (93%) than $GA_3$ (68%). $GA_9$ is also superior to $GA_3$ when applied to constitutively GA-deficient transgenic dwarf line 719 soybeans (Table 25). In two soil types (light-compact and heavy-loose), $GA_9$ resulted in greater percent emergence than $GA_3$, and equally high rescue of line 719 soybeans as compared to $GA_3$.

Based on these last two field trials, the GA compounds employed in these experiments can be ranked in order of potential for use in rescuing GA-deficient dwarf soybeans without decreasing emergence as follows: $GA_9 > GA_5 > GA_3$-3-acetate$> GA_3 > GA_{12}$. $GA_{12}$ decreases overall plant height.

Example 24

Half-lives of GA Compounds in planta and in soil, and Distribution of $^{14}$C-labelled GA Compounds in Seedlings The half-lives of $GA_3$, $GA_9$, and $GA_{12}$ in soil and in planta, and their distribution throughout the soybean seedling when added as a seed treatment, are investigated using $^{14}$C-radiolabelled compounds.

Determination of Half-lives and Distribution of $^{14}$C-Labelled GA Compounds in planta $^{14}$C-radiolabelled compounds are obtained from Lew Mander (Australian National University). $^{14}$C-$GA_3$ is dissolved in water:ethanol, 80:20, v/v; $^{14}$C-$GA_9$ and $^{14}$C-$GA_{12}$ are dissolved in 100% ethanol. Seeds of Asgrow 3237 soybeans are treated separately with solutions of each of the $^{14}$C-radiolabelled compounds (1.7–6.8 μg; 10–40 ppm; 111,000–2,000,000 dpm/seed) by placing one to four μl of the dosing solution directly on the seed coat ($^{14}$C-$GA_3$, $GA_9$, and $GA_{12}$), or on the hilum portion of the seed ($^{14}$C-$GA_3$). After evaporation of the carrier solvent (approx. one hour), the treated seed is planted in containers containing approximately 30 gm of Metromix-350, and transferred to a growth chamber. Plants are grown under a 12 hour light/12 hour dark regime at 92° F. (33° C.) and 75% humidity. The pattern of uptake and translocation of $^{14}$C-radioactivity in treated seed is monitored up to 12 days past initial treatment. For most experiments, three replicate plants are harvested at one hour after treatment, one day after treatment (DAT), two DAT, three DAT, six or seven DAT, and 12 DAT. At the time of each harvest, plants are divided into leaves, epicotyl, cotyledon, hypocotyl, and roots. The level of $^{14}$C-radioactivity in different plant parts is determined by extraction of plant tissues with aqueous methanol and scintillation counting. The extent of metabolism of the $^{14}$C-labelled GA compounds in planta is determined by HPLC analysis of plant extracts. The details are as follows.

Extraction and Quantitation of GA Compound Metabolites

The general extraction procedure consisted of blending the plant parts in a high speed polytron tissue homogenizer for 1–5 minutes with 10–20 ml of ice-cold methanol:water, 80:20, v/v, followed by vacuum filtration through a Whatman glass fiber filter. The filter cake is re-extracted as necessary using the procedure described above until an insignificant amount of radioactivity is removed. Prior to combining the extracts from each sample, aliquots are weighed and analyzed by liquid scintillation counting (LSC) to determine the amount of extracted radioactivity in each extract. Aliquots of the air-dried filter cakes are combusted and analyzed by LSC in order to determine the amount of non-extracted radioactivity. The extracts are combined and, when necessary, concentrated by rotary evaporation at a bath temperature of less than 35° C. to a small volume for analysis by HPLC to determine the extent of metabolism of the $^{14}$C-labelled GA compounds in planta.

High Performance Liquid Chromatography (HPLC) with Radioactive Flow Detection

The HPLC system used for chromatographic analysis of sample extracts comprised the following components: A Rheodyne model 7125 syringe loaded sample injector; a Waters model 680 gradient controller; Waters model 510 solvent pumps; a Waters model 484 variable wavelength UV detector (set at 210 nm); a Radiomatic Flo-One radioactive flow detector with a 2.5 ml liquid flow cell; and an ISCO model 328 fraction collector. Atomflow liquid scintillation cocktail (NEN Co., Boston, Mass.) is mixed with the column effluent at a flow rate of 9 ml/min., yielding a ratio of 3:1, cocktail:effluent. An Eldex Model B-120-SRM pump is used to pump the scintillation cocktail. The HPLC column is a Beckman Ultrasphere-ODS column (5 μm packing, 10 mm×25 cm). The column is eluted (flow rate: 3ml/min.) with 90% water containing 0.1% trifluoroacetic acid and 10% methanol for 5 minutes, followed by linear gradient to 100% methanol over the next 30 minutes.

Determination of Half-lives of $^{14}$C-labelled GA Compounds in Soil

Metabolic studies in soil are conducted with $^{14}$C-labelled GA compounds in order to investigate the route and rate of compound degradation in soil under aerobic conditions. $^{14}$C-labelled GA compounds are obtained from Lew Mander (Australian National University). The $^{14}$C-labelled compounds dissolved in 0.2–2 ml water:ethanol, 80:20, v/v, are applied to 50–60 gm portions of spinks soil (USDA classification Loamy Sand: 82% sand, 14% silt, and 4% clay) in 250 ml centrifuge bottles at a rate of 0.1–0.2 ppm (6–12 μg; approximately 1,200,000 dpm per soil sample. The soil samples are placed in a glass dessicator which served as a container for all soil bottles. The glass dessicator is connected to three separate trapping solutions in series, each containing 20 ml of ethylene glycol:ethanolamine, 2:1, v/v. Air is pulled into the glass dessicator and through the trapping solutions by house vacuum. The trapping solutions are used to collect $^{14}C$-volatiles and $^{14}C$—$CO_2$. Soil samples are incubated for eight days at 25° C. in darkness. For most experiments, duplicate soil samples are harvested 0, 6, 12, 24, 46, 72, 120, and 192 hours after initial treatment. Soil samples are extracted twice with 100 ml of water: methanol, 20:80, v/v, and the combined extracts are analyzed by HPLC under the same conditions as described for the determination of half-lives of GA compounds in planta, above.

The results are shown in Tables 26a and 26b, respectively.

TABLE 26a

Half-lives of $GA_3$, $GA_9$ and $GA_{12}$ in planta and in soil

| Gibberellin | Half-life (days) | |
|---|---|---|
| | in planta | in soil |
| $GA_3$ | 2 to 3 | 0.5 |
| $GA_{12}$ | <1 | |
| $GA_9$ | <1 | |

TABLE 26b $^{14}C$ Label Distribution in plant parts

| | | $^{14}C$ Label Distribution (% of dose) | | | |
|---|---|---|---|---|---|
| Time | Gibberellin | Cotyledon | Root | Hypocotyl | Epicotyl | Leaves |
| 3 DAP | $GA_3$ | 85 | 0.5 | 1.5 | | |
| | $GA_{12}$ | 55 | 3.5 | 1.7 | | |
| | $GA_9$ | 60 | 1.3 | 6.8 | | |
| 12 DAP | $GA_3$ | 72 | 2.8 | 1.4 | 0.2 | 0.9 |
| | $GA_{12}$ | 45 | 3.0 | 0.9 | 0.2 | 0.7 |
| | $GA_9$ | 54 | 1.0 | 1.0 | 0.1 | 0.3 |

As shown in Table 26a, the half-lives of $GA_9$ and $GA_{12}$ in planta are less than one day; the half-life of $GA_3$ in planta is two to three days. The half-life of $GA_3$ in soil is about one-half day.

As shown in Table 26b, $^{14}C$-labeled $GA_3$, $GA_9$, and $GA_{12}$ are taken up and mobilized by soybean seedlings. No compelling differences are observed in the distribution of these compounds among cotyledons, roots, hypocotyls, epicotyls, and leaves at either three or 12 days after planting.

Example 25

Evaluation of GA Compounds as Rescue Agents via Hilum Treatment

In the previous experiments, the effect of various GA compounds on transgenic, GA-deficient and wild-type soybean is evaluated by treating seeds with these compounds via imbibition. Several of these compounds are not completely soluble in water, which limited the interpretation of their utility in rescuing GA-deficient dwarf plants. The purpose of this experiment is to reevaluate selected, previously tested compounds, and additional compounds, by introducing them to the seed via the hilum. As shown by the results presented below, direct application of small quantities of GA compounds dissolved in an organic solvent to the hilum is an effective method of treating soybean seeds. As in the previously described experiments, comparison is made between activity on GA-deficient soybean seedlings and normal (wild-type) seedlings.

| Compound | Source |
|---|---|
| $GA_3$ | |
| $GA_3$-3-acetate | Sigma Chemical Co., USA |
| $GA_{12}$ | L. Mander, Australian Natl. U. |
| $GA_5$ | L. Mander |
| kaurenoic acid | L. Mander |
| $GA_{12}$-aldehyde | L. Mander |
| kaurenol | L. Mander |
| $GA_9$ | L. Mander |
| kaurene | L. Mander |
| steviol | L. Mander |
| $GA_{53}$ | L. Mander |

Soybean Seeds

A3237 soybean seeds are supplied by Asgrow Seed Company (Des Moines, Iowa). Seed of GA-deficient transgenic soybean line 719 is created by transformation of A3237 soybean with pMON29801 (FMV/antisense CPScc). Fifth generation seed (R5) is used for these experiments.

Preparation of GA Compound Solutions

GA compounds are dissolved in absolute ethanol at a concentration of approximately 10 mg/ml. Compounds are applied to the hilum of dry soybean seed at levels between 1 µl and 10 µl per seed as 1 µl drops. When multiple droplets are applied, each 1 µl droplet is allowed to dry before subsequent droplets are added. Ethanol minus compound is used a treatment control.

Seedling Growth

Seeds are sown the same day as treatment in 4-inch plastic pots (2 pots per treatment; 5 seeds/pot) containing commercial potting soil (Metromix 200). Pots are placed in a greenhouse set for 12 hr light, and day/night temperatures of 85° F. (29° C.) and 75° F. (24° C.), respectively. Emergence timing is measured by counting the number of emerged seedlings at different times after planting. Emergence is defined as the presence of cotyledons raised to soil level or above. After all treatments are emerged (5 to 6 days after planting (DAP)), hypocotyl length is measured. Both hypocotyl and first internode length are measured at 9 to 10 DAP. To assess the ability of a seed treatment to deliver biological activity beyond the first internode, measurements are taken on selected treatments after prolonged growth and development.

The candidate compounds are first evaluated at a single rate to determine if further evaluations are warranted. Four compounds, i.e., kaurenol, steviol, $GA_{12}$-aldehyde and $GA_{53}$, exhibited activity on GA-deficient plant tissue at a concentration that does not affect normal plant tissue which is not limited in gibberellin supply. All four compounds are biologically active on transgenic, dwarf GA-deficient line 719 in terms of both emergence timing and hypocotyl length.

Interestingly, $GA_{12}$ inhibited emergence timing and hypocotyl length. A surprising finding from further observations of the soybean plants in this study is that $GA_5$ continued to stimulate stem elongation past the first internode. $GA_5$ at an initial seed dose of approximately 10 µg/seed caused measurable increases in internode length up to the third internode, while $GA_3$ and the other compounds are not active beyond the first internode.

oversupply of gibberellin bioactivity. The activity previously observed with kaurenol is not confirmed at a rate up to 100 ng/seed.

TABLE 27

Effect of selected GA compounds applied to the hilum of transgenic GA-deficient dwarf soybean seeds and wild-type soybean seeds on seedling growth and development

| Compound | Rate (µg/seed) | Emergence timing | | Hypocotyl length (6 DAP) | | 1st internode length (12 DAP) | | 2nd internode length (12 DAP) | | 3rd internode length (20 DAP) | |
|---|---|---|---|---|---|---|---|---|---|---|---|
| | | L719 | A3237 | L719 | A3237 | L719 | A3237 | L719 | A3237 | L719 | A3237 |
| $GA_3$ | 10.1 | pos | pos | pos | pos | pos | 0 | 0 | | 0 | |
| $GA_3$-3-acetate | 10.1 | pos | pos | pos | pos | pos | 0 | | | | |
| $GA_9$ | 16.5 | pos | pos | pos | pos | pos | 0 | 0 | | 0 | |
| $GA_5$ | 9.7 | pos | pos | pos | pos | pos | pos | pos | | pos | pos |
| kaurene | 13.0 | pos | 0 | 0 | 0 | 0 | 0 | | | | |
| kaurenol | 8.3 | pos | 0 | pos | 0 | 0 | 0 | | | | |
| kaurenoic acid | 10.9 | pos | 0 | 0 | 0 | 0 | 0 | | | | |
| steviol | 13.3 | pos | 0 | pos | 0 | 0 | 0 | | | | |
| $GA_{12}$-aldehyde | 11.0 | pos | 0 | pos | 0 | 0 | 0 | | | | |
| $GA_{12}$ | 9.9 | 0 | neg | neg | neg | 0 | 0 | | | | |
| $GA_{53}$ | 10.2 | pos | 0 | pos | 0 | 0 | neg | | | | |

Kaurenol, steviol, $GA_{12}$-aldehyde, and $GA_{53}$ are re-evaluated at different rates to 1) confirm the results obtained above, and 2) assess their relative bioactivity. Previously evaluated compounds, i.e., $GA_3$, $GA_9$, and $GA_5$, are included in this study to broaden the information on their biological activity profiles.

The biological activity of steviol, $GA_{12}$-aldehyde, and $GA_{53}$ observed in Table 27 is confirmed in this experiment.

The unique longer duration bioactivity of $GA_5$ is confirmed in this second study (Table 28). $GA_5$ is approximately 10 times more biologically active on the first internode of line 719 soybeans compared to $GA_3$ and $GA_9$. Increased internode elongation at internode number 3 is attributed to $GA_5$ at a rate greater than or equal to 1 µg/seed. No activity is noted on visual inspection of the other treatments for the other compounds

TABLE 28

Evaluation of the rate response of biological activity of selected GA compounds applied to the hilum of transgenic GA-deficient dwarf soybean seeds and wild-type soybean seeds on seedling growth and development

| | Lowest rate where biological activity is observed (µg/seed) | | | | | | | |
|---|---|---|---|---|---|---|---|---|
| | Emergence timing | | Hypocotyl length (5 DAP) | | 1st internode length (10 DAP) | | 3rd internode length (20 DAP) | |
| Compound | L719 | A3237 | L719 | A3237 | L719 | A3237 | L719 | A3237 |
| $GA_3$ | 0.1 | 0.1 | 0.1 | 0.1 | 10 | 1 | | |
| $GA_9$ | 0.1 | 0.1 | 0.1 | 1 | 10 | 1 | | |
| $GA_5$ | 1 | 0.1 | 0.1 | 1 | 1 | 1 | >1 | 1 |
| kaurenol | >100 | >100 | >100 | >100 | >100 | >100 | | |
| steviol | 10 | >100 | 1 | >100 | >100 | >100 | | |
| $GA_{12}$-aldehyde | 1 | >100 | 1 | >100 | >100 | >100 | | |
| $GA_{53}$ | 1 | >10 | 1 | >10 | >10 | >10 | | |

In each case, the amount of GA compound producing a biological response on dwarf, GA-deficient transgenic line 719 soybean is at least 10 times lower than the amount causing a response on wild-type (A3237) soybean. The abbreviations in Table 27 are: "pos" is emergence faster/stem segment longer than controls, "0" emergence timing/stem segment length similar to controls, "neg" emergence slower/stem segment shorter than controls. Thus, these compounds are attractive as seed treatments for GA-deficient soybeans because they are less likely than commercially available gibberellins such as $GA_3$ to cause negative agronomic traits, for example reduced emergence, due to The experiments conducted in the present example incorporate several improvements over those described in the previous examples. First, the supply of GA-deficient soybean seed (R5 line 719) gave an approximately 95% severe dwarf phenotype. Seed used in preceding examples contained a segregating population of normal looking, intermediate, and severe dwarf phenotypes. Secondly, hilum treatment of the soybean seeds allowed direct seed treatment with compounds dissolved in organic solvents. Third, more data are collected for each treatment, increasing the characterization of each compound tested.

The results of this study demonstrate that intermediates in the biosynthetic pathway to endogenous bioactive gibberellins in plants (such as $GA_{12}$-aldehyde and $GA_{53}$, see Scheme 1) or derivatives (such as steviol, i.e., ent-7,13-dihydroxy-kaurenoic acid, note Scheme 1) are biologically active as seed treatments on GA-deficient soybeans.

Furthermore, these compounds are active on GA-deficient soybeans at rates at least 10 times lower than the rates that show biological activity on wild-type soybeans. None of these three compounds showing this type of activity profile have all the molecular attributes thought to be necessary for biological activity per se, i.e., a 3-hydroxyl group, a 7-carboxyl group, and the lactone bridge; thus, it is possible that these compounds are converted into biologically active gibberellins in planta. Plants limited in their gibberellin biosynthetic intermediates, such as plants blocked at CPS (line 719), might be expected to be more likely to convert exogenously applied biosynthetic intermediates downstream from the block than would wild-type plants where these intermediates are not limiting plant growth. This unique property of these GA compounds, i.e., relatively high biological activity on GA-deficient soybean compared to wild-type soybeans, may be advantageous in restoring normal growth and development to GA-deficient soybeans when added as a seed treatment, foliar spray, or soil drench because these compounds would be less likely to oversupply plant tissues that do not need additional gibberellins. An oversupply of gibberellin bioactivity added as a soybean seed treatment has been attributed to decreased seedling emergence due to hypocotyl arch breakage under environmental conditions that favor soil crust formation.

The results of this study also clearly show that $GA_5$ has uniquely long-lived biological activity in soybean. It increases stem elongation in soybean up to the third internode under conditions where none of the other compounds tested showed notable activity past the first internode. $GA_5$ may have a substantially greater half-life than $GA_3$ due to greater in planta stability of the 2,3 double bond in the A-ring of $GA_5$ compared to that of the 1,2 double bond in $GA_3$. The unexpected longer duration of biological activity of $GA_5$ suggests it may have an advantage over $GA_3$ in restoring normal growth to GA-deficient soybeans that remain short past the first internode.

Example 26

Effect of GA15 GA, $GA_{19}$, GA24, and GA44 on Constitutive Transgenic GA-Deficient Dwarf Soybeans and Wild-type Soybeans Previous experiments evaluated the, biological activity of late pathway gibberellin biosynthesis precursors (e.g., $GA_9$ and $GA_5$; note Hedden and Kamiya 1997. *Annu. Rev. Plant Physiol. Plant Mol. Biol.* 48:431–460) and early pathway precursors (kaurene to $GA_{53}/GA_{12}$). The purpose of this experiment is to evaluate potential gibberellin rescue agents occurring at an intermediate or middle portion of the gibberellin biosynthesis pathway (between $GA_{53}/GA_{12}$ and $GA_{20}/GA_9$) as seed treatments. These GA compounds are tested using hilum treatment and comparing activity on GA-deficient soybean plants and normal (wild-type) plants.

| Compound | Source |
|---|---|
| $GA_3$ | |
| $GA_{15}$ | Lew Mander, Aust. Natl. U. |
| $GA_{19}$ | L. Mander |
| $GA_{24}$ | L. Mander |
| $GA_{44}$ | L. Mander |

Wild-type A3237 soybeans are obtained from Asgrow Seed Company. Transgenic seeds are fifth generation (R5) line 719 seeds.

Test Solutions

The GA compounds are dissolved in absolute ethanol at a concentration of approximately 10 µg/ml. Compounds are applied to the hilum of dry soybean seed as 1 µl drops. Seeds are sown in 4-inch plastic pots (2 pots per treatment; 5 seeds/pot) containing commercial potting soil (Metromix 200) placed in a greenhouse set for 12 hr light, and day and night temperatures of 85° F. (29° C.) and 75° F. (24° C.), respectively. After all treatments are emerged (5 DAP), hypocotyl length is measured.

All four compounds evaluated, i.e., $GA_{15}$, $GA_{19}$, $GA_{24}$ and $GA_{44}$, restored normal or greater hypocotyl height to GA-deficient (Line 719) soybeans at a test rate of 10 µg/seed as shown in FIG. 41. $GA_3$, included in this experiment for comparison, caused overelongation of A3237 hypocotyls. Interestingly, the four new compounds provided only modest increases in hypocotyl elongation of wild-type (A3237) soybean. These four compounds therefore possess desirable properties as rescue agents for GA-deficient, dwarf soybeans; when applied as a seed treatment, they restored approximately normal growth and development to GA-deficient soybeans while minimizing overelongation of wild-type soybeans.

Example 27

Effect of GA Compounds on Seedling Growth in Epicotyl-intensive GA-deficient Transgenic Dwarf Soybeans The studies described above identified four GA compounds that are either biosynthetic precursors of bioactive gibberellins ($GA_5$, $GA_9$, and $GA_{12}$) or a gibberellin derivative ($GA_3$-3-acetate) that can restore normal growth and development to GA-deficient soybeans with higher emergence than $GA_3$ when applied as seed treatments. These studies are performed on soybean plants engineered to express their GA-deficient phenotype throughout the life cycle via the use of the constitutive FMV promoter (line 719, FMV/antisense CPScc). In contrast to the constitutive FMV promoter, the peak activity of the AX5 promoter is developmentally restricted to the soybean seedling axis (epicotyl) three to five days after the start of imbibition, with limited expression beyond the seedling stage of development. Soybean lines transformed with the AX5/asCPScc cassette therefore display an epicotyl-intensive dwarf phenotype. In these lines, inhibition of the hypocotyl is modest; most of the total height reduction in these plants is due to shortening of the epicotyl. Rescue of AX5/asCPScc soybean plants therefore presents different technical challenges from those required for rescue of constitutively GA-deficient transgenic dwarf soybean lines containing the FMV/asCPScc construct. Soybean lines engineered to express the GA-deficient phenotype during early seedling growth using the AX5 promoter, and not appreciably during the rest of the life cycle, have therefore been produced (line 46 and line 234, AX5/antisense CPScc). Line 46 and line 234 have shorter hypocotyls than controls, but the greatest effect is on the epicotyl of approximately two-week old plants. The purpose of this study is to evaluate the ability of four GA compounds, i.e., $GA_9$, $GA_5$, $GA_3$-3-acetate, and $GA_{12}$, to restore normal growth in AX5/antisense CPScc soybean lines when applied as a seed treatment.

Compounds

GA$_3$ is obtained from Abbott Laboratories (Chicago, Ill.) as Ryzup™. GA$_3$-3-acetate is purchased from Sigma Chemical Company (St. Louis, Mo.). GA$_5$, GA$_9$, and GA$_{12}$ are supplied by Lew Mander (Australian National University, Canberra, Australia).

Soybean Seeds

A4922 soybean seeds are supplied by Asgrow Seed Company (Des Moines, Iowa).

Transgenic soybean lines 46 and 234 are prepared by transforming A4922 soybean with pMON34439 (AX5/antisense CPScc) as described above, and selected based on first generation (R1) phenotype and molecular analysis. Line 46 plants are R2; Line 234 plants are R3. Seed from both lines is produced from greenhouse-grown plants.

Seed Treatment

The GA compounds are dissolved in ethanol and applied to the hilum of dry seeds as not more than 10 µl droplets with a syringe. If multiple applications are made to seeds, the previous application is allowed to dry before a subsequent application is made.

Plant Growth

Seeds are sown 1 inch deep in commercial potting soil (Metromix 200) in 4-inch plastic pots and placed in a greenhouse set for 12 hours artificial light and a temperature regime of 85° F. (29° C.) day and 75° F. night (24° C.). Pots are watered as necessary by overhead hand watering. Hypocotyl and epicotyl measurements are made for each plant at various stages of plant growth.

Summary

The GA compounds are first tested using a broad range of concentrations on R2 seeds of line 46. The results are shown in FIG. 42, where the error bar represents +/– two times the standard error of the mean (n=12–15). The lower dashed horizontal line represents the total height of untreated AX5 line 46 soybeans. The upper dashed horizontal line represents the total height of untreated wild-type A4922 soybeans. Measurements are made 8 days after planting.

As shown in FIG. 42, GA$_{12}$ did not increase line 46 seedling height at concentrations up to 40 µg/seed. GA$_3$, GA$_3$-3-acetate, and GA$_5$ and are similar in their activity at 1 µg/seed. GA$_9$ is approximately ten times less active in this assay than GA$_3$, GA$_3$-3-acetate, and GA$_5$. The four latter compounds rescued AX5/asCPScc soybean line 46 total height, with some hypocotyl over-elongation. GA$_{12}$ reduced plant height.

Based on the results of the previous experiment, a narrower rate range is selected to compare the effects of GA$_3$, GA$_3$-3-acetate, GA$_5$, and GA9 on R3 line 234 seeds. The results are shown in FIG. 43, where the error bar represents ± two times the standard error of the mean (n=7–10). The lower dashed horizontal line represents the total height of untreated AX5 line 234 soybeans. The upper dashed horizontal line represents the total height of untreated wild-type A4922 soybeans. Measurements are made 10 days after planting.

As shown in FIG. 43, GA$_3$, GA$_3$-3-acetate, and GA$_5$ produced a generally similar response in seed treatment rates between 0.1 and 1 µg/seed. GA$_9$ is approximately 10 times less active than these compounds. Each of these compounds could restore normal height to line 234 soybeans by producing both hypocotyl and epicotyl elongation; however, they did not maintain the same ratio of hypocotyl to epicotyl length as in the control line (A4922). These results suggest that GA$_3$, GA$_3$-3-acetate, GA$_5$, and GA$_9$ can each restore normal height to AX5/antisense CPScc soybean, but that they may not maintain the same hypocotyl to epicotyl height ratio as in wild-type soybeans, i.e., some over-elongation of the hypocotyl contributed to restoration of full plant height.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

Aach, H., et al., "ent-Kaurene synthase is located in proplastids of meristematic shoot tissues", *Planta* 202: 211–219 (1997)

Altschul, S. F., et al., "Basic local alignment search tool", *J. Mol. Biol.* 215: 403–410 (1990)

Aoyama, et al., "A glucocorticoid-mediated transcriptional induction system in transgenic plants", *Plant J.* 11: 605–612 (1997)

Aoyama, R., et al, "Molecular cloning and functional expression of a human peroxisomal acyl-coenzyme A oxidase", *Biochem. Biophys. Res. Commun.* 198: 1113–1118 (1994)

Back, et al., "Isolation of the spinach nitrite reductase gene promoter which confers nitrate inducibility on GUS gene expression in transgenic tobacco", *Plant Mol. Biol.* 17: 9–18 (1991)

Bensen, R. J. et al., "Cloning and characterization of the maize An1 gene", *Plant Cell.* 7: 75–84 (1995)

Bewley, J. D., "Seed germination and dormancy", *Plant Cell* 9: 1055–1066 (1997)

Briggs; S. P. and Bensen; R. J. U.S. Pat. No. 5,612,191 (Pioneer Hi-Bred International, Inc., Issued Mar. 18, 1997)

Briggs; S. P. and Bensen; R. J. U.S. Pat. No. 5,773,288 (Pioneer Hi-Bred International, Inc., Issued: Jun. 30, 1998)

Christou, P., et al., "Developmental aspects of soybean (*Glycine max*) somatic embryogenesis", *Ann. Bot.* 64: 225–234 (1989)

Comai, L., et al., "Expression of a *Brassica napus* malate synthase gene in transgenic tomato plants during the transition from late embryogeny to germination", *Plant. Physiol.* 98: 53–61 (1992)

Comai, L., et al., "Coordinate expression of transcriptionally regulated isocitrate lyase and malate synthase genes in *Brassica napus*", *Plant Cell.* 1: 293–300 (1989)

Comai, L., et al., "Expression of a *Brassica napus* malate synthase gene in transgenic tomato plants during the transition from late embryogeny to germination", *Plant. Physiol.* 98: 53–61 (1992)

Coruzzi, G., et al., "Tissue-specific and light-regulated expression of a pea nuclear gene encoding the small subunit of ribulose-1,5-bisphosphate carboxylase", *EMBO J.* 3: 1671–1979 (1984)

De la Haba, et al., "Antagonistic effect of gibberellic acid and boron on protein and carbohydrate metabolism of soybean germinating seeds", *J. Plant Nutr.* 8: 1061–1073 (1985)

Depicker, A., et al., "Nopaline synthase: transcript mapping and DNA sequence", *J. Molec. Appl. Genet.* 1: 561–573 (1982)

Dietrich, R. A., et al., "Downstream DNA sequences are required to activate a gene expressed in the root cortex of embryos and seedlings", *Plant Cell* 4: 1371–1382 (1992)

Dmochowska, A., et al., "Structure and transcriptional control of the *Saccharomyces cerevisiae* POX1 gene encoding acyl coenzyme A oxidase", *Gene.* 88: 247–252, (1990)

Don, R. H., et al., "Touchdown PCR to circumvent spurious priming during gene amplification" *Nucleic Acids Res.* 19: 4008 (1991)

Fraley, R. T., et al., "Expression of bacterial genes in plant cells", *Proc. Natl. Acad. Sci. U.S.A.* 80: 4803–4807 (1983)

Gatz, C., et al., "Regulation of a modified CaMV 35S promoter by the Tn10-encoded Tet repressor in transgenic tobacco", *Mol. Gen. Genet.* 227: 229–237 (1991)

Gatz, C., et al., "Tn10-encoded tet repressor can regulate an operator-containing plant promoter" *Proc. Natl. Acad. Sci. USA.* 85: 1394–1397 (1988)

Ghersa, C. M., et al., "Seed dormancy implications in grain and forage production", *J. Prod. Agri.* 10: 111–117 (1997)

Gish, W. et al., "Identification of protein coding regions by database similarity search", *Nat. Genet.* 3: 266–272 (1993)

Gnatenko, Z. P., et al., "Phytohormone content of acotyledonous embryos of soy seeds during germination", *Biol. Nauki* (Moscow) 11: 77–80 (1981)

Grossi, M., et al., "Characterization of two barley genes that respond rapidly to dehydration stress", *Plant Sci.* 105: 71–80 (1995)

Harada, J. J., et al., "Spatially regulated genes expressed during seed germination and postgerminative development and activated during embryogeny" *Mol. Gen. Genet.* 212: 466–473 (1988)

Hill, D. E., et al., "Complete nucleotide sequence of the peroxisomal acyl coA oxidase from the alkane-utilizing yeast *Candida maltosa*", *Nuc. Acids. Res.* 16: 365–366 (1988)

Huang, A. H. C. In: Lipases, in Lipid Metabolism in plants", Thomas Moore. Ed. (1993)

Komatsuda, T. et al., "Maturation and germination of somatic embryos as affected by sucrose and plant growth regulators in soybeans *Glycine gracilis* Skvortz and *Glycine max* (L.)", *Merr. Plant Cell Tissue Organ Culture* 28: 103–113. (1992)

Kul'shan, Z. P., et al., "Effects of gibberellin on the energy metabolism of germinating soybean seeds", Osob. Gorm. Regul. Protsessov Obmena Tempov Rosta Rast. Yakushina, N. I (Ed) pg. 114–123 (1983)

Lange, T., WO9428141

MacFerrin, K. D. et al., *Proc. Natl. Acad. Sci. USA.* 87: 1937–1941 (1990)

Mett, V. L. et al., "Copper-controllable gene expression system for whole plants" *Proc. Natl. Acad. Sci. USA.* 90: 4567–4571 (1993)

Miyazawa S., et al., "Complete nucleotide sequence of cDNA and predicted amino acid sequence of rat acyl coA Oxidase", *J. Biol. Chem.* 262: 8131–8137 (1987)

Nalawadi, U. G., et al., "Improvement in the seed germination of soybean varieties by pre-soaking treatments", *Indian J. Agr. Sci.* 43: 546–550 (1973)

Newman, T., et al., "Genes Galore: A summary of methods for accessing results from large-scale partial sequencing of anonymous *Arabidopsis* cDNA clones", *Plant Physiol.* 106: 1241–1255 (1994)

Okazaki, K., et al., "Two acyl coenzyme A oxidases in peroxisomes of the yeast *Candida tropicalis*: Primary structures deduced from genomic DNA sequences", *Proc. Natl. Acad. Sci. USA.* 83: 1232–1236 (1986)

Reynolds, S. J., et al., "Regulation of expression of the cucumber isocitrate lyase gene in cotyledons upon seed germination and by sucrose", *Plant Mol. Biol.* 29: 885–896 (1995)

Reynolds, S. J., et al., "The isocitrate lyase gene of cucumber: isolation, characterization and expression in cotyledons following seed germination", *Plant Mol. Biol.* 27: 487–497 (1995)

Sarma, P. S., et al., "Effects of gibberellic acid and naphthalene acetic acid on germination of soybean Clark-63 (*Glycine max* (L) Merrill", *Andhra Agric. J.* 25: 5–7 (1979)

Schreiber, S. L. and Verdine, G. L., *Tetrahedron* 47: 2543–2562 (1991)

Shen, Q., et al., "Functional dissection of an abscisic acid (ABA)-inducible gene reveals two independent ABA-responsive complexes each containing a G-box and a novel cis-acting element", *Plant Cell* 7: 295–307 (1995)

Shimizu, S., et al., "An Acyl-CoA oxidase from *Candida tropicalis:*", *Biochem. Biophys. Res. Commun.* 91: 108–113 (1979)

Sossountzov, L., et al., "Spatial and temporal expression of a maize lipid transfer protein gene", *Plant Cell* 3: 923–933 (1991)

Sun, T-P., et al., "The *Arabidopsis* GA1 locus encodes the cyclase ent-kaurene synthetase A of gibberellin biosynthesis", *Plant Cell* 6: 1509–1518 (1994)

Thomas, T. H., et al., "Some reflection on the relationship between endogenous hormones and light-mediated seed dormancy", *Plant Growth Reg.* 11: 239–248 (1992)

Ulmasov, T., et al., "The soybean GH2/4 gene that encodes a glutathione S-transferase has a promoter that is activated by a wide range of chemical agents", *Plant Physiol.* 108: 919–927 (1995)

Varanasi, U., et al., "Isolation of the human peroxisomal acyl-CoA oxidase gene: organization, promoter analysis and chromosomal localization", *Proc. Natl. Acad. Sci. U.S.A.* 91: 3107–3111 (1994)

Vogeli-Lange, R., et al., "Evidence for a role of -1,3-glucanase B in dicot seed germination" *Plant J.* 5: 273–278 (1994).

Wang, Q. et al., "Application of Ga3 and kinetin to improve corn and soybean seedling emergence at low temperature", *Enviro. Exp. Bot.* 36: 377–383 (1996)

Washio, K., et al., "Organ-specific and hormone-dependent expression of genes for serine carboxypeptidases during development and following germination of rice grains", *Plant Physiol.* 105: 1275–1280 (1994)

Weinmann P., et al, "A chimeric transactivator allows tetracycline-responsive gene expression in whole plants", *Plant J.* 5: 559–569 (1994)

Wilde, R. J. et al., "Control of gene expression in tobacco cells using a bacterial operator-repressor system", *EMBO J.* 11: 1251–1259 (1992)

Xu, Y-L, et al., "Gibberellins and stem growth in *Arabidopsis thaliana.*", *Plant Physiol.* 114: 1471–1476 (1997)

Yamauchi, D., et al, "Promoter regions of cystein endopeptidase genes from legumes confer germination-specific expression in transgenic tobacco seeds", *Plant Mol. Biol.* 30 :321–329 (1996)

Zhang, et al., "Application of gibberellic acid to the surface of soybean seed (*Glycine max* (L.) Merr.) and symbiotic nodulation, plant development, final grain and protein yield under short season conditions", *Plant Soil* 188: (1997)

Zhang, J. Z., et al., "DNA sequences that activate isocitrate lyase gene expression during late embryogenesis and during postgerminative growth", *Plant Physiol.* 110: 1069–1079 (1996)

Zhang, J. Z., et al., "Isocitrate lyase and malate synthase genes from *Brassica napus* L. are active in pollen", *Plant Physiol.* 104: 857–864 (1994)

Zhang, J. Z., et al., "Two classes of isocitrate lyase genes are expressed during late embryogeny and post-germination in *Brassica napus* L." *Mol. Gen, Genet.* 238: 177–184 (1993)

Zheng, G. H., et al., "Enhancement of canola seed germination and seedling emergence at low temperature by priming", *Crop Sci.* 34: 1589–1593 (1994)

What is claimed is:

1. A method of growing a transgenic plant comprising:
providing a transgenic plant or a seed or seedling thereof comprising a transgene, the transgene comprising a promoter and, operably linked to the promoter, a sequence that encodes an enzyme that inactivates an endogenous gibberellin in a plant cell, causing reduced levels of the endogenous gibberellin in the plant cell, compared with an otherwise identical plant or seed or seedling thereof that lacks the transgene, wherein the sequence is SEQ ID NO: 62;
applying a composition that comprises at least one GA compound that is metabolized by the seed or seedling to produce a product having gibberellin activity that is not inactivated by the enzyme to the transgenic plant or the seed or seedling thereof; and
growing the transgenic plant or the seed or seedling thereof to produce a phenotypically normal transgenic plant.

2. The method of claim 1, wherein the application of said GA compound is to the soil in which the transgenic plant or seed or seedling thereof is grown.

3. The method of claim 1, wherein the sequence encodes the soybean GA 2-oxidase 1 (SEQ ID NO:63).

4. The method of claim 1, wherein the promoter is preferentially expressed in developing seeds, during seed germination, or in early seedlings.

5. The method of claim 4, wherein said promoter is selected from the group consisting of the Brassica isocitrate lyase gene promoter, the soybean AX5 gene promoter (SEQ ID NO:7), the soybean Sle2 gene promoter, and the At2ox4 gene promoter.

6. The method of claim 1, wherein the GA compound is $GA_4$, $GA_7$, $GA_3$, or $GA_3$-3-acetate.

7. The method of claim 6, wherein the GA compound is $GA_3$ or $GA_3$-3-acetate.

8. An isolated nucleic acid construct comprising a promoter that causes expression of an operably linked nucleic acid segment in a plant cell and, operably linked to the promoter, the nucleic acid segment comprising a sequence that encodes a polypeptide having a GA 2-oxidase activity, wherein expression of the nucleic acid segment in the plant cell results in inactivation of an endogenous gibberellin in the plant cell, thereby reducing levels of the endogenous gibberellin in the plant cell compared with an otherwise identical plant cell in which the nucleic acid segment is not expressed, wherein the sequence is SEQ ID NO: 62.

9. A transgenic plant transformed with a nucleic acid segment, wherein the nucleic acid segment comprises a promoter that causes expression of an operably linked nucleic acid segment in a plant cell and, operably linked to the promoter, the nucleic acid segment comprising a sequence that encodes a polypeptide having a GA 2-oxidase activity, wherein the sequence is SEQ ID NO: 62, and expression of the nucleic acid segment in the plant cell results in inactivation of an endogenous gibberellin in the plant cell, thereby reducing levels of the endogenous gibberellin in the plant cell compared with an otherwise identical plant cell in which the nucleic acid segment is not expressed.

10. The transgenic plant of claim 9, characterized by at least one phenotype selected from the group consisting of a shortened hypocotyl, shortened epicotyl, and both a shortened hypocotyl and shortened epicotyl compared with an otherwise identical plant that lacks the nucleic acid segment.

* * * * *

SEQUENCE LISTING

```
<160> NUMBER OF SEQ ID NOS: 89
<210> SEQ ID NO 1
<211> LENGTH: 1265
<212> TYPE: DNA
<213> ORGANISM: Brassica napus
<220> FEATURE:
<221> NAME/KEY: misc_feature
<222> LOCATION: (1)..(1265)
<223> OTHER INFORMATION: N = any nucleotide

<400> SEQUENCE: 1
tcggcgtacg atacggngtg ggttgctttg atcgacgcgg agataaactc cggcatttcc      60
tccgccgtga aatggatagn cacantcagc tatccgatgg tcangggtg atgctactct      120 ctcttatcat gacgtctcat caatacctg gcgtgcgtcg ttgctctaac atcatggaat      180
ctctttcctc atcaatgcca caaggaatc atgttttta gagaaaatat cggaaagcta      240
gaagaagaag acgatgagca tatgccaatt ggattcgaag tagcctttcc ttcattactt      300
gagatagctc gaggaataaa catagatgta ccgnacgatt ctccggtctt gaagggatat      360
atacgccaag aaggagctaa agctaacaag gatacccaaa gagataatgc acaagatacc      420
aacaacattg ttgcatagtt tgggagggca tgcgtgattt agactgggaa aaactattga      480
aacttcaatg tcaagatgga tctttcctct tctctcctnc ctcgaccgnt ttcggattca      540
tgcaggaccc gagacagtaa gtgtcttggg gtattngggc aatgccggca aacgtttcaa      600
tggagggggt ccccaatgtn ttcctgtggg tcttttcggg catatatggt tcgtgggggg      660
cctacancgg ttngggnata tccgagatac ttcgaagaag agantaagca gtgtcttgac      720
tatgttcaca gatagtggac aggcaaggna tatgntgggc tagatgttct catgtncgag      780
anatcgacga cacaccntg gnanntagac tcntaagact tgatggatac ncagtttccg      840
cagatntgtt caagntcttt gagaaagang gagagttttt ctgcntcgcg gnccaatcan      900
accngnnggt gnctggtatg ttcaatctat accgggcatc ncaantagcg tttccaaggg      960
aagagatatt gtganacgcc caagaatttt cgtccaagta tctacaacat aaacaagaga      1020 nagggagtt gcttgataag tggattataa tganagactt acctgctcga gattgggttc      1080
acgttggaga ttccatggta tncaagcttn cctcgagttg agaccagatt ctatattgag      1140
cagtatggtg gagaaaccga cgtttggatt ggcaagaccc tttataggat gccatatgtg      1200
```

| aacaataatg aatatctgga attagcnnaa caagactaca acaactgcca agctccgcat | 1260 |
| cagct | 1265 |

<210> SEQ ID NO 2
<211> LENGTH: 2460
<212> TYPE: DNA
<213> ORGANISM: Glycine max

<400> SEQUENCE: 2

| aacactccat ggcttctcac ttccgccttc cgtctttctc ttcttctaac catttccttt | 60 |
| taacatcttc ttcttcttct tcttccatct ctcttcacca cttctccaaa tcctctctgg | 120 |
| gtgccgtgtc gtctgagact aacgacaaac aagagataag atgcagagca atatccaaac | 180 |
| cacgaacaca agaatgttca gacatatttc agggtagtct agcaacgtta aagtttcgtg | 240 |
| agattaatgt ggaagatgac atagaagagg agcaagacat tggggctttg gtggcaaatg | 300 |
| agatcaagaa gagagtggac actatcaaat caatattggg ttccatggaa gatggagaga | 360 |
| taacagtatc tgcttatgac actgcttggg ttgctctgat agaagatgtt catggaactg | 420 |
| gtgtccctca atttccatcg agtctagaat ggatagcgaa aaatcaacac cccgatggtt | 480 |
| catggggtga taaggaatta ttctcagccc atgatcggat tattaacacg ttggcttgtg | 540 |
| ttattgcatt aaaaacatgg aatatgcacc ctgaaaagtg tgagaaagga atggcatttt | 600 |
| ttagagagaa tcttggcaag cttcagaacg agaatgtaga gcatatgcca attggttttg | 660 |
| aagtagcctt tccatcactt cttgacatgg ctcgtggctt ggacattgaa gtgccgaaca | 720 |
| attccccaat ccttaataaa atcttcgcaa tgagaaacgt aaaactcaca agaataccaa | 780 |
| gagctatgag gcataaagtg cccacaagtc tccttcatag cttggaaggg atgtcaggcc | 840 |
| ttgactggaa agaacttcta aaactgcagt ctcaagacgg gtctttcttg ttttctccgt | 900 |
| catccacagc ctttgctctc atgcaaacta aggaccaaaa ttgccacaat tacttgaata | 960 |
| aagtggtcaa gaggttcaat gggggagttc caaacgtgta tccagtggat ttgttcgaac | 1020 |
| atatttgggt ggttgatagg cttgaacgtc taggaatatc tcagtatttt cagcaagaga | 1080 |
| tcaaggactg tttgagttat gtttacagat attggactga aaagggtatt tgttgggcaa | 1140 |
| gaaattcaaa tgttcaagac attgatgaca cggcaatggg tttcagacta ttaagattac | 1200 |
| acggttacca agtttcagcc gatgtgttca gaactttga gagaaatggt gaatttttct | 1260 |
| gctttacggg gcagaccaca caagcagtga caggaatgtt taatctgtat agggccacac | 1320 |
| aaatcatgtt cccgggagag agaattcttg agcacgggaa gcacttctct gccaaatttt | 1380 |
| tgaaggagaa gagagcagca atgagcttg tagataaatg gatcataatg aagaacctgg | 1440 |
| cagaagaggt tgcgtatgct ttggacgtac catggtatgc aagcctacct cgagtggaga | 1500 |
| caagattcta cattgatcaa tacgcggtg agagtgacgt gtggataggc aaaacccttt | 1560 |
| ataggatggc atatgtgaac aacaataact atctcgagct tgctaaatta gattacaaca | 1620 |
| attgccaggc actgcatcta atagagtggg ggagaattca aaagtggtac tcagaatcta | 1680 |
| gattggagga gtttggaatg aacagaagaa cgcttctatt ggcctatttt gtggcagcag | 1740 |
| caagcatatt tgagcctgaa aagtctcgtg tgagactagc gtgggcacaa accagtatct | 1800 |
| tacttgagac cataacatcc tatgttagtg atgcagaaat gaggaaagct ttcatgaaaa | 1860 |
| aattcagtga ctgtcttaac aggcgagact actccattgg ctggaggttg aacaggaaca | 1920 |
| gaacaggaca tggactcgct gagactttgg ttgccaccat agatcaaatc tcgtgggata | 1980 |
| tactcgtgtc tcacggtcat gaaattggat atgacatgca tcgcaattgg gaaaagtggc | 2040 |

```
tttcgagttg gcatcgggaa ggagacaaat gtaaaggaca agccgagctt ttggcgcaga    2100
caataaacct atgtggcggg cattggattt ccgaggatca agtgtcggat ccactgtatc    2160
agagtctcct tcaactcact aacaatctct gcaataaact tcgttgccac caaaaggaca    2220
aggaacttga gagcagcaac agcggcacga atgtaaacag catgatcacc caagaagaag    2280
agtcaaaaat gcaagaactc gtgcaattgg tgcaccaaaa atctccaact ggcattgatt    2340
tcaatatcaa gaatactttc ctcacagtgg ccaagagttt ttactataca gcttttgtg    2400 attcaaggac cgtcaacttc catattgcca aagttctgtt tgatgaagtc gtttaaaagc    2460
```

<210> SEQ ID NO 3
<211> LENGTH: 870
<212> TYPE: DNA
<213> ORGANISM: Gossypium hirsutum

<400> SEQUENCE: 3

```
agcttggtac cgagctcgga tccactagta acggccgcca gtgtgctgga attcggcttt     60
gtcataaacc cgagtgtttc ttgcccagga aattccatct tcagtccagt atctataaac    120
gtaatctagg cattctttaa tttctgggtg gaaatatctt gaaatcccaa ggcgttgcaa    180
gcggtcgaca gtccaaatat gttcaaacag gtcaaccgga tacacattgg ggactccccc    240
attgaatctt tgaacagttt tcattaaata tctgaggcaa ttctcatctt tggtttgcat    300
gagtgcgaag gcagtggagg atggcgagaa caagaaagac ccatctatgc actgcaactt    360
caaaagcttt tcccagtcca agtctggcat cccttcaagg ctatggagta gtgttgtggg    420
tacattatgc attatctcct ttggtatcct tgtgagcttt agatctctct ttgcatatat    480
gtctataaag acagggagt catacggtac ttcaatgtgt aaacttcgag ctatctccag    540
aagcggagga aaagccactt caaacccgat tggcatgtgc tcctcactct cgttttcgag    600
tttgcttata ttatctttga aaaacgacac ccctttctgg catttgtcag gatgaatacc    660
ccatgttttc aaggcaataa cacaagctaa agtgttgatc agacgatcat gtgccatgaa    720
tatttgtcta tcgccccagg atccatcggg gagctgattg ttagcgatcc attcaagccg    780
aattctgcag atatccatca cactggcggc cgctcgagca tgcatctaga ccgcccaatt    840
cgccctatag tgagtcgtat tacaatcact                                     870
```

<210> SEQ ID NO 4
<211> LENGTH: 2109
<212> TYPE: DNA
<213> ORGANISM: Triticum aestivum

<400> SEQUENCE: 4

```
gcacgagcca acacccttgc ctgtgtcgtg gctctcacaa agtggtctct tggccctgat     60
aaatgcagta gagggctctc ttttctggaa gagaacatgt ggaggctagc agaggaagac    120
ctggagtcga tgcccatcgg cttcgagatt gcgtttcctt ctctcctgga ggtggccaag    180
agcttgggca ttgggttccc gtatgatcac catgctctgc agtgcatata tgccaacaga    240
gaagtgaagc tcaagaggat tccgatggag atgatgcaca gaattccaac gacgatcctg    300
cattcccttg aaggtatgcc cggggtggac tggcacaaga tcctcaggct ccagtctagt    360
gatgggtcct tcctctattc tccttcggct acagcctttg ctctcaagca aactggtgac    420
gcaaaatgct tcgagtacat cgacagaatc gtcaagaaat tcaatggagg agttcccaat    480
gtttacccgg tcgatctctt tgaacacatc tgggtcgtcg atcggctgga gcgtcttgga    540
```

```
atctcgcgct acttcaagca agaaattaaa cagtgcttgg actatgtcca cagccactgg      600
actgaagacg ggatttgctg ggcaaggaac tccgctgtaa gagacgtgga tgacacagcc      660
atggccttcc ggctgctgcg gctgcatgga tacaccgtct cgccgagtgt atttgagaag      720
tttgagaagg acgggagtt cttctgtttc gcggggcaat caacgcaagc agtcactggg       780
atgtacaacc tgaacagggc ctctcagcta agattccctg agaggatgt gttgcagcgt       840 gcagggagat tctcgtatga gttccttaga gaaaggaag cccagggcac tattcgggac       900
aaatggatca ttgctaagga tctaccaggc gaggtaaaat atacactgga cttcccatgg      960
tatgcaagct taccgcgtgt agaagcaagg gcctacctag atcaatatgg tggtgagaat     1020
gatgtctgga ttggaaagac actctacagg atgccacttg tgaacaacaa cacctatctt    1080
gaattggcaa agcgtgattt caatcgctgc caagtccaac atcagcttga gtggcatggc    1140
ctacaaaagt ggtttattga aatggcctc gagacttttg gggtggcttt aagagatgtt     1200
ctgagagctt attttctagc tgccgcttgc attttcgaac caagccgtgc cacagagcga    1260
cttgcatggg ccaaggtctc agtgctggcc aacattatta ctaaatatct tcatagcgat    1320
ttatcgggta tgaaatgat ggaacggttt atgcacggcg gtctccatga aggaaatagt     1380
actatatcat ggcgtaaagg agatgcaaaa gaggacattc ttgtgggggt acttcagcag    1440
tttattgatt tattgcaca agagacacta cctgttggtg aaggaccaat gtacatcaac    1500
aatttgttac gctgcgcttg gattgaatgg atgatgcaac tgataaatag agaggatgac   1560
acatacgatt caagtgttat tcaagcaggg tcgtgcatgg ttcacgataa acaaacattt    1620
ttgcttctag tcaaaattat tgagatttgt ggtggacgaa tcggtgaagc atcatcgatg    1680
ataaacagca aggatggtgc ttgctttatt caacttgcgt cctctatttg tgacaacctt    1740
caccacaaga tgttactttc tcaggacacc gaaactaacg aggcggcgat gagccacatg    1800
gatgagaaaa tcgaggctgg catgcaggaa ctcacccaga actttctcca gacgcatgac    1860
gatggggcga acagcgagac gaagcggacc ttgttgagcg tcgtgaggag ctgttactac    1920
gcggctaact gccctcgcca tgtattcgat agacatgttt cgaaggtcat tttcgaacat    1980
gtgttttgaa agaaagaaag aagaattatc ctscaatggt agggatggtg gagatgggat    2040
ctgtatgtac atagagaaaa gaatgctgca agaggaagg gcgtattcaa aaaaaaaaa     2100 aaaaaaaaa                                                            2109
```

<210> SEQ ID NO 5
<211> LENGTH: 1030
<212> TYPE: DNA
<213> ORGANISM: Glycine max
<400> SEQUENCE: 5

```
atgccttcac tctcagaagc ctaccgagcc accccgtgc acgttcaaca caagcaccct       60
gacttaaact ccctacaaga actccccgag tcttacactt ggcacacca tagccatgat      120 gatcatactc ctgcagcttc caacgagagt gtccccgtta ttgatctcaa cgacccaaat     180
gcttcaaagt tgatacacca tgcatgcata acttggggag cgtaccaagt ggtgaaccat     240
gccataccca tgagcctcct ccaagacatt caatggggttg gggagacact cttctctctc    300
ccttgtcaca aaaacaaaa agcagctcgt tccctgacg tgctgatgg ctatggcctt        360 gctcgcatct cttccttctt ccccaaactc atgtggtctg agggattcac aattgttgga    420
tcccctcttg agcattttcg tcaactctgg ccccaagatt accacaaata ctgtgatatc     480
gtcaagcgat atgatgaagc catgaaaaag ctagtgggaa agctgatgtg gctgatgttg    540
```

```
gattctctgg gtattacaaa ggaagacctg aaatgggccg ggtccaaagg ccaattcaaa    600
aagacatgcg cagccttgca attgaactct tacccgactt gtccggatcc ggatcgggcc    660
atgggtctgg ccgcccacac cgactccacc cttctcacaa tcctttacca aaacaacata    720
agcgggttgc aggttcaccg aaaaggcggc gggtgggtga cggtggcacc agtccccgaa    780
gggcttgtga tcaatgtagg cgacctcctc cacatattgt cgaacgggtt gtacccgagt    840
gtgctccacc gggtcttagt gaaccggatc cagcaaaggc tttcagttgc gtatttatgt    900 gggcccctc cgaatgtgga gatatgtcca catgcgaagc tagtgggccc aaataagcct    960
cccctttata aggcagtgac ttggaatgag taccttggca ctaaagcaaa gcatttcaac   1020
aaggcactct                                                          1030

<210> SEQ ID NO 6
<211> LENGTH: 950
<212> TYPE: DNA
<213> ORGANISM: Gossypium hirsutum
<220> FEATURE:
<221> NAME/KEY: misc_feature
<222> LOCATION: (1)..(950)
<223> OTHER INFORMATION: N = any nucleotide

<400> SEQUENCE: 6
ggcttgtgcg aaggtactct ttccaagtca ccaaccatgg natctccaca agtctccttg     60
atatgggtgg agcacacttg ccgctcccct ttctctttac cagttcacca aaaacttaaa    120
gctgcaaggt ctcctgacgg cgtctccggc tatggatttg ccaggatttc ctcctttttt    180
tctaagctta tgtggtctca ggggttcact attgttgggc caccagacga gcattttgc     240 caactttggc cccaagattt cagctaccac tggtgagcac ccattgcaca catgcgaatg    300
cacgtgcaaa ttctgattat tattgattct ctttgttctg atattttct cttttgtggc     360 aacccccct tcccatttgc ttttcttaat gcaattagca aagattacaa tgaaagctat    420
ggacccacga agtagattag gagtagtaat ggagttaaaa aaaaacanaa accaacccac    480
ttgtcaagtg tttgcttgtt gtatcaccag cataatagca gcttaactgt tgcatacagt    540
attctgattc tttcgtaatt tgattgtttc atttgtttgt ttcttcctca gtgatgttat    600
taaggattac aagggaggaa ttgaaaaagt tagccgggag attgatgtgg ctcatgttgg    660
nttccttagg cataattgcc aaagaggata tcaaatgggc cggcccaaaa gctgacttca    720
aaggggcctc agcagcttta cagttgaatt actaccccgc ttgtccggac ccggaccgag    780
ccatgggtct cgccccgcac accgactcca ctctcctcac catcctctac caaaacagca    840 ctagtggggtt gcaggtcttt aaagagggag ccggatgggt cgcggtacct ccggtaccgg    900
ggggacttgt gataaacgtt ggtgaccta tgcatatact gtccaacggg               950

<210> SEQ ID NO 7
<211> LENGTH: 943
<212> TYPE: DNA
<213> ORGANISM: Glycine max

<400> SEQUENCE: 7
gtttcaaaca aaatgggtgc gtggagtttt ccaaaattgg ttgaaaagaa ttaaatttga     60
tcaagtacta tgagtattca aggccaaatc atggaaatcg caaatgcaat tcaacaggaa    120
agccttgtct gtgttaattt ctaatctaac ataataatgt ttcaatttc aatttagcca     180 actcaatttt tgagccaaat atcatatatg ttttcagcta gagtagtttg caagatccgc    240
```

```
atacgggcct taattagttt atactattat ttagtagcat tgcttcatta ggattaatgg      300
tttatttctt gaaagaaaga aaaaaaggt actaaactat taactaataa tttacttata      360
ctaccattat gtccataaac ttgatcagta agtgtataat aagtgatttg agcctagcca      420
aacatagcaa atctcataca actaaagtat atatgcagaa agcatttctt ggctcctaat      480
atggtatata tctaaatcaa ttctccagtg ttaagactct ttttctttgt tagttagcaa      540
ttaatcatga gtcaaaacca gaaactagct actacactcc catgccataa tgcgtaaaac      600
aattcaatta tttggtatgg caattgaaat tatttgtatt aacacctttc caaggagac       660 aaagacgtcg gtgcattgag aaatgtgaaa aaaaatatt atcacttgtg tggacttgtc       720
aatgctcccg ttaaatttcc aactttgcaa ctacaagaag acagcattca cctacacagc      780
aattgaaaat ccacaccgaa gattgacctt tgtacaacgg tgctagaaac cgcgtcacta      840
gtaataacta ttggattgag acatgcactt aacagtaagg cccccaacta gtataaaaac      900
cagttattgg gtgtgttact catcagcaac tacaacgtga gaa                       943
```

<210> SEQ ID NO 8
<211> LENGTH: 1077
<212> TYPE: DNA
<213> ORGANISM: Glycine max
<220> FEATURE:
<221> NAME/KEY: misc_feature
<222> LOCATION: (90)..(998)
<223> OTHER INFORMATION: N = any nucleotide

<400> SEQUENCE: 8

```
atggaattaa gtgcttccac tctagtactt taccctgcat cacagccacc acaagagcct        60
aaaaatgaga acaatggggg catagtttgn gactcaaaaa atttgnagca aatgcaaggg      120
gaaatgccca aagagttcct ttggccttct agggacttgg ttgacaccac ccaagaggag      180
ctaaaggaac cccttgtgga cctagcaatc tttaagaatg gtgacgagaa agctatttcc      240
aatgcagcag agcttgtgag aaaagcatgc ttgaagcatg ggttttttcca agtgataaac      300 catggtgtgg acccagatct cattgatgct gcatatcatg aaattgactc cattttttaag     360 ctcccattga gcaaaaagat gggtgctaag agcaaaacct ggtggtgtct cagggtactc      420
tggtgctcat gcagatcgtt attcgtccaa gttgccatgg aaagagacgt tttctttcct      480
ctatgatcac caaagcttct ccaactccca gattgttgac tacttcaagt ctgtgttagg      540
ggaggatctt caacacacag ggagggtata tcaaaagtac tgcgaggcaa tgaaggattt      600
atctttagta attatggagc tattggtrta ttwgkttggg tgtggatcgt gagcattatc      660
gaagattttt tcaagatggt gactcaataa tgaggtgcaa ctattatcca ccttgcaaca      720
gagcgaacct caccttaggc actggccctc acactgatcc aacctcacta accattcttc      780
atcaagacca agttggaggt ttagaagttt ttgtagataa caaatggctc gctgttcgcc      840
ctcgatctga agccttagtc ataaacatag gtgatacttt catggcattg tcaaatggga      900
gatacaagag ttgtctacac agggcattgg tgaacacata cagggagaga aggtcccttg      960
tttattttgt gtgtccaaga gaagaccaaa tagtgagncc cccagacaat ttgttatgca     1020
gaaatgagga aggaagtac cctgattcac atgtccaatt gttaggtacc ggatcca         1077
```

<210> SEQ ID NO 9
<211> LENGTH: 21
<212> TYPE: DNA
<213> ORGANISM: Artificial Sequence
<220> FEATURE:
<223> OTHER INFORMATION: Primer

```
<220> FEATURE:
<221> NAME/KEY: misc_feature
<222> LOCATION: (1)..(18)
<223> OTHER INFORMATION: N = any nucleotide
<220> FEATURE:
<221> NAME/KEY: modified_base
<222> LOCATION: (6)..(18)
<223> OTHER INFORMATION: I

<400> SEQUENCE: 9
tcggcntacg ayacngcntg g                                              21

<210> SEQ ID NO 10
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (10)..(10)
<223> OTHER INFORMATION: N = any nucleotide
<220> FEATURE:
<221> NAME/KEY: modified_base
<222> LOCATION: (10)..(10)
<223> OTHER INFORMATION: I

<400> SEQUENCE: 10
agctgatgcn gagcttggc                                                 19

<210> SEQ ID NO 11
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(21)
<223> OTHER INFORMATION: N = any nucleotide
<220> FEATURE:
<221> NAME/KEY: modified_base
<222> LOCATION: (3)..(21)
<223> OTHER INFORMATION: I

<400> SEQUENCE: 11
gcntaygaya cngcntgggt ngc                                            23

<210> SEQ ID NO 12
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(18)
<223> OTHER INFORMATION: N = any nucleotide
<220> FEATURE:
<221> NAME/KEY: modified_base
<222> LOCATION: (3)..(18)
<223> OTHER INFORMATION: I

<400> SEQUENCE: 12
ytncayagyc tngarggnat g                                              21

<210> SEQ ID NO 13
<211> LENGTH: 23
<212> TYPE: DNA
<213> ORGANISM: Artificial Sequence
<220> FEATURE:
```

```
<223> OTHER INFORMATION: Primer
<220> FEATURE:
<221> NAME/KEY: modified_base
<222> LOCATION: (6)..(15)
<223> OTHER INFORMATION: I
<220> FEATURE:
<221> NAME/KEY: misc_feature
<222> LOCATION: (6)..(15)
<223> OTHER INFORMATION: N = any nucleotide

<400> SEQUENCE: 13
ckraangcca tngcngtrtc rtc                                        23

<210> SEQ ID NO 14
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(22)
<223> OTHER INFORMATION: N = any nucleotide
<220> FEATURE:
<221> NAME/KEY: modified_base
<222> LOCATION: (4)..(22)
<223> OTHER INFORMATION: I

<400> SEQUENCE: 14
catnckrtan arngtyttnc cnat                                       24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
aacactccat ggcttctcac ttcc                                       24

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
ttaaacgact tcatcaaaca gaactttgg                                  29

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
cctcaatttc catckagtct agartgg                                    27

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
```

```
ccgtattgat caatgtaraa tcttgtctc                                      29

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gaatggatcg ctaacaatca g                                              21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tgtcataaac ccgagtgttt c                                              21

<210> SEQ ID NO 21
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(18)
<223> OTHER INFORMATION: N = any nucleotide
<220> FEATURE:
<221> NAME/KEY: modified_base
<222> LOCATION: (3)..(18)
<223> OTHER INFORMATION: I

<400> SEQUENCE: 21
ctncrrgarc tnccngantc ttaya                                          25

<210> SEQ ID NO 22
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(25)
<223> OTHER INFORMATION: N = any nucleotide
<220> FEATURE:
<221> NAME/KEY: modified_base
<222> LOCATION: (4)..(25)
<223> OTHER INFORMATION: I

<400> SEQUENCE: 22
gtcngtrtgn gskgknagac ccatngc                                        27

<210> SEQ ID NO 23
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(24)
<223> OTHER INFORMATION: N = any nucleotide
<220> FEATURE:
```

```
<221> NAME/KEY: modified_base
<222> LOCATION: (3)..(24)
<223> OTHER INFORMATION: I

<400> SEQUENCE: 23
gcnatgggtc tnrcnscnca ycangac                                        27

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
gtkcsaagrt actcwttcca wgtcac                                         26

<210> SEQ ID NO 25
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: N = any nucleotide

<400> SEQUENCE: 25
ntcgastwts gwgtt                                                     15

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
ttataaactg gtggtttctc agtg                                           24

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
gaagccatgt ttctcacgtt gta                                            23

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
aaatagcggc cgcgtttcaa acaaaatggg tgcgtggag                           39

<210> SEQ ID NO 29
<211> LENGTH: 27
<212> TYPE: DNA
<213> ORGANISM: Artificial Sequence
<220> FEATURE:
<223> OTHER INFORMATION: Primer
```

```
<400> SEQUENCE: 29
gaagatctgg ttctcacgtt gtagttg                                          27

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
gtggtagctg aaatcttg                                                    18

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
cctggcaaat ccatagcc                                                    18

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
cccatatcaa ggagactt                                                    18

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
catggttggt gacttgga                                                    18

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
agttagccgg gagattgatg tg                                               22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ccttaggcat aattgccaaa                                                  20

<210> SEQ ID NO 36
```

```
<211> LENGTH: 22
<212> TYPE: DNA
<213> ORGANISM: Artificial Sequence
<220> FEATURE:
<223> OTHER INFORMATION: Primer

<400> SEQUENCE: 36
cagcactagt gggttgcagg tc                                            22

<210> SEQ ID NO 37
<211> LENGTH: 41
<212> TYPE: DNA
<213> ORGANISM: Artificial Sequence
<220> FEATURE:
<223> OTHER INFORMATION: Primer

<400> SEQUENCE: 37
ccatctagaa gatctcatat ggctttgaac ggcaaggtgg c                       41

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
ccagcatccg gtacctcatt aagcagacgg ggcgctaata gtgg                    44

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
agcaagttca gcctggttaa gt                                            22

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
ttatgagtat ttcttccagg g                                             21

<210> SEQ ID NO 41
<211> LENGTH: 61
<212> TYPE: PRT
<213> ORGANISM: Consensus
<220> FEATURE:
<221> NAME/KEY: MISC_FEATURE
<222> LOCATION: (1)..(61)
<223> OTHER INFORMATION: Variant
<220> FEATURE:
<221> NAME/KEY: VARIANT
<222> LOCATION: (10)..(10)
<223> OTHER INFORMATION: I or L
<220> FEATURE:
<221> NAME/KEY: VARIANT
<222> LOCATION: (13)..(13)
<223> OTHER INFORMATION: L or V
<220> FEATURE:
<221> NAME/KEY: VARIANT
<222> LOCATION: (25)..(25)
<223> OTHER INFORMATION: C or N
```

```
<220> FEATURE:
<221> NAME/KEY: VARIANT
<222> LOCATION: (30)..(30)
<223> OTHER INFORMATION: S or T
<220> FEATURE:
<221> NAME/KEY: VARIANT
<222> LOCATION: (32)..(32)
<223> OTHER INFORMATION: I or V
<220> FEATURE:
<221> NAME/KEY: VARIANT
<222> LOCATION: (35)..(35)
<223> OTHER INFORMATION: P or T
<220> FEATURE:
<221> NAME/KEY: VARIANT
<222> LOCATION: (38)..(38)
<223> OTHER INFORMATION: H or Q
<220> FEATURE:
<221> NAME/KEY: VARIANT
<222> LOCATION: (39)..(39)
<223> OTHER INFORMATION: S or T
<220> FEATURE:
<221> NAME/KEY: VARIANT
<222> LOCATION: (61)..(61)
<223> OTHER INFORMATION: K or R

<400> SEQUENCE: 41

Gly Phe Gly Glu His Thr Asp Pro Gln Xaa Ile Ser Xaa Leu Arg Ser
1               5                  10                  15

Asn Xaa Thr Xaa Gly Leu Gln Ile Xaa Xaa Xaa Asp Gly Xaa Trp Xaa
            20                  25                  30

Xaa Val Xaa Pro Asp Xaa Xaa Ser Phe Phe Xaa Asn Val Gly Asp Xaa
        35                  40                  45

Leu Gln Val Met Thr Asn Gly Arg Phe Lys Ser Val Xaa
    50                  55                  60

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
agggctccaa gtgtccaatt ca                                      22

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
taaatctccc gttcgtcatc ac                                      22

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
ctaaaaagct tgctcataa acctg                                    25

<210> SEQ ID NO 45
<211> LENGTH: 27
<212> TYPE: DNA
```

```
<213> ORGANISM: Artificial Sequence
<220> FEATURE:
<223> OTHER INFORMATION: Primer

<400> SEQUENCE: 45
atggtgaaag ggtcccagaa aatcgtg                                27

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
gagagctgag agcgaaaggc a                                     21

<210> SEQ ID NO 47
<211> LENGTH: 31
<212> TYPE: DNA
<213> ORGANISM: Artificial Sequence
<220> FEATURE:
<223> OTHER INFORMATION: Primer

<400> SEQUENCE: 47
tttagatcta gggagagagg gattttatga g                          31

<210> SEQ ID NO 48
<211> LENGTH: 35
<212> TYPE: DNA
<213> ORGANISM: Artificial Sequence
<220> FEATURE:
<223> OTHER INFORMATION: Primer

<400> SEQUENCE: 48
atgcggccgc agaatattat atcgaccggt cggtt                      35

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
atggtgaaag ggtcccagaa aatc                                  24

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
ccttatcatc ttctctcata aaatc                                 25

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
ggcctccagg tggcattccc t                                     21
```

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
gaatctccca ttcgtcatca c                                          21

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
ggccacgcgt cgactagtac                                            20

<210> SEQ ID NO 54
<211> LENGTH: 37
<212> TYPE: DNA
<213> ORGANISM: Artificial Sequence
<220> FEATURE:
<223> OTHER INFORMATION: Primer

<400> SEQUENCE: 54
ggccacgcgt cgactagtac tttttttttt ttttttt                         37

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
tgtaatacga ctcactatag ggc                                        23

<210> SEQ ID NO 56
<211> LENGTH: 723
<212> TYPE: DNA
<213> ORGANISM: Arabidopsis thaliana

<400> SEQUENCE: 56
tatccaccgt ccgatcaatt ctttggtgaa gccaatcttt ctgaccaatc tgtgtcactg    60
acaagagttg gcttcggaga acacaccgac cctcagattt taacagttct tagatctaac   120
ggtgtaggag ggctccaagt gtccaattca gatggcatgt gggtttctgt ctcccctgac   180
ccttcagctt tctgcgtcaa tgtaggagac ttgttacagg tcaatgtctt ctttttttctt   240 tctttcttga ttacattttt tttattacat cattttttatt tgtggtgatt aaagatcgta   300
attaaaaaaa aaaattgtta gtcctaaacg aaatcagaaa ccgtaaaaat cgaacatata   360
ctaaactata accatttatt tataaaatca tcaaacaaga aaccataaaa gccaaaccta   420
aactaaacat taaacatgtt tttatctttc ttttggtcac aagatattac tttaacattt   480
tttctgtcat ttatcaatgt tgtggacctt atattaattg gttcttggat tttaaggtga   540
tgacgaacgg gagatttata agtgtaaggc atagagcatt gacctacgga gaagaaagcc   600
ggctatccac ggcgtacttt gccggaccac cgcttcaggc gaagattggg cctctttcgg   660

-continued

| | |
|---|---|
| cgatggttat gacgatgaat cagccacggt tgtaccaaac atttacttgg ggcgagtaca | 720 |
| aga | 723 |

<210> SEQ ID NO 57
<211> LENGTH: 4170
<212> TYPE: DNA
<213> ORGANISM: Arabidopsis thaliana

<400> SEQUENCE: 57

| | |
|---|---|
| tctagaatat tatatcgacc ggtcggttat tataatacta tctcacatat attatctttt | 60 |
| attttattca actagaggaa agcaagattc caaaaagaaa acaataaaat tgtattgtgg | 120 |
| atgttgaata gtataaagag gtcaaacttc ttttgcaaat tgggaatttg cgggttctac | 180 |
| tttagccaga agtctttgat cagctgaata tcccgaggaa tacaaattaa tatatgtgaa | 240 |
| agaggtttac gacgaatatt tggaagaata gtactatgca ttcttaccta aaaggtaggg | 300 |
| gaagtatatt acatgatggg gtgacaaaaa ataatattag gtgcaatgat ctaacacgaa | 360 |
| attgagtttt gagttagatg ttgaatgatg ggttcatatt aagcatttac atatgagata | 420 |
| atacatagag aacacgcatt ttgactattt atgtttaata tatatgtacc tacacttgaa | 480 |
| agtataaagg attttaacaa attcatctta acaatagata aaaaaaattc acaaaaaaag | 540 |
| aagaagatga aattctatca gttagtaact tcttaatttt attctgtaaa gtggtcgtag | 600 |
| ttgtattgct aaaaaattca tcatcagtta aaatgatttg tgtaagaaaa gaagaaagca | 660 |
| aaatttcagt gaaaaaggaa aaaccaaaaa gctaattgaa gtcttaattc tgatgcgttt | 720 |
| agaaaacttt aatcgtaaca aagcatcatg caatactctt tttcgttaat tatctacctt | 780 |
| tagtccttat aaatttataa gagtactcca ccaaacatag tattacccga atacccgttg | 840 |
| gtgcctaata catgcacgtg ataaccaatt ttaatttgcc aacaattctc tctcttgtgt | 900 |
| gcagtgtgta tataaatata gccacacata catacactaa tgttgaaaat ttcttcctta | 960 |
| tcatcttctc tcataaaatc cctctctccc tttctctaaa aatggtgaaa gggtcccaga | 1020 |
| aaatcgtggc cgtagatcaa gacataccaa taatagacat gtcgcaggag agatcacaag | 1080 |
| tgtcgatgca gatagtcaaa gcctgcgaga gtctcggctt cttcaaagtc atcaaccatg | 1140 |
| gcgttgacca aaccaccatc tcaagaatgg agcaagagtc tataaacttc tttgctaaac | 1200 |
| cggctcacga gaagaaatct gtccgaccag ttaaccagcc tttccggtat ggttttagag | 1260 |
| acattggact caacggtgac tctggtgagg tcgagtattt gctgtttcac actaacgacc | 1320 |
| ctgcctttcg ctctcagctc tccttcaggt agacgtatag taactgtatt tctagatata | 1380 |
| tacggttcgg gtttggtctc attttaacct aatcattatt aatattttaa tgaaattata | 1440 |
| ttgaaatagt ttatatatag ttgcatgtaa aatatacaac tgcatgtata gcttggatac | 1500 |
| gttcaaaagc ttatactata tatctaccaa acttcaaaaa tattaatgtg ataaatgcac | 1560 |
| atgattatta tatgtaggca aagtgcatgt ttatgttaat tattttttaa tgcatgctaa | 1620 |
| tatgtcagca taacagtata tataatttaa ttaagtgtta acttgtaggt ctacatttat | 1680 |
| gtaaaaggag acagttatag ctcatggaag cattaattat tgatactaaa tacaaacagt | 1740 |
| tcacctttta tgtatttaaa tagatatagg cttgttttc atttattttg gaagctttta | 1800 |
| aacaatacta gagtctggag aaaccaaacg taccagacat gtagtaaact aaaaaaatgt | 1860 |
| aatagtctct ctcaataaca gtgtatggat aagaattgtg tatctactaa tctacatgat | 1920 |
| acatgacatg tactatttta tatttgagct tttagaaaaa cttatatata ctacaatctg | 1980 |
| ctagtctttg ttctcaaata tactaactct tacgaagttg tataattgtt cgtactaatg | 2040 |

-continued

```
tttcaacagt tttttttttgt acttaactca ataatggctc aataatgatt cattttttgtc      2100
tatctttttt tttctttgat agaaaaaaac ccaacttctt tctgaaagta gaaatattaa      2160
ggttacgtgg atatatttcg tatatttcta taagtaacca aaaataaatg aatctcgtgc      2220
tgatgtgtga cgtatatgtt tgacagctcg gcagtgaatt gttacataga agcagttaag      2280
cagttggctc gtgagatctt agatctgacg gctgagggac ttcatgtccc acctcacagt      2340
ttcagtaggt taatcagctc cgtcgatagt gactccgttc tgagagtgaa tcattatcca      2400
ccgtccgatc aattctttgg tgaagccaat ctttctgacc aatctgtgtc actgacaaga      2460
gttggcttcg gagaacacac cgaccctcag attttaacag ttcttagatc taacggtgta      2520
ggagggctcc aagtgtccaa ttcagatggc atgtgggttt ctgtctcccc tgacccttca      2580
gctttctgcg tcaatgtagg agacttgtta caggtcaatg tcttcttttt tctttctttc      2640
ttgattacat ttttttttatt acatcatttt tatttgtggt gattaaagat cgtaattaaa      2700
aaaaaaatt gttagtccta aacgaaatca gaaaccgtaa aaatcgaaca tatactaaac       2760
tataaccatt tatttataaa atcatcaaac aagaaaccat aaaagccaaa cctaaactaa      2820
acattaaaca tgtttttatc tttcttttgg tcacaagata ttactttaac attttttctg      2880
tcatttatca atgttgtgga ccttatatta attggttctt ggatttttaag gtgatgacga     2940
acgggagatt tataagtgta aggcatagag cattgaccta cggagaagaa agccggctat      3000
ccacggcgta ctttgccgga ccaccgcttc aggcgaagat tgggcctctt tcggcgatgg      3060
ttatgacgat gaatcagcca cggttgtacc aaacatttac ttggggcgag tacaagaaac      3120
ttgcgtactc tctacgactt gaggatagcc gtttagacat gtttcgtaca tgtaaggact      3180
agtattcagg tttatggcaa agcttttttag taatatctat gaaatgtttt cgtctaacta     3240
tgttcccttta aaaagtttta agctaaacgt agacatgtta gatctgtgta cctagaacta    3300
ggagttgaaa gttttgtaat gtgttacctt aactttgttg aggtgaaatg tgatacccca      3360
ctatattaag gaagtgatat tagataaaac gattcaatta tgaagtataa gattcttttta    3420
attattgaac tgttaaagta gggatgagga tgaatataca ttacctgtta accgtttttac    3480
ctataaccat tttacttgta aaatcatctt tatattttct tactcgaatt tcaaatcttc      3540
ttcttctcca tctccttgat tatttatcat gggtacatac atgtatcatg tattagacta      3600
ttagtcgttt agtattgggt tgttattagg tacaacggcc ttttgggcct attgaatttg      3660
gataatctta attttccttt ttaaaatcag ttgtacaatc aaccatctta tatagttcat      3720
gtgcttgcaa cgttttttaga tatttgagat ccaatctttt acatttttatc tatataatga    3780
ctaaatggat tttatagtaa tcattattac tattttgcga gtgagtgcgt aaattcaact      3840
ttgtcaagac agaaatacac tttgaaaatg tcaataagta aacatgacaa tgtccacgaa      3900
tggtttatttt cttgaggttg ctttgcatac actctaatca taatttacat acagcttttg    3960
acatttgtct aactttagtt ctttataaag ttctaactgc ataattaacc tttgtaacct      4020
tttatagatt agactaattg attaagtttc ttttaatttt cataaaaccc cattaactcg      4080
tgcatcagtg catgtagggt tccctttttct actttatatt agaacaagtt cctaagcaaa     4140
gactttcgtt ttgttacttt attttctaga                                        4170
```

<210> SEQ ID NO 58
<211> LENGTH: 966
<212> TYPE: DNA
<213> ORGANISM: Arabidopsis thaliana

```
<400> SEQUENCE: 58
atggtgaaag ggtcccagaa aatcgtggcc gtagatcaag acataccaat aatagacatg      60
tcgcaggaga gatcacaagt gtcgatgcag atagtcaaag cctgcgagag tctcggcttc     120
ttcaaagtca tcaaccatgg cgttgaccaa accaccatct caagaatgga gcaagagtct     180
ataaacttct tgctaaaacc ggctcacgag aagaaatctg tccgaccagt taaccagcct     240
ttccggtatg gttttagaga cattggactc aacggtgact ctggtgaggt cgagtatttg     300
ctgtttcaca ctaacgaccc tgcctttcgc tctcagctct ccttcagctc ggcagtgaat     360
tgttacatag aagcagttaa gcagttggct cgtgagatct tagatctgac ggctgaggga     420
cttcatgtcc cacctcacag tttcagtagg ttaatcagct ccgtcgatag tgactccgtt     480
ctgagagtga atcattatcc accgtccgat caattctttg gtgaagccaa tctttctgac     540
caatctgtgt cactgacaag agttggcttc ggagaacaca ccgaccctca gattttaaca     600
gttcttagat ctaacggtgt aggagggctc caagtgtcca attcagatgg catgtgggtt     660
tctgtctccc ctgacccttc agctttctgc gtcaatgtag gagacttgtt acaggtgatg     720
acgaacggga gatttataag tgtaaggcat agagcattga cctacggaga agaaaagccgg    780 ctatccacgg cgtactttgc cggaccaccg cttcaggcga agattgggcc tctttcggcg     840
atggttatga cgatgaatca gccacggttg taccaaacat ttacttgggg cgagtacaag     900
aaacttgcgt actctctacg acttgaggat agccgtttag acatgtttcg tacatgtaag     960
gactag                                                                966

<210> SEQ ID NO 59
<211> LENGTH: 321
<212> TYPE: PRT
<213> ORGANISM: Arabidopsis thaliana

<400> SEQUENCE: 59

Met Val Lys Gly Ser Gln Lys Ile Val Ala Val Asp Gln Asp Ile Pro
1               5                   10                  15

Ile Ile Asp Met Ser Gln Glu Arg Ser Gln Val Ser Met Gln Ile Val
            20                  25                  30

Lys Ala Cys Glu Ser Leu Gly Phe Phe Lys Val Ile Asn His Gly Val
        35                  40                  45

Asp Gln Thr Thr Ile Ser Arg Met Glu Gln Glu Ser Ile Asn Phe Phe
    50                  55                  60

Ala Lys Pro Ala His Glu Lys Lys Ser Val Arg Pro Val Asn Gln Pro
65                  70                  75                  80

Phe Arg Tyr Gly Phe Arg Asp Ile Gly Leu Asn Gly Asp Ser Gly Glu
                85                  90                  95

Val Glu Tyr Leu Leu Phe His Thr Asn Asp Pro Ala Phe Arg Ser Gln
            100                 105                 110

Leu Ser Phe Ser Ser Ala Val Asn Cys Tyr Ile Glu Ala Val Lys Gln
        115                 120                 125

Leu Ala Arg Glu Ile Leu Asp Leu Thr Ala Glu Gly Leu His Val Pro
    130                 135                 140

Pro His Ser Phe Ser Arg Leu Ile Ser Ser Val Asp Ser Asp Ser Val
145                 150                 155                 160

Leu Arg Val Asn His Tyr Pro Pro Ser Asp Gln Phe Phe Gly Glu Ala
                165                 170                 175

Asn Leu Ser Asp Gln Ser Val Ser Leu Thr Arg Val Gly Phe Gly Glu
            180                 185                 190
```

His Thr Asp Pro Gln Ile Leu Thr Val Leu Arg Ser Asn Gly Val Gly
        195                 200                 205

Gly Leu Gln Val Ser Asn Ser Asp Gly Met Trp Val Ser Val Ser Pro
        210                 215                 220

Asp Pro Ser Ala Phe Cys Val Asn Val Gly Asp Leu Leu Gln Val Met
225                 230                 235                 240

Thr Asn Gly Arg Phe Ile Ser Val Arg His Arg Ala Leu Thr Tyr Gly
                245                 250                 255

Glu Glu Ser Arg Leu Ser Thr Ala Tyr Phe Ala Gly Pro Pro Leu Gln
        260                 265                 270

Ala Lys Ile Gly Pro Leu Ser Ala Met Val Met Thr Met Asn Gln Pro
        275                 280                 285

Arg Leu Tyr Gln Thr Phe Thr Trp Gly Glu Tyr Lys Lys Leu Ala Tyr
        290                 295                 300

Ser Leu Arg Leu Glu Asp Ser Arg Leu Asp Met Phe Arg Thr Cys Lys
305                 310                 315                 320

Asp

<210> SEQ ID NO 60
<211> LENGTH: 810
<212> TYPE: DNA
<213> ORGANISM: Arabidopsis thaliana
<220> FEATURE:
<221> NAME/KEY: misc_feature
<222> LOCATION: (766)..(766)
<223> OTHER INFORMATION: N = any nucleotide

<400> SEQUENCE: 60

```
taacgctaac ttatatcaac aataaaaaag tcctttttc cttttttcc ccccctgaaa      60
ctgttatgct ttcgaaattt cacttatctc tctgacgtgt ttagtttcat cctaaaagtg     120
tatatatata tagcttaatg tttctatgtt ttctcttatc ttataatata tgtatttctt    180
ataatgagca actcgtgatg atgtatgata tgtctgtttg acagctctgc ggtgacgtgt    240
tacgtagaag caattaagca gttggcgtgt gagatcttag acctcacggc tgaaggacta    300
cggctcccac ctcataccct cagcaagtta atcagagccg ttgatagcga ctcagttctc    360
aggcttaatc actacccatc atccaatcaa ttccttagtg gagccaaggt ttctgatatg    420
tctgtgtcat taccgagagt tggcttcggg gaacacacag accctcagat cttgacagtc    480
cttagatcca atagagtagg gggcctccag gtggcattcc ctgacggaag gtgggtctct    540
gtctcccctg acccttcaac cttttgcgta aacgttggcg atcttttgca ggtcagtccc    600
tatattcatt acccatttga ttctgtatat gttactttaa aaaaaaaaa aggttttcag    660
gtgctacttg aaaaacttaa aatgcaggaa tctaactatt aataataca tatcaacatg    720
taagaatcta ctaagattct ataaatttcc caactattat aactanaata ttaatcgatg    780
caaaatttct aggtgatgac gaatgggaga                                    810
```

<210> SEQ ID NO 61
<211> LENGTH: 123
<212> TYPE: PRT
<213> ORGANISM: Arabidopsis thaliana

<400> SEQUENCE: 61

Ser Ala Val Thr Cys Tyr Val Glu Ala Ile Lys Gln Leu Ala Cys Glu
1               5                   10                  15

Ile Leu Asp Leu Thr Ala Glu Gly Leu Arg Leu Pro Pro His Thr Phe

```
                    20                  25                  30
Ser Lys Leu Ile Arg Ala Val Asp Ser Asp Ser Val Leu Arg Leu Asn
             35                  40                  45

His Tyr Pro Ser Ser Asn Gln Phe Leu Ser Gly Ala Lys Val Ser Asp
 50                  55                  60

Met Ser Val Ser Leu Pro Arg Val Gly Phe Glu His Thr Asp Pro
 65                  70                  75                  80

Gln Ile Leu Thr Val Leu Arg Ser Asn Arg Val Gly Gly Leu Gln Val
                 85                  90                  95

Ala Phe Pro Asp Gly Arg Trp Val Ser Val Ser Pro Asp Pro Ser Thr
            100                 105                 110

Phe Cys Val Asn Val Gly Asp Leu Leu Gln Val
        115                 120

<210> SEQ ID NO 62
<211> LENGTH: 1359
<212> TYPE: DNA
<213> ORGANISM: Glycine max

<400> SEQUENCE: 62
ctcaatctct cttcttaccc atttcctccc cccctctttc tcttttcttg ttctgttttt      60
attttcactg ttctctgata acaacgttgt tagttgtcac catggttgtt ctgtctcagc     120
cagcattaaa ccagtttttc cttctgaaaa catgcaagcc cacgcccttg ttcgcgggga     180
ttcctgtggt cgacctcacg gaccccgatg ccaagaccca catagtcaat gcctgcaggg     240
acttcggctt cttcaagctc gtgaaccacg gtgttccgtt acagttcatg gccaatttgg     300
aaaacgaaac cctcgggttc ttcaaaaaac tcaatccga  aaagacagg  gctggtcccc     360 ctgacccttt tggctacggc agcaagagga ttggccctaa cggcgatgtc ggttgggtcg     420
aatacctcct tctcaacacc aaccctgatg tcatctcccc caagtcacag ttcattttca     480
gagaaggtcc tcagaatttc agggcggtgg tgaggaata  cattagagcg gtgaagaaca     540
tgtgctatga ggtgttggaa ttgatggctg agggattggg gataacgcag aggaatgtgt     600
tgagtaggtt gctgaaggat gagaagagtg atycttgctt cagacttaac cactacccgc     660
catgcccgga ggtgcaagca ttgaacggaa ggaatttggt tggatttgga gagcacacag     720
acccacagat aatttctgtc ttgagatcta acagcacctc aggcctgcaa atctgtctca     780
cagatggcac ttgggtttct gtcccacctg atcaaacttc cttttttcatc aatgttggtg     840 acactcttca ggtaatgact aatgggaggt ttaaaagtgt aaagcataga gttttggctg     900
acccaaccaa gtcaaggttg tcaatgatct actttggagg accacccttg tgtgaaaaga     960 tagcacctt accttcactc atgttaaaag gagaagagag tttctacaaa gagttcacat    1020
ggtgggaata caagaaggct gcgtacgcgt caaggctagc ggataataga ctcggcccctt    1080 ttgagaaatc tgctgctgat taaggaggca agtgtgtca aaattctact actcaatttt    1140
ggcacgtgtt gttaggccaa cttttttatt ttttatttt tttgggtgtg tgtatctagg    1200
ttccaaacag ttgactttac ttgagatata tagaaaatga ataggttgct tatgcacttc    1260
cttttaatcc ttgttctttt tcttgtttga ttgaagtgta atagtcacta ctgcccttct    1320
attatcaatg aaacgcaact ctagtcacag cttttcatt                         1359

<210> SEQ ID NO 63
<211> LENGTH: 333
<212> TYPE: PRT
<213> ORGANISM: Glycine max
```

<220> FEATURE:
<221> NAME/KEY: MISC_FEATURE
<222> LOCATION: (178)..(178)
<223> OTHER INFORMATION: Xaa = any

<400> SEQUENCE: 63

Met Val Val Leu Ser Gln Pro Ala Leu Asn Gln Phe Phe Leu Leu Lys
1               5                   10                  15

Thr Cys Lys Pro Thr Pro Leu Phe Ala Gly Ile Pro Val Val Asp Leu
            20                  25                  30

Thr Asp Pro Asp Ala Lys Thr His Ile Val Asn Ala Cys Arg Asp Phe
        35                  40                  45

Gly Phe Phe Lys Leu Val Asn His Gly Val Pro Leu Gln Phe Met Ala
    50                  55                  60

Asn Leu Glu Asn Glu Thr Leu Gly Phe Phe Lys Pro Gln Ser Glu
65                  70                  75                  80

Lys Asp Arg Ala Gly Pro Pro Asp Pro Phe Gly Tyr Gly Ser Lys Arg
                85                  90                  95

Ile Gly Pro Asn Gly Asp Val Gly Trp Val Glu Tyr Leu Leu Leu Asn
            100                 105                 110

Thr Asn Pro Asp Val Ile Ser Pro Lys Ser Gln Phe Ile Phe Arg Glu
        115                 120                 125

Gly Pro Gln Asn Phe Arg Ala Val Val Glu Glu Tyr Ile Arg Ala Val
    130                 135                 140

Lys Asn Met Cys Tyr Glu Val Leu Glu Leu Met Ala Glu Gly Leu Gly
145                 150                 155                 160

Ile Thr Gln Arg Asn Val Leu Ser Arg Leu Leu Lys Asp Glu Lys Ser
                165                 170                 175

Asp Xaa Cys Phe Arg Leu Asn His Tyr Pro Pro Cys Pro Glu Val Gln
            180                 185                 190

Ala Leu Asn Gly Arg Asn Leu Val Gly Phe Gly Glu His Thr Asp Pro
        195                 200                 205

Gln Ile Ile Ser Val Leu Arg Ser Asn Ser Thr Ser Gly Leu Gln Ile
    210                 215                 220

Cys Leu Thr Asp Gly Thr Trp Val Ser Val Pro Pro Asp Gln Thr Ser
225                 230                 235                 240

Phe Phe Ile Asn Val Gly Asp Thr Leu Gln Val Met Thr Asn Gly Arg
                245                 250                 255

Phe Lys Ser Val Lys His Arg Val Leu Ala Asp Pro Thr Lys Ser Arg
            260                 265                 270

Leu Ser Met Ile Tyr Phe Gly Gly Pro Pro Leu Cys Glu Lys Ile Ala
        275                 280                 285

Pro Leu Pro Ser Leu Met Leu Lys Gly Glu Glu Ser Phe Tyr Lys Glu
    290                 295                 300

Phe Thr Trp Trp Glu Tyr Lys Lys Ala Ala Tyr Ala Ser Arg Leu Ala
305                 310                 315                 320

Asp Asn Arg Leu Gly Pro Phe Glu Lys Ser Ala Ala Asp
                325                 330

<210> SEQ ID NO 64
<211> LENGTH: 1403
<212> TYPE: DNA
<213> ORGANISM: Glycine max

<400> SEQUENCE: 64
ctgctcagag cctcattaag ttttttctct tatacttatt cattgactct ccaaaagccc    60

-continued

```
tttaaacctc tctattcctc tctcacgtac cctcttcctt ccattcactc cacttcttaa    120
ctccccaaaa cagaaagcag caagaaaaat ggtgttgctg tccaaggcaa caacagaaca    180
atactcctac atcaagaact acatgccaac ggcattctcc tcaacaattc ccgtagtgga    240
cctctccaaa ccagatgcaa agaccctcat agtgaaggct tgtgaggaat ttggattctt    300
caaagtcatc aaccatggtg ttcccatgga aactatatcc caattggaat ctgaagcctt    360
caagttcttc tctatgccac tcaatgagaa ggaaaaagta ggccctccca aaccatatgg    420
gtatggtagc aagaaaattg gacacaatgg ggatgttggt tgggttgagt accttcttct    480
caacaccaat caagaacaca acttctctgt ttatggcaaa aacgctgaga aatttaggtg    540
tttgttgaac agttacatgt cttctgtgag gaaaatggca tgtgagattc ttgagctgat    600
ggcagaagga ttgaagatac aacaaaaaaa tgtgtttagc aagcttctta tggataaaga    660
gagtgactct gttttttaggg tgaatcacta ccctgcttgc cctgaacttg tgaatggtca    720
aaacatgata gggtttggag aacacacgga cccacaaatc atttctctac ttaggtccaa    780
caatacttca ggccttcaga tttttcttag agatggaaac tggatttcag tcccacctga    840
tcacaaatct ttcttcataa atgttggtga ttctcttcag gttatgacca atggaaggtt    900
tcgaagtgtg aaacacagag ttttgacaaa tggatttaag tctagactct caatgattta    960
ctttggaggt ccaccattga gtgagaaaat agtaccatta tcttcactta tgaaaggaaa   1020
agaaagctta tacaaagagt ttacgtggtt cgagtataaa aatttaacct atgcttcaag   1080
attggctgat aataggcttg gacattttga gagaattgtt gcttcataat atgctaaagg   1140
attacggggg catttgtcaa tacaaaatgg ggggttacaa tatatagtct atgtactata   1200
tatgtttttt tttttttttc aactttaagg ttatttatca attagaatgc ttcatagacg   1260
atagaatata taccccttt gcttttgctt caacactagt ggatgacgtc tgatgtagtc    1320
aacaatggag atttgttaat gattaaaagc ttgattcaaa ttgtaataaa acattataag   1380
aataaagtat atattccatg cac                                           1403
```

<210> SEQ ID NO 65
<211> LENGTH: 326
<212> TYPE: PRT
<213> ORGANISM: Glycine max

<400> SEQUENCE: 65

```
Met Val Leu Leu Ser Lys Ala Thr Thr Glu Gln Tyr Ser Tyr Ile Lys
1               5                   10                  15

Asn Tyr Met Pro Thr Ala Phe Ser Ser Thr Ile Pro Val Val Asp Leu
            20                  25                  30

Ser Lys Pro Asp Ala Lys Thr Leu Ile Val Lys Ala Cys Glu Glu Phe
        35                  40                  45

Gly Phe Phe Lys Val Ile Asn His Gly Val Pro Met Glu Thr Ile Ser
    50                  55                  60

Gln Leu Glu Ser Glu Ala Phe Lys Phe Phe Ser Met Pro Leu Asn Glu
65                  70                  75                  80

Lys Glu Lys Val Gly Pro Pro Lys Pro Tyr Gly Tyr Gly Ser Lys Lys
                85                  90                  95

Ile Gly His Asn Gly Asp Val Gly Trp Val Glu Tyr Leu Leu Leu Asn
            100                 105                 110

Thr Asn Gln Glu His Asn Phe Ser Val Tyr Gly Lys Asn Ala Glu Lys
        115                 120                 125
```

```
Phe Arg Cys Leu Leu Asn Ser Tyr Met Ser Ser Val Arg Lys Met Ala
    130                 135                 140

Cys Glu Ile Leu Glu Leu Met Ala Glu Gly Leu Lys Ile Gln Gln Lys
145                 150                 155                 160

Asn Val Phe Ser Lys Leu Leu Met Asp Lys Glu Ser Asp Ser Val Phe
                165                 170                 175

Arg Val Asn His Tyr Pro Ala Cys Pro Glu Leu Val Asn Gly Gln Asn
            180                 185                 190

Met Ile Gly Phe Gly Glu His Thr Asp Pro Gln Ile Ile Ser Leu Leu
        195                 200                 205

Arg Ser Asn Asn Thr Ser Gly Leu Gln Ile Phe Leu Arg Asp Gly Asn
    210                 215                 220

Trp Ile Ser Val Pro Pro Asp His Lys Ser Phe Phe Ile Asn Val Gly
225                 230                 235                 240

Asp Ser Leu Gln Val Met Thr Asn Gly Arg Phe Arg Ser Val Lys His
                245                 250                 255

Arg Val Leu Thr Asn Gly Phe Lys Ser Arg Leu Ser Met Ile Tyr Phe
            260                 265                 270

Gly Gly Pro Pro Leu Ser Glu Lys Ile Val Pro Leu Ser Ser Leu Met
        275                 280                 285

Lys Gly Lys Glu Ser Leu Tyr Lys Glu Phe Thr Trp Phe Glu Tyr Lys
    290                 295                 300

Asn Leu Thr Tyr Ala Ser Arg Leu Ala Asp Asn Arg Leu Gly His Phe
305                 310                 315                 320

Glu Arg Ile Val Ala Ser
                325

<210> SEQ ID NO 66
<211> LENGTH: 403
<212> TYPE: DNA
<213> ORGANISM: Glycine max
<220> FEATURE:
<221> NAME/KEY: misc_feature
<222> LOCATION: (178)..(178)
<223> OTHER INFORMATION: N = any nucleotide

<400> SEQUENCE: 66
attcttctct atgtcactca atgaaaagga aaaagtagga cctcccaatc catttgggta      60
tggtagcaag aaaattggac acaatgggga cgttggttgg attgagtacc ttcttctcaa     120
caccaatcaa gaacacaact tctctgttta tggcaaaaac cctgagaaat tcaggtgnct     180
gttgaacagt tacatgtctt ctgtgaggaa gatggcatgt gagattcttg agttgatggc     240
agaagggttg aagattcagc aaaaggatgt gtttagcaag cttctaatgg ataaacaaag     300
tgactctatt ttcagggtga atcattacgc tgcttgtcct gaaatgactc tgaatgatca     360
gaacttgatt gggtttggag aacacacaga cccacaaatc atc                      403

<210> SEQ ID NO 67
<211> LENGTH: 783
<212> TYPE: DNA
<213> ORGANISM: Gossypium hirsutum
<220> FEATURE:
<221> NAME/KEY: misc_feature
<222> LOCATION: (726)..(726)
<223> OTHER INFORMATION: N = any nucleotide

<400> SEQUENCE: 67
cccacgcgtc cgcttttgac tactaatcaa gaccccagtc tccatagctt ccaaactttg      60
```

```
agggtggctt tgaataatta tatgaaatca gtaaagaaaa tggcgtgtga gatacttgaa      120
atgatggctg atgggttgaa gatacaaccc aggaatgtgt tgagcaagct gttgatggat      180
gaagagagtg actctgtttt cagggtgaat cattacccac catgccctaa tgttcaacct      240
ttgagtggta atggcaatgg caatggggat gtgattggat ttggtgaaca cactgatcca      300 caattatct cagtgttgag atctaacaac acttctggtc ttcaaatctc tctaagagaa       360
ggaagctgga tttcagtgcc acctgaccaa acctcattct tcatcaatgt tggtgactcc      420
ttacaggtaa tgaccaatgg aaggtttaaa agtgtaaaac atagggtagt gaccaacagt      480
gtgaaatcaa ggctatcaat gatttatttt ggtggaccac cattgagtga aaaatagca       540 cctttgccat ctttgatgag aggtgatcaa caaagcttat ataagaatt tacttggttc       600 gagtacaaga aatctgctta taattccaga ttggcagata ataggctcat tcactttgaa      660
aaaattgctg cttcttaatc tcttttttta ttttcactt ttgagtagat ttttttttata     720 cttcanataa aaaatagga ttagggaaaa agtttgtagt atcaaaaaag cttgtgtga       780 tct                                                                    783

<210> SEQ ID NO 68
<211> LENGTH: 406
<212> TYPE: DNA
<213> ORGANISM: Gossypium hirsutum
<220> FEATURE:
<221> NAME/KEY: misc_feature
<222> LOCATION: (306)..(306)
<223> OTHER INFORMATION: N = any nucleotide

<400> SEQUENCE: 68
gaaaacagga caaccccagc cttatggcta tggtaataaa aggattggac caaatggtga       60
tgttggttgg gtggaatatc ttctcctcac aaccaaccaa gacccgaatc tccttggaac      120
tgaaaaccca gagagtttca ggattgcttt ggataattat atggcagcag tgaagaaaat      180
ggcatgtgag atacttgaaa tgatagctga tgggctaaag gttcagccaa gaaatgtgtt      240
aagtaagctg atgatggatg aacagagtga ctctgttttc aggctgaacc attaccctcc      300
gtgccnagag gtggttcagt ccttgaatgg aacgagcagt aatgtgattg gattcggtga      360
acacactgac ccacaaatca tttcagtcct aagatccaac aacact                     406

<210> SEQ ID NO 69
<211> LENGTH: 376
<212> TYPE: DNA
<213> ORGANISM: Gossypium hirsutum

<400> SEQUENCE: 69
ctagggtcgt cgaagcttag actacttcag taaagtcttc attttaggt aaaaaagaaa       60 cacacaaatg gttgtgctgt catcggcaac ttcaatgaga accaaaaaaa ccaaagcagt      120
agggattccc gtcgttgatc tttccctcga taggtccacc gtatcggagc taatcgtcaa      180
agcttgtgaa gactatggtt tcttcaaggt catcaaccat ggcgtaccta gtgatacaat      240
atcgagactt gaagacgaag gggttcgttt ctttgacaag gaagcaggtg ataagcaacg      300
tgcagggcct gcaactccat ttggttatgg tttaaagaac atcggtctta atggtgataa      360
gggtgaactt gagtac                                                      376

<210> SEQ ID NO 70
<211> LENGTH: 426
<212> TYPE: DNA
<213> ORGANISM: Zea mays
```

```
<220> FEATURE:
<221> NAME/KEY: misc_feature
<222> LOCATION: (26)..(44)
<223> OTHER INFORMATION: N = any nucleotide

<400> SEQUENCE: 70
cggacccttg ggcggaccct tgggcnattg cngtgcngga caantacttg gcggcggtaa      60
ggcgcataac ctgcacggtg ctgcagctga tggcgcaggg gctgggcctc gacgacaggg    120
acgtgttcag ccggctggtg ctggaccggg acagcgactc catgctgagg gtgaaccact    180
acccgccagc ggcggagacg aggcggctga cggggttcgg cgagcacacc gacccgcaga    240
tcatctccgt cctccgctcc aacgacgcgt ccggcctcga gatcacgctg cgggacggca    300
cctgggtgtc cgtgccctcc gacacggaat ccttcttcgt caatgtcggc gacgcgttgc    360
aggtactcca tagtcccatc taacattaca ttgctacttt attatacaat acacacatga    420
cctggc                                                                426

<210> SEQ ID NO 71
<211> LENGTH: 811
<212> TYPE: DNA
<213> ORGANISM: Zea mays

<400> SEQUENCE: 71
gtacacggtg gcggtgcggc ggatggcgtg cgcggtgctg gagctgatgg cggagggggct     60
gggcatcgcc ggcggcgccg gggacgcggt gctggcgcgg ctggtggcgc gcgcggacag    120
cgactgcatg ctgcgggtga accactaccc gccgcggccg cgctcaacc ccagcctcac     180
ggggttcggc gagcacaccg acccgcagat catctcggtg ctccgcgcca acggcacctc    240
cggcctggag atcgcgctgc gggacggcgc ctgggcctcc gtcccgcccg acggggacgc    300
cttcttcgtc aacgtcggcg acaccctgca ggtgttgacg aacgggaggt tcaggagcgt    360
gaggcacagg gtggtggtga acagcgagaa gtcccgggtg tccatggtct tcttcggcgg    420
cccgccgccc ggcgagaggc tgggcccgct tccgcagctc ctgggcgacg gcggccggag    480
ccggtaccgg gacttcacct ggagcgagtt caagaccagc gggtgcagga ccaggctcgc    540
ggaagaccgc ctgtcccgct tcgagaagaa gtagctagag gctacgtcat ttgcatgacc    600
gccggcggta ggatcgatta ccatgtatgc ttctctgtat atgtcagttg ccagctctag    660
ctactggcac tcccgtctat attagcggcc atgctcgtat tgtacgtgca cgtgtatgca    720
cgcatatggt gcaccacata cagggtatca tccaatgcta tctatccatg gagtaccaac    780
catgcatatg catggtcctg ttattagctt t                                    811

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
ctcaatctct cttcttaccc a                                                21

<210> SEQ ID NO 73
<211> LENGTH: 21
<212> TYPE: DNA
<213> ORGANISM: Artificial Sequence
<220> FEATURE:
<223> OTHER INFORMATION: Primer
```

-continued

<400> SEQUENCE: 73
ctgctcagag cctcattaag t              21

<210> SEQ ID NO 74
<211> LENGTH: 21
<212> TYPE: DNA
<213> ORGANISM: Artificial Sequence
<220> FEATURE:
<223> OTHER INFORMATION: Primer

<400> SEQUENCE: 74
tttgctcaaa gccaaaccaa a              21

<210> SEQ ID NO 75
<211> LENGTH: 1239
<212> TYPE: DNA
<213> ORGANISM: Lycopersicon esculentum

<400> SEQUENCE: 75

```
atgtctgttg ccttgttatg ggttgtttct ccttgtgacg tctcaaatgg acaagtttc      60
atggaatcag tccgggaggg aaaccgtttt tttgattcat cgaggcatag aatttggtg     120
tccaatgaga gaatcaatag aggtggtgga aagcaaacta ataatggacg gaaattttct    180
gtacggtctg ctattttggc tactccatct ggagaacgga cgatgacatc ggaacagatg    240
gtctatgatg tggttttgag gcaggcagcc ttggtgaaga ggcaactgag atctaccaat    300
gagttagaag tgaagccgga tatacctatt ccggggaatt tgggcttgtt gagtgaagca    360
tatgataggt gtggtgaagt atgtgcagag atgcaaaga cgtttaactt aggaactatg    420
ctaatgactc ccgagagaag aagggctatc tgggcaatat atgtatggtg cagaagaaca    480
gatgaacttg ttgatggccc aaacgcatca tatattaccc cggcagccct agataggtgg    540
gaaaataggc tagaagatgt tttcaatggg cggccatttg acatgctcga tggtgctttg    600
tccgatacag tttctaactt tccagttgat attcagccat tcagagatat gattgaagga    660
atgcgtatgg acttgagaaa atcgagatac aaaaacttcg acgaactata cctttattgt    720
tattatgttg ctggtacggt tgggttgatg agtgttccaa ttatgggtat cgcccctgaa    780
tcaaaggcaa caacagagag cgtatataat gctgctttgg ctctggggat cgcaaatcaa    840
ttaactaaca tactcagaga tgttggagaa gatgccagaa gaggaagagt ctacttgcct    900
caagatgaat tagcacaggc aggtctatcc gatgaagata tatttgctgg aagggtgacc    960
gataaatgga gaatctttat gaagaaacaa atacataggg caagaaagtt ctttgatgag   1020
gcagagaatg gcgtgacaga attgagctca gctagtatat ccctgtatg ggcatctttg   1080
gtcttgtacc gcaaaatact agatgagatt gaagccaatg actacaacaa cttcacaaag   1140
agagcatatg tgagcaaatc aaagaagttg attgcattac ctattgcata tgcaaaatct   1200
cttgtgcctc ctacaaaaac tgcctctctt caaagataa                          1239
```

<210> SEQ ID NO 76
<211> LENGTH: 412
<212> TYPE: PRT
<213> ORGANISM: Lycopersicon esculentum

<400> SEQUENCE: 76

```
Met Ser Val Ala Leu Leu Trp Val Val Ser Pro Cys Asp Val Ser Asn
1               5                   10                  15
Gly Thr Ser Phe Met Glu Ser Val Arg Glu Gly Asn Arg Phe Phe Asp
            20                  25                  30
```

-continued

Ser Ser Arg His Arg Asn Leu Val Ser Asn Glu Arg Ile Asn Arg Gly
        35                  40                  45
Gly Gly Lys Gln Thr Asn Asn Gly Arg Lys Phe Ser Val Arg Ser Ala
    50                  55                  60
Ile Leu Ala Thr Pro Ser Gly Glu Arg Thr Met Thr Ser Glu Gln Met
65                  70                  75                  80
Val Tyr Asp Val Val Leu Arg Gln Ala Ala Leu Val Lys Arg Gln Leu
                85                  90                  95
Arg Ser Thr Asn Glu Leu Glu Val Lys Pro Asp Ile Pro Ile Pro Gly
            100                 105                 110
Asn Leu Gly Leu Leu Ser Glu Ala Tyr Asp Arg Cys Gly Glu Val Cys
        115                 120                 125
Ala Glu Tyr Ala Lys Thr Phe Asn Leu Gly Thr Met Leu Met Thr Pro
    130                 135                 140
Glu Arg Arg Arg Ala Ile Trp Ala Ile Tyr Val Trp Cys Arg Arg Thr
145                 150                 155                 160
Asp Glu Leu Val Asp Gly Pro Asn Ala Ser Tyr Ile Thr Pro Ala Ala
                165                 170                 175
Leu Asp Arg Trp Glu Asn Arg Leu Glu Asp Val Phe Asn Gly Arg Pro
            180                 185                 190
Phe Asp Met Leu Asp Gly Ala Leu Ser Asp Thr Val Ser Asn Phe Pro
        195                 200                 205
Val Asp Ile Gln Pro Phe Arg Asp Met Ile Glu Gly Met Arg Met Asp
    210                 215                 220
Leu Arg Lys Ser Arg Tyr Lys Asn Phe Asp Glu Leu Tyr Leu Tyr Cys
225                 230                 235                 240
Tyr Tyr Val Ala Gly Thr Val Gly Leu Met Ser Val Pro Ile Met Gly
                245                 250                 255
Ile Ala Pro Glu Ser Lys Ala Thr Thr Glu Ser Val Tyr Asn Ala Ala
            260                 265                 270
Leu Ala Leu Gly Ile Ala Asn Gln Leu Thr Asn Ile Leu Arg Asp Val
        275                 280                 285
Gly Glu Asp Ala Arg Arg Gly Arg Val Tyr Leu Pro Gln Asp Glu Leu
    290                 295                 300
Ala Gln Ala Gly Leu Ser Asp Glu Asp Ile Phe Ala Gly Arg Val Thr
305                 310                 315                 320
Asp Lys Trp Arg Ile Phe Met Lys Lys Gln Ile His Arg Ala Arg Lys
                325                 330                 335
Phe Phe Asp Glu Ala Glu Lys Gly Val Thr Glu Leu Ser Ser Ala Ser
            340                 345                 350
Arg Phe Pro Val Trp Ala Ser Leu Val Leu Tyr Arg Lys Ile Leu Asp
        355                 360                 365
Glu Ile Glu Ala Asn Asp Tyr Asn Asn Phe Thr Lys Arg Ala Tyr Val
    370                 375                 380
Ser Lys Ser Lys Lys Leu Ile Ala Leu Pro Ile Ala Tyr Ala Lys Ser
385                 390                 395                 400
Leu Val Pro Pro Thr Lys Thr Ala Ser Leu Gln Arg
                405                 410

<210> SEQ ID NO 77
<211> LENGTH: 1161
<212> TYPE: DNA
<213> ORGANISM: Cucurbita maxima

<400> SEQUENCE: 77

```
atggctttga acggcaaggt ggcaaccgaa tccgctccct caaacttgaa tgaggagatg    60
aaagggagt accgtccgcc atttgggggc tccgacgagt caaaggtgcc ggaggatttc   120
atttggtcgg aaaagtttga ggcatccgag ttgctgccgg tgctggatgt ccaactatt   180
gacttggaaa agtttatgag tggcgacaaa agttatgtgg aagaggcgac aaggctggtg   240
gatgaggctt gtagacaaca tggcatattt tttgtggtga accatggagt ggacatagaa   300
atgatgggcc gtgttcatga ctgtatgaat gagttcttta caatgccttt ggatgtgaag   360
cagagggcta agaggaaggt aggtgagagt tatggatata ccaatagctt ctttgggaga   420
ttcgcgtcca atcttccatg gaaggaaacc ttttcccttc gctgtgtggc tgctcaaaac   480
tcctccgcgg ctcatgacta tgttcttgac actttaggcc catcattctc ccatcatggg   540
aaggcgtatc aagagtgtgg gatagcattg aacgagcttg gtacgaagat tgtggagctt   600
ttggggctta gccttggcat ttcaagagaa tacttcaaga atttcttcga ggacaacgat   660
tcaatattga ggcttaatta ctacccaaca tgcgacaagc cagaggttgt gttgggaact   720
ggccctcaca ctgatcccac ctccgtcaca atccttcacc aagaccctgt cagtggcctt   780
caagtgtgct ccaatgatca atggtattca attcctccaa cccagaagc ctttgtcatc   840
aacatcggtg acactttcac gtctctcacg aatgggattt acaagggctg catacaccgc   900
gctgtagtga attccatgaa tgcaagaaaa tcattggcct ctttctgtg ccatcgcat   960
gacaaagtgg tgagagcacc ggaggaattg gtggagaaga gtccaccacg aaagtatcca  1020
gattataaat ggccaatgtt gcttgaaatg acccaaaagc gttaccgacc tgattgcaac  1080
actttggaag ccttcaaaac ttgggttcaa gagggaaagg cgttggacac tgggtccact  1140
attaccgccc cgtctgctta a                                            1161
```

<210> SEQ ID NO 78
<211> LENGTH: 386
<212> TYPE: PRT
<213> ORGANISM: Cucurbita maxima

<400> SEQUENCE: 78

```
Met Ala Leu Asn Gly Lys Val Ala Thr Glu Ser Ala Pro Ser Asn Leu
1               5                   10                  15

Asn Glu Glu Met Lys Gly Glu Tyr Arg Pro Pro Phe Gly Gly Ser Asp
                20                  25                  30

Glu Ser Lys Val Pro Glu Asp Phe Ile Trp Ser Glu Lys Phe Glu Ala
            35                  40                  45

Ser Glu Leu Leu Pro Val Leu Asp Val Pro Thr Ile Asp Leu Glu Lys
        50                  55                  60

Phe Met Ser Gly Asp Lys Ser Tyr Val Glu Glu Ala Thr Arg Leu Val
65                  70                  75                  80

Asp Glu Ala Cys Arg Gln His Gly Ile Phe Phe Val Val Asn His Gly
                85                  90                  95

Val Asp Ile Glu Met Met Gly Arg Val His Asp Cys Met Asn Glu Phe
            100                 105                 110

Phe Thr Met Pro Leu Asp Val Lys Gln Arg Ala Lys Arg Lys Val Gly
        115                 120                 125

Glu Ser Tyr Gly Tyr Thr Asn Ser Phe Phe Gly Arg Phe Ala Ser Asn
    130                 135                 140

Leu Pro Trp Lys Glu Thr Phe Ser Leu Arg Cys Val Ala Ala Gln Asn
145                 150                 155                 160
```

Ser Ser Ala Ala His Asp Tyr Val Leu Asp Thr Leu Gly Pro Ser Phe
            165                 170                 175

Ser His His Gly Lys Ala Tyr Gln Glu Cys Gly Ile Ala Leu Asn Glu
        180                 185                 190

Leu Gly Thr Lys Ile Val Glu Leu Leu Gly Leu Ser Leu Gly Ile Ser
    195                 200                 205

Arg Glu Tyr Phe Lys Asn Phe Phe Glu Asp Asn Asp Ser Ile Leu Arg
    210                 215                 220

Leu Asn Tyr Tyr Pro Thr Cys Asp Lys Pro Glu Val Leu Gly Thr
225                 230                 235                 240

Gly Pro His Thr Asp Pro Thr Ser Val Thr Ile Leu His Gln Asp Pro
                245                 250                 255

Val Ser Gly Leu Gln Val Cys Ser Asn Asp Gln Trp Tyr Ser Ile Pro
            260                 265                 270

Pro Asn Pro Glu Ala Phe Val Ile Asn Ile Gly Asp Thr Phe Thr Ser
        275                 280                 285

Leu Thr Asn Gly Ile Tyr Lys Gly Cys Ile His Arg Ala Val Val Asn
    290                 295                 300

Ser Met Asn Ala Arg Lys Ser Leu Ala Phe Phe Leu Cys Pro Ser His
305                 310                 315                 320

Asp Lys Val Val Arg Ala Pro Glu Glu Leu Val Glu Lys Ser Pro Pro
                325                 330                 335

Arg Lys Tyr Pro Asp Tyr Lys Trp Pro Met Leu Leu Glu Met Thr Gln
            340                 345                 350

Lys Arg Tyr Arg Pro Asp Cys Asn Thr Leu Glu Ala Phe Lys Thr Trp
        355                 360                 365

Val Gln Glu Gly Lys Ala Leu Asp Thr Gly Ser Thr Ile Thr Ala Pro
    370                 375                 380

Ser Ala
385

<210> SEQ ID NO 79
<211> LENGTH: 1041
<212> TYPE: DNA
<213> ORGANISM: Cucurbita maxima

<400> SEQUENCE: 79
atggataagc ttcctgccgt aggccttttg actcctctgg acctcaacac agttgaggct    60
gttcctgaat ctcacgtatg gcctcacctc gatgaatcat cgcagaagtt caaatcggac   120
aaaacggtct cgatcccggt tgtcgatttt aacgacgaca atgtgttgga gctcataggg   180
aaagcctgcg aggagtgggg aatgtttcag ttgattaatc atggtatccc gaaaacccta   240
acagcagaaa ccgaggaggt ggctcgatgt cttttcgctc ttccaaaaag ccagaagatg   300
aagacattaa atgttcccgg aaccgccaac ggctactgca tggccagatt aacgaagcat   360
catgacaaaa tgatgtggca tgaaggattc accgtcatag gttctccggt tgatgatttt   420
aagaaactct ggccatcgga ctaccaaccg ttctgtgata agtggaaga ataccaactt    480 aaaatgaagg ctttagctga taagctaata agcttaatct tcaagtatct tggcatctcc   540
gatgaagaga tggtgaagaa gttgtcttac atcgacccgg ccaccggaaa accccacttg   600
gctttgcgct tgaactcgtt tcctccatgc cctgaaccaa gcaaagtcat gggcctcgcg   660
gcccacactg acacctccct cttcaccatg cttcaccagg cacgcagaga ggggctacag   720
atcttaaacg agaaagaagg ctggcttccg ctggctccga ggagagacgc tctcatcatt   780

-continued

```
aacatcggcg acttcctcca aattatatcg aacgggcggt ttcatagcgt tcctcaccgg    840
gtgatgatac gagagactga gaagactacg atgtcgatgg catatttctt tcatccacca    900
ggtcatttat acgtagcacc ttattgtaag ccattgagtg aaaccctaca gactcccatt    960 tataaggag tgaacgtgaa agaatatttc atcatcaagg ctaaagcctc ggggaaggga   1020
attgctgccc taacaatatg a                                             1041
```

<210> SEQ ID NO 80
<211> LENGTH: 346
<212> TYPE: PRT
<213> ORGANISM: Cucurbita maxima

<400> SEQUENCE: 80

```
Met Asp Lys Leu Pro Ala Val Gly Leu Leu Thr Pro Leu Asp Leu Asn
1               5                   10                  15

Thr Val Glu Ala Val Pro Glu Ser His Val Trp Pro His Leu Asp Glu
            20                  25                  30

Ser Ser Gln Lys Phe Lys Ser Asp Lys Thr Val Ser Ile Pro Val Val
        35                  40                  45

Asp Phe Asn Asp Asn Val Leu Glu Leu Ile Gly Lys Ala Cys Glu
    50                  55                  60

Glu Trp Gly Met Phe Gln Leu Ile Asn His Gly Ile Pro Lys Thr Leu
65                  70                  75                  80

Thr Ala Glu Thr Glu Glu Val Ala Arg Cys Leu Phe Ala Leu Pro Lys
                85                  90                  95

Ser Gln Lys Met Lys Thr Leu Asn Val Pro Gly Thr Ala Asn Gly Tyr
            100                 105                 110

Cys Met Ala Arg Leu Thr Lys His His Asp Lys Met Met Trp His Glu
        115                 120                 125

Gly Phe Thr Val Ile Gly Ser Pro Val Asp Asp Phe Lys Lys Leu Trp
    130                 135                 140

Pro Ser Asp Tyr Gln Pro Phe Cys Asp Lys Val Glu Glu Tyr Gln Leu
145                 150                 155                 160

Lys Met Lys Ala Leu Ala Asp Lys Leu Ile Ser Leu Ile Phe Lys Tyr
                165                 170                 175

Leu Gly Ile Ser Asp Glu Glu Met Val Lys Lys Leu Ser Tyr Ile Asp
            180                 185                 190

Pro Ala Thr Gly Lys Pro His Leu Ala Leu Arg Leu Asn Ser Phe Pro
        195                 200                 205

Pro Cys Pro Glu Pro Ser Lys Val Met Gly Leu Ala Ala His Thr Asp
    210                 215                 220

Thr Ser Leu Phe Thr Met Leu His Gln Ala Arg Arg Glu Gly Leu Gln
225                 230                 235                 240

Ile Leu Asn Glu Lys Glu Gly Trp Leu Pro Leu Ala Pro Arg Arg Asp
                245                 250                 255

Ala Leu Ile Ile Asn Ile Gly Asp Phe Leu Gln Ile Ile Ser Asn Gly
            260                 265                 270

Arg Phe His Ser Val Pro His Arg Val Met Ile Arg Glu Thr Glu Lys
        275                 280                 285

Thr Thr Met Ser Met Ala Tyr Phe Phe His Pro Gly His Leu Tyr
    290                 295                 300

Val Ala Pro Tyr Cys Lys Pro Leu Ser Glu Thr Leu Gln Thr Pro Ile
305                 310                 315                 320
```

```
Tyr Lys Gly Val Asn Val Lys Glu Tyr Phe Ile Ile Lys Ala Lys Ala
                325                 330                 335

Ser Gly Lys Gly Ile Ala Ala Leu Thr Ile
            340                 345
```

<210> SEQ ID NO 81
<211> LENGTH: 30
<212> TYPE: DNA
<213> ORGANISM: Artificial Sequence
<220> FEATURE:
<223> OTHER INFORMATION: Primer

<400> SEQUENCE: 81
cttgtctaga atgtctgttg ccttgttatg                                    30

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
gtaacctagg aaatagaaac ttctctccgt                                    30

<210> SEQ ID NO 83
<211> LENGTH: 33
<212> TYPE: DNA
<213> ORGANISM: Artificial Sequence
<220> FEATURE:
<223> OTHER INFORMATION: Primer

<400> SEQUENCE: 83
tctagatggc tttgaacggc aaggtggcaa ccg                                33

<210> SEQ ID NO 84
<211> LENGTH: 30
<212> TYPE: DNA
<213> ORGANISM: Artificial Sequence
<220> FEATURE:
<223> OTHER INFORMATION: Primer

<400> SEQUENCE: 84
ggatccggtt ggtttaagca gacggggcgg                                    30

<210> SEQ ID NO 85
<211> LENGTH: 19
<212> TYPE: DNA
<213> ORGANISM: Artificial Sequence
<220> FEATURE:
<223> OTHER INFORMATION: Primer

<400> SEQUENCE: 85
tttttttttt tttttttv                                                 19

<210> SEQ ID NO 86
<211> LENGTH: 32
<212> TYPE: DNA
<213> ORGANISM: Artificial Sequence
<220> FEATURE:
<223> OTHER INFORMATION: Primer

<400> SEQUENCE: 86
ggatccatca tattgttagg gcagcaattc cc                                 32

<210> SEQ ID NO 87
<211> LENGTH: 31
<212> TYPE: DNA
<213> ORGANISM: Artificial Sequence
<220> FEATURE:
<223> OTHER INFORMATION: Primer

<400> SEQUENCE: 87
gtctagatgg ataagcttcc tgccgtaggc c                            31

<210> SEQ ID NO 88
<211> LENGTH: 815
<212> TYPE: PRT
<213> ORGANISM: Glycine max

<400> SEQUENCE: 88

```
Met Ala Ser His Phe Arg Leu Pro Ser Phe Ser Ser Asn His Phe
1               5                   10                  15

Leu Leu Thr Ser Ser Ser Ser Ser Ile Ser Leu His His Phe
            20                  25                  30

Ser Lys Ser Ser Leu Gly Ala Val Ser Ser Glu Thr Asn Asp Lys Gln
        35                  40                  45

Glu Ile Arg Cys Arg Ala Ile Ser Lys Pro Arg Thr Gln Glu Cys Ser
    50                  55                  60

Asp Ile Phe Gln Gly Ser Leu Ala Thr Leu Lys Phe Arg Glu Ile Asn
65                  70                  75                  80

Val Glu Asp Asp Ile Glu Glu Glu Gln Asp Ile Gly Ala Leu Val Ala
                85                  90                  95

Asn Glu Ile Lys Lys Arg Val Asp Thr Ile Lys Ser Ile Leu Gly Ser
            100                 105                 110

Met Glu Asp Gly Glu Ile Thr Val Ser Ala Tyr Asp Thr Ala Trp Val
        115                 120                 125

Ala Leu Ile Glu Asp Val His Gly Thr Gly Val Pro Gln Phe Pro Ser
    130                 135                 140

Ser Leu Glu Trp Ile Ala Lys Asn Gln His Pro Asp Gly Ser Trp Gly
145                 150                 155                 160

Asp Lys Glu Leu Phe Ser Ala His Asp Arg Ile Ile Asn Thr Leu Ala
                165                 170                 175

Cys Val Ile Ala Leu Lys Thr Trp Asn Met His Pro Glu Lys Cys Glu
            180                 185                 190

Lys Gly Met Ala Phe Phe Arg Glu Asn Leu Gly Lys Leu Gln Asn Glu
        195                 200                 205

Asn Val Glu His Met Pro Ile Gly Phe Glu Val Ala Phe Pro Ser Leu
    210                 215                 220

Leu Asp Met Ala Arg Gly Leu Asp Ile Glu Val Pro Asn Asn Ser Pro
225                 230                 235                 240

Ile Leu Asn Lys Ile Phe Ala Met Arg Asn Val Lys Leu Thr Arg Ile
                245                 250                 255

Pro Arg Ala Met Arg His Lys Val Pro Thr Ser Leu Leu His Ser Leu
            260                 265                 270

Glu Gly Met Ser Gly Leu Asp Trp Lys Glu Leu Leu Lys Leu Gln Ser
        275                 280                 285

Gln Asp Gly Ser Phe Leu Phe Ser Pro Ser Ser Thr Ala Phe Ala Leu
    290                 295                 300

Met Gln Thr Lys Asp Gln Asn Cys His Asn Tyr Leu Asn Lys Val Val
305                 310                 315                 320
```

```
Lys Arg Phe Asn Gly Gly Val Pro Asn Val Tyr Pro Val Asp Leu Phe
                325                 330                 335
Glu His Ile Trp Val Val Asp Arg Leu Glu Arg Leu Gly Ile Ser Gln
            340                 345                 350
Tyr Phe Gln Gln Glu Ile Lys Asp Cys Leu Ser Tyr Val Tyr Arg Tyr
                355                 360                 365
Trp Thr Glu Lys Gly Ile Cys Trp Ala Arg Asn Ser Asn Val Gln Asp
        370                 375                 380
Ile Asp Asp Thr Ala Met Gly Phe Arg Leu Leu Arg Leu His Gly Tyr
385                 390                 395                 400
Gln Val Ser Ala Asp Val Phe Lys Asn Phe Glu Arg Asn Gly Glu Phe
                405                 410                 415
Phe Cys Phe Thr Gly Gln Thr Thr Gln Ala Val Thr Gly Met Phe Asn
                420                 425                 430
Leu Tyr Arg Ala Thr Gln Ile Met Phe Pro Gly Glu Arg Ile Leu Glu
            435                 440                 445
His Gly Lys His Phe Ser Ala Lys Phe Leu Lys Glu Lys Arg Ala Ala
            450                 455                 460
Asn Glu Leu Val Asp Lys Trp Ile Ile Met Lys Asn Leu Ala Glu Glu
465                 470                 475                 480
Val Ala Tyr Ala Leu Asp Val Pro Trp Tyr Ala Ser Leu Pro Arg Val
                485                 490                 495
Glu Thr Arg Phe Tyr Ile Asp Gln Tyr Gly Gly Glu Ser Asp Val Trp
                500                 505                 510
Ile Gly Lys Thr Leu Tyr Arg Met Ala Tyr Val Asn Asn Asn Asn Tyr
            515                 520                 525
Leu Glu Leu Ala Lys Leu Asp Tyr Asn Cys Gln Ala Leu His Leu
                530                 535                 540
Ile Glu Trp Gly Arg Ile Gln Lys Trp Tyr Ser Glu Ser Arg Leu Glu
545                 550                 555                 560
Glu Phe Gly Met Asn Arg Arg Thr Leu Leu Leu Ala Tyr Phe Val Ala
                565                 570                 575
Ala Ala Ser Ile Phe Glu Pro Glu Lys Ser Arg Val Arg Leu Ala Trp
            580                 585                 590
Ala Gln Thr Ser Ile Leu Leu Glu Thr Ile Thr Ser Tyr Val Ser Asp
            595                 600                 605
Ala Glu Met Arg Lys Ala Phe Met Lys Phe Ser Asp Cys Leu Asn
            610                 615                 620
Arg Arg Asp Tyr Ser Ile Gly Trp Arg Leu Asn Arg Asn Arg Thr Gly
625                 630                 635                 640
His Gly Leu Ala Glu Thr Leu Val Ala Thr Ile Asp Gln Ile Ser Trp
                645                 650                 655
Asp Ile Leu Val Ser His Gly His Glu Ile Gly Tyr Asp Met His Arg
                660                 665                 670
Asn Trp Glu Lys Trp Leu Ser Ser Trp His Arg Glu Gly Asp Lys Cys
            675                 680                 685
Lys Gly Gln Ala Glu Leu Leu Ala Gln Thr Ile Asn Leu Cys Gly Gly
            690                 695                 700
His Trp Ile Ser Glu Asp Gln Val Ser Asp Pro Leu Tyr Gln Ser Leu
705                 710                 715                 720
Leu Gln Leu Thr Asn Asn Leu Cys Asn Lys Leu Arg Cys His Gln Lys
                725                 730                 735
Asp Lys Glu Leu Glu Ser Ser Asn Ser Gly Thr Asn Val Asn Ser Met
```

-continued

```
                   740                 745                 750
Ile Thr Gln Glu Glu Ser Lys Met Gln Glu Leu Val Gln Leu Val
            755                 760                 765

His Gln Lys Ser Pro Thr Gly Ile Asp Phe Asn Ile Lys Asn Thr Phe
    770                 775                 780

Leu Thr Val Ala Lys Ser Phe Tyr Tyr Thr Ala Phe Cys Asp Ser Arg
785                 790                 795                 800

Thr Val Asn Phe His Ile Ala Lys Val Leu Phe Asp Glu Val Val
                805                 810                 815
```

<210> SEQ ID NO 89
<211> LENGTH: 352
<212> TYPE: PRT
<213> ORGANISM: Glycine max
<220> FEATURE:
<221> NAME/KEY: MISC_FEATURE
<222> LOCATION: (97)..(314)
<223> OTHER INFORMATION: Xaa = any

<400> SEQUENCE: 89

```
Met Pro Ser Leu Ser Glu Ala Tyr Arg Ala His Pro Val His Val Gln
1               5                   10                  15

His Lys His Pro Asp Leu Asn Ser Leu Gln Glu Leu Pro Glu Ser Tyr
            20                  25                  30

Thr Trp Thr His His Ser His Asp Asp His Thr Pro Ala Ala Ser Asn
        35                  40                  45

Glu Ser Val Pro Val Ile Asp Leu Asn Asp Pro Asn Ala Ser Lys Leu
    50                  55                  60

Ile His His Ala Cys Ile Thr Trp Gly Ala Tyr Gln Val Val Asn His
65                  70                  75                  80

Ala Ile Pro Met Ser Leu Leu Gln Asp Ile Gln Trp Val Gly Glu Thr
                85                  90                  95

Xaa Phe Ser Leu Pro Cys His Gln Lys Gln Lys Ala Ala Arg Ser Pro
            100                 105                 110

Asp Gly Ala Asp Gly Tyr Gly Leu Ala Arg Ile Ser Ser Phe Phe Pro
        115                 120                 125

Lys Leu Met Trp Ser Glu Gly Phe Thr Ile Val Gly Ser Pro Leu Glu
    130                 135                 140

His Phe Arg Gln Leu Trp Pro Gln Asp Tyr His Lys Tyr Cys Asp Ile
145                 150                 155                 160

Val Lys Arg Tyr Asp Glu Ala Met Lys Lys Leu Val Gly Lys Leu Met
                165                 170                 175

Trp Leu Met Leu Asp Ser Leu Gly Ile Thr Lys Glu Asp Leu Lys Trp
            180                 185                 190

Ala Gly Ser Lys Gly Gln Phe Lys Lys Thr Cys Ala Ala Leu Gln Leu
        195                 200                 205

Asn Ser Tyr Pro Thr Cys Pro Asp Pro Asp Arg Ala Met Gly Leu Ala
    210                 215                 220

Ala His Thr Asp Ser Thr Leu Leu Thr Ile Leu Tyr Gln Asn Asn Ile
225                 230                 235                 240

Ser Gly Leu Gln Val His Arg Lys Gly Gly Trp Val Thr Val Ala
                245                 250                 255

Pro Val Pro Glu Gly Leu Val Ile Asn Val Gly Asp Leu Leu His Ile
            260                 265                 270

Leu Ser Asn Gly Leu Tyr Pro Ser Val Leu His Arg Val Leu Val Asn
        275                 280                 285
```

```
Arg Ile Gln Gln Arg Leu Ser Val Ala Tyr Leu Cys Gly Pro Xaa Pro
    290                 295                 300

Asn Val Glu Ile Cys Pro His Ala Lys Xaa Val Gly Pro Asn Lys Pro
305                 310                 315                 320

Pro Leu Tyr Lys Ala Val Thr Trp Asn Glu Tyr Leu Gly Thr Lys Ala
                325                 330                 335

Lys His Phe Asn Lys Ala Leu Ser Thr Val Arg Leu Cys Ala Pro Ser
                340                 345                 350
```